US008492087B2

(12) United States Patent
Suematsu et al.

(10) Patent No.: US 8,492,087 B2
(45) Date of Patent: Jul. 23, 2013

(54) METHOD OF JUDGING RISK FOR ONSET OF DRUG-INDUCED GRANULOCYTOPENIA

(75) Inventors: Koji Suematsu, Tokushima (JP); Koichi Hasegawa, Tokushima (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 379 days.

(21) Appl. No.: 12/833,611

(22) Filed: Jul. 9, 2010

(65) Prior Publication Data

US 2010/0273176 A1 Oct. 28, 2010

Related U.S. Application Data

(62) Division of application No. 10/563,818, filed as application No. PCT/JP2004/010722 on Jul. 28, 2004.

(30) Foreign Application Priority Data

Jul. 29, 2003 (JP) ................................ 2003-281937

(51) Int. Cl.
*C07H 21/04* (2006.01)
*C12Q 1/68* (2006.01)

(52) U.S. Cl.
USPC ......... 435/6.1; 435/6.11; 435/6.12; 435/91.1; 435/91.2; 536/23.1; 536/24.3; 536/24.33

(58) Field of Classification Search
None
See application file for complete search history.

(56) References Cited

PUBLICATIONS

Office Action issued Apr. 14, 2011, in Canadian Patent Application No. 2,530,168.
Emmanuel Dias Neto, et al., "Shotgun sequencing of the human transcriptome with ORF expressed sequence tags", Proc. Natl. Acad. Sci., vol. 97, No. 7, Mar. 28, 2000, pp. 3491-3496.
André Pawlak, et al., "Characterization of a Large Population of mRNAs from Human Testis", Genomics, vol. 26, 1995, pp. 151-158.
Brookes Anthony J., The essence of SNPs, Gene, vol. 234, pp. 177 to 186, 1999.
Martin Eden R. et al., SNPing Away at Complex Diseases: Analysis of Single-Nucleotide Polymorphisms around APOE in Alzheimer Disease, Am. J. Hum. Genet., vol. 67, pp. 383 to 394, 2000.
Murakami Yasufumi et al., "Bioinformatics no Jissai", Kodansha ltd., pp. 210 to 211, 2003.
Schacher Daniel H. et al., Developmental Expression of Insulin Receptor Substrate-2 During Dimethylsulfoxide-Induced Differentiation of Human HL-60 Cells, The Journal of Immunology, vol. 164, pp. 113 to 120, 2000.
Dolores Bernal, et al.; "Insulin Receptor Substrate-2 Amino Acid Polymorphisms Are Not Associated With Random Type 2 Diabetes Among Causasians"; Jun. 1998; Diabetes, vol. 47, pp. 976-979.
K. Iwamoto, et al.; "Identification of a single nucleotide polymorphism showing no insulin-mediated suppression of the promoter activity in the human insulin receptor substrate 2 gene"; Aug. 2002; Diabetologia, vol. 45, pp. 1182-1195.
Xavier Jeunemaitre, et al.; "Haplotypes of Angiotensinogen in Essential Hypertension"; Mar. 1997; Am. J. Hum. Genet. 60; pp. 1448-1460.
Eden R. Martin, et al.; SNPing Away at Complex Diseases: Analysis of Single-Nucleotide Polymorphinsms around AP E in Alzheimer Disease'; Am. J. Hum. Genet. 67, pp. 383-394; May 2000.
Anthony J. Brookes; "The essence of SNPs"; May 1999; Gene 234; pp. 177-186.
Michele Cargill, et al.; "Characterization of single-nucleotide polymorphisms in coding regions of human genes"; Jul. 1999; vol. 22; Nature Genetics; pp. 231-238.
William E. Evans; "Pharmacogenomics: Translating Functional Genomics into Rational Therapeutics"; Science; Oct. 15, 1999; vol. 286; pp. 487-491.
J. Claiborne Stephens, et al.; "Dating the Origin of the CCR5-3 Al S-Resistance Allele by the Coalescence of Haplotypes"; May 1998; Am. J.Hum. Genet. 62; pp. 1507-1515.
S. A. Tishkoff, et al. The Accuracy of Statistica Methods for Estimation of Haplotype Frequencies: An Example from the CD4 Locus; Jun. 2000; Am.J. Hum. Genet. 67; pp. 518-522.
GenBank Accession No. AL162497, revision history (printed Mar. 4, 2009).
GenBank Accession No. XM_007095, revision history (printed Mar. 4, 2009).
Berliner, N. et al., Hematology, vol. 2004, pp. 63-79 (2004).
Sugiyama, E. et al., J. Clin. Oncol., vol. 25. pp. 32-42 (2007).
Hahn, K.K. et al., Am. J. Health. Syst. Pharm., vol. 63, pp. 2211-2217 (2006).
GenBank Accession No. AL162497 (Jun. 2001).
GeneBank Accession No. AF073310, *Homo sapiens* insulin receptor substrate-2 (IRS2) mRNA, complete (Mar. 25, 1999).
Andreas Fritsche, et al., "The Prevalent Gly1057Asp Polymorphism in the Insulin Receptor Substrate-2 Gene is not Associated with Impaired Insulin Secretion", The Journal of Clinical Endocrinology & Metabolism, vol. 86, No. 10, 2001, 1 front page, pp. 4822-4825.
Hisanori Haga, et al.,"Gene-based SNP discovery as part of the Japanese Millennium Genome Project: identification of 190 562 genetic variations in the human genome. Single-nucleotide polymorphism", Journal of Human Genetics, 47(11), pp. 605-610, 2002, JSNP: http://snp.ims.utokyo.ac.jp/index ja.html.
Office Action issued on Apr. 22, 2013 in corresponding Canadian Patent Application No. 2,530,168, 2 pp.

*Primary Examiner* — Jeanine A Goldberg
(74) *Attorney, Agent, or Firm* — Oblon, Spivak, McClelland, Maier & Neustadt, L.L.P.

(57) ABSTRACT

Means for determining the presence of the risk of drug-induced granulocytopenia in a human is provided.
A method for assessing the risk of drug-induced granulocytopenia, including detecting a polymorphism of the human insulin receptor substrate-2 gene of a subject, and determining the presence of the risk of drug-induced granulocytopenia of the subject by use of the genetic polymorphism as an index.

8 Claims, 1 Drawing Sheet

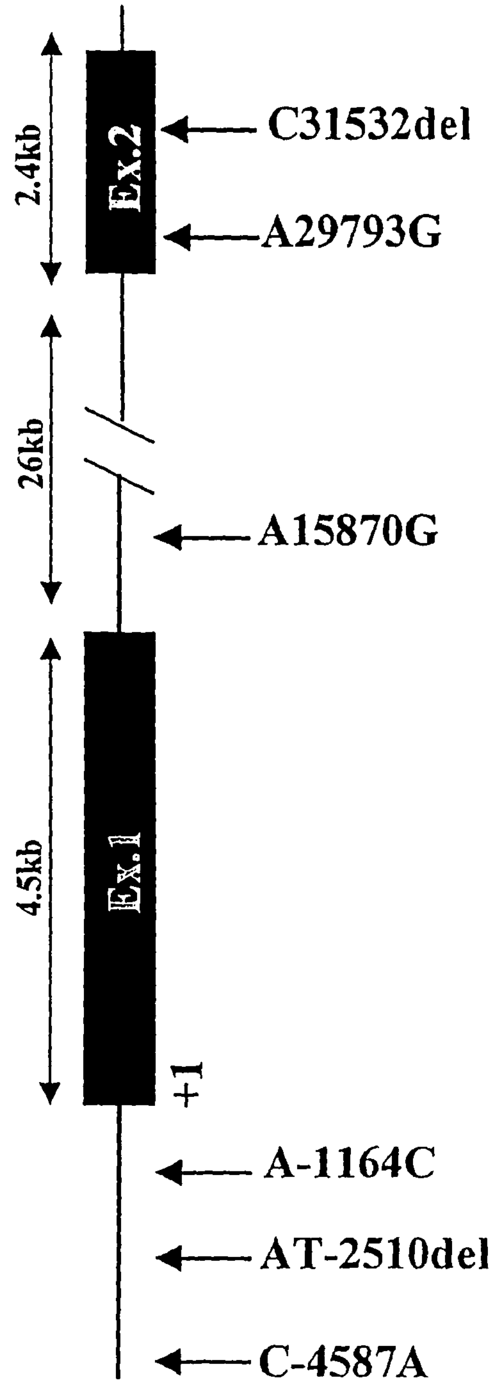
2.4kb
Ex.2
C31532del
A29793G
26kb
A15870G
4.5kb
Ex.1
+1
A-1164C
AT-2510del
C-4587A

SEQUENCE LISTING

<160> NUMBER OF SEQ ID NOS: 19

<210> SEQ ID NO 1
<211> LENGTH: 22
<212> TYPE: DNA
<213> ORGANISM: Artificial Sequence
<220> FEATURE:
<223> OTHER INFORMATION: Synthetic DNA

<400> SEQUENCE: 1
accactgtat ttgtgacaac tc 22

<210> SEQ ID NO 2
<211> LENGTH: 22
<212> TYPE: DNA
<213> ORGANISM: Artificial Sequence
<220> FEATURE:
<223> OTHER INFORMATION: Synthetic DNA

<400> SEQUENCE: 2
aaatatggat cagtctcttt cc 22

<210> SEQ ID NO 3
<211> LENGTH: 21
<212> TYPE: DNA
<213> ORGANISM: Artificial Sequence
<220> FEATURE:
<223> OTHER INFORMATION: Synthetic DNA

<400> SEQUENCE: 3
atgttcattt tatgagggag g 21

<210> SEQ ID NO 4
<211> LENGTH: 20
<212> TYPE: DNA
<213> ORGANISM: Artificial Sequence
<220> FEATURE:
<223> OTHER INFORMATION: Synthetic DNA

<400> SEQUENCE: 4
aactgccaat ccagagctgc 20

<210> SEQ ID NO 5
<211> LENGTH: 20
<212> TYPE: DNA
<213> ORGANISM: Artificial Sequence
<220> FEATURE:
<223> OTHER INFORMATION: Synthetic DNA

<400> SEQUENCE: 5
tctcaccaca ccgcttcaag 20

<210> SEQ ID NO 6
<211> LENGTH: 20
<212> TYPE: DNA
<213> ORGANISM: Artificial Sequence
<220> FEATURE:
<223> OTHER INFORMATION: Synthetic DNA

<400> SEQUENCE: 6

-continued ccacattttc ttcaagcacc 20

<210> SEQ ID NO 7
<211> LENGTH: 20
<212> TYPE: DNA
<213> ORGANISM: Artificial Sequence
<220> FEATURE:
<223> OTHER INFORMATION: Synthetic DNA

<400> SEQUENCE: 7
gagcttgctg ggatctgaac 20

<210> SEQ ID NO 8
<211> LENGTH: 20
<212> TYPE: DNA
<213> ORGANISM: Artificial Sequence
<220> FEATURE:
<223> OTHER INFORMATION: Synthetic DNA

<400> SEQUENCE: 8
atgtgactcg gcgttacgca 20

<210> SEQ ID NO 9
<211> LENGTH: 18
<212> TYPE: DNA
<213> ORGANISM: Artificial Sequence
<220> FEATURE:
<223> OTHER INFORMATION: Synthetic DNA

<400> SEQUENCE: 9
ccttgcagtg gaagcatg 18

<210> SEQ ID NO 10
<211> LENGTH: 21
<212> TYPE: DNA
<213> ORGANISM: Artificial Sequence
<220> FEATURE:
<223> OTHER INFORMATION: Synthetic DNA

<400> SEQUENCE: 10
ctatcccgat tcctagatgt c 21

<210> SEQ ID NO 11
<211> LENGTH: 21
<212> TYPE: DNA
<213> ORGANISM: Artificial Sequence
<220> FEATURE:
<223> OTHER INFORMATION: Synthetic DNA

<400> SEQUENCE: 11
gactcatctg tgactaactc c 21

<210> SEQ ID NO 12
<211> LENGTH: 19
<212> TYPE: DNA
<213> ORGANISM: Artificial Sequence
<220> FEATURE:
<223> OTHER INFORMATION: Synthetic DNA

<400> SEQUENCE: 12
cctagatgtc agcttgccc 19

<210> SEQ ID NO 13
<211> LENGTH: 20
<212> TYPE: DNA
<213> ORGANISM: Artificial Sequence
<220> FEATURE:

-continued

<223> OTHER INFORMATION: Synthetic DNA

<400> SEQUENCE: 13
tctggaactc cagagattgc 20

<210> SEQ ID NO 14
<211> LENGTH: 25
<212> TYPE: DNA
<213> ORGANISM: Artificial Sequence
<220> FEATURE:
<223> OTHER INFORMATION: Synthetic DNA

<400> SEQUENCE: 14
tgctgagcgt cttcttttaa tggta 25

<210> SEQ ID NO 15
<211> LENGTH: 22
<212> TYPE: DNA
<213> ORGANISM: Artificial Sequence
<220> FEATURE:
<223> OTHER INFORMATION: Synthetic DNA

<400> SEQUENCE: 15
gaggcttttt tagaggaaga cc 22

<210> SEQ ID NO 16
<211> LENGTH: 21
<212> TYPE: DNA
<213> ORGANISM: Artificial Sequence
<220> FEATURE:
<223> OTHER INFORMATION: Synthetic DNA

<400> SEQUENCE: 16
catgtcatgg agggagcatt c 21

<210> SEQ ID NO 17
<211> LENGTH: 20
<212> TYPE: DNA
<213> ORGANISM: Artificial Sequence
<220> FEATURE:
<223> OTHER INFORMATION: Synthetic DNA

<400> SEQUENCE: 17
gcaaaagtct tcctgcttcc 20

<210> SEQ ID NO 18
<211> LENGTH: 143409
<212> TYPE: DNA
<213> ORGANISM: Homo sapiens
<220> FEATURE:
<221> NAME/KEY: misc_feature
<222> LOCATION: (1)..(143409)
<223> OTHER INFORMATION: AL162497 an antisense strand

<400> SEQUENCE: 18
gcaaatcaaa accactgtgc gatatcacct acacccttta ggatggctat taccagagac 60
aagtgataaa tgtttgcaga gtgtggagaa aagagaattc ttgtacactg ttggtaggaa 120
tgtagattgg aagagccatt ctggaaaaca aaatggagct tccttaaata aatgaaaaat 180
agaactacca taagacccag caaccctctt ctgggtatat atccaacaga gaggaaatgg 240
ctaccttata aaaatattgg cactcccatg tgcactgcag cattatttac agtagccaag 300
gtatggaaac cacctaagtg tccattgaca gacaaatgga tgaagaaatt cctcgatgag 360
attggagatt attattctaa gtgaagtaac tcaggaacag aaaaccaaac atcgtgtgtt 420

-continued

```
cccactgaca tacggaagct aagctatgag gatgcaaagg cataagaatg acacaacgga    480
ctttgaggac ttagggggaa ggctgggagg aggatgaggg ataaaggact acaaatatgg    540
tgcagtgtat actgctcagg tgatgggtgc gccaaaatct cacaaatcac cacaaaagaa    600
cctactcatg taaccaaata tcacctgttc cccaatacct tatggaaaaa taaaataata    660
aactaaaata aataatgtca catatgtaca acagaatgtt atttggacct cataaagaat    720
gagatcatcc catatgccac aacatcgatg aggctagagg acattatgct aagtggaata    780
aaccagacac agtaagaaaa atattgcatg atctcactca tatgtggaat ctaaaaagaa    840
aaattcaaat ggagatagaa aataaagcag ggttctgggg agatgcaagt tggaggacac    900
aacgtagccc acatgcaaga tgaacacctc tagagatttc aggcacgaaa tgaggacact    960
aagggccctg accaccctgg agtaagagct gacactactg ccttcccctg cctcggggga   1020
tcatcaccag ccacccagtg ggtgaagagg aacagtaaga aagaagccat ggggcttccc   1080
gcaatagctc ggtgtggtag agtctatcta aatgcagaat actttgatgg aggttactgg   1140
ctgggtcact gccactgagt ctctatcagg agctgggaca gggtggctcc catgcctggt   1200
tccacagcca gagaccttgc tgagtgacat gcagatttga gggacatggc tcatcttcct   1260
gcctgctact ctctagggct cactgatgaa tttctagtga cagtgtgttc tagaagttag   1320
ctctaactat aaaacatttt ttcaggtctt ccactttctg aacaatctga tcctaaagcc   1380
actgtgtgta tccaaacaag gggatatcc gcaccgatgg aagggaccac agaggaacat   1440
agtgagcaag gatgggattg gggaggttt gcaagagccc gagctgggca ttggtagggg   1500
acggtggcgg tccacatggc tgggtcatgg tgtcagagcc ccagtgcaat gaggaccggg   1560
ctcctgcagg agtaggacca tgggactttc agcctgagta gggtagagag agtgtccaag   1620
caggggaagg gactgaatgg aagggtggca ggcacccaga aaaatgaatg gggtttaagg   1680
gggaagcagc tggagcaaag tgtgcctctg ggcagggcaa ggagggcttc ggtgtaggaa   1740
gggaggaaaa ggggctttca tgtgggcgga tggtccagac aggaatggca cagcattact   1800
gggcagggag gatgctggcc tgggatgcag gccagtgcct ggcctcagag atcatacaga   1860
atttggaatc ggactgtgca gggggaggtg gcaatgctga tagaaaatgg caggggtggc   1920
acagggtgtg aatgagagtc acaaatatac aaaggaagaa agtggggtgg actctgaggt   1980
gcttgagtga actgaagata ttagcaccaa ctcatggctt tccatataga cagagctaga   2040
gacaaacata gacataaaca tctgtgtgtg tgtgtgtgtg tgtgtgtgtg tgtgtgtgtc   2100
tatatgcata tgctgtccag ctctgtgcac tgaggtacac ccagatcatg gtatctaaag   2160
cccattctcc tcttgggatt cagctctttt tggagaacca gctgacccat gatccagagc   2220
aggcagggtc cacaatgact cagaaacatc ttgaggacct gctcagagaa tgacaacaca   2280
cgggccagtg ggaacagctt ccaaacccca gcaaaggtga acagtaagat aagtaatgat   2340
aattccaggt tataatccaa taaataagat agaaaactac acatccatac tgacataaat   2400
acaacataaa tgaataaatt aaacgttgaa tgaagagcag agtatttaca cagttttaag   2460
ctagtcctcc atgtaatact aattaattac aaaggaagaa aggagtgaag aaaccacaga   2520
caccacctcc atcaggtcac cagtgtgaac atcgtcagta accgggcaaa ttgcagtcct   2580
gccgacctga gagcacggag tgaggcggtc ccagggtcgc tcctgggttc tcctgccaag   2640
gacgctaaac ctgaatctgc tcatgaggaa gcatcaggca gccccgtgct gggggaaatc   2700
ctgcaatgta actggcctag agccattaga gtgtcaaggc cacgaaagtc acagaaagac   2760
tgaggaactt ttccaggtga atggagccta ataaaacaca acagccaaat gcagcatgta   2820
```

-continued

```
gctctgagat ggttcctttt gtttttaagg atgtctgggg gcaaatatga acagggtctg   2880
agaattaggc attaggaata tatcaacgtt gattatctga ttctgttaac tctactgtgg   2940
ttgtgtagga gcatatttgt gttggtacaa aatacacact aaagtattcg tattcaggga   3000
tgacaagata tcatgcaggc aacttactct caaaaggtcc agcaaaaaaa aaattatttc   3060
tgttgtcctt gcaactattt tgtaagtagt ttgtacttgt taggaaaaaa aaaattcaga   3120
cttcttataa ctaatatcct tatgtgtgaa gaaatgataa aaatttccaa tgaaaataaa   3180
ttcccaaaca cctgggcagc ctctgcaccc atttggtaaa ctcctggctt tcatgcgctg   3240
tagttttgac ctgcagtggt tcccaggtca catgagtctc tgctgtaatg agacaggtat   3300
gcctcacgat gtcagtgcat ggcatcatga tgaaaacccc cctaagtttg ccagtgtcct   3360
cagtaaagga cagtgagacc aacagatgat atccatcagc tgccaaccca ggagggctgg   3420
aaagattgcc tagccctacc agtgtgggtc aagtaatttt tgttcttgga atctagtcaa   3480
acgaacaccc aataggaaga gatcagagaa tcttaggacc caggataagg gcagcactaa   3540
aaataaccaa aggtatcatt tattctgtgt gataaacctc ccactcaccc catcgcgtgc   3600
catcatcgca atagtctggg gaagtgagta ccgttactat ctcatatggg ccatgagaaa   3660
ctgaaagctc agaaaggaac tccaacaaat ttacaagaaa aaaacaaaca accccatcaa   3720
caagtgggtg aaggatatga acagacactt ctcaaaagaa gacatttatg cagccaaaaa   3780
acacatgaaa aaatgctcat catcactggc catcagagaa atgcaaatca aaaccacaat   3840
gagataccat ctcacaccag ttagaatggt gatcattaaa aagtcaggaa acaacaggtg   3900
ctggagagga tgtggagaaa caggaacact tttacactgt tggtgggact gcaaactagt   3960
tcaaccattg tggaagtcag tgtggcgatt cctcagggat ctagaactag aaataccatt   4020
tgacccagcc atcccattac tgggtatata cccaaaggat tataaatcat actgctataa   4080
agacacatgc acacgtatgt ttactgcagc actattcaca atagcaaaga cttggaacca   4140
acccaaatgt ccaacaatga tagactggat taagaaaatg tggcacatat acaccatgga   4200
atactatgca gccataaaaa atgatgagtt catgtccttt gtagggacat ggatgaagct   4260
ggaaaccatc attctcagca aactatcaca aggacaaaaa accaaacacc gcatgttctc   4320
actcataggt gggaactgaa caatgagaac acatggacac aggaagggga acatcacaca   4380
ctggggcctg ttgtggggtg ggggtagggg ggagggtagc atttagagat atacctaatg   4440
ttaaatgacg acttaatggg tgcagcacac caacatggca catgtataca tatgtaacta   4500
acctgcacgt tgtgcacatg taccctaaaa cttaaagtat aaaaaaaaaa aaacttggct   4560
actgtcactc caccgtgtgt attcatctcc taagggagat gcttacattc aaagggggtg   4620
caattattct ctctctctcc ctcacagagt aggaacctga gacacagaaa tgatcagcgg   4680
gctgcctgag atcacatggc taatgaggga tgaattgaac attctcaaat tctcattcac   4740
caccaactcc tcatgtcctg tgctgcccca cctcccaggt gggacttgca ggtcttttaa   4800
gaacttgcat tcattgacac tattttgacg acagtaaact ggtagcaaaa ttaatgtgag   4860
cacattcaaa tacaatttat tttttaagca gcctgggaga gtggaaaaag cactcctggg   4920
ctcagcctcc atcacctgct agctgtgagc ttctgtacaa tctcttcact ttttccaatc   4980
cccccaatgt ccttccttag attgaaatcg actctttaga atcagcacat tcaaggaggt   5040
aaagtcacag cttgtcttgc agcccaaacc tcccatccaa taggcccatg gcaaagaacc   5100
cacaggctgg gagcttcgca tcaggcgtcc ttgtttttgt ttgagccttt tctttcaaat   5160
atatggataa tgaccacgtt tggggctaaa cataaagcat tctattcatt aggaccatgt   5220
```

-continued

```
cacggacttg tggcatgtgg gaaatattac catggctacg gaggaggtgc gtgtggatgc   5280
tggcagcggg gagggagccc atgcctgcct ggttgctgct aaacaataag tcaatctgtg   5340
tttcactggg gtgttagtgt tctgttccct ctcacctcct ggagaccaag gatgtctccc   5400
tgacatcaag ctgagcagtg ggaagctgag atatgagaga agaaagggcc tccgggggac   5460
tgtgtgcagg tgatggccct ggagcttcca ttcaattatt ccaccagcat gcaccgagtg   5520
actgccatgt gcaaagcaag ccagcagtaa gctacattct atcaaggaga caatatggag   5580
aaactctgca aggagcttcc acacaccgga tgccctttca tcactcaaag acatagtttc   5640
catgccagtc ttagggcagt aagtgaaagg ctacaattag aacagacgaa tcccaaaacg   5700
cagagcctct gctgtgcgcg aaccatgagt cagcacctcc acggtgcact aagcgtgagc   5760
tggcacctcc acggtgcact aagcgtgagc tggcacctcc acggtgcact aaccgtgagc   5820
tggcacctcc acggtgcact aagcatgagc tggcacctcc acggtgcacc aaccgtgagc   5880
tggcacctcc acggagcact aaccatgtgt aggctttgaa ctagtctgtt ctggaacctt   5940
gctttgctca ggaggttttt tcctgttcct tccctgtgtc cagtcctctt gagagaggaa   6000
aaccaaacca tgctgccgct attccctttc ttgataacaa tctgaaatca ttctggccaa   6060
actgggatgg gcacagtgct tttccacatt gactttttt ctgcttccca tgtttaggct   6120
caaatttcta aaacggacca gagatgtaaa agggatattc aagtataaag tcctgtataa   6180
acgtaaggca taaatattat gatcctcatc actttagga gagtgaggta gaatgatgat   6240
tttaaaaatt aggaacaaag ttacttcttt gatctcttta ttagccactt ctaataatcc   6300
ctgtcccact catcctaaaa cctccagccc cctccagtct cccatccagc cacacacaga   6360
attaccacaa tctaaatgcg ccctttgaat cagacaatac tcctattgct attaataata   6420
atatattggt tagtcaccat tataaagatt ttacaaaata catttatggc atcaccagcc   6480
aacacataac aggttacttt tattaagttg catttgttat ccctgatctt cacaggattc   6540
ttacaagaca ggtattaata tgcccacttt tatggttggg gaaggatgat tcacagttac   6600
ggaaacttgc tcatactcag gaggaagcta agccatcttt ctggcccact accattgttt   6660
gatttcacag tgctggacag ctggtgtcac cctcagaggc cataggtaac cacatcccca   6720
gatccttaac agccaggccc cccgccacca cataactttg ggaaacacgg aagcccggaa   6780
tgcagcccca tgggctctaa tccaggtcaa ctgggtggga caccccgccc ccgcgtacag   6840
gcacccccac cccgcccctg ctacctctct aggtctgaaa gccccagcaa taagtctcat   6900
cggacccgag ctgcgattat ttatgccttc ctttcatctt tgcttcggtc tcttggtcag   6960
ggtgatttct tcatcctttt tgtagaaggc ttccctttgc attagcagct ttgctatagt   7020
tctagaataa atgagcacag gaagaagacg ctgtcatacg ggaccgatcc gtgtccacat   7080
gaagtcatca gatcggtatg ggtgagtggc aggcaaatcc ggtgtgggga agcggcaaag   7140
cctgaggagc ctgcacttat caaagattaa acactttcag gttctttaaa ggacaaactc   7200
tgagttttcc cagcgtagta tttgagctat ttgagggtct gaaaagatat cacacaggtt   7260
accctgcgtt ttgacagcct ttccttactt taatccaagc ctgtggcaaa ctggttgtaa   7320
actattactg aagaaatggc tctatatttc tattctctct ctctttctcc ctctcttccc   7380
gtttgaaatg aaaacacagt tctttcatta gctcattaaa aaatttactc ctttgtgaat   7440
attttgaaat cacagagcag atatatattt tatatcaaag actccagtga aatattgatc   7500
acctgtgtgt ttcactccct aaattcacca taactgtgcc tacgtggctt gtttcaaata   7560
cacatcttac cctccagttt gaagtttaaa tcattgtggt aggcgttgta cagaggattg   7620
```

-continued

```
cttttttatt ttctgtgctt aagtgcaggg cagccaaaac aagaacataa ttatatcgtc   7680
agagtcgata agcgcatcaa gcctctatca gatcttgctg ggctcagcaa ctgcctcaca   7740
ggaagtgctg ggagctcttt ccgccaccaa atccatttgg ctctatttag gaactaagta   7800
caggaaggta gttattgtac aagattagtt tcctgtaggc cataaattgg cagtagcaga   7860
aaaatacagg atgaatttat tagcgtgcaa ggtcagctag aaggaagaca aggctgagcg   7920
attgcgcttg ttttctttca tttagcccac ctcctggacc tcagggctga aaaagaccct   7980
ctaactactt aattacttct taatagtttt aagcaaattc aaaaggcctg cgcgttgcta   8040
agtgcctgag gtaagagctg cctgggctag gttaggaatg cctgtttgga ctagagtttc   8100
tgaaacctga ctaggcccct tataatctga ggctttgtga gttttctgcg tttttttttt   8160
tttttcctg ccttatttgg tgttgattgg ccaagcattt actttgaagc tagaatttta   8220
tacttgggaa taaaggagta gcttctaata gtgaaaatat aaaatccatc aagtcaaaaa   8280
tattgtttcc aaccagaggt atgataatgt gataaacatc tctgtagata tttgctttaa   8340
agagaacaag gacagattgc atttaaaaaa attttttta aagaatacca cttcaaaaac   8400
actcatttaa aggtagccca aaaggtggaa tgacctcctt acacagacat ttctaccttc   8460
aaggagaaaa cctcgctcag ttacctgagc ctctttacca tgttagacac atgtaattca   8520
cattttaatt atactcagca tctgcagtga gttatgggag acccctcctt ctccatccct   8580
gcttccactg ggcctgctca cgctgcctct cctcacagat accctggtgg agcatacagg   8640
gctggatgcc tgaaagtaga aaggcagagt cctctctgtt ccttcctaga agacaaccct   8700
gttttggaat atgctttcct gatttcttag taaactgcag cactttgatg ctgtaaaaag   8760
cctcatgatc agctagcacc agctcctgtc ctgccatttg caaacaaagg gcccagttaa   8820
ccttcactgg gtgaggccat cctcccctga gggcagcccc gaggggtgag aggagcctga   8880
gggaggaagg cccgttcaga gacagacagg gctgctgttc ccggaggtcc aagggatgtc   8940
actgcttctc tattgtggac atttgtccaa gctgtactgt cttgataaaa gagtttgaga   9000
gcatttcgaa agcgcaggtc ttaaaacaga tctccaggtg aatttcacag ccccttccc   9060
cagagcacag acgcagagta ccccacacag tgttcaggtg cccagccttg ctctggggta   9120
gggtgggggc aggcattgca acgctccgac atttgctgaa cgactgggtc acagtagctt   9180
ggctgatttt ctgttcctgt cactccctgg agatgtgggt ctgaggtgag ctctggcacc   9240
aagcctacct ctctggcatt ggctagagcc tccgtgtcag gccagagtca acctctcgta   9300
acctttccaa agccaattat cacaacacag attcagaaat taagggagaa gttcaaagcc   9360
caaattgtgc cagaaggagc cttcgcaagg cagtctgagg ccaagcagtc gcaggcagtt   9420
tcttcattta ctcaccaggg aagctgaagc ccggcattcc tgaaacaaag atagcttttc   9480
ttttccttcc catgttgttc tgaagtaggt tttagccaat cccaaaaaat ctcaaatcaa   9540
caaattttta gccctaaata atgatgggcc caattacctg ctctctgcca agcatacgac   9600
aaaaaaaaaa aaaaaaaaaa aaaaaaaaaa aaaaaaaaaa aaacataaca caattcttca   9660
ctgaatctcc tggatttctt agtccaggca ccctcagaga catatgctta gatcctacgt   9720
ctgcttctat agaaaataca aaggaacgta gctctggaaa ggagggagcg tgagattctg   9780
agccagaaat gttcctgata gactttgaaa atgatttgga agttcttgct gactatctcc   9840
ctgctatgaa gccgccccga gttagatgtg aagactaaag tggaagcctt cagcagcctg   9900
tcctcaccag cctgctcctc tgtcttccac tctaccctgg gctgcgaccc tgagcagagc   9960
agccagctgc agtgttactc cattgctgga gggctcctct gtgaacccac aggaaggtcc  10020
```

-continued

```
ctgcctcaca gtgggtgacg gtgcatcctc cacctgctga gtggtgtgac ctccacacct  10080
gctgggacgc atggtggctt gaacctcact gtctccactt tgcccagcag caatcttgcc  10140
tttctccccc cacctcaaga cacccaccac ctacctctgt ggcttcacag ggcagatgcc  10200
ctgttaagtt gtggtgcctg tccccagcac tgtttagggt tttttttgtt ttttgtttgt  10260
ttgtttttgt tgtttttttt ttgacggagt ctcgctctgt cacccaggct ggagtgcaat  10320
gccaagatct tgctcactgc aacatccgcc tcctgggttc aagcgattca cctccctcag  10380
cctcctagta ggtgggacta caggtgccca ccaccaagcc cggctaattt ttgtattttt  10440
agtagagacg gggtttcacc atgttggcca gactggtctc gaactcctgg cctcaagtga  10500
tccgcctacc tcggcctccc aaagtgctga gattacaggc gtgagccacc gctcccagca  10560
catgttatta aagtcatgga caccaccaag tgctcagctt cagaacagcc atgactgtaa  10620
ctgttagacc caggaatggg aagaggaaaa agagtcttca gggccaccaa gttcttttgc  10680
tgcaaatctt gaaaggttat cagaagcata aaattgatta tcttcaccca cacccagcaa  10740
ccacacacac gcactcctga cttagggaaa gttatatgct gtcgaagaac cagcggtagc  10800
aaatgctttt cctcaccagt gagttcagaa aatcctgcat ttatctggcc caaagtccgc  10860
atctcagata aagtctgaac gtgataactg cagaccaaca gcagtcctat cccaaagctc  10920
agtcaaagcc actctcaagc cagagaacag acaggactca gacagggtca gaacacaaca  10980
gtgcaacatc actgaggaag taaacaagtc accaaagaaa caccagagaa attcgtggac  11040
aatattccag gcattaccat gttagggcta gcatgttaaa agacagcata ttgtattggt  11100
gtgttttttt aaattcttac tgaaaagtta gaaaatgagg aaacaaaatg tggtatatat  11160
ctctttaatg gaatattatt tagtcataaa aaagaaatga agtgctagca cacactacaa  11220
cgtgcatgaa cctttaaaca ttacgttaag tgaaagaagc cagacacaac atataacgta  11280
tgattccatt tatatgaaat atccagagta cccaagtcaa tcatgacagg aagtggacta  11340
gtagttgtaa gggactagga gtcaagagaa atggggtgtc atggctatgg ggcttctctt  11400
tgggatgata gaacattctg aaattagatg gtgaagatgg ttgccaactc tgtgaataca  11460
cgaacaacta ctgaactaca ctccttttaa aagttggtat catgatatgt gaattacatc  11520
tttatggtga taaaataaat gaggggcggt ggcagaaaga aacagaaatg aattccctta  11580
tccaatatgt cttcacattg gccttcatgt tgagccactt ttatgcagca atctgagaca  11640
aaggccacta ggacttggat gggtacccaa tgttacaatg aaaccttcaa gaggacctag  11700
tcaactcagt ttcctggcta gctgacatgt ccctctttga gttttagttt taatgaacct  11760
gctaattcca gtggaactaa ggcctctaga aagaactgcc aacttggtca agaccttagt  11820
agtctgaata acgttggcct ggaaaccatg cacgtttacc tattttgtaa caaaacccca  11880
actcaatgaa atgtgtttgt ctttaactag tctcagggga tttacatttt gccatctata  11940
gggcagggtt tcctggccaa cttgagctgg atttgcaggc aagcagattt cccaacctag  12000
gtactctagc tttgtgttcc cttatgcact tttccaatga ccggatgatg gcaagccccc  12060
tggctcagat ccccaaattt ccacatcagt aaatgttgag aaagaaatta tatttcttaa  12120
ttgcttagaa accgaagaca tacaggggaa atggcatcgt gtcctacact cgtggatctt  12180
gaagacatga aacagaccta ataaaataag aatataaaca gacaacagag atttcgtctc  12240
tcccaatcgt caggcatttc agtggatctg tgctccttgt gagccgctct acggtggtta  12300
agtcaaagaa aaaaagcaca cttcccaggg cgacaacgga ctctctatta gaacctgtat  12360
agtttcctag ttttcccttg tttataccta gtttcccatt attatctaca aagatgtttg  12420
```

-continued

```
ccagttccag tccttaatga tccatgcata cattcctctc tgggttctga cctctctccc  12480
ttcagtctca cctctgcatc ctgcctaatt gtggcttatc cttcagcttt gccctgttga  12540
ttcttgatgc caattcctgg agaggctaat cctcaactct ctcatccctc aaaagaaata  12600
aacaaatgaa ttccttccac attctgctga ccataatcac tgaaggatgt gcacagcgag  12660
ggctaattgc ttgctggctg gctggttgtt tggttggttg gttggtttgt ctctatctca  12720
gcaatctctg attaattcat cgttccctct tctaaattct aggacctgga aaaaaatgcc  12780
tgccacatac gagaaattta acaactatat gctagatgaa tgacggttaa cagaactttg  12840
tggcttaaat ttgagacaca aaactatgtt gtaggctcta cggatcctta aatgtaagaa  12900
ctgggttttt tgtttatttg acttggtttt tgtcccaaca tctctaccca agctctatgc  12960
ttggtgtgcc caagcataga gctaggagac aggacacttg ggcttgaatc ctggctgcca  13020
caggtctttt gatgacctca gataggggat gcgtcctctc agatggacag tcagctacat  13080
agaagcagaa actgacaagg gactcaagga ggaagctcca acttgaattt cagcctaaag  13140
gacagtgcaa tgagtatctc ctggattccc agtttctggg accatgtgtg ctccccacac  13200
ttcttggaaa tcatctgttg atgaatctgg cttctccact ggagtatgag cccctgataa  13260
tgaaggctga gtcttgttta cctccaggcc tgcacatagt aggcacataa tgaacagctg  13320
cagacaagct gaacttcaaa catcatttga aggagagtaa agtctgagtc agatctttag  13380
tatcagttgt ttcctgttaa aaataacatc ttttatttga aaaactgttt caagattgtc  13440
tgccagggta aaagtcaagt caagttcctt gctgttccca gtgtaagaat aacatgagta  13500
aaattcacag tataacccgc tgggactctc agaaatctcc ttgttctttc cttaaggctc  13560
atgatgccat agtaaagact atgaacaacc aatccatgaa ttctattaca aaactaaaaa  13620
taaacagggc agtgctgtgt aattttttaa aggcactatg agtataccag ataaatagtc  13680
tttgttggca gtaggaataa aaacttccaa tactcctgca aagttataag caaaatttgt  13740
tagcttcatt ttttttattt tgcagagcaa ttctattatt attgaatagc atgtgatgtg  13800
gtttggctct gtgtccccac ctaaatctca tctctaattg taatccccct gtgtcaaggg  13860
ggggacatac ctggtgggag gtgattggat cacagaggag gtttcccaca tgctgttctc  13920
atgatagtga gttctcatgg tttaaaagtg gcagttttcc ctgcacgctc tctctctcct  13980
gccgccatgt aagacttgcc ttgcttcctc ttcatcttcc accgtgattg taagtttcct  14040
gaggcctccc cagtcatgca gaactgtgag tcaattaagc cttctttctt tataaattac  14100
ccagtctcag gtagtatctt tcaagcagtg tgaacatggg caaatacatc acgccatgat  14160
gataattacc gtttttaagt gcttatgcct gttaagagct gttttactca tattacctca  14220
gtggaactct cccattcctc agtaaggtag ccactggtat cacctctatt tgacaggtga  14280
tgacacctgt acacagatct ggtaagtgtg aggattgaaa tttaactcag gctgtcttgt  14340
cctagcactc ccacctccac atgaacctct tagcactgcc acaataatca aagcacagct  14400
gtcagagatg gcaacccagg gcaagatgat ttttttattc tacattttgt atattgaacc  14460
tttagagcat taaacagtaa atgccagagc ccaacttata aggtctatga aaaggtcaaa  14520
gtctcctttt acttcatcac cactggagaa aaacctaaac aataatagta accaaagtcc  14580
atgtcttctt ttagaagacc aaaattttga gttcctctat tatgagtctt tgatggagac  14640
ctgcttaatt ttctttctgg ggatttacaa caaatctatt ttttttaat tcttcattct  14700
ctgtttttgt aatggtttta agggataatt actatttttt taaaaaaact taatgagtta  14760
cagaacagtg atctctactt aaaattttgg tacactgctt tcactggtaa cagtatgggt  14820
```

-continued

```
tcgtgctcca accccagctc tgccacttac agaacactgg ggacctgggc caagttattc  14880
aacttctctt tacctcagtg ttctctgtaa aatgggaata acaatagaac ttctggtatt  14940
aggctgttat gaggattaaa aaaaattcat atttacaaat tgcttagaag agtgcctggc  15000
atataataag tggctctgaa ggtgtttgtt ggataaaaaa caacttttgt ggtaattttg  15060
ggctggagga aggacaaaca agcaaacgtg ctgagccgag aagactcagg ccgcacacct  15120
cccgttggtg gtgcacatta tagatcctgc cagaactgaa gagagaagct cacacaatag  15180
ggtgaaaagg ctgggcttga agtaaggttt tgctagggag aatcagatta gaactgcatt  15240
tcagaaaatc tgatctggca gggatggatt ggagaaacaa aaaactggag gtagaaaaga  15300
atagccagga gttagaggta caacccatct gtgaatcaag ggaacccaaa ggcagatggg  15360
gttggaatga gggtgaaaca gagagaaggg aatgggaggg ttggggggag gcactggggt  15420
aactctcagg ccgagaattg ggcagcaagg gctcaaggct tctgcaagaa acaggtaaaa  15480
ggggagctca tttgaaagca aggttgagtt caaatgcttt gaatagttta tgtcaaaggc  15540
aagggtgggg gttcaggtgg agatggatac cgtgcagttg aaaacatgga ctagggttca  15600
gcagtcagag ggattaaact ggggatgtgg aagtcgtttg cctagaatga aagttgacat  15660
cttagaatgg atgcaattgg cttagattga ggaaagacta gatgagaaaa gagggttaag  15720
ggaaaagcct gagagaacaa catttagggg ttgggaagga gaaaaagaac cagtggaagc  15780
aagagagatg aagcaaaaga gcctcaggat ggagctttcc ggaaatggag agtttccact  15840
gggtcagact ctgcagaaac tgcagaggct aatagattaa gaaagccatc agactgggca  15900
gtaatgtggt tcctagtgac actcagcaag caacgtcagt cattcaagga gatggggtga  15960
gtagatgata agaaagtaga taaatccaag cttcccaaac tgcagaggat aggcctatgg  16020
ttcccaaact acagtggata gatctatggt tcccaaatta cagtacctag ttctcatagc  16080
tttttacggg cacgcttact cccacaccca tctcactggc catgatttaa tcagaagacc  16140
acaaataagt gtaagcaaga ctaggagatg cagcctttat cccagatgat gacgcactca  16200
gctaagcact gagaattctg cacctaggaa ggaaaacgga catctggtag acctcagctt  16260
cctctgcctc atgttgggac agattattta ttaagaaatc caaaagctag gcatggtggc  16320
tcacgcctgt aatcccaaca ctttgggagg ctgaggcggg cagatcattt gaagtcagga  16380
gttcaagacc agactggcca acatggcgaa accccgtttc tactaaaaac acacacagaa  16440
aattagctgg gtgtggtggc acatggctgt aatcccagct actcaggagg ctgaggcagg  16500
agaatcgctt gagcccagaa ggcagaggtt gaagtgagcc gagatcgcgc cactgtactc  16560
cagccctggc aacagaacaa ggctcaatct caaaaaaaaa aaaaaaaaat tccaaccatc  16620
aatgggcagg aagggataag ggattggctg taaattgggg gatggcaaaa atcaaaagtt  16680
agtcttttgt tttctttttg ctttttttatt gttttgtctt ttcctcataa tttgggatct  16740
gtctaaatat ataggtaaaa caacagagaa acacagcagg ggtgctactg agaaagattc  16800
ctaaagagat gggaaggaga aactccaatc caaattccat acatgcaagg ttattttta  16860
agtcttgaga acagataaag taaaaagtgt tgctttgata gactagtcag aaatttaaag  16920
tttctataca tgcagaataa tatatcatat ttgtttcctg acccttctat aataaagtac  16980
cacaaactag aggcttaaat gacagaaatg tattgtctca cagttctaga ggctagaagt  17040
ctgagattca ggtgttggat ctgccagaca gcatggctca cacctgtaac tccagcactt  17100
tgggaggcca aggcaaacag atggcttgag cttaggagtt caagaccaac ctgggcaaca  17160
tagagagacc gtgtctctac aaaaaataca aaaattagcc aggaatgttg gggaacactt  17220
```

-continued gtggtcccca ctactcagga ggctgaggtg gaaggatccc ttgagcctgg gagccggagg 17280
ctgcagcgag acatgattgc accactgcac tccagcttgg gtgacagagc aagaccttgt 17340
ctcaaaaaaa aaaaaaaaaa gtcaccggat ccttccaagg gaaaatctgt tccccgtgct 17400
ctcccagtgt cttctggcct tggcctccct tggcttgtag gtggctgtcc tctctctgtg 17460
tgtcttcaca tcatcttctt ctacaggtgt ctctgtgtcc aaattttccc gttctataaa 17520
aacatcagta atattctact agaggcactc taatggcctc accttaacca tctgcaaaga 17580
ctcaacttct aagcgaggtc acactggtga gtgagcatgg agagttagga cttcagcatt 17640
ttgggggaca caattcaacc ccttaattta agaacagtta tgacaatgtt tctatttaaa 17700
aacaaattcc attgttatat aatttcctac ctaatgctat aaaatcccca atttcattca 17760
ttgaggttct ctataaaaat ttaaaatgta attaatactt ctgtacttct gtcaaacatt 17820
ttatatattt gctttggaaa gtttccttat ccatatacat ctgaacacaa attggcaacc 17880
aattttacta aagccaattt tacataagga cagagaaatt atgttaaaat tcaaggtcaa 17940
cattcaaatt ctgaatctta atcaagagta attatgaaag caaatgttat gtatcacatg 18000
gaaagctgta taggaatgta cggagcagct ttattcatca tcacccaatg gcccaatggt 18060
ggaatcagcc caggcatcct taacagctga ttggtgaaat aaaccatggt acctccctac 18120
tgaggactgc cgttcagaaa cgcaaaggaa ccaagtacta atacaacacg ttgaatgaat 18180
cttcagaaaa ttatgctgag tggaaaaatc taattctcaa agatgacata tgattctttt 18240
tttgtaacgt ttctgaaatg acaaagtttt agaaatggaa gacagattac ggtacccaga 18300
agttagggat gggggaagtg gggtgagagg gaagaggcta tggaattgtt cagtgtcttg 18360
actctggtag tgaatataaa aacttacaca ggagagaagt ggatagaact taacacacac 18420
agagacacac acatacacat gcacacacgt gtgcacacag gcacgtgtac acacatgcat 18480
gtgcacacat gtatacacat gcaggcacac actcgcaaat acacatgcat acacacacac 18540
acacacacac acactactgg cactactgag gaaatctgaa taaaatcagt ggactgtgtc 18600
aacgcccata tcctggctgt aatagttcca ccatgttttt gcaaaatatc accatggggg 18660
caagtgggta cctcaagtct ctctgtatta tttcttgcaa ctgcaggtga atctacaatt 18720
atctaaatga aaataattat ctaaatgaaa agtcaattat ctaaatgact atttttgtaa 18780
tgaaaaatag tcatctcgag ccttggcttt atgtattatt aaacctattt attttgaaaa 18840
caatttttat actttttaac tacagagctg tgatgaaatg caatacaaat attataaata 18900
ttattttttt aacacatcaa ttagtcacca caaagacaaa aagcagagtt aaaaggaaaa 18960
gtcaaagagg aaatgctatt ctaggaaact aaaatagcaa aacaacatcc aggtagatta 19020
gagatgagaa agaagactaa agagaatcca ctcagataga tagatagatg atagatagat 19080
agatagatag acagacagac agattaaata ttaggtactc tggtccttga ttgaaaacta 19140
agattcaaag ccatttattg tgggttcata aatctcccct ttataataaa aactctacct 19200
cattattcaa ttgatttcat tatttctagc agacttataa aggctaaaga aaaaagtagc 19260
taatgttgaa aacccacaag ccttatttac aaattacatt ccaaatagaa attcttttcc 19320
atttatgcct ctgaacaatt atcatattaa atgcaaactt tgctcacctc tctctgtatc 19380
tgaattgtca cattgtctca atcaggttca gcctgaccac cctgcttaag attgccctta 19440
gcgcatcacc catatctttg ttttcctgtg tgtacaatat ttatgatatt ctaccatact 19500
gcattatgta cttattatgt ctatagttta ttatctgtct tcttcttcca gaatataagt 19560
ttaataaggc agggattttt tttgaagggg cgggggaggc atacgttaat gtacctggaa 19620

-continued

```
catagtaggt gcataatcaa tatgtatttg ttgaatgaat gaattttagg cattctatgg  19680
tccaattttc agtgcaaact ttttaggtag agactaaaaa aggaaataaa actgtgtgta  19740
acttcttgtt gttgttgcca ttgttgcaca gacattgttt ttatggcata aacactcaga  19800
ctgaggcaag aacaaaggag tcgaccttgc catccctaca ataaagttcc taagcaccta  19860
taatgggaaa aacagtgtga taaatgttga aaagtatttt aaaaaaccaa gacatggtca  19920
tgttcttggc agtttacagt ccagaaggaa tgccaaaaca catccacaaa taccaacccc  19980
accagctata aaatgatcaa taccataaga gagatatagg caaattctac caaaaaaaaa  20040
aaaaaaaaaa aaagagctga ctcctgagtg gagggcatct gggactggat ttgaggatgg  20100
aatagcactt cagtttatgg agataaggta ctttctggga gggaaccttg tggagaagct  20160
gaagcctcag cccatatggg gagctttgat tggcttagga agcagagatg ggacacgaaa  20220
ggggaagagg taataacggg tccagatgag aaggtccagg gactaaataa ggaatatcgt  20280
acatggtgaa gagccaagac ggtgtgcagt taactagaaa acacagaatt acacaatagt  20340
gctaattgta acctatgaac catagagcca aggttcagca atgggggcat gtgccattag  20400
ggcccagagc agtggtgctg gttgtcatgc tcagaagcaa ggcaagggtc tccaagctac  20460
cttctccaag cagaattgtc tccaggtgtt ttatcagctc ttcccctgcc ctcatcagac  20520
aaggacatca atgatggtct gtgtcgtgga gaccctacat acttcctgga tgtattgggg  20580
ttagatgtga tgggtattaa gggtggaaaa cagagttatg tattcacaac ggagttatgt  20640
attcacatga gatgtgtttg ctgtaactaa ctgcacttgg gttccatcgc agttcaccat  20700
ctctgtttat ttcccgatag agttcaaggc ttaggctcag tctgcaaagt agaatctacc  20760
tggctgttca gatgatgagt agctggggca aaaccttgtc ttctggatac tttaccaact  20820
ttccagccag cttctccacg aatcccaaca ttgcacacaa gtgaacatgt gtttccaaac  20880
acaaggatgg actgtgttga ctgcccatcc tctccagcca cctgtccctc atcctgcacc  20940
agggcatgct cttgtgaaac agcacaccaa ggtcaggggg catggcagag ctgtgagcag  21000
gaccagtggg agcgccacat tccaggcaca gggcctaaac aatgacattg gccacttcgc  21060
ccacatcctc cttttggcta tgtgcgatgc aaaaacttaa acaagtttct gctttaaatt  21120
gtaaatgcaa caaataaaaa catttatact aggcttgtat tccagagtat tattttgtca  21180
tctttttgtc aacattttaa gtaaatttca gtaacacatt tttccttttt tataatcatg  21240
gctgattgcg tttttttttgg gggggaggcg ggagacagag ttttgactct tgtcaccggg  21300
gctggagtgc aatggcacag ccttgattca ctgcaacctc cgcctcccgg gttcaagcaa  21360
ttctcctggc tcagcctccc tagtagctgg gatcataagc atgcaccacc acccccagct  21420
aattttatat ttttagtaga gacagcgttt caccacgtta gccaggctgg tcttgaacta  21480
ctgacctcag gtgatccacc cacctcggcc tcccaaagtg ctgagattac aggtgtgagc  21540
caccgtacct ggccctgatt gctttttata cataaaaaca gaaaattttt aaaattagat  21600
caacatacag aaagagcttt aatttggaaa gaatttccaa attgttctaa taactccttg  21660
tataacatga aaaccagatt tataccataa caacgtatgt atttgttcat tttggggatt  21720
ttggaaggaa aggggctttt tccataatcg tatgtcataa tcattgtcat cacccactga  21780
actaaacact taccatgcaa tagttatttc atgtcttcct catagatgtc cgggactgat  21840
gatttattca tcttattttc cagctgatgg aaatgaagtt tagagtggcc aaacactgcg  21900
attacatagc tgacaaacct caggtttatg attccaaatt ctatgctttt ccccaaacac  21960
tgcattcttt gcacatagcc agtgctggtg tgtacacaca catacacata agcacagagc  22020
```

-continued

```
ctgcgaagtt ctgaacacca agcggttcac tttagtgcct cctcctttc ttctacaagt  22080
tacaagctcc ccccaacgtt atttcaagca gagggtactt cagaactaaa acagtatctg  22140
acagtgcctg gctcaaacac ttccaattcc ttcctagagt aagtaggaaa gcacagaaaa  22200
ggataaaaac acaagcacag acaggtggac ctgtcgatcc acaaacccc tgccagactc  22260
tgggagatgc tggtgacagg aaaggacagc agacctggac cgggaaacac aatccacagc  22320
cttgtgcaga ggctggaatg aagtgcgcag gcggcttgag ggaggagccc cacacaactc  22380
tccttaccta ggagctggct cacctgaccc actagagcac agcaactggt tttgtgaaag  22440
aaaaaaagaa aagaaaaaac agtgataaat aacataggtt caattgtttt gacagtaaaa  22500
ctcattccaa aatacagcag aggcgtgtgt cctccacgtc tcgccttccc cacagagtga  22560
gcccttcatc tctccaaggt cagtctgttt ttagcccaac gttgcttgaa cctgtcatct  22620
tccctccaat tgcaccatca ctgtcaatgc tcccaccatc acagtgctcc caccatcatt  22680
agccctccct tggcttccta gaaaggtcac cctgctttaa tcttgcacta ttttaatgag  22740
ttctgcactg aaatcaagag tgtcttcaca aataccaacc tgagtctcct ttcctcatgc  22800
tcccatactc atgaggggct ccaccaatgc caacacgtgc ctcctttccc catgctccca  22860
tactcacgag gtacaaagcc catgctcacc tttttacct ccctccctcc agtccacacc  22920
tggccatctt gtcctccccg agcttggttc agctaaatag tccctgaatg catcaagttt  22980
gttctcagcc cctcactcat gagctttctg ctccctttct ctgcctagaa tgttcccatt  23040
ccctcggtcc tccttcactg gacttactcc ttttcatcct ttcagatgta gctccaggaa  23100
aacctcccac cacccgtagg caaagtcaga gtgctttctc cactgcagtt ctgaagacat  23160
tccccacacc ccatcacaag cacagttgag ctgtgatcag gtgctcatgt ctcctctacg  23220
gtaaactcct ggtgatggct tcggtcattc cttcaaaagc tttttatgag cccctatccc  23280
acagccagca ctcccaacat acagcagtga aagcacaggc tctgtgactt cgatgctcgc  23340
aaataggcaa ttgtataaat aaacaagata attgctgaga atgatggatg cttcacaact  23400
gtagcttttt cttttctatc ccccaagatc caaccccatt tttgacattt aaaaaaaaat  23460
gctcaataaa tgtgttagat gaatataaaa tggcaagtac catcgtgatg acggtaataa  23520
agttttgagt gtagaaaatg agtgataaac agaaatacag agaggaggag aaggaggaga  23580
tgaaggatta aggagaaatt taacattgaa ggtttagaga aggtttttc ttgactttt  23640
aagacagtgg caaaagggta gaaaacagag ggaagatgac agattcgttg atacattgat  23700
aggaaaaaaa gcagtattga gtgccttctt gaaaagcaaa aggaataact tctctgatat  23760
gagcttaaaa caggtatgtg aacaggtaga aatgagttgg tagaaaagta acctgaaagt  23820
tgagggggtt tgtcctgatg tatctgtttc ctttaaaaag tcaaaatcac agttgggtgt  23880
tcagtgtgga gggtggggaa gggataaggt aggagttggg ggaaaatgaa aatggtgaaa  23940
gtatgcaatg accgttgtag gcaatgggaa aggcagcttt ctagaagctg aaacaggaca  24000
cccctccccc cagcccctgc cagcagcatc aatgcagcca catccctggg tataaactct  24060
gtgacttccc atggaagagc tctacaagct gaggtgcaga gagggaacac tcgctaccaa  24120
gaaaaactca aagcctgaca ggtctttggg tcatgaaagc aaataaacca caacaggagt  24180
tcacgtcttc agaaaatgac ttgtgctggt gtctaatgat gcctggggct gtggggtggc  24240
aggtgcaagg tcagagccaa aaatataatg cagtttggaa gttttgctcc acaaagcgaa  24300
gaagagtcat tagtttcaac tccaccaagt caggcaaaca cagtatataa gatcatttga  24360
ccctgcttcc agaacgattt ggcctaaccc agcagcctgc agttctccga cttatctcca  24420
```

-continued

```
ctgtataaaa tatttcctaa tgttttatga cataactaat ctgctagcac tgggctttgc  24480
tcacacaccc aggatcaggt caatccacct gtgtaacagg gcccattcca ggacacacct  24540
gtcatcgccc caaatggtaa ccctcttagg caccccaaga ggaagtgagg gatgggacac  24600
atctaggtca gacctcagca gacatgatta aaaagagatg tgtagttgga cagacagctc  24660
gcacactttt gaaaatggca cgcaggagaa accaccttcc ccttggcttc ctcgcattag  24720
gtttcactgg atctgaataa atgttacgtg gctctctgtg gcccagcaaa tacaaaggct  24780
ggagcattgt ctgtgctggc ctcagtcacc gcctcccttg gaaaaaccaa gtgtgaggca  24840
gagacattgc tcctgtggga aaagcaactt ggcccacagt caagtctaag tttgtaattg  24900
gagcaggaag gggtgggtgt gttttcagca gaggcaggtc aactagggaa aaggtgatgt  24960
ttacttcggg gctggggaaa gcagatttgc tgcgtggaaa gagctgaaat agcagcaaat  25020
gccaccgtgc ccgtgcaagc agctccagcg aagaaagaca gctctatcgt gtttaggcga  25080
aaggggaaag ttaggcaacc gtttggaatt aaaaaaaata aaatccggag cccactaagc  25140
ctgtgtcaac gggcgaaaat gaagtgaagg gttgagaaaa tgaactgggt atggcagccc  25200
caagtccacc atgggacagc cacctaaggc tggacccggc ctctgtgcag gttagaaatg  25260
cgaaaactcc actcagaatc aagcttggag caagcctcac atgcccagca ggggagaggg  25320
tggaaggagg agtgggaggg agggagaaag gaaggaagag gctatgtgga tttttaaaaa  25380
tccagatgct agtgtagaag ggatcattgt gctttctcca ttgatttact tatgcttctg  25440
gaatttgcca ttcactgcat aattgcaacc ggaatgttat ggtgctcttc attaaaaatc  25500
tcttggagca agttgagcct ttattggagg ctaaatataa atgttgttgg accaaaggta  25560
cagcggtaaa tctggacttt tgtgtgtaca gtgtaatgtt gtggctgaca ttttggggtg  25620
tgaccacgtg gtcaaaatga actgaagcac tgaaacatta tttgggacaa tcagatcaat  25680
ggaaagagct gctcttcatc ccacaggaga aaacaaagtc ggcttaagta aaacctactc  25740
ctccttattt tctgtagcac atttatgtgc ataaattgtc ctgaaataaa gaactcaaat  25800
catatttttg attgtcccat aaagccagat gtctaaacaa gggttcttaa aattacttag  25860
ggaatgaaac atcagaaagt tacgaaacat gataaaatat caatgtttac ctctgttttt  25920
tgaactaggg ttattttagc gattaaaagt atggcaacat taaaatcacg caatacaaat  25980
tcacaactat gagcacagct gtccatgaaa atccagctgt caggctaact caggtagcta  26040
tttccaaggt actcggttga gagtttggta cttgttcact gtttttctta tcaatttaag  26100
tgctttccag cagagaagca gtagaatttc caaagattta agaaaaagtt attggggaac  26160
tttttaaatt gaaaaaagcc tatccctttt ctcaaccttg tatgtgcacc tggaaacgat  26220
cattatctca ctttaatagt aaaaccccag gttcagcctc cagagtacac gttttccaca  26280
ggaatcaagt tggagaacca tcgtcctgtg atgtttttca cttcccatgc tctgtcttag  26340
actatattag aaatgtattt ttagaataca gattttctgc tacaagaatg aagccactct  26400
tatttttctc tttgctctga tttcaggatc tatttttata ttattctatg tacattttat  26460
aagacaccaa agataccctt ttgaagaggt ataaataagt tgcttaaata caacacaaac  26520
aaaaaacaaa cactaattca ctctaaactc tggagtctag aaatttagca tttaaaactt  26580
ctatttagtc atttatgtaa tcattcattc agtgaataat taaagcaaac taattctact  26640
ccaaacattg gttcagtcct ggttattaag cacataccaa ggatgctgga catagtaact  26700
cacacctgta atttcagcat tttgtggggc tcaggtggaa ggatcactta agcccaggag  26760
ttcaagatca acctgagcag cacagtgaga cccaacaaaa aatttagaaa ttggagctgg  26820
```

-continued

```
gcacagtggc tcacgcctgt aatcccagca ctttgggaag ccgaggcggg ctgatcacct  26880
gaggtcagaa cttagagacc agcctggcct atgtggtgaa accctgtctc tactaaaaat  26940
acaaaaatca gccgggtatg gtggcatgca cctgtaatcc cagctactca ggaggctgag  27000
gcaggaaaat cgcttaaacc tgggaggtgc aatgagccaa gactgcacca ttgcactcca  27060
gcctgggcaa cgacagtgaa actccgtctc aaaaaaataa taataataaa ttaaccaggc  27120
attgtggtgc ccacctgcca acccaactac tcggaaggct gaggtgggag gaccacttaa  27180
gcccaagagg cggagtctgc agtgagccgt gatggcacca ctacactcca gcctggacaa  27240
ccagggcaag actctgactc aaaaagcaag aacaaaaaaa aaaaacaggt gcctggtcac  27300
agagaattta cattctggaa gggataaaca ggagataaac aatgcaatat gcatttaata  27360
aaataaaatg tcagatgcta gtgttattga aaactggcag gatcaagggg acagaaagaa  27420
aaattcttct tagagtggta agggatggcc ttgcagataa agtgacattt aaacgggaaa  27480
ccgaaagaaa aattcagggc aaagcacaca gctatctggg acaagagcat tccaggaagc  27540
aggaagaggg accagcaggt gcaccggctc tgggcagggt ttgctcttta accctcctag  27600
aactaattgg tccacaaagc ctttgtacct tttacacatt taaatagcct ccaaatgact  27660
tcttttatga gataagcaca aagtcaaagt cctttggatt gaacatttct gtcttttcaa  27720
aattccaata tcacctctac cagaaactcc tgttggcttg atctcagatg caagtttcaa  27780
agcattctct ttatggtttc cactaattgt gctcttattt actttccctg caccagggac  27840
aaagaaagat gagctcctgt ggtgttggaa attcactgtg acttcgggca gaaggcctgc  27900
tttgagaacg tacctaattc ctgccaaagc tcatccctgt atttcctcaa aattgttggc  27960
gggtttctca tttgaccgag atttctttga aatcaacagc caggaaaaac aagtaaacaa  28020
gcaagggcag cctcccaggg tcacccacac ttggtgaaca gtagccagga tgggagcacg  28080
caggccgcgt tgtcctccgc aaaggcctgg gtttccatgg tgctaggtct gcaaagggca  28140
gtgttcaaaa tcaagccact gcgtggtgaa actagcaccg caaaacccca aatgctttgg  28200
gtgttggttt tacaaaggat ttacactatg tcgtgggcat agaggttcta cctgatcact  28260
ttttggaata actccaggat gctttccatc tctcactaca aatctcacat cacctctctc  28320
caggcctcag ctgctgtttc tcctaaaaat atggcagtgg gaggggatgg ctgagccctc  28380
tgaagtttta ctaatatcag ggcgcaaaca cttgcctcga aatgacttcc ttctcctgtg  28440
caataacaaa attaataaaa gctcggtggc cactaccaga tagtgacttt ttcatagaaa  28500
tgtagagaac atcaccataa tccttgtcca actgtgataa ctccaacatt tatattaagt  28560
taagtgattg aggtctgcag tctttgcttg ccatagtcaa ctgtacagca atatatttta  28620
tttcctaatc atgcccccag aaacccctgt ctggaatatg ctattggaca gaggacataa  28680
tatgcaaata catcttatcc atcataaaac caaagctaag gctggaagca aaaaggacat  28740
ttgtttgcaa ctcagctctt ctcttcagac tccccatttc ccagctcatg ttcctctgag  28800
tgcagcgtct gcatctcacc atcagaggga aaacctccac gcagcagtgt ctttaactgt  28860
ttgacttcat tgcttttcaa aatttttctt aaatcattga aaatatctta gaagtcacag  28920
taagaggtag aatgggcttc catagcatct aatgttttaa ttctttaaaa actatctgag  28980
gcgaatgtgg caaaatgcta agatacagca aagctgagag gtgaggactt gagtgttcct  29040
tagtctgtct tttcgcatgc atatatttaa caataaatac ccaatagtaa tagatattta  29100
ctaatgaaat gcattagtga aaacatccct ggatgttgtg acttcaacta attgatagag  29160
ctaaatatat ctgcatactg ttttcatgta cagcatttgc aattcatgtt tagacttcct  29220
```

-continued

```
ccctcctctc cccagaagtt tccaaaaggc aggccacgta attgctttac attatggtat  29280
ctatttttttg ttaattgatg tcttcttgtg gcaggacctt tcttcccgct atcctgagac  29340
tcagcagctg cctgtgggca tgtaacccag tggaggccat cagctggtgt ggtccccagt  29400
ctcagtgagc aagggctgcc tgcagcctgg ggtccatggg ctaaggccct tagctgattg  29460
cacacagact caccagggct tagacacaaa ggagatggat gctgaatatt tcacctgagt  29520
gtcacctgct ttctgttttc tttttgaact gccctagaaa tccctcctca agaaaattca  29580
tcaaacgaaa ccaaagcagg gtatttctgt cgtctcttct gcttagtact gtcctcttta  29640
caaattgtta gttgtctcaa cattacatat gagtctactt tagggctgtg aagtatatta  29700
ttcaacattg atttttcctt ccttcagcac tggcgaccct ggatcactgg ccactgttta  29760
aatcaccctg tgctggcttc ttctgagccc gttagcacca tgtggtagcc ccagtgccga  29820
tggcatccca gcctgcatcc aggtcagagg aggcgcatgc ttccgtcacg cacgggcaca  29880
ctcctccacg aagaacccca gttcaccggg gctgccctca tgccataaaa acagaggcac  29940
tgccggccgg gcatggtggc tcacgcctgt aatcccagca ctttgggagg ctgaggcggg  30000
tggatcacca gccaggaggt cgggagatcg agaccatccc tggctaaaat gtgaaacccc  30060
gtctctacta aaaatacaaa aaattagccg ggcgtggtgg cacatgtctg tagtcccagc  30120
tactcaggag tctgaggcag aagaatggca tgaacccggg agacggagct tgcagtgagc  30180
cgagatcgtg acactgcact ccaacctggg tgacagagtg agactccatc tcaaaacaaa  30240
aacaaacaaa caaaaaatac gaaggcactg ccattaggac agagtcagag agagccacac  30300
acctgacatg tggcctctta agaggacaga gacgtgctct gctggaagaa ggaaaacgtt  30360
agaagaggtc agttgccttg cctggccaca tcagtccagt gtggactgat atatatctta  30420
tattccaatt tctttacttt tcaaacatgc ttttagccca gcacagaact gtgtgtctct  30480
ctttacggca gggaggggaa agtgcaaaga tgagatcaaa atcaaacatt tcaagattgc  30540
gaggaagagt tggaaattgg tacttttcac ccttctcttc ccctaaagtc attctcacct  30600
ttccctcagc tcacaggcga aaggagggta cctgacaatc ccctcaaggg gaggttcagc  30660
agatacaaat gaggactgaa caaaatatta gaacagttca aagaaaaggt gactgcaagt  30720
tggaaatcat aaacatcacg tgttcataca ttacatactc atgcaccaat atttgcttta  30780
aggataaagg cttttcttaa aaatggatca gggccgggca tggtggctca cgcctgtaat  30840
ctcagcactt agggaggcca agatgggtgg atcacctgag gtcaggagtt caagaccagc  30900
cttgccaaca tggtgagacc ccatctctac taaaaataca aaaattagcc gggtgtggtg  30960
gtgcatacct gtaatcccag ccacttggga agctgaggca ggagaattgc ttgaacccag  31020
gaggtggagg ttgcagtgag ccaagatcat gccactgcac tccagcctgg gcaacagaaa  31080
tggatcagtc gattagagtt cggcacttat tattattatt attatttggc atacataaca  31140
ctgaaagtgt ctattcctaa attctagttg agatgtcttt cagtaactta ggaagccatt  31200
gggaaacaat ctgaatgcaa actttttcta gagtttttgt ttgccaattt ttcacaatca  31260
tcacatctag gtataactta acagagaaaa gtttgtgact cgactatact ctttccaaag  31320
ttttaacttt acaaaaaaca gcttgatttt cccctaatag ttctttatta tgtatgcatc  31380
ccatatatgt ttatatatgt tcaagtgtac aacaaaaatt cacaaaatac tataaaggat  31440
gtaccttgtg attttccatt ctagcccaag gaagttgagc cagttctatt ctttcaaatg  31500
cagaccacga cccattaaat tgatttaaca acctgcaaat agtcaggctc cccagcatga  31560
aaggcactgc ttcagtagct gtctgtaagc accaagcagt gagggcagag aggagaaccc  31620
```

-continued

```
ctgagcacct ccccatacca ccgactgcat ctcagtgtaa tgtcccaata gctcagagga  31680
aacatagcaa atgcttaaag tatcaacact actgaaatca atgatgtaat ctttgaactc  31740
acagttacac ttgtctttgt tttgtgaaag catacaaatg tcttgttctc catcaagaca  31800
ggaaaagagc acacagacag cttcagtgcc tgctcctccc tgtgctcaag gttcactcca  31860
ttcttccaat ttttttcctc taagttcaga ggctggcaaa ctgcagtcca tgggccaagt  31920
ctggccagtg cctgtttttg tcaaattgcg tcggaacaca gccacgctgg atttgtgtgt  31980
gtgttgtctg tggttgtttt caagctgcag cggcagagtt gtttgatcgg agaaggtctg  32040
ccacacaaag cccaagacat tcacgaactg gccgaaaaga tggctcaccc cccgcactaa  32100
gtcatctcct agctctgaga aaatggcgat cctctgagaa ctcagaagct ctttccccat  32160
attaaattat ttgctcacaa acttgtttac tgggataaga agaaggtggt attatttcca  32220
ttgccattta tgcatcagag caaacaaatg atcaagtcag acttagagat aggacatatc  32280
ttacaggttt gaaatgaacc ctttccactg tcttagttta ctttgctttg tttaccacag  32340
taacagagga aagaaatttc agggccctgc aaccatgttc atattttttc atctcatgtt  32400
tagttctaaa gatatatgta atatacgcat cacactttat actgtagtta tgtttatatt  32460
aaaatacttt aaattgctta ccttcaagta aaacttgtgg tcccagaaaa ctcagagctt  32520
caagaaacca gtgacattaa atagagccat atttcacctc aaagtgccat accgctgttt  32580
gaaaacatgg aagaagaaat ggacatcacc aggaattatg aggaccacct catgcccact  32640
gagggtgttt ggggacagca gctacctggg ctgggatgaa gggaatggtc ttgcctgggg  32700
tacagaaaat ttctgttaaa agataattca tacacgataa gtaagccaag caaaactggc  32760
ctgcttttat cccaacaaga gagtcattcc aaacacagtt agtgatgaaa cagtcctaca  32820
cacacacaca cacacacaca cacacacaca cacacaatca tttgttgatg aaagttctaa  32880
ataattgctc ttgtgactgt tgagttttca ttacatatat ttgggtgtgt gtgtgtgcgt  32940
gcacgtgtgt gcgcgtgtgt gatgggttga aatgcatcgc ccaaaaagct atgttcaagt  33000
cctaacccct ggtacctgtg aaggtgactt tatctggaag tggggggtct ttgcagaagc  33060
aatcaagtta agatgaaacc atactgaagt atggtgggtc cttcatccaa agtgactagt  33120
gtcctgataa gaagagggga agaaaaccaa gacaacacaa gagaatgtgg aagatgtgaa  33180
catggagcag agatcaggca atgtgtctga gagccaagca gtaccccgat ggccccagcc  33240
accaccagaa gctggagaga ggcagggggc cgattccttc tcccagcctc caaaggaacc  33300
agccctgcag acctccagcc tcgagaacca tgaggaatac atgtctgtta ttttaagcca  33360
cacagtttgt ggtcatttgt gacagcagtc tggcgaaact tatacaccta tgcaagcttc  33420
aatcaattca tttgtatctt tatcacttaa taaacatcat actctacagg aaagttattc  33480
cagaaaactc caagttattc agctgaccct ggcacacagg cacccagccc cccgccttca  33540
tgtgaacgga aggagctgga tggagtaaac tattaacact ggttccaggt gcttctccaa  33600
ccccggggat aatacatatt ctcgcactta aaccttagat tctaaattaa acgtgacagg  33660
acagtgcctg tcaaaataaa ggaacacaac ttgacttatt ttaattcagt catcagaggg  33720
gaccatttgg aagtttgtgc ttaaaatcta aaacagtgca acaggggaca aactgcacaa  33780
tgtaatattt ttgtttagta aatgcaaatg tcagttcata aaacatttta ctgaatctga  33840
aaaatttttt taaaaataga aatgtataat tttaactgat ttctactcat tttaatatta  33900
aaagaaatat aaatatataa tatatataaa tataaattta tatataatat ataatatata  33960
atatatattt aatatataat atatattata tataatagtt atatataata tatagttata  34020
```

-continued tataatatat atttcatata taatatataa tatatagtta tatataatat atatttcata 34080
tataatatat aatatatata tatcatatat aagttatgta taatatatat ttaatataca 34140
atatataata tatatattta atacataata tatagttata taatatatat atttaataca 34200
taatatatag ttatataata tatatttaat atatatgtta tatataacat atatttaata 34260
tataatatat agttatatat aacatatatt taatatataa tatatataaa tataaataaa 34320
tataaatata taaatataaa tatatattat ataaatataa atatatatta tataaatata 34380
tataatataa atataaatat atattatata atatatatta tataaatata aatatatatt 34440
atataatata tattatataa tataaatata tattatataa tatatattat ataaatataa 34500
atatatatta tataatatat attatatatt atataatata tattatataa atataaatat 34560
atattatata aatatatatt atataaatat aaatatatat tatataaata tatattatat 34620
aaatataaat atatattata taaatataaa tatatattat ataaatataa atattataat 34680
aaaatattta ataaataata ttaaagaaag tcattactac tactgagtct tacatgatca 34740
ttactaaaag taattttgtt acgtgcagga gagaagtgtg gaaaatcatc tgtactgtat 34800
atcacatgtt ctgactacac cttagtggga gcagccacgc tgtgagcact ctctcttagt 34860
tattcaacta tgcaaacaca tagcaatcaa gttaagatga aatcttcact aggctttgag 34920
gttgcagaga tgacacaaac atgcaggcac agagtcctgt taagcaacct gtagtgtgtg 34980
cgaacgacca acatgtaagt gattattccg gctctggctc ccaaacctgg ctgggcctca 35040
gagtcaacta tgaatcttgt ttaaaaaata caagcatcca ctctcaaaaa tggtttcaca 35100
ggctcttatc aaggtaaaca tgcccttacc acatgactca acaattctgc tcctgggtat 35160
ttatcccaga taaatgaaaa tatgtcttca cacaaaaacc tgtacatgaa tgtttgttgc 35220
agctctgttc ataattgtcc caaactggaa acagctaaaa tgcccctcca aaagtgagtg 35280
aataatcagc tgtggctcct ccacacaatg gaatacaacc cagcaaggga caaacatgaa 35340
tcaacaactt agatggattt tacaggcatt acggtgagct aatgaagctg acctcaatag 35400
gtgagggccg tatgattgca ctggtatgac agcattggaa agatacatcg gcagtgatgc 35460
aggacagaat agtgggtgct ggcgtcagaa ttcaggaggg tgagcctata aagggatagc 35520
cccaaggagt tttgggggtg agggaattgt ttgtaacctg attgtggtag tgatcacgca 35580
aatctatata tgagtcaaaa ttgatagacc tatgcactaa aaagaaaaaa gtcaatttta 35640
ctgaatggct gaagggccca tgcagtagtg cataaagact caagaagcag gtggcagggc 35700
tgtacagagc tagaaagagg tttcaaatgc attctggagg caatagggaa actaaaaatt 35760
tttcctcatg agacagacat gattagatct gggttttagt aggatcattc tgttgacaga 35820
ttgaagatgg attggaggtg gttacatgga agagaaggaa gtcaattagt attccatggc 35880
aagaaagatc aattaagggc aacagataat gaattcagct ctgtacatag tgagttagag 35940
acactcacag ggcattgaag caaagatgtc catgggggtg gaagacagga gtctgaagct 36000
ccggaaagag ccccaagcta atagtaacag tatggtagtt gaatgcatgt gtacagatga 36060
agttgtcttg gatgaactgt atgtagggtc agggaggaaa aaagcagttt gggattagag 36120
tcaaggggaa ctgcattatc tggaaaaaaa gaaaaaaaca tatagagaga aagaagaaac 36180
tgataatgtg tagtcacaga ggagtgcttc agaaactaaa ggaagaaaga agaaaggagt 36240
caacggtttc cacccctagt gcatgagtct ggatgctatc gtctaactgc acagaataag 36300
caactgggct gtacacagaa tcacaaagcc acaggatttg gccaccaaaa gagatctatg 36360
tgatcgccca gtccaaaccc tcattcaata gctaaggaaa ctgaggccaa ggaagactag 36420

-continued

```
ctggtttgtt tgaggtaaca cagctaatgc acggtaaggc tatggcaggc atccaaactg  36480
ccagattgtt ggaataaaac aattgaattc ttcaacaagt cttccataag aaaatttaaa  36540
tttcaatcaa cacattatcc ccaccagttt cccttacatc cacttatgag agaaaaccat  36600
cttctatccc aacacagaaa agtaagaacc aggatgactg gattcatccc atttatctac  36660
ctgttgctta catcagtaga tgccaatcta cctgattaat ccatttactt tcctctttct  36720
gtccagtagg agaatacaaa cagattttga actacccata tagctcccca aatttggctc  36780
ctagataaat ttatcagata tttgtggtgg aaattctatt tttcctcagc cttgactttt  36840
ctgttttcta ttgcaaaata tttctcactt gctactcacc aggctatgga gagactgtga  36900
ggcacacagg atttcctaca aaaggggcca cttacccaaa ctttctaatg gcttaacaac  36960
tagaacatat aactttttaa aaatcttaca cgtttcaaaa atgtacaatt aattcattgt  37020
aagaccaaca ttattctttc cagaagggtt aaatgtcaag catttcagct ccaaattttt  37080
ggctcatttg attctttctg agtaaatctc agttaataaa aaaaatacac aatgcaaaca  37140
tgccaaaatt gctttctgat ttagagattc cttaagaatt ttattttgca tagtaaattt  37200
ggatggaaat ttgtctctaa aaatatagca agaagataaa ctagtctaga actaaagcta  37260
tagacattta aatgagtgtg atgctgtgaa aatctttctt ggataagaga aggagtgtga  37320
aaagcaaaca aagacggcag atcaataaca tgggaacgag agaaagatct ggcgagttct  37380
gaagtagcca ctggaatggg caagagggtt catgagcaaa cttgggtcct ggcggaagtg  37440
gtgtgttagc aggacattca tacgtgagta ggtgtcagag gcatagaaga gaagttcatt  37500
tcaggataag agaagaatgg gctgtgaaaa caaaaggtat attttggaaa gctcagtgac  37560
acacagctca taaataagtg gaagatgagg caggacaggg tgcagacttg tgtcatgttg  37620
ccagaatttg ggtatgtctt taaatgcact gagagtgtct gaggttctag aggagcggta  37680
tgattctacc tcagcttctg gaaaggggtt ccagcaacag tgtctttgta aagagaccat  37740
cacaaaaaga tccaagtgaa ggaaaatggg gcccgaggca gtcatgtgag tgaggagagt  37800
aggaaaagaa ggcagagaga aggatttggg agatatttca gagggagaag caagaggacg  37860
tggtataggg gaagggtcag acaggtccgt gctagggatt gacgtcccgc gggagaggct  37920
gacgttccta cccggcagct gggacagctg cagttatcag cagctcaaat gtgaaataca  37980
ggagaaaagg cagcagggaa ggaaggccca tcagattagg gcacggtgag ttctgatgac  38040
tgcccagatg tccagagagc ctttggaaat tcaggccttg ccattcatag aatgacatca  38100
agatgtaggt ctatcactcg aaatcagcag gtttgaaatt atcagagtgt aggaggtttg  38160
tctagacatt tgctttaagg ctttggcagt ggaagaaaaa cccaaaatac actcaggagg  38220
agaatatggg gtagggagac attatttttt aataactaat tacaatccct ggcaagagtt  38280
ttgctggtaa ttttacttcc tactgtggtt gctatccatg gatgtactat acatataaaa  38340
gagataatat caaataactt gtttctgtga catactaaaa gaagaagtat gaaaaatatt  38400
ctacctcatc taaaattctg ataccttcat attttggaaa ggcacatacg tattaaagta  38460
tacaactgtc aacaatttgt aaatattcca caccaagtgg ctgctaggca aagccttacc  38520
ttgtgttgat atgacatctt ttatttcttg agtcctattg caaaaattta aaagatttct  38580
cgttatatct ttttcatgtc gctcacactt tccaataagt atgtgccaag cttttattct  38640
tcaaggtcaa caaaccctgg cttagccatc ataatcaatc aaactgcatt tttacaaatg  38700
taagtttcag ccatctgata aaatgagcaa ttctgcaatg ttttgtggtt tttttatttc  38760
cgtttgaaaa caactcattt tagaggaact ctgttccctg tggttcttag tcatccttat  38820
```

-continued

```
cccagaaaag agtaatttt cagtgtccat tctcactaac tctggaatat attgtatgat  38880
tagctaactt tgaacctcaa atacttacat taaaagtgca gaaaccatga tggtttgaat  38940
agttttgttt tgtgatttag aattcaagta gagctggata ataactgaca acataaaatg  39000
tggaatccac aaagagtcag tatgattcaa agttcaccat tctaattcaa ataaaatttt  39060
aagaattaaa actgatgtcc agcccaatat agaagctcaa gcaaattcaa atggctgatg  39120
gaggagctgg cttggctcca atttttctat tcctcaagtt acttttgaga aaaataatac  39180
atataaatga aaacataaca ttactggaaa agagaaaaat gaaaatagcc atggaataga  39240
aatgttgaaa gcttcttccc aagcaagcct agaaaaagct ctgagagcaa agtcaaggag  39300
gcaaagacct tgccatgagt caaacattag ggcgagagct ggaacggctc actacagctc  39360
ctaccaccaa tcccccaaaa tagagtcgaa aaatgacggt cggagaaatt gtttctccca  39420
aagacaaagc ccaaagacta gtttttaaag aaaattaatt tgtcggtgaa cttacagggc  39480
ctaaaagaag cacagcagat cttcgccccg gcaaacccac aggggcgctg tggagtttct  39540
tcatttttga gagaaacaca acctcttgga catccatcag cccctccatg aaacgtctgc  39600
tctagcaaag ccaccgatcc aaggctcaag agcgctactt tactttccac gaggccctgg  39660
ctggatgttc agcaggtgct ctgataaaaa gcaggccccg tatgaaaacc agcagggaac  39720
agaaaacgca gcagggctct ccaatctcat gccaaggtag gtgaggctgt gctgtcccca  39780
gcaggcgcgt gcagcgctgc taagtgatgg gaatttcaga gcaaaagaaa agatgggttg  39840
tttttgttt tgttttgttt ttgtttgttt tttctttaaa ggtatatgta ttggtttttc  39900
aaacagttac taagttgtta gggcatgcat aattatgtcg tttggctcta actacttata  39960
cacagaactg ttaagaagtt gctctggcct agggccactg taaaaaaatt actgaaacaa  40020
tgatagagac ttgaaccaag aaagcgagga agtctctgtg ctgtagttat cggctctcag  40080
gaaagaaaaa ccctcctggc ttggcagctg gcccaggagg ggcgtgggca ggaggaggtc  40140
cccaggctgc tggatagttc ttcctgctgt tggagcctca tccacagaca caggcctgta  40200
gttagccagg cagggaggag gctgagcagg aaacagatgt gcctggctgc aaaggaaacc  40260
cacaagcaat caaccccatc ttcattcata aaaaagaacc aaatcaagtg ccacccaata  40320
caggaggcaa ataccagggt ggaggataat gtgaacaaat aaaacagctc acctgagagg  40380
aaatagaagt aataataata ataaaaatcc aacttgatac tgagagatta gagaggaaat  40440
tgcacccata aaattagaat tagctacaat taggaggagg aggaggtagg gagggtaagg  40500
aacagggaat aagaagataa cagcacttac gaaaaaggaa gaggtatggt aaataaaatt  40560
taactgacaa aatgaaaatt aaatggaact gccaagctgg ctgtccagaa gaggggctgt  40620
tccaccatgg agaccaggca gctagagggt cgagccaaag aaacctccca gatctaaaag  40680
gaaaaataaa cagacgaatg aataaaaacc taaaagtctt gcaagatata ttcaggaggg  40740
tcaaactaat agagactttt acaaatagag aacaaaaata ttagaaagaa atactaggag  40800
aaatgattga agcctctttt ctggagctga agttccttat acagtgatcc actgagggct  40860
gtgtgtccac ccacaggtcc cctgataaaa cttatagacc ccaaaataaa agaaaaactc  40920
taaaagctcc cacaacacag aaggggacaa catgctgtgt aggaaccagt ggctgccatc  40980
agaagctaag aagacgcaca aaggttgtga aaaaggtccc gcagatcttg gccttaggtc  41040
acgcttcgag tagtgggagt tttggtgaca gatagcgttt cccttgctac aggtttattt  41100
attcaccttg tttcaaagag aataaaatat gcataattat aataccatgt gctgacgtgg  41160
agggacatcc atcacatgaa aaacaagttg caaaacaaat ggataatagg atcctactga  41220
```

-continued

```
gcttaaatac acatacacag gcacaactag acaaataggc agatagatag ataataggta  41280
ggtaggtagg tagagagaga ggaatttaaa aatatctaga atacgtagca gacagctgag  41340
attggggagt agaggaggtg aagatgtttg cttttaatct tcaccacttg atactctcat  41400
tttttaacag agtataaatt tcttttgaaa ttaaaaaaat tatcgtactt ttagtggaat  41460
aaaagcagca tcaggcacat agtaggtaat taatcaatat ttgttaaatg aatgcgtgaa  41520
tgcaaaatat atgcctttct accatcagaa gtatagctct attcaaactt tcttcagtat  41580
ctcctgtagc actgacaaat taagttttct gtctcttctt aagtcatatt tggtaatata  41640
ttttcctaga aattcattca tttcagctag atatcaaaat ggattatctc atggctgtgg  41700
actgcaacct cctttccata ttgcttgttt tacataagaa acacatacat attttctttt  41760
tgaaaccctg ttataaaagt actcgacaaa ttgtattagt cagttttcac actgctgata  41820
aagacatact ggagactggg caatttacgg aagaaagaga tttaatggac ttacagttcc  41880
acacggctgg ggaggcctca caatcatggc ggaagataaa gaggagcaag tcacacctcg  41940
gatggcagca ggcagagaga tcgatctggt gcaggagaac tcctctttat aaaaccatca  42000
gatcttgtga gacttactca ctatcacgag aacagcatgg gaaagacctg cccccatgat  42060
tcaattacct cccactgggt ccctcccaca acatgtggga attcaagatg agatttgggt  42120
ggggacacag ccaaaccata tcacaaatgg taactcaatg taattttttt aacagcacta  42180
tgagccgtgg gaatccaagg catgagacaa gaaggctgga cagcgttcct ggatcacaca  42240
gctgagtacc ggtgaagtca acccagtgtg cctcggctaa gggactgctc tcaccactat  42300
gcctctcccc agtgtcctga attctaatgc tgaatatttg tatgttctct gcttttctct  42360
tagccttcca aagatttgtc atcagtagta tttaatatca aagaataaag gtttgaatta  42420
ctatatttgt tatagttttt caggttctaa gtcattaatt tctactatat cttcgttttc  42480
ttactcatgc ttttgttggg gctttttaaa ttattttttg cttctgcagt aacatggata  42540
tttcatttgc aactttctta taaaaacctt gaaaacttac aaagttttct cctagcacaa  42600
tgtgggttac attccatata ttatggcatc ttctaaacaa tctctttatt cagttttaat  42660
tttctctatc attttctttg agttaacagc tcatggatta ttcagggagt atttttagtt  42720
tccacatggt tttagatttg gtgttaaact ttttattact taaattctat tgtttattgt  42780
caaaatatgg cttatgggaa tgctttgtat tgagcttttt tttgacacag aagctataat  42840
caatgtttaa ctatacgatg cacatttgaa gacattttct ttaaagaaat actgagtaaa  42900
taaaacatat taattattca gttctctgta aagtttatgt acataacata aaaagtagag  42960
atattgttaa gtagcctgtt aagactgtgc tttgccagtt tcttattgca tttataacaa  43020
cttttatgtc ttttgatgct gttatttggt ttttaaacat ctctggctac tacattctca  43080
taataaatta tactttagaa aattaatata aagtagccct cgctcattcc ttattttctc  43140
tcaagttcca ctttgtatga tattaatatt gcactttggg gttcatttta tttttttgtct  43200
tacatttaag aatttactca tctattttct atgtcatttt gcttcgtaca catgtatgtg  43260
tatataaaat ttaatatgac aatatctttt gtaaaggaag tttgacccat ttatatttac  43320
tgtatattat catgagtgat cttcttgata agagttctga aacacacaca catattactt  43380
ttggcatcat tcactgctat taacacaggt atatgacatt ttaaaaaata aatcaccctg  43440
atctaactta aggcttcaaa tcgttcattt atacatttgc tccaggaata ttttgtaaag  43500
tctctattac atcatggaat tgtactagcc actgaaaacc ctttggtgaa aaagatacat  43560
atgagttgcc atcttgaagc ttaccttcta aaaatactaa cagcaggaca acaatgcaaa  43620
```

-continued

```
tctgtgtgct ttctatccaa gggcactgtt ctctctgctt tacttacttt attaaatttt  43680

cacaactaaa tgactttcta ccaatgagca aattgagaat cacagagttt taaaaacata  43740

cctattgtta tctactttgc atgtggtaga tccaagttgc taatgtatat ctgaacacag  43800

agccggtcac tatgaacatg ctacccacca acatgtgctc tctctctctt cgggctccaa  43860

gctttccata acgcttccag gttgccaaac cgtcaatccc agccactttg aagacccctc  43920

ctaatgcttc cctgccattc acaactacac cttgtggtga ctgaacagct gttctgtttc  43980

gcttcaggct gttttcctgg gaaccaccag ccattcctcg tgcccactgg gtcttactct  44040

cactggcccc atggaccccc tgaggttgtc agtgacttct gttgggttcc aggtacaggc  44100

acccttttgcc acagagatga cctctggaat gttctcagcc tccttccatg ccctccatgt  44160

acctgtggga atgtcttgat gctttccatg ccacagtgac aaggacagca agctcagatc  44220

ctcactctac ctatttgagc tgtgcagtca ctagcactgt gagaagacca ccctgaagtg  44280

ccggagcagg ggcatcctac aaggccgtat ttgtgcactg cccctctgcc cttgacaggc  44340

gaccctccat ctttctggat ttttgccatg cactcccacc ctcaccccac atcctgccca  44400

tcaaccttga ggagaaggcc ccacacttgg cgtggacagg acctggcact gtgctgcttt  44460

acactctgct ttgccttccc tgccccatgg tgtggcaccc gacaggccat ccctcttctc  44520

tttctgttcc accacacctt ccagacacaa aactctatga tcaattacac tttgcctagc  44580

tttgaatatg ccaaaaaggg agcttcccaa actgggaaat atttttcttt ctctacaaag  44640

cttggccttc gggcctcgtg tgtttctgtg aactcagata gcttcattag catgcagaac  44700

ctgcccatcc ttccccgtat gagtaaaccc gctgtctgca tcctggcagg tcaccctcct  44760

ccctgtaggg caggaggctg cccaggttgc gtaggagaag cccatatacc gggaaatgca  44820

aagcataaaa ttacatcagt gtatctcaaa actgtttgcc ctatttcgta acaactcgag  44880

aagtacatgg cacggtgaca tcaccaaaga gaatatttgc ctactttgaa actgaaaaaa  44940

aaagattcct gaaggagtaa tgctcgaggt gagttttgaa gaaccatagg aagcacctgg  45000

tggaagagga agttaatttt ctttccgggc aaaatgaatg gtgtctgcaa atagccagag  45060

gccacaggag catctgtgtt taaacaactg aagaaagccc acagggctgc agaacggaga  45120

gagaacaaga ggcataagga gatgccagac agtgggcttt ggcagggcag ggaaggcttg  45180

cgtttgtcag gcgtggccat gtctccctgc tctaaaggga aggagaggaa aaatgggagg  45240

ggccggcagc ggatactgtt gcggcagctc tggcacagag cacataagat tacaaaatct  45300

gatgcctgct agggttggtt tcatgcccct ttcagctgac gcactcatga tccacaggct  45360

gaaggaggca agggttgtga gccccaggtg ccagctctgc ccaaggaccg aatcccggct  45420

cccttcctgc gttaccccac cttcttccaa gcggccccac cctcaactgt ggaatttaat  45480

tctcccagaa ggcctggcac ggtggcttac acctgtaatc ccagcacttg gggaggctga  45540

ggcgggcggg tcacgaggtc atgagattgc gaccgtccta gccaacatgg tgaaaccccg  45600

tctctactaa aaatccaaaa attagctagg tgtggtggcg cacgcctgta atcccagcta  45660

ctcaggaggc aggagaatca gttgaacccg ggagttggag gttacagtga gctgagatcg  45720

tgccactgca ctccagcctg ggtgacagag tgagactcca tctcaaaaaa aaaaaaaaaa  45780

attctcccag acatgctcag agccaaagca agcaaaatga gggtcctcca ctgagtgatt  45840

ctcctgcacc ctccttagct gtccaccaac actgcctcca gttgtcccaa gcctgaaatg  45900

cacttgagaa cacgtcctca aatccagtgg aaaagtctac attattttgg gagaacagag  45960

catcagacag agctcccaac cccaccgctt cctgtccttt gccttgagga cctccctcag  46020
```

-continued

```
ggtagggggg cctgtgggcc aggagtgggc agcccagccc cttcgatttc acaactgcct  46080
ggtttcctct ctggtggaaa tgcacaggtg gtgacaaaac tggatgaatt tcatcttctt  46140
tactcttgtt ttagagctgt gagttcgagt cagttacggt gtgtgactta ctaacccatg  46200
tttgcatctg tgtgcttctg atcttcacac acgctgagca cattaggggc gccttcctgt  46260
ggaccgggcc ccacactggc aatggggcag gcgcacagtt cctccaaaga acctcacagc  46320
tgtgccttgt cctctgagaa aaggtgtcag ccagttccac tggacagccg gcactgtcag  46380
aaatcctacc ttagcagctg gaccaaggtc tcaccggaga agatgtgtca attcaatttc  46440
aaggtccttt tatacaattt aatcaaaggt catcattaga aaaaaaaatc atgattaaga  46500
aacgaataaa attcaagtca tactgttacc tctgttttaa acaaaacaat gtttctttac  46560
atataaattt ttatttcaaa acatttgatc ccaggaaagt ctttcacaat aagtgagttt  46620
ttagcagacc aggagagtca tcagtggata agagttctgg ggtgaaggtt ttcacaaagt  46680
gccctagatt gttgatgata ttttaatcat ctatccttgg aatacaatgg acataaaatc  46740
aagaagtgta ctgaaccttg aatgaaacag cagaatgaac tctgagtccc agaaaacacc  46800
taagaactaa gaatgcgttt ttaatgctca tgaaaaacaa atggcaatat agaatgtggg  46860
actaaagaat ggttacttga agccagaagt gggtgttctg caggtgaaac ccaagcgcgg  46920
cccctcccca aggctccttt ctgtgttgtg agtgccccac tccccaggga cagcactttg  46980
ttttctttca gcttttctga catcatatga tgcaacctga tgcaaagcaa agcgataggc  47040
atcttgtcac aggagaaatt cacagagagg aggggggcac gctgcagctg gtgcggaaat  47100
tctcaagaga ggcctgggag tggagctgag ccgttgcaga ggaaggtgga gaacctcttg  47160
agaagttcat ggacacatag cgtggttcag aagaaaagtc aggttccagt gattgaagaa  47220
aaaagcgaga cattattgca ggcaaggatc tccatgttgg gatacaaagg caatgctgat  47280
ttcaggatat ctgtgtacgt ctgtgtgtca tgggaaggga ggctgcagtt ggacacgaat  47340
agaacatctg ctcaggacga ggacacgtgg gatcacatcc tcagagcccc gtcgtcttca  47400
gagcccttct ctaggctgga ggcagtgagg acaggatggg agtgtctcct cccttccctg  47460
tttcccaggg agcatggcca gcttggtgac tgtcacagca ggtgagcagc aaactcccag  47520
gccagcaggg aggggcgact gtgagcagaa tgacagccac atggtaggtg tgtactttag  47580
agcaggggcc tctcctcgag gttaccccag ctcatgcccc agcagatagc ttggtgggag  47640
tgctgtgcct gaccctccca taacctacgg agcccaggtg gggagagtca ctctccagat  47700
cttacataaa agatgtagca cctcacacac tgctgttaca gagcagataa taaatattca  47760
tgatatgcaa ttgaatagtt atttaaaatg tttatctatg gatgaatgaa tgaactgaac  47820
aaagagcaaa atatacagac aagtaaggtg tcacaaagct ggctctgagt aaccagcctg  47880
ttatcaaatt catttgtaca gtaataaaag aaaacatatc ccaccagcca tgtgccaggc  47940
actgacatgg gagcttcaca catatgaagg cgcagagcaa tcggcacaat cctctgcttc  48000
atggaagagg aaacaaaagc cccaagaggc tgggccggga gcctgaggcc cagcggggcc  48060
agcttcgggc cacctcactg tgtttcaagg cccgccgtcc atcactgcgg ctgtcacaat  48120
ccctgtcttt tcttggttgt catatttgct tctcacctca tcatgtctat tttccatgtg  48180
gttcaagctt ttaggttaca tggctaatag gttaacccaa ataaaccaca ttatggcttg  48240
tttattgctc tctgtacagc actactaaga cgggtgttaa acccaacttc ctcctcgtga  48300
aagaacacct aagcctggaa acttcccact tcgctgttca ttataaggtt cgaaaaacac  48360
aaactccatg acagtgcttc agaggtgctt tccagcagct ctaggcacaa ggagtactat  48420
```

-continued

```
catttgaggt tttcaggatt ttatgttaga tgaagcagag ttagtaaaat cattttaaat  48480
tttcttctaa agaactatca agattgtaag gacattcaaa aacaaatttt atgtacatag  48540
tactaataac atccacgtat ttccaaacat ctaaatactt gaaattgtat gtaatcagca  48600
agtatcatag tataccttta tcatgactga taaaaccttt ggaagctgag taagtaattt  48660
tcaaaaatta ttagttcctg aaagaccctg aaatctgttt cataaattgg aaatgaaatc  48720
tagctattaa ttcaagatcc tctagataaa tcataccctg ggcaccttga aagaatcaaa  48780
gattttcagt actttttttcc acatactcaa ggtataatat tataagacaa gaaaggagat  48840
agactgaggc ttccatttat ctactactca ttaatcattt attgagcatc tacactgggt  48900
cagatattat gttaggtatt gtggatacaa agatgaatga agcaaacttc ctgtccacaa  48960
ctcattgtaa ctagagagaa taattttagc aggggagaag tagaattgta agttgggaag  49020
gcagatttga acaacagtgt ggtaaatctc aaatattaga ctaaaggttt tatcctgtaa  49080
ttattggaga atagggaatt atttggaaaa taaaattaac ataaaagaaa taattaaaaa  49140
catactacca gcgccggaag tagctttaga gcaggggtcc gcgagctcca gggcatggac  49200
tggtaccagg tccatggcct gttaggaact ggctgcaccg cagaagatga gccacaagcc  49260
acggggagca ttaccaccta agctccgcct cctgtcagat cagcacttgc attagattca  49320
ggaacattgg agcacaaaca ctattgtgac ctgtgcatgc gagggatcta ggttgtgcac  49380
tccttatgag aatctaatgc ctgatgatct gtcactgtct cccatcatcc ccagatggga  49440
ctgtctagtt gcaggaaaac aagctcaggg ctcccactga ttctacatta cggtgacttg  49500
tataattatg tcattatata ttacgatata ataataataa aaataaagca cgcacttgaa  49560
tcatcccaaa accatctccc cacccccagt ggtctgtgga acagttgtct tccatgaaac  49620
cagtccctgg tgccaaaaag gttagggaca gaatatccag cctctactct catcccctct  49680
ggactggagc cactttatat ctagaaaggc gatttatttg ttttgttctc tgcagtgcct  49740
ggtagaaagt aatccactca atatatgttt aataaataaa tgaaagaaac aggaaagtat  49800
aaacccaagt aactgattta atgacttgcc tgaggtcacc ctgaagtggc caaaccccag  49860
gttccctgtt cagctatgac cagagcccat tcttcattca ttgttaaaca taaactagat  49920
gttttatcca cacagagata gctatctaga gatatgaact tccagaaagt tgaccgtatt  49980
ttttgtttac atgtggatat ctgatatctt gaaaatatac acatttagtc attaagttta  50040
aaattaaaat ataggcctaa aattttttgg agccatactt ccaataataa tattatatgg  50100
atgcacaagc tatattacat attaggaaaa acaataaagc cccaaaccta cagatttctc  50160
tctctcacac acacacacac acacacacac acacacacac acactgctca ccaagattgt  50220
tgattctcca gttttccaaa cactttgttt ctctactgta gctctaggtg aaacaagact  50280
gatcctgagt ttatagctgc tgaagctggg tgatgactcc atggcttctc attagaccat  50340
ggcctcttca tctgtatatt tttcaattgc ccattaaaaa atgtttttaa attgagagcc  50400
aaaaaagagt atccattaac aaataaatgt atcattcagt cggcttattt agcagcagtc  50460
agaagaaaac tccttctgaa ctgagcaggt caggcatcta tatagaattg tttcttggca  50520
gatggctgag ctgtccagga gtaccaaatg taggcacctg cccaaggtaa cttaggaggt  50580
tttcccctta gaagggagag agagagagga ggatggagaa cgtctctgca atcccttata  50640
tcttattgca taactttctg ctgaatggag agctgcctgc ttgtttcagg gagaatgtca  50700
tttttttata cccaaaactt aaaaaacaat attgttatgc agaaaagatt taaaaaattt  50760
ctagagttgt aagtgaaaac taaattacta ggaatcattc atcaaatttt accaactcta  50820
```

gattctgatt ttatttttgt atgtgtgcca aaatagatgt ttacccatgg gtacagatca 50880
caaccaattt gcaagagcaa gtgggaagaa agctgactac tccttcacct ctgctgcact 50940
tcctaagttt gaccattgat atctgaagat agaagtcaca tgtgcatgtg tgaatataaa 51000
atataccttc ctcaattaaa tatacaagac aaagccactt taggaagcat attctcagat 51060
tgttggctgc agtctttgac caacccaaat aaagattaga tagttgtaac tgtaagagct 51120
gaagaaactg aaaactgagc atatttcctg aaattgtgag catagttaag tgtcttcact 51180
ttttcagaaa aactgaaatg ggatgaggag acaaaacccc tcataaccta aagctctgtt 51240
attttttttt tttctttttt ggagatgaag tctcattctg tcgcccaggc tggagtgcag 51300
tggcgcaatc ttggctctct gcaacttctg cctcccgggt tcaagcgatt ctcctgcctc 51360
agcctcccaa gtagctggga ttacaggcga gcgccaccac accagctaat ttttgtattt 51420
tcagtagaga ctgggtttca ccacgttgtc caggatggtc ttgatctcct gacatcgtga 51480
tctgcctgcc tcggcctccc gaagtgctgg gcttacaggc atgagccact gcaccgggcc 51540
ctgaactata tacatttcta tctgcacatc taatgtctag tatccgctga ccacagaata 51600
aactcaataa atgtttgctt ttgaacatat aaatcattgt tgttataact ctaattatat 51660
gagaataaat ggaagatact ggcataatct atatacatat ttacatatat aggtatatgt 51720
catctataca ttgttcatac agatttgagc agaaaacctt aatgagcgaa ccctgacaca 51780
tggttgcttc agctttaagt gtgtccaaat gtctaagaaa atatggaata gaatttgtaa 51840
tagggtttta agatcaatgc ataaaatatg tcactatgtt tatgaaagca tagaccgcct 51900
gagctgtaac aggtacagag ttctggaaat atgaattctt cctttcacac actattaaga 51960
tgtcctgcag gagtcgaatc gttttaatgt ttctgttctg gatgaaataa gccacattta 52020
cgcagctaca atctctagct aacacagatg agtaataagt tttaggccga aatgattgtg 52080
atgtgatgct ttcaagtgag gaagtgccgt ccagagtcac tggctctcag aattggaggg 52140
aaattcatgc agtggggaag ctcacagagg atctcgctaa agactgagtt aaatggcctg 52200
gaactcaact tacaagcagg ttaaaaaata acaaccttcc ttccttgtct agctccttta 52260
agtgaagtat tttctatctt ggaggcctct tttgaaatgc aatactcctg agagtggtca 52320
caccttaagt tatcagctaa cactttccga gggattagca gacagccggc agagaaaaag 52380
aaatgggatt taggcaaaat gcctgagggc tggaggggag acactgcctg gagaaaggtt 52440
aactagtctg ttgatttgct gatagacaaa tttcacgtac tccagagcat ttggtctaca 52500
gtggagactc ccaaattctg gattctataa caccaccaaa aagcctacaa tttcccagat 52560
tatcttgcaa gcaacttaag tctgcatgga atacaaacaa aataaaccca ctattggcct 52620
ttgtataatt gaaaattatt aactttactt agaacatatt caaattattt ctgaggattg 52680
tttatataca tgagatcaga ctttttaaat tataaatgca ttttaagaag gtaaaggaca 52740
cagtaaaaat atagcaagtc ttaataagcc tacacagtga aaactcatca gattcttcta 52800
gattgcaact aagatacact acaaaaaacc ccagatgggc caggcacggt ggctcacgcc 52860
tgtaatctca atactttggg aggccgagaa gggcagatca caaggtcggg agttcgagac 52920
cagcctggcc aacatggtga aaccctgtct ctactaaaag aaacatttct gttccgtatg 52980
aaataaacca cactcacaca gctacaatct ctagctaaca catacaaaaa ttagtcgggc 53040
atggtggcgg gcacctgtag tcccagctac tcaggaggct gaggcaggag aatctcttga 53100
acccgggaag cggaggttgc agtgagctga gatggcgcca ctgcactcca gcctgggcga 53160
tggtgtgaag ctccttctca aaaaaaaaaa aaaaaaaaaa aacccagatg tgccctgcct 53220

-continued

```
taggattttt tgacttaaca atggcacaaa agcaacacac atccagtgga aactgtattt  53280
ccagagctga aataaccatt ccgtgtttca ttttcaagag gctgttcagt caattatatg  53340
agatattcaa ctcattatta taaaacaggc tttgtgtgag gtggttttgc ccaactgtag  53400
gctaatgtta agtattccga acacgtttac ggtaggctag gctaagctat gacgtttggt  53460
aggtgtattc aatgcatttt cgacttacat ttttagttta caatgggttt ataggaatgt  53520
gtattagtcc attctcatac tgctataaag aaatacctga gactggataa tttataaaca  53580
aaagaggttt aattgactca cagttccaca ggctctccag gaagcacggc tcaggaggcc  53640
tcaggaaact ttcaatcatg tgcgggcgaa ggggaagcag gcacatggct ggagcaggag  53700
gaagagagtg aagcgggagg tgccacacac ttttcaacaa ccagaactca ctgtcacaag  53760
aacagcaagg ggaagatcca cccccatgat ccaatagcct cccaccaggc ccctcttcca  53820
acagtgggga ttgcaataag attttggcag agagacagac ccaaaccata ccagatgtaa  53880
ctgtatcata agttgaggga cattggtata tagcttatat aatagaaaaa gagaatttct  53940
cttcagtttt aggaatcttt tttttcccca ggagcctatt tttaattgtt cttactactc  54000
tgggtatagt atgttacagt cttagagtat ttatgcttta tcttcaaatg tcagcttaca  54060
ctgatcaatt tagggcagaa gcctgttata gtcctttctt ggaaccacac cacatagaag  54120
aaataatttt tttttaactt ttttttgttt tatgcttttc tgatactttt tcctacggac  54180
ttcctggagg caacaaagct aaacaagctc ttcaaagttt aatcgacctc ttcggatcta  54240
tgactgtatg ggtaggccct aatggactta aatattatca aaagttgctg agcacaggct  54300
ttgtaagtgc acatttcgtt aatattgcct ccacttctcc atttatgatc atggggaaca  54360
cacgcagcac agacagaagg tatctcccca ctccattttt ttcattgatt tgtatcttct  54420
tttgccatga aacttttcac tatcaccaat aacaaagagc cagacagaga tgaatttaca  54480
ttcattacct taccttattt ttaaccttag gcaaccataa tcgtgagcaa gtgaagggtc  54540
aaagctatta gtattcctaa atgaatagta gatttatttt gaaagtgatc attaagagga  54600
aatgtgctta ttccttagtg ctttaatttg gcaaacacat ttgagtttct cttgtgcccc  54660
aggtaccgtg ctaggctctg ggtgtcaaag gataaggaca aacacagctg ttgcctctca  54720
agatctagca taaggcaaca attagtaaac tgggtctaat ttgtgaaata gcagtatgtg  54780
aattctgttg aaaaatactg aactcatgcc caaaagactc ggtttatcat cccagcgttg  54840
acatttacta gttatgtgac cttgaacaag tcactgtgtc tccctcacct ctaggttttt  54900
ctcccaaaaa gtgtgacatt tgaccacaac tagatgattc ttttctgttc caaagctgta  54960
tgattccctg gtcatagtca agcccatcga tggggaaaac tagaatagaa cttattggat  55020
gggtaccatg catgccatca tttaacgtcg ccttgtcctc tgggggccgt tatcccacag  55080
gactccatgg cttcctgcct ctctaccatc tcctctctct gtggaagcaa gggtcggctc  55140
acagtttgga atctcaattg ttgagaaagt gtaattgttt acaaggacag accaatgagt  55200
aaaaccagcc atattttcac acacacaaaa aggggcgata gatctcaact tctcattatg  55260
gataaaaatt tcaaaatatc aagtcaggtg aaggacatgt gcagcgagga ctggtgtgac  55320
ctcaggactc agcatttatt ttacctcatt agtgtaagaa tgtcacaaga ttgacaggaa  55380
cagcaattca atcaatcggc ttcaatcaag gctaccaaaa atgagagcca atctcttgcc  55440
attagatttt gggcttcaaa caattttagg aagaagttct attcgctagc tgtataaaca  55500
ctagaaattt attgcctgaa atctttgtat gaaagattat tccctgaagt ctttgtctga  55560
aagttttgcg tgtaagatta gcaaatcttt ttaaaaagca ataaatatca aacaataaga  55620
```

-continued

```
aaaaggaagt tgagaaactc aaagaccaca gtttaatctg gaatggatcc actggaaaag  55680
tatattgtta acatgagttc atctaaacgt acacgctaac ttgtagcaac tgagtttcaa  55740
agcccctccc tcattctgcc cccactggca aacaatttct aggtctgcta ggagaaaaag  55800
atcttcaatt gcctcagtga gaggatgggg gcagaaagga gcctcaaatc ttccatgtcc  55860
acataaaccc ttagtcatct gtcacatgtg aaatccctgc tgtcagccct gacccacatg  55920
gcaggagcca ggctcattct gaagcaacac ttgttgctgt tgcaaggagt gacctgttca  55980
tataaaagcc tacttcacag tgccaggcta acttttgttc agggacaaaa tcctctgttg  56040
ccagaaacaa caacagcatt tgctcctcag gtcaacgtaa tacctcacta atgagattac  56100
cttcttcatt ctaacagatt tttctgctat gtggagacca agaatatgag aatgcctact  56160
taatttaatg tcctctgaat attatactga tttgaaaaaa aaaatactgt tgtttcaatg  56220
ttgctgttga catttgaggc agagggacag tttacaatgg gacacgcagg actcacatcc  56280
agtgagtagg aaggactttt tcagcctggg ggaaaataag acaaagtgat ggttaaaggt  56340
gatggctcca gagtcacagg tgtgggtttg aaccctgggt ttctcatcta ctagctgtct  56400
ggtcttggat aagtttctta atctttaaat cttagtagtg ctggtaatat gaaggtttgg  56460
gtgagattta agtaagattc tgcactaaaa gcaattttca ccataccttg cacgtagcga  56520
aggcctacat ttccatatat atattattcc tatttgtatt acattaccat ggctgtcaca  56580
acaaagtacc ccagacttgg tggcttaaac aatagaaatt gattatctca cggttctgtg  56640
ggccagaagt ccaagatcca ggtggtggca gggctggctt cttctgacat ctgtgaggga  56700
ggctctgctc caggcctctc cctggctgta gacgcctatc ttctccctga gtctctccac  56760
atcgtcttta ctctatgctt gtgtctatgt gcaactttcc cctttcgcta aggacagcaa  56820
ccatagtgac cttgattacc tctctaaaga ccctgtcccc caaatataat catattatgt  56880
gatgctggga gtttcaaatt tcatcacata aatttggagg agacacaatt caatccatac  56940
tgctgttgat ataggtaata ataacaacta ttattagtat catgtttaga gcagaggtca  57000
tccactccag aaaactgcat gtctttgaaa tgggaaattc tttcctagtg cctcgaacgt  57060
aataaatgac ttgaagtggg taagaagagg ctacaagaat gaatgagtga gtgagtgaac  57120
gtaataaatg acttgaagtg ggtaagaggc tacaagaatg aatgagtgag tgagtgagtg  57180
aatgtaataa atgacttgaa gtgggtaaga ggctacaaga atgaatgagt gagtgagtga  57240
gtgaatgtaa taaatgactt gaagtgggta agaggctaca agaatgaatg agtgagtgag  57300
tgagtgaatg taataaatga cttgaagtgg gtaagaggct acaagaatga atgagtgagt  57360
gagtgagtga atgtaataaa tgacttgaag tgggtaagag gctacaagag tgaatgagtg  57420
aatgagtgag tgaatggtgg gcaggatatg aggagcctta aggatttacc tccagcaggg  57480
atggggcaag tgaccaatgg agctccaagc atctgcggga ggtaaacagc agatgtataa  57540
aaggagcctt ctcgagagcc tgcaggtcta agaccacagc gataggagga cagggcaaga  57600
acctctgttc cagaaggatt gggaccagga agaaagctgc agagaggcag gctcgtgctc  57660
acctgcagtc atgcccatct tgcccacctg ctgtctgcga ctaggccaac tcctaaacct  57720
ctctgaagct taagacctgc cacagtgggc tgtgccagag ttggagtgga gactcactga  57780
gatcatctag aagaggcacc tgcctcaaag ccttcaggta atacccacac ataaacctta  57840
gggtttttcc tacctgcaat tctgtgttct ggccccttca cgatgaccca gccagcctag  57900
gcatcaagcc acggaaagtc ctagaggaag tgggacctgg ctgaagtggg tataagcatg  57960
tagagaccaa agctggcaga agatgacccc ggctatccat ccccatattt tgggaacttc  58020
```

-continued

```
ctggaggaag ccatcctacg aggtgcccca gaggaaagga acctattttt aatgaggtta  58080
cattgtaact aaattgatag cagggaggga gaaacagaag cttctgaggg agtataggtg  58140
tggtggatat ttgataatac tctgaaatat ttttggtctt attttatttg cttttactac  58200
aagaaaagaa aatctgcttt atttagaaag ccatttagaa gtccttactg gctaataaat  58260
acataataag taaatattta ttatacttat tataatatat ataatactat ataatatata  58320
aatactatat aatatagtaa tatatattaa gtaatattgt gacttcttag gaaagtcaca  58380
ttatacattt attagccaac ttaaactcaa aaatgagaaa taagaatgtc cttttataaa  58440
ataaacaaga cacacaaaaa aatctaactc caaatatcta attcaagctg ctgattgaaa  58500
gttggattgt aagtggcccg tgggcaactt ctacttccta ctacaaaata tgttgttttc  58560
cttgcaaaag agtacttgga aattcttcca ggcaacagca aattcagtaa gcagatgagg  58620
gactctgact gattaatata aatgagagtc tagaacagca gaactctgga aaatgagcaa  58680
gtaaagaagc cctgaaaaag aaaaagcaat aaagcttgcc tgttgattca ggaaaacagc  58740
ctccattgtt actgaaactt gattcacagt tgatggtgag ttatggaaag ggcaaaagga  58800
caaaatcctt ttataaatat agttctgtag ggcatgggaa gcaatcaaat ggtgctgtga  58860
gactgaacac aaatcatgct tttttcaagg ataattattt tgaatcaaca acctaagtat  58920
ttccagtgca cttctgcaag acaaatattt tcttgggatg aaaaaataaa tatgttttgc  58980
aaagaaatcg agaccatatc caaaaaggct gaaaagggtg tgtgtataca catatatacg  59040
cctatataaa cacatcatat atggtctatg tacatacacc acgtgacacc atgtatcaca  59100
tacatgcaac atataccaca caagctagta ataattattt gtaccaaatc tatttcttaa  59160
gactgtaata ctgtgttcac acagtcacca tttagagata tattatcaca gtgtcaatca  59220
ccaggactac agactattct tatagcttgc tgaagtttag ttttgtactt agaaatcaga  59280
gctgatctct catacacagc aggaattaaa tatttaacag ttctccatag aacttcataa  59340
aaaaagagta aaggagacag aaattactgc ttttgtagaa gaagaaaatt agtgctttgt  59400
gtaatattta cagggactgc tgatggagtc tcaaagcaag aattgttttt tagggtaaag  59460
aagtgaattg gcaatacctg cgttactgga cagtccttaa ctccttggtg gtattctgtt  59520
taggaccttt ggtgaagggt cagtcatggg attttgaagg gtgcattgat ctcatcagga  59580
aacattctgc tgccattgta acccttgccc actgtgattt tctctaaaag agtggagact  59640
ttttagaaca cggaatgact ccaacaaggg tcagactcta acaaccaaac aacaacaatc  59700
aacaactact tcacagttct cagagatcag ccctgccacg ggaaacgcac agtaaagcaa  59760
gagcagggtt gacattctct gtgaaatggc atcaggcatg actctggagc aatcttacag  59820
atggatagcc ttgatctcct tccaccagtt ggctaaagga ttgaattttt tactatctgt  59880
aggagatagt ctatgatctt gttccaaata tctgaataaa ctttaagaac cacagtgcaa  59940
tcacttggac acgatcccag atccatccgt ccattcatcc atccacccat ccatccatca  60000
ttcacgattg actcaatatc ctgctgggag ctgggaaaaa agagacatga agtatccctg  60060
cctctgagca gctttcagtg cagatggtat gccagggaca atatacaaga cagaatagag  60120
ttcattcaag tattctatgt tttgttattt agttttcaaa tatgaaccct ggatggaacc  60180
aggctttgtt cccccaagtt atcagctaaa gagaaagagc tcagccaagt gacaaggtgt  60240
tgccgcagtg ataactcaat tttgtggttt tcagaaatgc agaagaaaga aggttggaaa  60300
gaatgggctg gcactccccg aagagtgggg ctcaaagttc tggtctcagc agatctttga  60360
gggagacgta gggtctaggc cggcaaaacc agagagaagg ataggctttt agatgctcat  60420
```

-continued

```
cccacccaaa accatgaaat aatctcccct gtctcctgat tagtatttgt cagcctcatt  60480
taccccttaag atttgtgcaa atgaaaaacg ttaaatgcag ttcctggatc agtaattaaa  60540
cataattatt tcagtggaag agatttttgt tttcataatc tcctctttgt ctgcatagag  60600
ccagctcttg gttacatctg ccactgatag cctttgctct gtttacttta aagaataagc  60660
cactgtttga tttggtttct tgttttcaat atgtaaaccc tggtctcttg attccccatt  60720
ccaggaagga aaaaataaaa gaacaaggct ctttaaatat cagagccatg atgacttaac  60780
agatacacgc aggctcaata ttttatgtaa cagccactta ggaaaatgcg taagaatttc  60840
ccagctggca gccctgattt ggcaggtgta cctcaattga accaatcgct tttcatctgg  60900
ctgtcaattt gtttggtttt tctggctaca ttgcaccaga gtctgtgtgt attccaaaag  60960
gtcgttcacc tattccacgg ttcaaaggga tcattctgtt cacttaaagg gtcactgtaa  61020
tcatatattg aaacatagct aagtacgatg agctagaatt ttaggagggg taaaactaat  61080
aggaaaatcc aggagtataa accacaaaac acacataaaa aaagagataa aaacagaaaa  61140
cataattcct caattaaaaa aaaaaaggaa ccaaaaagaa aaaaaatcta taacaaacca  61200
cactgtagga gtctcactat acactaaaat taacaatcac agctggggta aatactttat  61260
ttattttatt catattctgc actggcagca tattctagtt gcctgtttga tttcattaat  61320
ccaaagcaaa agagaagtag agatttatgt aaatttcatg ttatgctcag attgtaaggg  61380
agccactaat tgaacttcag gtcttcctta ttggaaggaa gacctgaaga tgaatggctt  61440
catgaaataa tcgtaaatga ataattcccc cacatccgta agtcagccta cttctgtaaa  61500
cagaaaaaca aggtagtagt cccatagtct atttttaat ccagaaaaag tcattcttgc  61560
agcaagaata agggaaacta tgtcccaaaa ataccaggtt ttccagatat agggatcatg  61620
tttgaccaaa acaacccttg gcctaaaaat actgctatat tcaaataaga ggagttgctg  61680
ttatttaatt ttactatact atttatactt acatgggatt tttataatga tactactgtg  61740
gttttcacag atgtttggct tgtaaaaatg ctaaagatta caatctttag gtcaccaact  61800
acctgtattt atggaggcta caggacagag cacagaacag ccaggaagcc aaaacgcgct  61860
cgaattacct ccagcactta ctgccgcggg actcaaaccc gagtcctttc tgggactgct  61920
tttccttgaa cataaaaatg ggggtgatat caccttccac agggatctcc taactgtaca  61980
gagggcttag cacactgtct ggcactcaga ggccttgctg gatcgtgatc cgccccctcc  62040
agtcagcgac tgagacccct cactggttca agggcaaaca cagtgctgag agctgtgtgc  62100
ctggatcccg ccagcaggtg tgctggggta gggaatggaa gtcaggcatc ttgatctcca  62160
tatgtatcca ccgatggaca ccctgcctgc ctttcactgg gctcacccta aaatggtgaa  62220
caaagaaaac agctctcacc tctggagcca acacggaggg gtgggtatga gtgcagatgt  62280
ggtgggggtg ctggtggagg cttgctgccc atctggcttt tcctgttatt gacatgctca  62340
gatgaaagtg ggccctgttc acaaacatgg catccattcc tgggactcat cccgagcaga  62400
acctcaaata aaaaccagaa caaactacac taatttgctg aaccccaaat ggagccaaat  62460
tcaaagctct tacgaaacta caaacagaac cacagtttca aaaacaccag gaaaatagtc  62520
tcaacaagac attacctaca tgaaggatgt ctgaaatcta ttttagtgta aaaatgctat  62580
aagtttactc tcctactttc taaaattact gaattagtta ttaaaataac aacctaagta  62640
atctgactgt aaattgagcc atattttatt taccctaaga tctctcaatc aaatggagat  62700
ataacaaggg ttatcaattt ctactgcatc tattcctgta acatattaaa tctccatctc  62760
cttgagagaa gtacattgat ttttccacag gagaattttt ttctagctcc aagaacagct  62820
```

-continued

```
gagggctgca aaactgagca gatggccaca tggaagaatc tgcttggttg ataagatagt  62880
ttaaaagaaa aatcacctga ctgcacatcc caaatacctg tcaaagtagg tcatgaacac  62940
tgcttgattg gaacaaacca aaatatttaa tggatcgaat cttccagagt tcatgataac  63000
tgccccacca aaggtctggg cttaagcact gatgtttcct ttaattataa agcccagatt  63060
gtaaggcaaa cacagccctg ccagtgtgtt tgtaggtcca gtcagtgact gtgctgcgtc  63120
cacaatggtc tttatcattg tcacttgttt gacctgacta taactgagta aagcatcatc  63180
attacaaaat gcagcatgcg ggatagtaat cacctaaaga tatggttcaa gcacttcacc  63240
aacctctgaa cctgaatatg cctaatgaat tttgtaaacc ttacaaaaag tgaagccagg  63300
tgattatcag aaaaaagaca tgtgtcatac taaagaaaga gcatgttctg gacctgagaa  63360
aacagcagtg cagaagggaa tgtcttttct ccacagtgat atgtggccac agccttgaac  63420
agcaaatttg cagattaatg aagatagtaa aatagatcac atcctcctgc ctccaggtat  63480
aatattttat tcatataaga gctatgtgag ccttgattta tatgaacttt cattagtagg  63540
caaaattcaa tcataaggtt tcctcttttc acctctaggc gtccttaaat tcaacacaca  63600
gtcaaatggt gattggcttc ccctctccct aggtaatacc ccaccccccca gcctcccaaa  63660
aaagacagaa aaagaggaaa atgaaaaaca agcacgttag aaaggtggcc agacaaaacg  63720
gtttgcatca acaacataac ttctgatttg ttctcccgct gggacagtct aatgcagcct  63780
cattcagctg tgcattttca atattattca acagagccca ctcaggtcaa agtagagtct  63840
tttccttcac aagtacagag atacaacact aggtttacgg gagggctatt ttcaatcttc  63900
ttgagcggta atgtgtttcc attatggttc catctatttg tgatctataa tgctttccaa  63960
atagccccaa atttcaaaga agctctagtt ggttccaaat ggaaatgaga ttacatattt  64020
agtattattt tattctcaaa tgttagattt aattaggttg ggagcattca ttcatctgcc  64080
cattgtgttt gttgacttca ttaagggaca atcacagaat tgcagggaag tccacgtagg  64140
gccccccaaa ctgcgattgc ttttagcttt tataaaccat taaaatgtaa gtcaagcaca  64200
taaatatatc tgctatgaaa agaagtggta ttgctaagtt ccctgataga tgatgacagg  64260
acttctcaga attcgaaggc cagtgtttta atcttcaggt tctctcaggt cacgtgcttg  64320
ccaatgacat tggaccagga atctccagag gtgagaaagc ccggccaac cccaaatgca  64380
gctcttgctt ggtgaaagca gagatggggt gaggacaggg acacaggcag aaccctgccg  64440
cgctccagct gagctgctca cttgccactc ccagagaaaa caggaggatc gacctttctc  64500
tatgcaacgt ctaaaattaa tttggtgctt aaaatcagag gtgggtcaag cagttgatta  64560
cctgaggttg cctttggact aacaaaggcg tctcttcagc atggtgaatt gctctgatgg  64620
ccctgggccc ggagcagtga tttgagaaaa tcacccatgg caaccattag gcaatgagtc  64680
tccattgact gccaaaatct cactgaatat tgaaggaaaa gagaatttat atgtaatcca  64740
attcagagca acaacaacaa caacatcaac aattcaatgt tccccagttc ttcatgggaa  64800
aacttcaatc caggtccaaa gagagctgca agaacagcgc agttcacaca gaaagtctgc  64860
attcacaggc tgggctgggg tcgcaactct gcgggcctcc ccaccctgcc acgctttgta  64920
ctgctgtgtg attttagcgg aggcatttag ctcacacagc cttagtttcc tcatctgtaa  64980
aattgaatag ctaccttcta ggctttggga gaatgcaatg gaaaaagaat cttgcctagg  65040
gcatcatcag ctcagtaaat aatagttatt atcatgatga ttatcctcca ggtagctgtg  65100
atgtgtagaa gcccagaacc aagtagcaca ggagacagag gtagttaatt caaccctcct  65160
ccaatacaac tgagtgccct aattatccga atagaagctc cactgcagga aaactctgtt  65220
```

-continued

```
ttggagctca aggaaagacc tacaagggag aaccacagag ctgtaattat cagctgaaag  65280
aggaaggaag ttctaatctc acagagccct tggagacttg tgaacacccg aagcttggag  65340
aaggcttcaa cagggaacaa acggtgaaag ccacacaaaa atgaacttag cagcaggaag  65400
gagtactcca cgtgcccctg cacctctcac caaagggata cagatatgtg atgggtgttt  65460
ctgtaatata tgcctcattt tccaatggaa aacctccata tacacatgag tgcatggaga  65520
ggtcatagtc actggtcaag gagttagaga tgagtgggga aaagtgatag ggtgagcatc  65580
ctcaatctgg ccccacccta tctggcgcca gacacctaat gaaccacctt tactggggga  65640
gacagggtca aggatgaagc aatttcctct tcatatctag ctatcattta ttctacatag  65700
ttgatgcagg caatatgctg gctgtttgaa gcaggtgata tttctaatcc acacaatggc  65760
ctgaaaggta agtattatgg aatcacttat ctggataaat aaaacatgag gttcagagag  65820
attacgtaac tggcctagat caataggtgg gtaggcagac aggtaggcag gtagatagat  65880
atagagattg aaatatactt taaaaacact ctgtttgccc tacattcctt gctttagata  65940
ggattctgaa tgtggggcgg gcaggaaagc tgtcagtcac gaagggagcc tgcccaccac  66000
aaggcgagtc atgtgaccca ggccagagaa tcaggttacc ccacagggaa catcagtgat  66060
tggcccaggg gtaagcaggt agctcatgta gcaccagagt catatttttg aagtttttat  66120
ggaagttgga aagatctctt ttggaaatta ccaactccag agaggatgtt agcctgggag  66180
tgccaggaac tttctgtgtc actggggaaa gcgagacttg attctccgga tatcattgac  66240
catctgggtc ctgtggtgcc tgacgctatg agttctcaaa gtggggcccc caaagcagca  66300
gcagcagcct catggccttg ctggaaatgc gaattctcaa cctcagctcc cagactcact  66360
gcattacaaa ctctggaaga tggagctgac tcagtgagat ctctttccaa gctctctaga  66420
tgggcctgat gcttattttg aaaagcactg ttctaggtca atccagggaa ctgttaaact  66480
tcatgagcca atagataccc ctcttcttgc ctaaactttg attataataa aagaaaaata  66540
cagcaagata gttttgaggg ttttttaata aaaatttaca attatttttt aatcgcaagt  66600
aaacttaatt attttaccat taaaacctct tcaacacaga aattcctttg aggtttttag  66660
ttttgttctg tgtttgtttg tatgtgaggc aagacacccc tggatgcttg caaagaagag  66720
gcaatttgaa gtgaaacagg cagatgtaca atctgatccc ataagtgacc cactgcagaa  66780
cagacagctg gacatatgga catatgcagc tgcctgtcat ttatacacga gagttaaaca  66840
gttggcaaag agagtctggg ccacagagtg gtgagctggc tagaggtgcg gatctagcca  66900
ttggataaca ctgtacttaa aacacaaaac tctatccaag aagaggaaat gattgaatac  66960
gaagtatttg aaaaaagatt tgaaagactg aaaatgaaac acttccttac attcgctaag  67020
tgagctgaga aagaattgcc cagaagggtg atacggaggg ctagagaatg aagacgacag  67080
ggagtggaag gagagagccc acctacatgg cacccagctt tgcagaggct cctgaagaca  67140
caaggttgaa ggccctggac tcaaaaattt ccttgactct gccaggcaag agggttagct  67200
gtttcagcag agggtagagc caagcgaaag ctggagagtg aataagaaat gctaggagca  67260
attgcgtcag gtggggcaac caggactgtg tttgccttcg gaccagggct gccgagtaca  67320
gatagcaggt ggtttatgtg aggcctggag caggggtcat tgcaggagac ggggttgctg  67380
tgtgcctata aatggagtga aaaagtgagt gcaaagaaat ggaaaagtta ggagatgcag  67440
cataacctgt gaatcatgat ccctgacaaa gtggggaggc tcatgggtgc aggtgtaggt  67500
gtgtgtgtgt gtgtgtgtgt gtgtgagatc acatggctgt ggacagaggt gggctggaac  67560
ccctaacttc caggaaactc caggttcttt tcttcttcta cccataggtc tgcattgtgt  67620
```

-continued

```
ttttctaggg tcactcatct attcatccaa caaatattca acaagcacct gttacatacc  67680
agattattac atacatgtgg cagtgcacgt aactgtgaag ctgtgtacta cagctgcagg  67740
gcgaggactg gggctttagc tcccaccttg tgcaatgtgg gatcttctcc atcgtcatat  67800
caagccaccc cacgtgtatt taatgtaagt tggaacactg tgcttgctac aaaagtcagc  67860
ttcagaagaa gcccctccgt ggatcaccac ctccctacaa gctgcagtcc taatctccta  67920
tgtcaaaatc agggactgct gctgccccgg ggggtttaga gatgaagacc cagactctga  67980
ctgaggagtc tcccagtgaa aggaaggagg cagaagccca gtcaccagtg acgccaccca  68040
gctgagtgga ccgcgcagag ggaggcggac gcagggcact ccaacatgga cctgagaggc  68100
acacactgca atgcaaatcc tccacgatag tccacaggat gtactgggag aaactggaag  68160
gccacaggag aaacgtttgc tcacgaaaac acaggcattt catgtgcctg gagcacggga  68220
tgaagaattc cttagacttt gagtgccaag ctagtgcttg gactttcttc taaaggtcat  68280
gggtgagccc ttggggaatg tggagaccac tccggcctgc gatggagaag gaaattgtgc  68340
cagaagctgg gaagtcaaag ttaaccctcc aggctagatg taagtaacgc gtggggctgc  68400
acatacggct gtggcagagg aaatgggaca gagggattga ttttagtaca gaaatcctaa  68460
ttgggcttaa agtaggtatg ggaaaacccc tgaaagtgtg tgctgatctt ggtatgtgca  68520
gatattattt tcctcctggg gtaaacttta attctcaaag gagtctatga cccccaaaaa  68580
agtcatctcc ctacttgaaa gatgcttgag tgtctaatgg ccaggagcgg gtgttggtgg  68640
gataccaagc ggtgggagga acacagtatc gtcctcaagc ctctgacttc tcctagacag  68700
ggtagctaag aggacttttc agatatgttg cttttgaggt gtctgtgagg agagggaggc  68760
aggaaacgca ggcacacgca ctcacagtgg acgcgtcttt agaaagctgc acattctcta  68820
attgagttaa ttgttcacgc actgaatgga gctgtttctg ctcaagctag ggaaagactt  68880
gtcagctgtt tcttcacttc catgaccttg gaaaatccgc tgtctccacc agacactgat  68940
ccttggcaca gccactattt gatacactta actctgctca ggattttaga tctcaaccca  69000
ggaaatgagc tacagtctca ccccaggcaa gtacagaaca ttttcctaac caggagagac  69060
gcctgtgtca cacattccaa aggtagccag cagctaagaa agccgcaaca aaggaaatca  69120
aacagctctc tctcccctaa acgctgcttt caggcaagtt ccaaacaaaa atggaggatg  69180
cactgcaaat taaaaacaaa agcctgccag tcaaaggcag tgtttttaaa cacagaaaga  69240
gcaataccac tgcagggggc agataaaaga gcttttgagc atctcagaag ctactcacac  69300
acaaaagcac ctctgtgcct tcaaacagga tctcctagaa gtttcccaag gtttcataac  69360
ccaaataccg ctggtagtga tgtggtttgg aaattaacct tgcttttctc cccactgctg  69420
ttttacatat taattaaagt gttttcctca gatcaggaac gcctgcaggc tggctaggtt  69480
ctgcagaagg tgcctcattt tcctgccgct tcccgccccg gccccacttg tgcatagttc  69540
aatgattaaa acttccccag gtcagctgta gacgcctccc ctcccttaac tgccatcgtg  69600
atatagaaca cacactttaa tgtggctttt aaaaagtaat cgcttcccca ccccccaaga  69660
aagataggtc gtgcagagct aatttcggga agccatttag aagaaattgt tgagaaggca  69720
ttgaagtatt tgggtccaac tctgcttacc tcattcatgg acctgtttct tttcttttt  69780
ttcttttcca gtgcttgaaa taggtgtgca aacaattcac atattataaa tacgttgact  69840
tgggccgggt gtggtggctc acgcctgtaa tcccagcact ttaggaggct gaggcaggag  69900
gattacttga ggtcaggagt tccagacaag cctggccaac attgcaaaac cctctctcta  69960
ctaaagtaca aaaattagcc gggcaaggtg gtccgtgcct gtaatctcag ctactcagga  70020
```

-continued

```
ggctgaggca ggagaatcgc ttaaacccag gagatggaag ttgcaatgag gcgagatcac  70080
aacaacccac tccagcctgg gcgacagagc aagaccctgt ctcaaataaa taactaaaat  70140
gaaaataaat aaattgattt gttttcattc atatattttg gggatacaat ggagcttaaa  70200
gtttgaaaac caaaacggag ctggccacca aaggtgtgga tttggtcaac agggtgtgga  70260
ctccagcagc ccgtgtcact ctcagactcc atgtctcaat ttgaatgttt ccatgtcact  70320
taaaaagtag aatattcata gtgatgttga agatacaaaa gatataccag gattaatttt  70380
ctagtcaatt ttatgtgtct gtgacccaag acaataaaag ttaagtcatc gttagttcct  70440
tagttgctgg acactttagc ccaatatacc accttcaatt ttgaattatt atttggactg  70500
tgttcatgag attcttggag tatgttaaat caacacattt ctttgtaatt attgagaacc  70560
ttttgttccc tataaaatca agtgtacgat gatgtaaact ataaaacgca aattgtaggg  70620
acaattggta atctgcagtg aaaataaagt caaaatagca aagagcagat tattctcaaa  70680
tttatgtaac agagttctta catgtggaag tggatacaag tattagcaca ttcagttgat  70740
gtactgaaaa taaaatgaaa ctatttttct acttactact tgcttgtgaa atccaaaggg  70800
gtgaataaga gccaggattc attgtcatga gtgtaggggt gccctgggaa ggaggcctcc  70860
atcccacgtg tcagtggcgt catcagaaat tccatgatcg tcggcttatt ctttgcacac  70920
gtgtctacag ggtccctccg cacaccgact tggtgtcctc caggatgcag aaaacccaaa  70980
ttaaactagt ttaatgaata aggaaactaa gtggctctta ggaccataag ccctgcggtg  71040
acgcctgctt cagggctgga ggagctaagt gttctctggt tcaccaaagc ccccagttct  71100
ttccgtctgt cactcatagc ttcggcttcg tccccggctc actgccagtg gtaatcaggc  71160
tgcccaagaa cttctgaaat ccacagcccg gtgtttccaa acgaattatc agtagggttg  71220
gaatcccttc tccccagccc cagccccagc aaggccctcc aacgccactg cagttccctg  71280
gatagcagga agaggcctga gccggctctc ccggagctcc aggtgcagag tctccccaca  71340
tgggagtcag tgttctcaga gcagcatttg ttgacctgag ctaaccaagt tctctaactg  71400
aaagcctggc tgtgtaaagc cacagatgtc tggcattaga atagctcaag gacaggagaa  71460
aaaactgaca atcagtccag aacggcatcc caggacttct gctctgagga gaaaacagga  71520
ctaaacccca gctgaggtct atttccaact ccaagattct gcaatgttat ctctgtttaa  71580
aaagatatcc cactttttga tgacagtgtg tctggaattg gtgggttctt ggtctcactg  71640
acttcaagaa tgcagctgcg gaccctggcg gtgagtgtta cagctcttaa aggcggcatg  71700
tccggagttt gttccttcta ggtgggttcc tggtctctct ggctcaggag tgaagctgca  71760
gaccttagcg gtaagctgtt acagctctta agtcagcgcg tctggagtcg ttcgctcctc  71820
ccggtgggtt cgtggtctcg ctagcctcag gagtgcagct gcagaccttc gtggtgactg  71880
ctacagctca taaaagcagt gtggacccaa agactgagca gtagcaagat ttattgcaaa  71940
agacgaatga acaaagcttc cacacgacag acacaaaccc taacagattg ccaccgctag  72000
ctcggagagc ctgcttttct tcccttatct ggctccaccc acatcctgct gattggccca  72060
ttttacagag agctgattgg tctgttttac agagagctga ttggtctgtt ttgacagggt  72120
gctgattggt gcgtttacaa tcctgagcta gacacaaagg ttctccaagt ccccaccaga  72180
ttagctagac acagggtgct gattggtgca tttacaaacc ttgagctaga tacagagtgc  72240
tgattggtgt attcacaatc ccttagctag acataaatgt tctccaagtc cccaccagat  72300
cagctagaca cagagtgctg attggtgcat ttacaaacct tgagctagat acagagtgct  72360
gattggtgta tttacaatcc cttagctaga cataaagatt ctccaagtcc ccaccagact  72420
```

-continued

```
caagagccca gctggcttca ctcagtggat cccgcccggg ggctgcaggt ggagctgtct  72480
gccagtccca cgctgtgcgc ccgcactcct cagcccttgg gcggttgttg ggactgggcg  72540
ccgtggagca gggggcggcg ctcatagggg aggctcgggc cgccaggagc ccacggcggg  72600
ggtgcggggg caggctcagg catggcgggc tgcaggtccc gagccctgcc ctgcggggag  72660
gcagctaagg cccggcgaga aatcgagcgc agcgccggtg ggccggcact gctgggggac  72720
ctggcgcacc ctccgcagct gctggctcgg gtgctaagcc cctcactgcc cggccgctcc  72780
gagtgcgggg cccgccaagc ccacgcccac ccggaactct agctggcccg caagcgccgc  72840
tcccagccct ggttcccgcc cgtgcctctc cctccacacc tccccgcagg ctgagggagc  72900
cggctcctgc ctcagccatc ccaggagggg gctcccacag tgcagcggcg ggctgaagcg  72960
ctcctcaagc gcggccagaa tgggcgccga ggccgaggag gcaccgagag cgagcaaggc  73020
ctgtgagggc tgccagcatg ctgtcacctc tcgacagagt cacaaagcat ttactgaatg  73080
cctactgtat gccaggccct tttctcaagt ctgcttaacc aggagtgaag aaggctgaca  73140
ttaccgtcca tgtcacattc tggtaggaga gggatacaga gaacactaca agtaggtgaa  73200
ataggtagta ctttaaagaa tgagaacaac atggaaaagg aggctatgaa atactgagaa  73260
tatggctgga gttttcattt tagataagta aatagccaaa gaagccttga ctgaggaagc  73320
agccagccct gtaagaaagg agacccctgc catggtcctg agacaagggt ttgagtggtt  73380
tccgcaggag gcatttccag gaggggaagg agggaaacaa cgagggaaaa gtacaaggtg  73440
tgctcacccc tgaatgagtc cccggggcaa cccggatcca cctgtccagg ctcctctgag  73500
cacgtgggga gcacgtggag agggagtggg ggagtcgtgg gggagcgtgg gcagcgcttg  73560
ggggagccgt tggggacttg gggagagcgt ggagagccgt ggggagggcg tggcggagct  73620
gtcggggagc cgtgggggcg cgcgtggtca gcacttgggg agcgcattga gagccgtggg  73680
gagcactgag ggaggatgcg gtggccacgg ctgcgtggca cccccaggcc atggccagga  73740
gaccctcggg cggcgcaggt gccggaagca gcgccatccg tgctatggac gggtccccc  73800
aattggcagc ggtctcgggg gtgagccaga ggatggggtg actgagaggt ggccgatgtg  73860
gggatggtgg ttttcaaata gaggcgagat cggagcagga gctgggaacc aaaccagaag  73920
gttttcagga cgtggttaga ctttgaagcg gcctaaggct gtggcacatc tgacccactt  73980
tctcaccaac attgcggtgg cttcttagta aggaacgggc tgaaaggggt aagggaaagg  74040
gtgggggcag ggcactggga aaccaccatt gccaacatcc aggccaggca ggggcggcag  74100
gggctgggcc agggcgcagg ggacccgact cttgctgcgg ccgctgggaa gagggaattg  74160
ccatagagcc agaacaggag gcgctggggc agggctctgc tgtggggcgg ggtgctcagt  74220
ttgggacagt gttgacactt ttggagatca tcagccatcc cagtaggtga ctccaggagg  74280
ccactggata tacagctctg ggaacaaaaa acggaatcat cagcctattt acaactctgg  74340
aatggatgag atggctgtga cgactggcag cagctgcgcc tgagccctca gcacctgcag  74400
ggtcccatgg gaggtgaggg ctgtaaggga gcaagcaact cctctccctg gagcaggcgg  74460
gcagggagaa cagaccgcca ctgtgctgct ctcaaaacca agtgcatggc cggtcggggt  74520
ggctcaggcc tgtaatccca gcactttggg aggctgaggc aggcaggtca cctgaggtca  74580
ggagttcaag accagcctgg ccaacatggt gaaccccctg actaataaaa atacaaaaat  74640
taggtgtggt ggcacacacc tgtaatccca gctactcggg aggctgaggc aggagaatcg  74700
cttgaaccca agacgcagag gtttcagtga gccgaaattg tgccactgca ctccaacctg  74760
agccacagag tgagactttg tcttaaaaaa aaaaaaaaaa aaagtgcaga gttgctttac  74820
```

-continued

```
atctttacat agaggagaat ggtgtaagac gcagctattt ggtcaaacct atgtgattga  74880
aacatttgca tagaaagaga gagagaaagg atgggagaag aaaatataaa ctaaataact  74940
ctccttttc tttgctggct tgtgtgtttg catttatgaa caccaacatg aaattttgaa  75000
ccttaaatct agtataaaaa tatggaacag ccagcttcct agagtgaggg caccattctg  75060
tgtttgctgc cggtggacct agtgtgggtt ttggcgccaa tgtccttttc tgctaaaaca  75120
acttggcctc ttggaaggaa acttggactc tgttgccctg actcaaactg ttgtttcatt  75180
tcttatgatg tctcctcatg ttaaaaaaaa aaagaatgtg gacattatgg gtttaaacat  75240
aattttgaat gaatgaggaa attctggtag agggtttgtc ataatgcagt atcaattggt  75300
taggtcttct aaagaaacat gtagggttct cttaggaact ggttcattaa atctaaaagg  75360
caaaaaaatt aaaacacact tttgatatat ttgttggagt tacatataat catatctttc  75420
aagagcagat gtgccaaaat atacacaaca gagtgtagct gggtgacccg aactgaccac  75480
gaaagtcatt tatcaaaatt caaagttagt tccccacagg cctgaatttt cagacctaca  75540
cacaattcca caaacaaatg atggtaaagt cccaaacacc acattcttgg agggatccaa  75600
tgctattggc actgatgctt taatcagaaa gaggctcaaa cccactggag ttaagctctc  75660
tgaaagtctt tgctccttgg caaccacgag caaacctcta cagctgactt ttttagagta  75720
ttttttacat ttttaaaagg attatttctg aattataaaa ccaccgttac caccttattc  75780
ttgtaactct aacttattat tttgagtcaa tttataaaac ttgattcatg agagtcaaga  75840
ttcagggtag gccagacagt cactcattcc taccctcaaa gagcatacac tcaaatagag  75900
aatgaaacac gtgccccaag tcagaggtaa atattataag caaaagccaa agtgttctgg  75960
gtcaaacact ttttgggggg tcagtgaggt cttcatgcag gggtaacagt ggagaaaggc  76020
cttcaaggat ggggaagatt ttcccaggca gagttaagaa caaagagaaa gcagtttgcc  76080
aggagacagg gaagcaagtg tgcagggagt gaatttgagg ccttcctaac tctgggtgtg  76140
acagcagagg ggacctgccc atgagctgtc cgagatgcag ccaaaggttt caccgcccac  76200
gtgataaggg gctagaacac tgaagtgtag aatttggact ttattcagta agaacgggga  76260
agtactgggg gtccctgagt agagaagtgg gatcctgcaa gctgagcatc acaatgattc  76320
gtcaggtgat gtctcagagt ttctctgaat ggcacataaa ccagagacag gaaggtgagt  76380
ccagccgttt ctgtggccca gcaagaagta acaagtaata agtaaagtgc tatcagtggg  76440
aatggcaagg gaggggcggt tacaagtcac atttcagaca ggagttgatt ggatgtgggg  76500
agggcccaag gatgtgggga gggagctgtc agaaataagt ggccctctaa attttagccc  76560
cagtgactta gagaaaatgg tcaagagatg gaattggttt tcagggaaga cactgatcca  76620
ttctggacat gttgaattta agatgccatt aggaaaacca aattaaggca ccttgcaggg  76680
aaattgcaca tgtaacatcc tggcttctgg gatttgagag gtggctgcaa agagagaaag  76740
gcagtaaggg atctccagag aaggagatca cacaggaagg aagtgaggga tgggaagtca  76800
ttgttgggaa gttgagggtc aaggacattt agagagcaga gggagaaaga aggggtggcc  76860
attgcactag ccaaagaaaa tgttcagcca ctcgccctgc agggaaggcg aggggcaggg  76920
tggctgcgca tagatgtgga attagccgga ctcagggtga agccatgatt ctgctagtgt  76980
ggtcttgtaa cctgggacat ctatctgagc gccctgtcag cgcttctctg cattgtaaat  77040
gggagttgtt gcaagggtga aataagacgt aaggtgtttg gtgcaaggtc ttgtgacaac  77100
tagcactaag gaatggtgcc tatgaccttt attaggcagg aaggagtcaa cagagtgagc  77160
tgctgctgca gggggttggg agctcttgca acggtggcat cgagaaggtt gtcaacacag  77220
```

-continued

```
ccctgtcaac ggctgagggt ggcagagtcc atattgcaaa ggagcacggc ataagtggcg  77280
aggcaagaag tagatggatg ttctattttt tcctttctct atctggacaa aggtcttttt  77340
ccttccaagg tgtagctgga ttttctctct atagagcttc cctggggcgg ttccattttc  77400
tagtgtctcc atgagtcttt gttctttata tgaggtccca atgatgccat ccactcattt  77460
gctttctcac aggcatgttt tccaccagcc acccacgctg attagcttga gagtgactca  77520
aggcaggaac gatgcccttg tcgtagaaca gcctctgatc gagtgcttgc tgaacagctg  77580
gctagctctg agcatgaagc aaaatgcagg aagctggggt gtgtgaggag gagcagggac  77640
agcttaaaga agagaggagg gagaggaggg ggactcctgc ttggggcacc ccacctcctg  77700
gatatgagat cacttgtgtg gagcaggcct agtagcaggt aagtgggccg aaggggaggg  77760
agtgaaaaag tccatgtatt gagtcacctg aggtgtcatt taaagagaca ggaataacaa  77820
aacatcaatg ggacctaagt tgagattaga attaccgact tgacttgtag tgtcacctgc  77880
cacccagggt gaggaatgtc ccttaccaca aggtcacctg gggtctgaga tttgaaatct  77940
gtcagccttt ctgggctggt ctcttgcctc agtttatgct cacacagctg cctcaggatc  78000
agtgtggaca gaaaggtacg tgagactgtg caacggagat gggctgggag aatgaggaag  78060
aggggaggga caggaggtgt ccatcacctg gacacgggac tgaacaacca cacaacctca  78120
tggcggacac cagcacacct tgacctttgc tcataagtct gtgagtcggg atggggggct  78180
ggcgacggct catcctgctg ggcttcctac gtgtctgaga caaccggatg gactggtgcc  78240
ggctccgtgt ggtctctctt catctcgcag atttgcctgg gcttgtttcc cagcagacag  78300
cttctgagga taggtttggg acgggcacct gccacttcct ccacattcca ttggccacag  78360
tgagttgcaa ggctggccag actcaggagt gcagagaaat accctctact tccagatgag  78420
aagagccaca aagtgacatc accgcaggct ggatgcaggg cagggcaaga cagcggaacg  78480
cgtgggctgt tttgacagtc agtctacccc aggatgctcc aggaagggga aaaggacaag  78540
ggaagagggg cgctgtggcc aagcagggga acttctgtgt tcaaaatctt ggagatggat  78600
cactttcagt tcccgataag gcttagtgta tggccctgag acttgccgtt tgatactata  78660
atctgtcata tacaatgtaa cttagtgaat tgggtaaagg atcttcaggg tttattttga  78720
atggttgtca tttattataa aattaattta ttttataata attttatcta attggctggg  78780
catggtggct caaacctgta atctcagcac tttgtgagag cagattgctt gaacccagga  78840
tcttgagacc agcatgagca acatagcaag acctcatctc tactaaaaaa aaaatccaaa  78900
aaattagcca ggcgtggtgc catgtgcctg tagtcccagc tacctgggag gctgaggtgg  78960
aaggatcgct tgagcccagg aggtcaaggc tgcaataagg tatgatcatg ccactgcact  79020
ccagcatggg caacagagca agaccctgtc tccaaataat aatttgatat caatttgtaa  79080
taatttattt taaaagaatt gtatgaagga cccatgcctt ggggcatagg ggcactgata  79140
gaaggtaggt gatcagtata gatatttgct gcattaatct atttcagtca cctgtgagat  79200
gattcaggta gaaggaaagt gaggccccga gaggtcaaat gtttgctgag tcccacacag  79260
gtgaacacac ttttctcctg gatcctagtc taccccacct tcttttctcc ttttgaaaat  79320
taatgttttg taagtgatta aaaagaaaaa tgatcgggct gggcatggtg gttcatgcct  79380
gcaatcccag cactttggga ggctgaggcg ggcagatcaa aaggtcagga gtttgagatc  79440
agcctggcca acatagtgaa acccccgtct ctactaaaaa tacgaaaatt agtagcgtgt  79500
ggtggcacac gcctgtaatc ccagctactg gggaggctga ggcaggagaa tcgcttgaac  79560
ccaggaggca gaggttgcag tgagccgaga ttgtgccact gcactccagc ctgggccaca  79620
```

-continued

```
gagtgagact ctgtctcaaa ataataataa agaaaggaaa agaaaatgat tgaagacaca  79680
gtgacattaa gtttcataat ttttatttaa tccaagtcta tccccaaaag gattatgcct  79740
actgtactat attatacggc atgaaataga tgatcctgta acataaggga tcagattcta  79800
tgccaacttc taacactgtg gcttaagaag tcagacccaa gaatgttgtt caattatttt  79860
atcattagcc taatttattt ccaccctgga tttttccatg ataactaatt ccacacttcc  79920
tctggatccc ctctttcagt ttcaggattc aggaatggct tcggggaaag agcccttatg  79980
tttttgcttt caatccactt gtgtttccct ttgtcaagag acaaatggga actgcacccc  80040
caaactgcat gatgttcttg gcagagaaaa tccccagacc acagaggagt ggtatctgca  80100
gaagatagaa cgagaggaag cagctcaaag acaaggttcc agaatgagct tgcaccatgg  80160
gatgcagcca gtggacagtg actgaccagg aaacacctgt gatggcaagc ggcagtgacg  80220
agcgagtcag aggtgaccgt gccggaattg aatgtgcgag cactgctgtt ataaaggaaa  80280
agaggaaagt gcaggcaagg acttttattc tcatgtgctg attataccaa ttcatataga  80340
tgacgtctgt gtgggcattc agatgggcat tttcagttca aatgattgtg tgaacatgaa  80400
tcgcctaatc aaaattagat ctttattttc tcctttccca gtcgtaccct cagcccaaca  80460
acatttaaag gtgaatggat gtgcaatatt ggcacgaatg gacgtgacac acagtaggcc  80520
tttgtgcacc ctggaaggga gggcagattc tgcttcaagt gtgctggaag acatgggagg  80580
gatctgaact ggctgacgct gcactgtagt agggagaatg gagtggaatg aggggaagga  80640
tgccaggggg aggccactta ggaggctgct gtgtagccca agcaagaaag gatggcgact  80700
tttctatcag gggaagggat gagaggaggt tggactgaga ccgggatatg ctctgaggtc  80760
aaggcgacag agttgctgaa ggatggaatg tgggctgtga gatggaggag tcctggcgag  80820
tgctcggctg gttggcctga gtgtgtggac ggctggtggt gccgtttatc ggtgcagaga  80880
aggctggtgg gagggcacct taggggtggg ctgggtgggt ctgttcagga aagaccacgc  80940
tttgatcatg ttggttttga ggcatgtgca ggctaggcat gtggagatgc agagtggatt  81000
tgagtgccat cggcatgcag atggactcag gccatgcgat cttgtgagat gccagcccag  81060
gtcttgttcg gaagaggcag agtatgtttg gctgcaatgg ctgagtgggg cttagattca  81120
gcaggaggag caggccatgg cagggtgaga ccttctgttt gagaagctag gcatggggca  81180
tccatggcac agccctggga gttgccgcgc aggcagcagt ggatgtgagg gtggaagtca  81240
aagttgagga tgtagatgag ggagctgaag tcatgggggg atgagggcac ctggggaagg  81300
ggtgtcaagc aagagagcgg tgcacagatg agaactctga cctttatgag atgggagaca  81360
aacgtgcgga tgaaaggtgc ggtgtcacac aaactccagt cgagaggcaa taaatatctc  81420
acatctcagc tgcatcgtcc tttctaacca agcatggaaa ttctgtctgg caagccgtca  81480
ggtacatttg cagaaaagga gaaggaaagt cattgagggc cacactggag tgagacagga  81540
tcagcaggaa gggaaagaat caagaccatg atgtttacat gacttctggt tacttctccc  81600
caagctccag aaggcaaatc ttgcatggac ctctggcatg catgggtggc tgcagagagg  81660
cctagagaag aggcattcat ttggggtgag gctcctcctc tctttcaggg attttacagg  81720
gatccttcca gccagtgggt ctgtgctgga tcctccacca gacaccccta gtcagggcgg  81780
aggccctcag cactccagcc tcagagccca gacagttctg gttcccagct cccttcctgc  81840
catgtctgtg agtccatcct cctgttccac ctcaggactt gtaaggcgta ttactgtgcc  81900
ccctgggtaa ggcagagttt gaggaagaac gaataaggtg agggccactg actttcagga  81960
tttagctcct cttctcaaca tgcatttcct gtctactgtc tgcttcacat cacccacccc  82020
```

-continued tcactgtccg aaatgcgtgc cccagcccaa catcagcatc acccaggagc tggttagaaa 82080
tgaggctctc aatctccacc caacctcctg aatcagactc tgcattttaa cgagatcgcc 82140
agagagattt gtgtgcatgt tgacatttga aaagcattat taggcacagt ggctcacgtc 82200
tgtaatccga gcactttaag aggccatggt gggcaggatc gcttgaggcc aggagttcaa 82260
gaccagcctg ggcaacaaaa gaaaccccat ctctacaaaa tatttttttt tttgagatgg 82320
agtctcactc tgttgcccag gctggaatgc agtggcatga tctcagctca ctgcaacctc 82380
catctctcag gttcaagcga ttcttctgcc tcagcttccc aagtagctgg gattataagc 82440
gtgtgacacc acgcccagct aatttttgta tttttagtag agacggggtt tcaccatgtt 82500
ggccagtctg gtctcaaact cctgacttca tgatccaccc gcctcggcct cccaaagtgc 82560
tgggattaca ggcatgagcc accacgcccg gccaaaacat ttttaaacat tagccaggtg 82620
cggtgcatgc ctgtagtccc agcaactcag gaggctgagg tgagagaatc ccttgagtct 82680
ggcatttcga aactgtggtg agctctgata gcacctaatg catgccagcc tgagtgaaag 82740
agtgagaccc tgtcaagaaa gaaagaggaa aggaagagag agaggaagga gaaggggaag 82800
aggaaggaaa gaaggaaaag cagtatcata tattatttaa tgacacttca cccaaggttt 82860
tccaaataaa aacatccaaa gaaactagac aacaagcatc cttacctttc aataaaggac 82920
tcacttgaca attttaggta tgtgccaaag caccaaagca aattgttgat gttcagctta 82980
gtaactgaca tggcttcaat acctacccgg catggtgctt cgctcactct ttaaagacta 83040
cctttatgca cttttactat ttcactgcca cgctaaacat ctaagcgatc atatccttat 83100
gcctactgat tatgaagtcc atgacattca acaacatcaa ccctttgccc actgccccac 83160
ccgacttgaa ccaagttttc ccaagttcaa ttcctggggc ctttgatagt ttcatgcctt 83220
ctccacgtgc cagagacaga gaagagtgag ctctatcgtt tttgggggtc tactagtttt 83280
gcctttatta tttagacagc ttcaggtcag cttcttcctt gtataccagt cacaagtggg 83340
tttttatttt acaaagaaaa catagaagtt atcattttct agaaaaaggt acaataacta 83400
tttcaagaca tattttagat atacttacag gcacaccttg gagcagttca ataattaaaa 83460
atttcatctg tctgcctgac cgccaatgca aaggaaacat aattaaaagt ttttttgttt 83520
cttctccaag ataatagttt ataaagtagc ttaatgaaac actgaaaatc cagaatggaa 83580
gaggacgtgt gaaatcccct ttccggtgtg aacttattct taaacaatca aatgaaagtg 83640
cccgtcagcc tttgcaagat gctaaccatc tggcccctgc atcctgtctg agtcacccga 83700
taaatagctg caggttgttt taagcacact gcgccctgca caagctgttt tgctctgcta 83760
ctcactgccc ttaggtgcag atatttacac ccggggttga gcatattttc agccacacct 83820
ggatgcctcg aggtaattag gaggaaactt ttagcggaaa ggaaacagca tacctttgag 83880
tagcccgatt gtgtatgcag gagaaaggtt aagtaggaag agaggggagt tctctcctga 83940
attgagtagc tttgcttcct attggaaaag tgtgcaaatg aaaggaagta gaaatgctaa 84000
aaagctctgt gactgcctcc tgctgtattc aattagcctt ccagaggatg ccagaaggaa 84060
ggctcaatta ccagagcggc tccaggactt aagagaaggc tggagggcaa accaaagggg 84120
ctgccatctt gcagacctgg tgtgagacca aggcggggca gctgtgtgat tggattatac 84180
acgggaacct tactttagtt tctattgcat ggccagagct atgcatgcca ccttttgcat 84240
ggagtcttga aaagtcacct aattttaata aagcagaagg ggaaagcgat aagaagaggg 84300
agagtgcatc tctctgaaat gcctaagcat cggccttgcg ggaaccggcc tcatcgagga 84360
gcagggccac caccgttgga gcatcggagg agcatcggag gagccctagc tctggcctct 84420

-continued

```
tggctggacg tcactgtttc aggccgagca gataaaagca gaaggcattg accgtgagcc  84480
aagagctcag tgttttcaga aaatggactg gacgggagga aagagtgtga gtgtgctttg  84540
agagcaataa acaaactatt ggctgccggc cagggaggag tgtgctgaca tcttcaagcg  84600
gatcctcgaa agctccacag agcggctgag gaagcctcct tagggctgtg gatggggtgg  84660
cggggcaagg gctgccgtgg cgccatgcag cagtgggcat cgggcctcag ccacacccag  84720
cagggaggcc aacagcagaa tcccaggcaa acgcccctag ggttcgcccc tcatgcctcc  84780
actccctggc ctggctctct gaagggcagg gcggtggagg agaagcagag ccaggcggtg  84840
ccctccgcca gctctagctc aaaggctgct ggggctgacg ggtggagctt gtgtagacga  84900
agccccttac cctggaagtg aaggttatgg ggtttcctgg agggagggca ctgggcctcg  84960
ctcttaactg aggcttcccg tcccccgagg gagggtgatg aagggtgtcc agacacatcc  85020
acggggacaa aggaggttgg caaggctgac cgcaggagtt tctcctctaa tgcctttcaa  85080
atgaacaggt ctgtgtcgct gctccgggag cgcctgcgct cacatacccc gcggtgcaca  85140
gttaccaacc agatcctacc acgccactgc ggacatcgcg gtttccggga agtctctggc  85200
cttcgtatga aaagacagcc cgacaggttg aattctttaa aaccttatct ttggttattt  85260
taataggata tgacaatctc ctctcctcag catgtcgata aatgtttatt gccctttact  85320
gtgtgagagc aggggtcctg ccgccgcttg tttttatttt cttttagacg gcgtgaacat  85380
ttttagcacg tgtaaccaat gatggtaatt aagattataa taatgctgat gccaacattt  85440
atatcagtgg atacagaaaa tacacagcct gattattttt tattactcgt acccataaaa  85500
ttaaagatct taaacatggg atggagggtg catccgcatc aagattttgt tagcatgaga  85560
ccgaacccat tcagccacgg ccttcatcag aagccttttg agtgatgaga cagtgatgag  85620
atagctcgcg ttatcctgca gcacagagct gcgcctggtc acggcagggt gcaccggctc  85680
tcgggcttca gacaacagct tatcagtacc ttgcccgtgt gcaaggacag tactccttga  85740
tgccctgaaa cctccgctcc tactaactgt ccttggacac gtcggcatac agagaatcaa  85800
tcgtactctc agcagtggtt tctgcagcaa ctctgggtca tggaagaagc caagtgcatt  85860
gttgaaacag cagagcccag gcagtgcccc gatagaaacc aggtattgag tgcttgcacc  85920
cgttcctgtg caggcgggcg tcacgcacac cttctgctgg aagacacact gtctacgtga  85980
acgcccagcc tccctgtgcc ctgccttgtc ttgtggaata tgtcggcacc cccaaagaat  86040
acaccttcaa agccaaaggg gagtttctgt ctgtctgctt cacactgtcc ttcctcctct  86100
cccacccctt ctctgtgtga agaagtaaag caaagctctt aatgatcacc cttaaatggc  86160
aagactttga tagactgttt ctataatagg ttctcattga aacatgggag ttctaaatag  86220
agaactgtta aaaagtggaa tgagagatga gggaccgagt cgtggccctc cttcctggtc  86280
tccaccatgt caagtatgcc tccaccccgg ggcctttgca cctgctgcgc tgctcttcct  86340
tcaggtcccc acagtaggcc ctttgggaac tctgatcaag tgttgccttc tccgagaggc  86400
cgcctctgac catcccctgg aaaccagcct tctctccccc acgcctgggc tattcctccc  86460
ggttcttatc ttcatcttgt gtttcatatt tgttttactt gctgatcacc agaagaaggc  86520
cttataagtc caggcactca ggcttcctct ccactcgatc tccagtatcc agaagcatat  86580
cggatgagga ggagaatgca atagaaatta gtcgcagaaa tcaatcatgg agaaaggaaa  86640
tgttctcagt gaggtgtttc aaatatgcag cgtacaagac ttaagtggaa gactcactta  86700
taaagtagct gactcgccca gcagaggcac ccatttttat actttcccct ttcacctttc  86760
ttgtggataa agccagtgtg atggctggag cttcaggagc cacgttggac tatgaggcac  86820
```

-continued

```
cttgaagaca gaaaggtgtg cactgaaaat gctaaagctg aatgacggtg ggaaggtggg  86880
tcctgggaag tgatggaaac cccgtgccag ccttggaatg cccacatctg tctagtttca  86940
tctgagagaa taaaacatta tatatgttcc agccattgtt gttttggctt ttctgctata  87000
tatagttaaa ggtttcctat acatatatca gagaaccatt gggattcaat tttagtcact  87060
tattataatt caacgaatgc actttacttc tctgagcaat gttatgcctt cataaagcca  87120
ataaaacagc gtaattgttg aagaaattgt gcaaatatag aatacaatca ttcaaggcaa  87180
cctagtctct tagcctgcga gtgttctaga tgtatacaag acaaatgcat tcattcaaat  87240
attcaacaaa tatttgttga gtacctacta ctatgtgtcg tgtattgtgt taggttcact  87300
aaaacacagt aggaaagagc tggaattgga ataaatgctt tgaattctga ctcactgctt  87360
attagttgtg accctgagca aggtgtttaa cctttctgag cttcagtttt cttaatagca  87420
cttagttctc agaggtgtgt gaatatggaa tgagaggtag ataaatgtct gaacagagtt  87480
gctcagcggt tacagtaaca cagttttgct agctaccatg tctgcaatgt gatcctttcc  87540
atcaaggagc cccctcgtgg gagaaacaca gataaacaga taatacagtg aaacttggaa  87600
ggtgccgtaa cagaagggta agcagagtgg tttgagaatc tggagaagtg ggtcactagc  87660
tctgtttagg tgagttgaaa tcaggttgca ttatagtcat tggaagcatt cactggatat  87720
ttccagtttt ccttctcctg acacatggta gagttgtctt gaagagtcag tacaagtctc  87780
tagatgaaga aagaggtttc aacactctag ggcaaatgaa atttttatgc aaagccgagt  87840
cataaaagga ttaaaatttg gtgataggat cagtgcaact gtgaccaacg ctgggttcat  87900
ggggtggtag aaggcagaag gtgagtctgg ttaggtagat agggttgtat atttagggca  87960
cctttgtgca aggtgaattt ccccagagta atttgaactt gaaaaccact catcaaaatc  88020
tcctgattca ataaataaga aggctggaga aatgtcacaa acttctttgg aaaggcgtat  88080
gggacctaag agtgatctac atagccaatt tgttgctcat ctataaagac aacaggcaaa  88140
ttacctctca aatatgagag agctcaggga acagagcata ttaaaaagtg tctggaaaga  88200
agttttgagt tgtttgtttt cagtaacaaa atccaagcaa ttaatagatg gttaaaaaat  88260
aagcatgttc aaagaacggg tggcatgaaa tggatcaatg taaatgaagg ataagtattt  88320
taaactcata ggaattacat tacagaaaaa atgtattttt ttaccttgaa aatgcagaaa  88380
ataatgtaac tgacaaatgt taaggtgggg aaaaaggaga aaggagaggt gaatggaaat  88440
gagatgatga atgtcctcag atttcaaagg aagaagtgaa gcaatgctgt atagcattta  88500
aatggtattt ttaaaaatgc ttctaacttg ttgcatacct ttcctcaagg gatcttttag  88560
gaaatagtaa ctcttggtag ataaacattt gtttttaggt tcagcaattc tttgtctttt  88620
cattttatgt tctcctcctt acttgagcta ggtgcacttt atgtgctcta ggaaggctta  88680
ggtgcagaca cagggagggg tggagcggga gggacagggc cttgaagatg tgtctgggga  88740
attaggcaga agccagttca tatagtgcct tatgtctcag gcctaccacg ttcaggaact  88800
ttgacttttc ctaaaagata atgggtgagt ggggaggaag gagaatttga attatacatg  88860
catttatttt ttttttcttt tttgagacag gatctagcta tattgtgcag tttggccccc  88920
aactcttggg ctcaagtgac cctcccaact tagcctccta agtagctggg actacaggtg  88980
ccagcaagag ggcccggcta tttgataaag atcactttgt cactttggct gtcctgtatt  89040
taaaaacctc tttaagcaac atgatttaga gctgctctat cagcatgatc ttatgatctt  89100
ataatcttat gaatctggac tattcaggat ggacctcata ctctgatcct tccttcaaat  89160
ttcagatctt tccttcagat tcctaaatac tactttggta aacactttac agactaaact  89220
```

aggcagaaaa aactatggtg attctttttg ctgattaaat ccatgctcag tagttctctt 89280
atcctcagag aagccaggat ctcaggcttc aggccatgcc ctgtgcaagt ccaggggagc 89340
tgttgacatg agcaacaaag gggtggctg cctcctcagc tgtgcgatgc tgagcccctg 89400
ggggaagggg ctggtcgaga ttatgtggtc tatgtcccct ctcccatcac tacgaagaaa 89460
gacagctgca aagtcctatt ttttaaggcc tccaggcaat gaaatcaaca attatttcaa 89520
agttgatatt taataaccct cgttattatc aaattatttt ttatggaaat cggacacatt 89580
tttctaattg tattctaccc ctttctctgg ttttatcatc ttttgaggag gtcagctgac 89640
taatctttat tttatctata gcccctaatg ttatcaatgc taatcaatca ccacgtagtt 89700
tcctcttttc cagtctaaat agtcctagct ctttgatgta ccttcaaatg tccaattttc 89760
caatccttta tatcttgatc ttttataaaa cagcttccca tgttgcacaa aatttaataa 89820
caaaagcaaa gatacgtgaa gcctatagtg aagcaatgac gccatcctct ttttgaccat 89880
gctagattca taattttgtt ctacttttac cctattttaa atcccccctt tcaaaatcgc 89940
tgtagatgga gatcatacat tagagatata attgcatttg aaaaggatgg ccctttcatt 90000
ttctgctgtt atagcagaca ctgttagttg ctactgaagt gacagtactc ctttttcctg 90060
gtttccaatg cccagctttt gttcaactgt ctcttcatgg gatgtggaca cctcccagcc 90120
ctggagggtg catctctttt agtgtaaatc agccatctcc ttcctcataa tcaatggaac 90180
caggagcttg ggacccaatc ccagacaatg gaagtgaggc agaggcagct ggtggtgggg 90240
tggctctggg gtcatttgca tcattccaaa aagacacccc aggaagagac actgctttgc 90300
tggacattgt tatgagatga catgctgcct ggagctgccg caaccatctt agaaacacag 90360
ggggccaagc gtctgaaatg aaagcaaaga tcgggaggat ggctgagtag aaagatgaag 90420
agatccaggg cttctgtgca cgccacttag ctgcctaatt aaccagccct gggcttcctg 90480
ttgtgtgagt taacacatcc ctttgcaatt tagtgatttt cactgtgtgg tcccagacca 90540
gtatcagcat catctggaaa tttttagaaa tgcagatttt ggggccctac cccagacttg 90600
ctgagaagag tctaggagtg gagtccagca atctgttttt aacaagcccc tccagataat 90660
tctaagaagt cctgaagttt gagaactact gctctgagct tgctacagtc tgaatgtctg 90720
tgtcctccca ccactcctat attaaaattt gaatccccaa agtgctggta ttaggaggtg 90780
ggggtcttta ggaagtgatt cagtcatgag ggcagagctc tcatgaatag gattagtgcc 90840
cttatgaaag ggaccccaga gagctaggtc aacccttctg tcacgggagg gcactgagac 90900
agtaccatct atgaagcagg cagcaggcct tcaccagaca ccacattata gcagcttgtt 90960
cttagacttc tcagcctcca gaattgtgag ggaaaaaaaa tactattgcc tataagctac 91020
ccagtctatg gcattttgtt atagcagctc agatcagcta agagccattg aattgaggtt 91080
tcaattactt gcagctaaat gcatgctaat taatacagct cctttattgt tttatgcatc 91140
ttttctagaa aaatctatca atcagtatgt tttctgtcaa tgtcatctga gaattaagtg 91200
tcataaccag aaagatctgg agagacagga gcacgttgta cagttcctga tatgtatttg 91260
acacacccag acaggctgga aaagagctgg ggtaggtttc ctggggtata agtaattttc 91320
gtaaaaattt agaacttttt gagttccaag gtgaaaggag aggattttga aatgcagaaa 91380
aagaaaagtt cagaggcaca aactcagaca gagctcctgt cagaggaacc aagtgcctaa 91440
aataggacag agtctccaga tgcagcggaa aggctgtgag tcatctgacc gctcaggtag 91500
gaaagcggga ccagtgtgaa atgaaggagg cactaatgat aagaggacaa gaaaccacca 91560
aattgctatt tagggtcatt gggatctgca gagggaaaca aggctgaaga gacaagagga 91620

-continued

```
aagacacagc tgtgagggtc aaaatctaaa aggagctcct gaagggatgc ttaatgtttt  91680
caagctatca actgcagcat gctaggtcta tcatctgtgt atcattgcca aagcaagacc  91740
cataaacatc agatttcact tggttataga attcagagaa atactactgg ggcaatgaca  91800
gggaagagac actgcacatt ctcagtggag gaatcgtccc ctctgtcctt caactggtgc  91860
catccaaaag ttgctatgtc aagtaatgct agcttcactc aaatgctatt acccctggtc  91920
aactcacagt gatatgcact aatgagcaac ccatctaatc tgtgaagcaa tgcttaagga  91980
aggtttgagg aaggacgagc tgcagatcag ctcaaggatg ggactcaaat atcatgacag  92040
taccatgagc taaggtgcct cttgcaagct gcctgtcgag gccatcagtg ggttagaacc  92100
aaattcttcc aaaattattg cagcctgcag tcttctcatc ttgtcatata acacttaaca  92160
ttctggaaaa ggccctgcat tggttttgag tggtatttcc agaatctgtg gacctttgaa  92220
acaactccat tttgctgtac tttctccaca atggctcttt cagataaatc acttgtccgt  92280
tcctgcctta gatgaggcct gtggaatgac tgcatcattt gccctttcat tgttgaaatg  92340
gttatcagat ttcaggtata tcaagacttg cagatcaggc ctcttactct gtgtgactaa  92400
caggctcccc cagaacaaac catccaggca caaacagggg atgcagcctg tggctatccc  92460
atcacaggtt tccacaccac agtgtgagtc catcttgctg acttaacaac cgtaatttaa  92520
aaatcacctt ccaaattgca ctgattttat ttgttcaaaa gataacacac acattattac  92580
atgactatca ttttagggca aagtggatgc acggacaaat gtttcaagca aggaggtaaa  92640
actctcctgg ataaaaattc acagcatcaa ttttctattt tctgcttcct gaattgcatt  92700
ttcctggatc tgatgatttt cttctttgta ttcttgatgt atgcatcggt atgtcttctt  92760
ctgtgtttgt gtcatggagg cagcattctt cttctttttt tttttttttt ttgagacgga  92820
gtttcgctct tgttgcccag gctggagtgc aatggcatta tcttggctca cggcaacctc  92880
tgcctcccgg gttcaagcca ttctcctgcc tcagcctccc gagtagctgg gattacaggc  92940
atgcgccacc acgcctggct aattttgtat ttttagtaga gacggggttt ctccatgttg  93000
gtcaggcttg tctcgaactc ctgacctcag gtgatctgcc tgcctcagcc tcccaaagtg  93060
ctgggattac aggtgtgagc caccacgccc ggccggagga agcattctta atgtatgcat  93120
tggtacatct tctgtgtgca tgtcatggag ggagcattct tgatgtacac gttggtgtat  93180
cttctgtgtg cacatcagga agggagcact aagcagaggt gcataagcag attctggact  93240
gcagagctgg ggagcggtcc tggttttacc actcatggac tgtgtgctct cacacaagtc  93300
tcttagcatt tttgtacctc gggctcctcc tctgtagaat gaggatgaca attcttacct  93360
cctaagattg tcatgagcta tcaagaagtt aatatttgtt atgtatttag aatggcatcc  93420
agcacgtcat aaggactctg ttttgtagag tacatcgaat gttctgtttt gttatataac  93480
acatttactt ttcataaatg ttgttatctg gcaggtattt tttggcttcc agaataaaag  93540
ttttaaaatt aaaagggggta tccaagtatt tttaggagcc tagtatttcc tcacttactc  93600
ccaaactcta aaagtagatt ggctttatgt taaacagaga attcgtacag aaaaaatctt  93660
caggactgta ttcatttcat aaataatgta ctttatttta ttgcatatgg ctattaagga  93720
gggcatccat gatcaataca gactaaatac aatgcactat tctagtccag tttattctcg  93780
tctccagcag catcacattg acccctatat acagcgtgta cagtggaaga cagagcaaga  93840
taagttaagt ctcttgtcat atcacaatag caagaaatat atttaacatc ttgatatcca  93900
gaaacaatac gtacccaaaa agaaaacact gtttaataac tgttaaagtt tatatagcaa  93960
aaaatatttt aaatttaagg taagtcaggc aaaatgtaca aagacccaat atacattgtg  94020
```

-continued

```
aagttttagc aaacataaca tttatacatt ttggttccat tctgtaaact aaattaaaaa  94080
tgtaaatatt gcatatgcct ttttgtgaaa tgtacaggat agaggaaaat ttagcatatt  94140
atcatctgtg tattttgctt gttttaagct gcagtatgaa cacgaaccat ctgtatagtg  94200
tcatgactac tctacggata gagggcgagt taaatatgcg tcaatacact gctttcagca  94260
gggtccatat tcagtcccta tcgtacctgg ggggagttac aaagcaaata ccacccattg  94320
atgcctattc ccaaaactaa ataaaaactt caggattttt atacatctta ataaagtata  94380
tcatacactg aaattgacct tccagctaac attatatggc ctatgcactg ctgtgatgta  94440
taatttcaga aaagtaaaac cttaaaaatg ttcagggaga tcactttaca ttcaactttg  94500
tcttgcaata caatcctctg ttctaaagtt cagcacggaa gcaggaagac ttttgcattg  94560
ccattaaata tatttttaag acattgaatt ttttggtctt cctctaaaaa agcctcattt  94620
tattaatgca ttattctata gcgatagata tctattatat atttatatat atttttctaa  94680
aaacaaaaca aaacaaaacc aacaacttac atctccaatg aattagtgta acctctccat  94740
gactatcaga gaagataggc actggggaag cccccacggg aggagaggtc gacagccctc  94800
caatcaagtg tcgagggagc agaaaacggc agaacattct gccggtcaag ttcagcagtt  94860
ttaggtaaca tctgcgagaa ctgccacaca ctggtatttt cagaatactg aaaacataaa  94920
acaagggtag tcttgtccgg aattttttcg acaagtaaca tgtactgcga gattgctttt  94980
cttctttttc tttttccatc aataacatag gggctggaat gcctcttttt atcagtttct  95040
ttctttcctt ttttttttt ctttttgttt tttttgttca gggcagcctc actggttgac  95100
ataataacat tttattaaag ataatacgtt ttttaaaaat caaatctgcc aaacccggac  95160
caccctggaa ttgctagcac gcctacaggg atttttggtt acagaaaggc atgcccaaga  95220
ttcaggagag cagagacatc tgagcttgta aatagaataa aaggcgtttg caatgtgaag  95280
tacctacata aacatctaca tcgagaagat taaacaagtc tgttaaaggt aaaaagagat  95340
attcatcccc ttcccaaagc ccttccctcc cacctcccac tacccaatac agttgatttt  95400
caaaagtagg ttgcttcagt tacatataat aattattatt tagtaatccg tcttcaaagt  95460
ccaatcccaa atttcacttc cattgagaaa tgtcagtccc acactgggct cggtgtggac  95520
gtaaacatcg caggtacctg cactggaatc caacaagcag ctgtctactt ggaccatttc  95580
aataaggccg aggaccgcgc tccagacaca cagcgcaggg gctactacag gaggtcctgt  95640
gggacccccg ccacggaaat ccggctttac cttgaactga ggtaggactg tggtcgtttt  95700
gagtgtaagc cagtaaatac cagattttac cacttccata ggtacgggtg cactctccta  95760
gcatgctgag ggttatatct gctttgccaa aaggaaaaga agaagaaatt aaaagacact  95820
ggccacaatt taagaaggcc aatgaaaaca tccaattttc ttgagaataa cttcttcagc  95880
taattttgtt aaaacaaaac aaaacaaaac gcaaacagca caatgatgaa tgccccatcc  95940
gggaacaagg gaaagaggca ggtgaccttg ccttgttggt gcctcatcta acagagtcca  96000
cagatgtttc caaacacagt cattgctcag atccaaaaga aaactgcaag cagcttcggg  96060
ctgaaacagt gctgagcgtc ttcttttaat gatactctct gacatgtgac atcctggtga  96120
taaagccaga cagatcttca ctctgaaaaa gaaaggaggg aagttagcag agaccctcag  96180
gagaacagag caatctctgg agttccagaa agggcccctc taacccacag ctaggacctg  96240
ggtcattttc ataaactgat gacctttgag aaagaaacat gtattcattc tgttttccag  96300
aggtgagttc agtgggaaaa ctctgagttt tcctggaagc agagctgtta ggttcatggt  96360
gagttgtcta gacagttagg ttcgtatttt caatttaaga aaaatattcg catgtgtttt  96420
```

-continued tgtgaatcat tctgtcgaac aagatagaaa aagaagggcc agttcctagg ttgcactgcg 96480
tgtctgtgtg atggaatgac ccctgtaact ccttaggcct tgatgcttcc tgtgttgtgt 96540
gggatacaca gaatccactt gccttcctcc cagggctgca gagatgaaaa actatgacac 96600
acattacaat gctctgtaaa ctatgtttat tctacaaatg tgcattatgt tatgaaagtg 96660
gagtaactaa taactccaca cttctgccct cagaaaactt ccaaccggat catctacctc 96720
tttttgaacg tgcccagcaa tggaaggttc ctgcacggcc tcatgtgttg ttgcataacc 96780
ctcaacatta ggaaagggtt atttttatcc actcaaactt tcatatgttc cagtttaagt 96840
aatttaccct ttcgctgtgc tcagagggga cagggactga ggacacgtgg ccagatctaa 96900
ttgcttcctc ccttccagga tgaaggatca aaattcttta acctttctca atttccagtg 96960
ttttaggcct atttttactt gatatattcc ttcttcaagg gacagaacaa attggaagat 97020
tttgaccttt cacagcgtgc tgttttcttc tttctaagct tcttggcttt ttaaccaaaa 97080
tgacatactg ttcattttca tcactcagca acatgagggt gagcaccgct ttgctctcaa 97140
acaggtacat ttccttcctt tgcagatgca tttataccaa ctgcatttct ggacactctt 97200
ctaaaatcct ttagaattct gatcctagcc tcttatcata ctccctgact tacttttttg 97260
tgaaccaaat tcttttctct ccatcttaag tttagaggac tgaactcaac aagacagaaa 97320
cttccagtgt gccctgaagc tgagagtgag tccctcaaaa ccacatctcc ttatgaactc 97380
gaggcactac atgctatagc cccccaaaaa ccccaaaagc tttacagaaa aaatacttgt 97440
caatatacaa agtggacatt ttaaaattcc ctacaacgcg acattctgag gctgttttat 97500
ctattttatt tattattatt attagtcttt tttaagatgg agtcttattc tgtcacccag 97560
gctggagtgc agtggcatga tcttggttca ctgcaacctt cacctcccag gtttgagcaa 97620
ttctcgtgtc tcagcctccc aagtagctgg gattacaggt acgtgccacc atgcctggct 97680
aatttttgta tttttagtag agacggggtt tcaccatgct ggccaggcta gtcttgaact 97740
cctgacctca ggtgatccac ccacttaggc ctcccaaagt gctgggatta caggcgtggg 97800
ccactgcggc cggcctatct tgttattttt aaaaagcttt atgtccatta taaatttaat 97860
aagtaaacaa tgttctgcca atgaacctta acagaattaa tttcttccta aggaaagatc 97920
tgtctttgag ttatctgatt cattattgtt gtgattttca atcccaggag acttcagtga 97980
gaatctaatt gtttgtatcc cctaaaaaaa aacaggcatt tgctaaaaca caccttgaga 98040
cttgtaattc accctaaaat gagcttgcat tttgtccctg agaccctgat ttgggaagaa 98100
tcccatggcc accacaagca ggtaactgag actctgcaaa tccattgaca gaagaatttc 98160
taatcaattg cttattttat tttgacacta acaattagct aaatgtggct gaattatctc 98220
atgttaactc taagtctgtt attttgaaaa cagctaaact agtaagttct tcagtttctc 98280
aaacttaagc actttgtcat ataaatggcg ggtaaattat tgctgaaaaa aattactttc 98340
cattttcatt tgtgatttca tgaggccact gacattttca ttgttttttt taggatgctg 98400
tatcgctgta atattcaact cttatcatta catctttgcg agctccaatt aagttgaaca 98460
tgtaatttta ttttttggaa gtagaataca gttatcaaaa cgttaatttc taagcattag 98520
cattatgcaa gaaaagagct gataaatggc aaggaagtaa ttcatccatg catttattca 98580
tgcaatgacc tttcaacaat tttctttttt taattctact ctggtgcaag gcctcactga 98640
taacttgggg gaagatggct gacaaaaaaa aaaaaaaaaa gaaggaaagg ggaaaaggaa 98700
gggcaagcgg aagaggaaga ggaaggggaa gaggaagggg aaggaaagaa aaaaaaagaa 98760
ggagggagga aggggaaagg gaaggagaag ggaggaagga agggttatta caggaagatg 98820

-continued

```
aacctgttaa tggcacactc aaaggacaca agagagctga ggtgagggag accagaaaca  98880
ggatgaccac ccgctcagag ccaggcatgg gggtgtcagc tgtgcagcgt ttcacacaca  98940
tctacatgca cacacgtgca ccagagcaag cacaacgtgc atgtgtctca cctagcctgt  99000
ctcctgttag gttaatacaa ccgctttcaa cggccgcctc ctttcacggt aaagcgagaa  99060
ctgtggtctg ggtgtgctca gcgggcacag gcctgtggtt ttgctcccca gtgccctgcc  99120
tctcacagac ctgcttgctt agacatcccc ccaccccagg aggctgaggc tgattccagg  99180
tgaccctttg ggatgcttgg aagcgctcgc ggtgatttaa acagaattaa ccagcagaaa  99240
caatcctttg cggaggtgca aaagggcagc gaggaaaagg ctggagcaca cctcagattg  99300
gacccagatg actaggacct gccagccgca gcagagggat tgggatacaa cagagaccta  99360
agaagcatca gtactaagaa tttatggtgg aaaaaaggga tctgttttga aaccctaagt  99420
atcattttta ttcatttgtt agagaaagaa ggtctaagac agaagccatc tgcctgaact  99480
gatgtctcaa ataccttttt ccaattgagc tggtggtaga atctttgcca cacatactat  99540
taaaggcccc aggcataggg ctaaatgatt aacacgtgca agggctcagg agggctctct  99600
gtagttcaca cacagctttc agacaccaaa caccaagagc tggtgcccct ggttgaaacc  99660
accacggcaa cacgatacct accacccacc tgacagccac ccactcatca gtgacactcc  99720
cctaccccag gaagaagaaa gctggaaaac actccagaga ttcaaaccta ggaatgagag  99780
taaacttttg cctttatatt catttacttt caaagtaact gaagttatcc ctcaccctga  99840
aaatcagcct ggttcatcct gaccagggga aaaaaacaca ccaacaattt tctaacacta  99900
atcatctgac atcctcaacc tttaaatatg atcaaacttc aggcttcctg aagatgagat  99960
tccagcaaaa atttatttgt tgtattatct gtgttcattt tagtagaagc aaagaattat 100020
taattttatg gctgttctac cctgaatatt cactaagaag gaagagattt tctgaattca 100080
tcagctgtaa tggcaaaacc aaaaagaaaa caataagact cacgtgttgc tcatgaacac 100140
aatgacagaa caccacacac cagttctgct gctacaggta atctatataa aaaatgtaaa 100200
cttactgata ctcattgaat ttgtcacatc gctcattaca cactgtacta ctctgtccct 100260
tagacgttgc tttgtgagga aatccatcca cagacgtatc cacgtagagt tatttgagca 100320
aataaaacca acaaacaaaa acacttttag cagagatgag agttgttcca tgtgacatgt 100380
cgtgcagtgt atccactccg catctccttt ctgctgtcgc ttgtgacaga tgacattcat 100440
acgtgggata cagtcccctg tgccactcac cataatgccc tgcagatggg caataattcc 100500
tccccttttc tcctccactt acaagagcaa tcagaatgca aatgaaggag agagctgtca 100560
gtaaaagctc caccttcaaa ctgctcaact tgactccccc gaaagagaga aaggaggaaa 100620
gaaaacaaat cactagaaaa cattgtgatt aagacaagga ggaaagcttc cttgtaatat 100680
atggaacaat gtcccaacaa tgacatgtca cacggagctg ggcaccatga ctgcaatcac 100740
attacagaaa actgaagtgg gcatcaagcc tagaacatgt tggaaataag gtcaatttgc 100800
tccagccaat aaaatcaggc agcattttcg gcacacagtc tgactcacca atccttttc 100860
ttcataattt ctcctgacaa tttgggtttg gacatgtttg cctccaatgt tacatttcga 100920
tgttcaaaat ccaggatata cacctgggtc gtggcagctc tgcccaggga ggccccggtc 100980
ctctctgcag aggggcttac ggccaccacg tagggcccca tggcacggct gtgggacatg 101040
gggcctcaca ggcctttggt gagcaacact ggaccaccca gaggccaaat tcatggagta 101100
ggtaaagatg ctttcacatt ttcagccata gctgaattag gagtgttaca aatactgatg 101160
tacttgacaa aatgaaacga tacacttctt aaaattaaaa tttgtatttc tagtagcaaa 101220
```

tgtgattccg aaagcaagga aaccttccat gagctcaaac atatcgtaca ggtacatctc 101280
agtgcccagt ttcagccttt tatgttaaac acagaattac aagggaaaat tgacttttca 101340
gttgcaggag caattctgag aaaaataaac ccgataattt agtatctcca gactttacta 101400
aagcaagaca ctctaagaac atgaaaaaaa aaaaaaggta aggttgggta tgataacaaa 101460
agccagagat tctaggaaaa acggttactt gaacttttct tttaaattgg aaaaaaaact 101520
aacttaaaag gaaaatatgg aagaataagt tccccatgac aaacaggggc aataacttgc 101580
tttcctgctg ccctccttga gaaagactga aaacattctt ttctatgagc tcatcacttc 101640
cactgacaat taaaatcatt tcattttgaa tgcttgttag taaaaaaaat tccgaatatc 101700
aagttgcaac ttgatgttaa tgacacaata caaaatagga tgagacaatc tagttgtctc 101760
acaggctgga tttagtaaaa ggtatctccc cctttaactc ctgtttaatc ctgcacataa 101820
gacctggtct taatcatcca aaactaggaa aatcaggcct cctaaacttt tacctactgc 101880
acttccaatt ccctctacac attcaacttt cctatacagg agcctgtata aattttacag 101940
tgcacggcta cagcagattg tgtaacacag aatgtacacg gttcttttct gagtgttatt 102000
gttaaaaacc ctgccatgtg catgaagtga gctattcgtc tatggcaaga attgcccact 102060
gcccctgcag cagccgccaa tgccatagga gaaacagtat cgatgattct tctgcacaaa 102120
cacctgagat acaaaaagtt ccaagaattg cgggtggacc ctttctttta aattatgaaa 102180
tgttagaccc tttttagtta aaacccagac caggaagcac gaacaacttg ctgaagcctc 102240
cctgccagtc tgtggaagaa cagggtcctc aacttctccc agaacacttt cctctctgct 102300
cccctttggt gacaatgaga tgggtgggac agggcaggag cagagacacc tgcaactgtc 102360
acctggggcc ccagagtgtc aacttccaca gtgaaccact agctctttat aaaactctcc 102420
tcgaaggaca ttaaacagca tgctagcatg tcacaagatt cagtgaagcc tgtgagtcga 102480
tgagggtgtg ctccatggtt ggtcttcctt gccagctgat gcccaggccc tgccttctca 102540
cctccctgtc cccagcagcc agcagcctgc tggtcaggtc cttagtaaag cttataggta 102600
ttaaattgaa gcgaaaaccc catgtggttc atgccatttc tcacaggcag aaatgctcaa 102660
taaagttttc taaaagagaa caaagttttc taaaacagaa cgaagcttta ggactgcgtg 102720
agacccagaa gaaaagaaaa ccctttccag cccacttgga gagtgacgtt ccaagcagag 102780
gtcagtaaag taaggccaga tctggcttgc ctgtctctgc aaataaagtt ttatttgggc 102840
acagccgtgc tcacgcattt acatatggct gctttcacac cataagcaga gtggagcagc 102900
tgtgacagag actgcatggc aatgaaccta aactctttac tacctgacct ttcacagaat 102960
gtttgttaat ccttcaagga gcacatgaac atggcaacct ttactaagga agacaatgcg 103020
aagaaaaaca ggcaaatttg tcagaaaaac accatatatt tccatctgtg tgttatactg 103080
ggaaactaat tgatatccct ttgaaaatta tctgcaagct tacgtacttt agaaatgcaa 103140
tactatctac taaaaaccac actatcctgt tacagaccct actgaaaaag aggacacaca 103200
tcacaaaatc atttatgaag ccagcacact tttggaatga atttctctta gctaccgcta 103260
ttctatttga tttttcatgc ataacacaaa agtgctcaat aaatctaatc attgctaaat 103320
acatcctaca ctagcattct tcctttaaca gaagtaaagg tttatatatg agatctacaa 103380
ctcattaagg gtccaaatct tttctctttc ttgggtcatt tgagaatgtg aatgtaagca 103440
ttatgcttct gccctaagag tatttgggcc aagtgatata aggtgcatta aaatcgcaaa 103500
tagccaatga acgacgtaat tctttcctca gacttaacac atgtttatac gtatggtttt 103560
cttactaatc taaaaaaatt ttatgtacac cataacaatg tttatattgt ttatatcaga 103620
aattataaaa cctaattata tttttgctgc caaattaaga gaatgtagaa taattattta 103680
ttcacaatat atccatctcc agatagcctg ttgttatata tcatttcaac tggacctttt 103740
ttctacttta aaagcttaaa taactgtagg taaatccccc ctcctcggtc tataacatct 103800
atgtgatata ggatttcagc tttgtctctc cagggacaaa tccatctatc taatttaaaa 103860
gcctcctaag aatcaccacg tagcctttaa ctgagccatc tactagagtc aaggttgaag 103920
ggtcaaatcc tacttagtca ctgaagcgca ggctctcttt gcagagatca aagtgcccat 103980
tcttcctaat cggccatatc aaaaacatcc tgctcttccc tgggagccta ggaatgactc 104040
catgccccca tctctgtact ttaaactaca tgccattccc acgactctca ggatacaggt 104100
gtgaaaggcg ctgtcgccac accagagccg ggtccccagg gctagcatct aggaaccact 104160
tcttaccagc tgtgtaatct ctacagctat gtctctaagt ctgctccctc ttatgaagat 104220
gggggcacta cctctcccac cctgaattcc ccagtggagt cacagggaac ctgtcaaatg 104280
agatttcatg tataaaatat ataaataatt aataccaaaa atgcgtatgt tctttcattc 104340
ataaagaagc acatgctact agcacaactg gcattttgtg gttggcttcc ctttgctttg 104400
tgcaccttca aataatgtat acatgtaacc acatgctgtg ttctcaacta cagacttctt 104460
aagaccaggc agccctgtgc tgccagggaa agacaggctc ctcccaccct tatgttctgg 104520
ctaatttgtg gagagccaca gtggtgtctc ttagtgcatt tgtcatcaca gctcttcctc 104580
gttcaaaatt gtattcgtga atgataccac gaacaaccac aactgcaagc agcaaataaa 104640
caactgccga atgcacaaaa acaatggcaa attgctccta aaataaaatg aacaaacttg 104700
ttttaattgg acagaagtgg aacagaagta gaattgtttt tctgggggta actctaggcc 104760
atttaaagct gcaaagagtg cctttgccta gctgctttct tcatgtcctg aggacaggac 104820
aaaatgcccg ggaaggggcc tcacatgtct actactcagg cagctgccca cagagaacat 104880
gaatcccttg ccacgtcaca catgccaagc acacacaatg catcatcaac aggctgggct 104940
ccgcctggtc caggccactg ggggacagca cttcccttct ctctgctcta tacaaaaagg 105000
tgccctaaaa tgcaggccga catttaagtt cctctgccac aaatgacaga gatttacatc 105060
taactaaagc actatttatt gaaatttcag taatgcaaaa tggaaaacgc caagctacca 105120
actatataaa gttcatttac tggagaagca aataaaataa gacagcagca gctgatcacc 105180
agtccttgcc caaggatgtg gagacagagg aaatccacat ctttggctcc tcttccccaa 105240
caagcatgta gatatcccag cctcaaccac cctgactcca actccccacc aagcatgtag 105300
atatcccagc ctcatccacc ctgactccaa ctccccacca agcatgtaga tatcccagcc 105360
tcaaccaccc tgactccaac tccccaccaa gcatgtagat atcccagcct catccacctt 105420
ggatccaact ccccaccaag catgtagata tcccagcctc atccaccctg actccaactc 105480
cccaccaagc atgtagatat cccagcctcc tccaccttgg ctccaactcc ccaccaagca 105540
tgtagatatc ccagcctcat ccactttggc tcctcctccc caccaagcat gtagatatcc 105600
cagcctcaac caccctgact ccgactcccc accaagcatg tagatatccc agcctcatcc 105660
accctgactc caactcccca ccaagcatgt agatatccca gcctcatcca ccttggctcc 105720
aactccccac caagcatgta gatatcccag cctcatccac cttggctcct cctccccacc 105780
aagcatgtag atatcccagc ctcatccacc ctggctccga ctccccacca agcatgtaga 105840
tatcccagcc tcatccaccc tggctccgac tccccaccaa gcatgtagat atcccagcct 105900
catccaccct gactccaact ccccaccaag catgtagata tcccagcctc atccaccttg 105960
gctccgactc cccaccaagc atgtagatat cccagcctca accaccctga ctccgactcc 106020

-continued ccaccaagca tgtagatatc ccagcctcat ccaccctgac tccaactccc caccaaacat 106080
gtagatatcc cagcctcatc caccctggct ccgactcccc accaagcatg tagatatccc 106140
agcctcatcc accctgactc caactcccca ccaagcatgt agatatccca gcctcaacca 106200
ccctgactcc gactccccac caagcatgta gatatcccag cctcaaccac cctgactccg 106260
actccccacc aagcatgtag atatcccagc ctcatccacc ctggctccga ctccccacca 106320
agcatgtaga tatcccagcc tcatccaccc tgactccgac tccccaccaa gcatgtagat 106380
atcccagcct catccacctt ggctccaact ccccaccaag catgtagata tcccagcctc 106440
atccaccctg gctccgactc cccaccaagc atgtagatat cccagcctca tccaccctga 106500
ctccaactcc ccaccaaaca tgtagatatc ccagcctcat ccaccctggc tccgactccc 106560
caccaagcat gtagatatcc cagcctcatc caccctgact ccaactcccc accaagcatg 106620
tagatatccc agcctcatcc accttggctc tgactcccct gcatgtgacc cactggcact 106680
gaaacagtgc acaagtcata ttcagttact gcacatgccc tttcagccaa aatgccaaag 106740
tgtctataaa gttactcaaa aacttaagtc taagcagagg aaacatacat tctttagcct 106800
cggtagaacc taaaatggca aagatcttgt agacattttc caatgctcat gggctgggag 106860
gagcctcaca caccagagga cccagatctg cgaaatgctt tggtcaggga catggaggga 106920
ggtttggatg agtgggcagc ctagaaacgt gggccccaac ttctcctgga gggtccagca 106980
gggtgccctg agtcaccagc agttggattc agagtgagga caggcccctt gctcctgcct 107040
ctcaggccca gggacagagg ccagaggctg tgcaggtcag tgtgcaccct ggctcctgtc 107100
caggcgggcc acaccgggaa tgtggccaca aacacgtctt ctgccctccc ctcctgtcca 107160
gcaaggagaa ggaggtgtgg aaggagaaaa tacccagcaa cataaagatt ccatttccca 107220
aattgccaga agtttggaaa ggggagaact gatcaattaa tgataaagaa aacatttcct 107280
acacgaaaag gaagttggac tgtgtggtga ttgacacagt cacatttcct ggtttcccaa 107340
ggctgtgcct gagtccttga aggcctttaa gaatggattc aagagagatg taactttcta 107400
accaccttgt tagtaaccaa ggtgacaaaa ctgaggatca agcagatgcg tacagaatag 107460
acagtagttc tgtcctgtgt gttacagact taatgccttc tcttcccaga gagcatcacg 107520
cagtgatatt ccattctgga aaatcagctc gaccattttt cctttttttt tttttttttt 107580
ttttgagatg gagtctcgct ctgttgccca ggctggagcg cagtggtgca atctcggctc 107640
gctgcaacct ccgcttcacg ggttccagcg attctcctgc ctcagcctcc taagcagctg 107700
ggactacagg catgcgccac cacacctagc taattttttct atttttagta gagatagggt 107760
ttcatcatat tggccaggat ggtctcaaac tcctgatctt gtaatccacc agccttggtc 107820
tcccaaagtg ctgggatcac aggcgtgagc caccgtgcct ggcccagtgt gaccatttaa 107880
acatttctag ttacatgatt ttgtaatatt caatatatat gaaatttcta gaaaataatt 107940
gttatttccc tcattttgct tagagaatga tggaccattt tacaaattct acttggaata 108000
actagcaaca cagttcaagc agataattca agaattaggt cctctttcac cattagtttt 108060
ctacatattt caggaaaact aagtcaaatg gagcctaaat tctgaagata gacctaaatg 108120
ctcaaccaca tttttaaaat tatgcaggct acaaataact gcacacagtt ggctggagcc 108180
catttattaa acatgcactt tcctcaccag caggctaaga ggacatcagg gcacccgtac 108240
acacctagcc ctcaccttcc ccaagctctt acgccctcag caaaacccat gcccttggct 108300
ctttcctgtg aagccaggat ctctatgaaa caaatggaat aatacattgg aataatactt 108360
tttctgcaca ttttttctaa cttctataat tttcatttcc aaattagctg aagagtgaaa 108420

-continued ttgatttgtt tgataagccg atggttagca ggtcctagtt aaccataatg cacggggcat 108480
cccgcctcaa ggcagagttc gaaataagcg gattcagctt ttagtctgtc agagggaaag 108540
accttgtctt ttttttttta aatgacggct gtgtgttacc agaagataca gaatcaggca 108600
ggagccaggc ttgccaggac cacatcctct ctctacagac tgggaaagtt tctccaacag 108660
caggagccag gctcaacggc ggggcaggca tatacatggc ctaccatctt caggcctcag 108720
attttccatt aaaaaacagg gataacaaca agatccaacc ctacgcatag gttattggga 108780
ttcaatacca tttttaaatg tcttatgaat tataaggtac gctacaaacg ttaagttttc 108840
agaataaggc atgtcattcc atgattacaa acttgtgctt ttgttttgca gtttatcctg 108900
taagcacgtc ccagtagttt ccccaacctc aatggtacct cagcgtcttc attccactag 108960
atcacttcta ggtcttttca aattttatat acttttgagg aagaaattcg agttgacgta 109020
tactctacca agtaaccacc accacccagg gataccacca ccatgatgat ggaattgatg 109080
gctacagtat gaaagttttt aaaagctctg catattattg ttcccaagga ctctatctcc 109140
ctcacacact gtgacatgtg ggctaacatc agtagcacgg ctggccgggc tcaattcctc 109200
ctggtccctt actacctctt tctcttcact ttctcctttg agccttagct ctccatgcca 109260
gccacactgg cctccttcct gttctggaac ataccgggca acctgctgcc ccagagcctt 109320
tgcactgctg ttcatcccct ttgcctactt ggattcctcc cttaacatct gtaagaccgg 109380
cttcccctga ccttcaggtt gcttggctca aatttccttt ccccctctc ccttccctgc 109440
ttcattgcta gagcatttca ccacctgtag tgcttcatct cctaaatgca catccaaatt 109500
aagtttactt cctaggtttc aaaggcagac agctcactga agactcgccc actttctgtt 109560
attcttttta gcttgaaaaa ccaaatctgt ttctctctag cctattcttt catattgctc 109620
aaatggatga agtatttttg agatagtcta tatgcaacaa ttgtcatctt tgtaatgaaa 109680
acatgcagaa atttaacagt ttgaatacat ttaaaaatta aagggagatc tcaccatttt 109740
tgccatcgtc ctttctgccc ccaactttct acctttctca agcaacccat aagtaaagtt 109800
cctatttttc tttttttctg aaaactgcaa aaggtggcaa aaggtgagaa tgggaggaga 109860
ctcatctgtg actaactccc ccatcagcct cacgggtggg tgacttggag ctccccaacc 109920
caatgggact tccttctttc gcctacactg gccaccacca tggagggcag ggaggccaag 109980
agcggcaagc agccctttga gccggtgggg gctgtggctg gcaggaaagg agggggcttt 110040
cctgaacagg ctagggatgc ctatagaaag aatgtgatca atacccttaa cgcagccttt 110100
ggggctgcct acaaaaagga gccaagaaac ctgacaatgg ggaagtttct ggaatactac 110160
catttacaac aaagactgag cacagaatga agtaccagga gagcttggag gcaaggccgc 110220
caagagctca gggcaagctg acatctagga atcgggatag cagcagaatc aaagctacta 110280
tttttcagag aagaaaactt acaaacacta cctcatctga tgcaccccag gttcacgcag 110340
gggtgaaggg gtgaaacatc tgagtggtcc cagctgtgaa tgggaccagt actgtgaatg 110400
ttccagcaag gatatccact gtcgcagcag agacatcccg tgaaacatcc cattctctgt 110460
gctcagccaa gattgcctgc ggggtggaca cttatgaaaa ggatcagagg ggctgcccag 110520
aaaatggtgc ccggtgggat gctgccaagt tgactctgaa ggcacctagg gaacagaggc 110580
caggcttcac atttcttctg catctcccag gacatctact cttgtgctga cacacgctga 110640
actctcaata cattgattgg cttaaaatat caactgtgtt ctgcgttttg gaaatggctg 110700
aagacccagt gattctaaac agcccagcga acctggacag atcaagactc acacagatga 110760
atgtgtatca cccagacttg ttctaagaac ttcattaaat gctccctgct gggaaaactt 110820

```
ggacatttca ttgcagtgat tatttcatct cgaactagga acactgataa gctaagctgc 110880
aaataacagt aagacggcaa actgaaccaa ggtgtgtcct ttctactgga ccactgaaac 110940
tttcatctgt ccccaaacac caaaatgccc ttacatgtag aagctacaaa acctttagga 111000
gaaattctca tttaaaaaac ttgtcagaac aaataatctc aacaatgtct ttgcatcaat 111060
gaatgcaaat tcatggatgt ttatatctaa aagggttttg tgtagccttt gtatctagta 111120
ttttcatgca gttcaatatt aatatttaat ttttttctct tttgctttct cagccagcta 111180
aattaaagtt agttttctga aactgcaatt aaaataaatt tacaatcctg gatttataat 111240
actttaaaag agaaaaagag atttggtact tttgcaacta acacattttg ctaaagcata 111300
ctcaaatata ctttcagttg aactatacat ttagtagatg tctacttgac aacataagtt 111360
atttgtacaa gtctcagcac actcacctga tatatagaac tggaagaggg tatgggtagc 111420
ttatggattt gttttctgtt tcatttgcgt atgtaaaacg ttattttagg ttgcttttat 111480
gcaggaagac aataaaaagt gaatacctac tatcatacca gaataaaact gaagcaaagc 111540
actttagtaa tttattttt taaaatgcac caaaggtgtg gggtaagaaa ctgaccacaa 111600
gactctactt ttccaggaat ttctgctgtc tgggaagttc agaagccctg caatgtccac 111660
agtaaactag ggtcccagta cctccatttc tgacctcttc aaacagaaac agtctctgct 111720
caatacactc taatccacga cttgcttaat cctgcttatt gcgtggagtt tctaaaggat 111780
tatgtgcatg gtttttaaat ttagtaaaga aattctggcc tatttccaaa acttttctcc 111840
ctgcttcaca attcccctta tttatccatc catctgggta tgggaagtcc cgaacaaaga 111900
aaggagggca gagaggctca cccggcatgc gctgggccca ggcagcgcag ggcagtcatg 111960
ggtgagggtg gccactgaga tgacgggatc gggggcggct tctgccgcag acccgggaat 112020
tcacgtggtc agatggtccc tgacttcagt ccctatttc ggtggttcat agcacggagc 112080
ggtgcaggta ggtgcacgct cttcccaggt cctctgcaga aggcaaaagt tcccagaggc 112140
acccaaacct tgctggggaa aaggcttctg gccgattcat gaagaccccc agaccacacg 112200
tctgcatcag ttttcctgac taaattggtg ggtgctcaac aaacccatca ctgcaacaca 112260
gggcgctccg aacgtggctt tcttcttaac ctggaagaag gtccgtaact ccattcgccc 112320
ggatagcaaa actgctttcc tgctttgctc atccagccag gtctccaatc tcacctgctg 112380
tttggtgggt cacggcgctc accgttgggg gtgctggcca ggaaggaggt actgtctctt 112440
gatgctgaga ggcctgacag cttgcacaaa gcaaacactg cactgcccac aagagttcca 112500
ggccacagat ttgcctatta cattttttttt ttttttttt gagacggagt ctcgctctgt 112560
cggccaggcc ggactgcgga ctgcagtggc gcgatctcgg ctcactgcaa gctccgcttc 112620
ccgggttcac gccattctcc tgcctcagcc tcccgagtag ctgggactac aggcgcccgc 112680
caccgcaccc ggctaatttt ttgtattttt agtagagacg gggtttcacc ttgttagcca 112740
ggatggtctc gatctcctga cctcatgatc cacccgcctc ggcctcccaa agtgctggga 112800
ttacaggcgt gagccaccgc gcccggccgc ctattacatt ttttaaagtg tgaatatctt 112860
aagaattttt atgtgtttgc taaagtgttt ctttctgctt ttgaaagtga ggttataccc 112920
acgtcattag aataatggca gcttctgtga aattaaattt gtatgaaaac tatttatctt 112980
catataaaaa tccagctaaa tgattttttt cctgagaatt aaaaaaaaag aaaaaaacaa 113040
gggctgttaa aaataaaaag gcactgacaa aatactcaat tccccagaag ataaccacct 113100
agcaacaact gattagttag ttattggtcc ttaggcaaat tctaaattga ttagttttca 113160
aataaactca ttaaataggt taatgactca tttcttagaa aaatgttaat ggacttatcc 113220
```

-continued

```
ataatgggga atatatgata tttcacttat agaacaagca cctgtcttag agacacagag 113280
agcagtgacc gaatgcaccc gctgactcat cactgtgtca ccgcccaggc tgaacctgtt 113340
acacagagcc gccttcaatt ctgctagata atctaggcct ttcgatttca ctgggggtct 113400
tcatgaaaca ataactttgt ttccttttct ttgataaagt aaatacatga ccttaaatat 113460
ttgccaaatc ttctccccac tcagtagaca ccgtccacat agtcatgaac agccatattt 113520
ctctgattta taacgcgttt cttcattaag gaattctgca ttctctattt ctggctttca 113580
gggtttcttt tagtctatgg atgaagaaag ttactaaaat gttccaaagt aaaaagacta 113640
atatcatttc cacaaatact aagttgttct aaagagcata ggctgtatcc tgggagaaag 113700
ttattcatca agatacaaag aaccaactga gatgtgtcat tgtttgtatc acattctcct 113760
actctttctt gatgatatct acaaacaact ctaccactaa ttgaatcagt gaccttgact 113820
aagactccgg acctcacaca gcctctgttt tcacaacctt aaataactaa gttacattct 113880
atcaacggtt ctcaactctt ccttctcaga acacccttgt atatttttt cgtattgtca 113940
ccacctgagt tgcaagagtt ttaatgtatt tgatggtggc ggtggtgggg aggtatctta 114000
ccaagtatca tatacagttt gctttaccaa gaggtaatga aagacagcca gagcaatcta 114060
agttttccac tttgttgaca catctagagg tccaggaagc atgactggag tccccagaac 114120
agatccatca ccaacttgat ggtcaacttt aaaattcact agtaacatca cagccttgaa 114180
aatagtatca aatactaaac tctccaaacc ggaggatgta aaaactgatt tcaataaata 114240
gagcgctttc ctaccagtct tcctcctcaa tggtccccat tttcctttga attgataccc 114300
agtggaagaa aaagggggag atgattaact atcactccag caaaatatta acttaaatgt 114360
tgcttgaggc aagggtctag gataaaatcc taatgtaatt attgcatatg agcttcccaa 114420
gcagacaata tgacattaga gaactgggct agggatacca agatgttatg aggttgaacc 114480
cgacactcct tctcctttttg gctcagagat ctggagcaag tcatctggcc tctccacact 114540
gtaggttctt gattccaaag aatggggttc atggtggttc tgcctatgcc ataggatttt 114600
ttggaatatt ataccatatt gtatatagga aaatgtctta ccactataaa gggaagaaaa 114660
acaccctttg aattttacac aactctttta accccaagag aagagtggca ggcagttatc 114720
cgtcaatatt gatcagaata atggtacatc gtcattgcat tcaacttcaa taagattctt 114780
tcaaaatctt cagttgccag ttgtctacca agttgtggga ttatctgtta cacttatact 114840
ttggaggcca aagattgact tatttaagtc catagaatgc atacagaaag cactgtatca 114900
tattcttaaa tattaaagat taagcattaa tactatgcaa aatctttctt tttttttttt 114960
tttttttga gactgaattt cactctttgt tgctcaggct ggagtacagt gtcgcgatct 115020
cagctcactg caacctctgc ctccctggtt caagtgattc tcctgcctca gcctcctgag 115080
tagctgggac tacaggtgca tgctaccatg gctggctaat ttttgtattt ttagtagaga 115140
tggggtttct ccatgttggc caggctggtc ttgaactcct gacctcagat gatccaccca 115200
cctcggcctc ccaaagcgct gggattacag gcatgagcca ccaagctcat ccaagaatga 115260
atcattctta acataaacat aaggatttta aggtaacaaa atcacacagt ataataggat 115320
tgtaaagtaa caaaatcaca tagtataatg aactatatca taatatctgt ttttatgcat 115380
tgaaaacaat tgaaatttca taccacaccg taataactga ctcaagtatt tgtactaact 115440
gtatagggat aaagtagcag tagactatgc ttaagttata aagtttcaac atgaacaaag 115500
aacacatcat taatccttga atttcagtta tggagaaaaa tatcatatcc agcctcctgg 115560
agcatgactg gatgagatat tatggaaaca cacacacaca cacacacaca cacacacaca 115620
```

-continued cacacacaca caccagcccc aaatatttgt tgctggaaaa cctgatactc tttaaaatga 115680
atattaaaag atccagcatt aggccgggcg cagtggctta tgcctgcaat cccagcactt 115740
tgagaggctg aggcgggaag atcacggggt caggagatcg agaccagcct ggctaacacg 115800
gtgaaatccc atctctacta aaaatacaaa aaattagcag ggcatggtgg catgcacctc 115860
tagtcccagc tactcaggag gcggaggcag gagaatcgct tgaacccggg aggtggacgt 115920
tgcagtgagc cgagatcaca ccactgcact ccagactgag tgatagagtg agactccgtc 115980
tcaaaaaaaa aaaaagaaaa aaacccagca tttacagggt gcaatgcgtg tgatcagtta 116040
tctttaaaaa atatatcgtg ggtcaaaata tttgatcaaa tattccaaat ttcagtaaaa 116100
acacagtaag caaggaatat tttataaacc ttgtgtatat agatatcata tatgacataa 116160
gaaaactgga cagagtttcc aaggcttcac ctttacccat tcaagtttta cagtgtcttt 116220
ggacacataa aagtgactct atacaaactt agtattttcc tagtctaata gaaaattaat 116280
cagaaccacc aaattgacta ttttatcatt tgtaaacatg taacccataa gttttaatcc 116340
aatctatttc agaattctta tgtaatgaat tcacttaagt aataaagcta taacacacag 116400
aagcatcttg cattatttgc acctacagag caaaatgttg gtatacaaca tatactccaa 116460
ctctttctac actaaccttc acctatgcat tgtattttag cacccagtta atgtaagtct 116520
ctgtagctat cttgaaagaa attgaaatca gtagcaatca tcaaccccat catctcctcc 116580
atgccaaatg atgactttac tagttttctt cagaaaagtc tagcactgaa ctctgtgtac 116640
aataatctac ctgaaatgag tcagaataac cactgcagtc ttgaagaacc cactcaaact 116700
aaatatagaa agagtgtccc tatctaaact tggacagcat tcttttcaca aaaatcatga 116760
tctgacagtt aatgtgttta taaccaatac ttttggacat tcagaaaatt ttgttttcat 116820
ttgttcatta aaacgccaac attaaaacgt tttgttcatc ttgtatagaa atatacattc 116880
tgctgtcatc cgtactagag aaatgaaaca gagaatccac ctgcattaca gctgtccaaa 116940
tgcaggatgg ggggcggggg gcacagcact ttgcctcacc cagtgttttc ctcattctac 117000
ttggcaatgc agatgaaaga ataaagttac attttccctt aagtttataa ggtgaaatgg 117060
gaacacttga ttctgtgcta ctccccctag aaaaaaacca aaacaaacaa acaaaaaccc 117120
tttctacttg ccaaatctga taccaaaatt agctcttaga actacgtttc taaagaaaat 117180
gcattagtgg gaattttaac agaaaaccca ttatactcat gctgttacta aaacttttcc 117240
aagttcttct cttcagaaaa aagagcctca ttttaaatac tcatacttct aaagaaaata 117300
aaatatcaat tctctactaa gattcctttt tgggtggtag aaaaacaaaa gaatcacgca 117360
ttttcctact atgtttgata agcacagtgc taccatcaaa actgcaggaa tgaccaccct 117420
cattaaatcg accccaaaga atgaaccccc agactaaaca atgagtagtc aaacaacctc 117480
agggttctgt ttttctttca atgcattcgg cattaagagg cgatttttaa aatgtatatt 117540
ctaattatac attttcatct tgtcaacatc tcttaatata aaaaccagta ataaaaggta 117600
atcagaagtt cagtcttaac atagtttcag gattaccata ctgttttccc taattgttac 117660
tttactatgt aatttagaac accactttgt tacaatctgt tcataaatat ctatgaacag 117720
atcttaagtt acataaaggg ggaaaacaat ggctcttggg agcctggagc ggaactagca 117780
ataagcagta aaggtaagca atttttaagg tgctggctcc attttcagac tatgctgtta 117840
ctgtttgttt caatttaaga gcacccattt acaaaagtgt ctttcctgta tacattcatg 117900
gtttcaaagc aataagtatc aacaactgga tttattagca tcttccttta gaagagctta 117960
aaacactctt gatgtttatg acctcattta ccttccagcg gccttgtgac acagaaaggg 118020
gaggattata attacccca ttttacagac agggaaagtg agaaggcagg attaagtggc 118080
tctcccatag acacacaatg actcattaag atcagcaact agaaacctgg tttcctgatt 118140
cctggtttag tgttccacat actatgcttc cttctatgaa gtactatttt tgtaaaggtt 118200
tctctttcaa taaaggaaac agaacaagtc atgtgacttt cattcacgaa agccggtgtg 118260
tgttttcatt agcaccttag ttgtctgctc ctgcgaatag ggcagcagca gtgcacgcta 118320
ttgtcttatt atggccagag ccagccaact aaagcaaact agcacccgcc acagcaaaca 118380
gaaaacttgt gtggtttgtc aatcacctca ctggatttct gaatttagga aaattctctg 118440
ctttacgact tcaaaaggca aaacttttca acataaatcg tgattttatt gtccctttgg 118500
aaacatatct cttatcattc tttcccctta agaaatgata atccttttat tcaacaaaat 118560
ttaaatatgg atactttcag tagtaattct gatctaatct gtcttataca tacatacata 118620
tatatacgcc aattttagaa taaaatccct aaaatcacta aaaaggaata ctaaaacagc 118680
aaattttatg gcattcatca atctaccatc ctaacacaaa aacatataaa gttaatttta 118740
aaaatcagtt ttaaagcaca ggaaattcag tagcgtcttt ccaattccca aacaacaacg 118800
aaacctaaca aattggttag agttttccac atgcacacac accaaaaaca catgataagt 118860
aaccttaacc tgccctcaaa taagatgcat aattttgagt ttgctctgga ctaataaaaa 118920
cagatgtacc tgagatatac tttttaactg gctcttgcac tgaaagccca cccccattca 118980
cgattctatt gtaaacaagt gccagacatg gctggaacct tacctctctg ctatcactta 119040
tgcaaatacc aaacattacc cacataaccc caaaattatt ctgcatcagc atcactaacg 119100
aggtcttccc atgcagaaca ggaagagctc agggtggaaa cacaggccac ttctaagagc 119160
caggcagggc agggggccgc ccaggaagtg ctttctctat ttcatcttca aagaaatgct 119220
ttgcaagtcg gccttctaca aatcatttcc tcaaaggaca ctgatctact gtgaactctg 119280
tatttatgag catcccaaac aaatttctag tgcatgtatg agttaaataa aagtgggtat 119340
ttatcccaag ttcctaaatg cttcctttct gtctcaacgg accacaactt tggtgctacg 119400
tggactaagg tgacactagc ctttcctatt ctgctgttct ctgtgttcaa cttactttac 119460
tagaaaccca atggggcaga tatttctttt tttttaaatg tcgttgggca tggtggactg 119520
actgcagttg tctattttga tttaaaagat ccttttactt cttagaagag ggttcatcat 119580
gatacccaca caaacttcgg acaaacagca gccccagtga tctctcatct ttgttcagca 119640
gctacagaac acaggcttct gtctggactt cagaatcaag aatcctatgg gctgaaagga 119700
attttacgca ggtgggaaat cttaaacaaa agctcaatcc agtctctaaa taaacttatc 119760
tcttagagtt caacattttc actagcctga aaagggcatt atttcctatt tggaccccaa 119820
ttctgaatgt atcggcttca tcagaaacgc cttgcgtccc tccaggcctg gaggcacaaa 119880
ttccagctta tggcgcctgc tatggcagag cccactgctg gggccccagc tccacccagt 119940
ccaggtttgt cccaccagct ccactgaaag caggaaaagg tgttatgttc ttggctgttt 120000
tctgattaga atcagattcg ggtaagatgt aatttacttt catgttcact ctggcatata 120060
cccatttgtg cagaccataa atatgtgtgt ttttccccac tcaattatac tgctgctgct 120120
gctgctgtgt ttataatggt ctgtgtctta taaggcagct aatccttcaa ctttctgaca 120180
cactagcaat agtgtataag taactccaac caaagtgacc ttcagctgag aatcactgtt 120240
cacaggatac attctggcga cttccaatga tttaattgga tgctgaagca ccacactcct 120300
gataattctc tgtgactctt catcttctag tatacggttt taataaagga aatagctttt 120360
ctctattaca ctagaataac agggagttca ccccacagct ataattttaa atcccatgga 120420
ccgacagtcc taagtatact ataaaacaga tgctggattt agatagcact aaactggtct 120480
atttaagaac aaaaggctgt gaatctccag cccaccttga tcctcatctc atgacccttg 120540
aagactgttt acaccttagg ctcacatcta atccagcatc caaattttac tatatgtttc 120600
actgttccca caaagcctct atcctgctag gaaccctaca aagaaaacag ctacaaaatt 120660
aaataaagtc tcccgaattg agcattcacc tttccctctc atctccccga ccccaaacac 120720
cattcaaagt ttagacagcc agaatgcacc accagctgca ttctgcatca gctctctctc 120780
ctcatggata tttgatcaga acgggaagaa caataccagg caccctccta tccaattgtt 120840
cttgagaaga cctgtgtttt ttgtctttcc cttgttttct ccaaagcact gattgtaaat 120900
cctggctgca cattcaaatc acctggacaa ctctgaaaaa tgtccgtccc tgcctcctag 120960
ccatctcatg tttcacttca acgggtctgg ggtgaggccc aacaggtaat ttttcaatcc 121020
tccccaggtg agtctcacct ggggcagggt cctcacaggg tggtcccccg gccagcagca 121080
tcggcattat gcggagactc actagaaatg cacagcctgg gccgcgcccc aaagctacag 121140
catcggaaac tgcggggtta acacaggcca gagatccatg tttcagcaaa gcctccaggt 121200
aactcccaca tatgctcaag ttgaacacca ctgcattagg ctgtgtgcag ccttaccgtt 121260
tcaccccttc cgagaaaaac aatgcctctg atggaaaagc tcccacagtt tgtgtgtaaa 121320
acggaaatgg ttaactgtcg ctattagcag ccatcaaaat ggatgctcat ttcttaaatg 121380
actttcaggt ctgaaccttc aagctcacca agaatcaggc ggagcccagc tccaggaaca 121440
cagggaaagg tgaaagctgc ggctgagggc agcggtccgg acccgaggtc cttccagaag 121500
gacggaccca cgcagccgga tgaagacagt cgggtgcccc gcggcctcta gtgtggccgg 121560
tctgggagaa cttccactgt gttaagggac agggggctgt gggacgcaca gaatgggtga 121620
atgggtgggg cctcaaaaaa tcagtctccc tcccacgcgg aaaacgtcac attcaactcc 121680
aagacgaatg ttcctggcaa gttctctgaa ggaagagaac agggcagccc gcagaaaaac 121740
aaaacaagga gccagtgcca ggctgtcggc ttctgggtca aggtccccaa aaagtgggag 121800
cagtgaaacc caagaggctc cctcagcgcc ccgcccctcc ttcccgccag acgccaaggc 121860
aaagggcctc ctcacctttc acgatggtgg cctccttcaa gtggtgggac aagaagtcaa 121920
tgctggcgta ggtgttggca gggggcaggg caccgggacc cggccccccg cacccgccgc 121980
cggtgctgcc gacgcccaca gcgctgatga gacccccgag gcttcgggtc cggccccagg 122040
agctcttgtc tcccggctga ggaagcggcg gcggcggcgg ctgcggctgg ggtggcagcc 122100
cgggctcctc cctcacgtcg atggcgatgt agttgagacc attctggaag ccggcagagg 122160
tctctctgcg catgggcgat ccaccgctcc caggacaacc gaccaagccc ccgggctgac 122220
ccggggtcca cggccggccc tgcggtgcca aagggggcgc cggctgcaac tgtcgtgggg 122280
aggtgggcgg ctcgtcgccc cctccagggc cgacacccac gccgccctcg ctgcttttcc 122340
tgagagagac attttccacg gaggccgagt tgtggcgctt ggggttgtgg gcgaaggacg 122400
gggacacggg ggtgaccgtc gtggtggagg agaaggtctc ggaactgtgg cggcggcggc 122460
ccccctgcgg gtctgcgcgg atgaccttgg cgccgcggtg ggggtccggg ggctggctgg 122520
cctgcaggaa ggcctcgact cccgacacct gctccatgag gctcagcctc ttcacgcccg 122580
acgtcgggct ggccacgcgg gcagcttctg gcttcggggg ggccgcgata ggttgcggcg 122640
gggtggcggc cacaccaaaa gccatctcgg tgtagtcacc attgtccccg gtgtccgagg 122700
acaacgatga ggcggcgccc gggccctggg cggtggcaac ggccgaggcg gggggcaggc 122760
ggtacagctc ccccggggcc ggcggcggtg gcggcggctg cagagacgac gacggggacg 122820

-continued

```
cggacggacg cgggggcaac ggcggatacg gggaggaggc ctcgggggac aggaggccgt 122880
ccaaggagcc cacggggtgg ccgctcgggg cgcccggctt aggagacttg ggggagctga 122940
agtcgaggtt catgtagtcg gagagcggag accgctgccg gctgtcgctg ctggtgcccg 123000
gggtgcctga gcccagcgac gaggccgggc tgctggcgga caagagcgag gaggacgagg 123060
ccgccgacgc cagcagggga ggcgcgggcg gcgacaggcg ggccccgggc tcgccaaagt 123120
cgatgttgat gtactcgccg gggctcttgg gctccggtgg cagtgggtac tcgtgcatgc 123180
tgggcaggct gggcagcccc tccagggaca ggcgcgtggg cctcaccgcc cggccgcgct 123240
ggcccaagaa gccctccggg cggccgccgc taggccgcac gggcgaaggc actacagggt 123300
gagggggctg cgtggggccg gccccgaagg cgctggccgc ctggctgggc cctggcgtgg 123360
cctgaggctc cagacgctcc tcctccagga tgcgccccac gggggagctc atgagcacgt 123420
actggtcgct gtccccgcca caggtgtagg gggccttgta ggagcggggc aaggagctgt 123480
agcagcagcc gggaacgccc ctgagcggct ccccgccggg gtgcagggct gcggagaaga 123540
agtcgggcgg ggtgcccgtg gtgaccgcgt cgctggggga cacgttgagg tagtccccgt 123600
tgggcagcag cttgccatct gcatgctcca tggacagctt ggaaccgcac cacatgcgca 123660
tgtacccact gtcctcgggg gagctctcgg cgggcgagct ggccttgtag ccgccccccgc 123720
tcgccgggaa tgtcctgccc gccgcagagg tgggtgctgg ccccgcaggc cccgcagaag 123780
gcacggcggc ggcggcggcg gcggcggccc tgggctgcaa gatctgcttg gggcgcggaca 123840
cgctggcggg gctcatgggc atgtagtcgt cgctcctgca gctgccgctc ccactgcccg 123900
cgagggccgc gccgggcgtc atgggcatgt agccgtcgtc tgcccccagg ttgctgctgg 123960
agctcctgtg ggagccgatc tcgatgtctc cgtagtcctc tgggtagggg tggtaggcca 124020
ccttgggaga ggacgcgggg caggacgggc agaggcggcc cgcgctgccc gagaaggtgg 124080
cccgcatcag ggtgtattca tccagcgagg cagaggaggg ctggggcacc ggccgctgcc 124140
gggctggcgt ggtcagggag taggtcctct tgcgcagccc tcggtccagg tcctgggccg 124200
cgtcccccga gacccggcgg taggagcggc cacagtggct caggggcctg tccatggtca 124260
tgtacccgta gaactcaccg ccgccgccgc cgtctcgggc cgggggcgtc tccgcgatgg 124320
actcgggcgt gttgcttcgg tggctgcaga aggcgcgcag gtcgcctggg ctggagccgt 124380
actcgtccag ggacatgaag ccggggtcgc tgggggagcc cgaggcggag gcgctgccgc 124440
tggagggccg ctggccgggg ccgtggtgca gcggatgcgg cagaggcggg tgcgggccgg 124500
gcggcggcgg gtaggagccc gagccgtggc cgctgctgga cgacagggag ccggggctgg 124560
tggcggcggg cggcgagtgc gccacgggca tggacatgga gcggctgtgt tgcagcgcgc 124620
cccctgccgg cagcagcgcc accttgctcc cgcggccgcc gcagccgccg ctcagggtgt 124680
gcgagcggct caggggcgcg cgcaccggcc cggggctcag ggggctccca gccaccgaca 124740
ccggcctggc gcccgcggcc gccgctcccg ccgccgcgcc gccgtcgccc tcgctggcgg 124800
tgcgcacccg gcacgagctg cacttggccg ccggcggggt ggcggccagg ctgtcggtgc 124860
gcgagcggcg caccaggccc gtctggctgg ggggcaggtt gaccaggtgg tggtggcggc 124920
gcgcgccggg gacgctgatg gggtgcgtgg ccgacgaccc cgacgattgg ctcttactgc 124980
gcggccggaa ctcgaagagc tccttgagcg ccttcatggc ctccaggatg gtctcgtgga 125040
tgttctgcgc caccaccgag tcgtccgcct gcatccacag ctcgccgggg cctgtgacgg 125100
ccgagcggcc cacctcgatg aagaagaagc tgtccgagtg gccgcagcgg cggatgttca 125160
tgagctgcag cgtcaccgac ggctgctcgc agttgagctt cacgaagccg atggtgcgcg 125220
```

cagacaggca cagacggtac acccccgtca ggttcttgct ctggcccaga cccttgggct 125280
tcaggttcac ctgccacacc tcacggtagg cggccgtggc gggagccacc agcccgtagc 125340
tgtcctcggc cccggcggcg ccggcagagc cgcccagggc gccgggcagg gaggcgctgc 125400
aggacgcggc gggcgcggcg gcggggggcg cgtctccggc ggccgcgcgg ccctcgctga 125460
ccaggtcggt gagcgcgcgg taccagccct cctgctcctg ctcgttctcg gcggccacgg 125520
cgaagtactc gtccttggtg tagagggcga tcaggtactt gtgcttggcg tcggcgcgct 125580
tgttgatgtt caggcagcag tcgagagcga tcacccgttt cggcgcgcct gccttgctcc 125640
gccacttttt ctcgctctcg tagtactcga gccgcggcgg ttgcggcgcc gaccccccgc 125700
ccgccgtcgc ctcgtcgccg cccgcgccgg gtccgcgcag cacgaagaag cgcttgtggc 125760
catgcttctg cttgcgcagg tagccgcact tgcgcacgct gtggttgttg ttgttgttgt 125820
tgttgttgag gttggggccg tctccgctcg ccggcccggg cggcccgtgc cgcggcgggc 125880
tcgccatcgc gggcgcttca ggccgcgcgg cccgggcccg gcgcccaggg gttggggcga 125940
ggggcggagg gggcgcgggc gggggcggct ccctcccacc cttgcgcccg gccgcccgcc 126000
cgatcacgcg tccctcgggc ccaggcggtg gggaaggtcc ggggaggccc gcgggggcca 126060
gcaccgctcg gcggcgccgc gccctccgcg ctctggggct cctgaggatg cccggcgcgg 126120
gcggtggccg ccccccctccc cggctgcctg cggccgctgc ctcctcgggc tctcgggcgg 126180
cgccggggga cgcgctcgct gggccgggag tcggggtccc cgagccgcgg ggccgagcct 126240
aaggcgcgcg cggccgcacc ggggctgctg ccgccgcgtc gcgctccggg aagccggggt 126300
gcgcccgggc gctcggggtc cgcgccgccg ccggggctgc tgctgctgct ggtgttgctg 126360
ctgctgctgc caacggcgac ccgggctcgt cgcggtcccc gccgcacagt gagtaacaca 126420
tcgcgcaccg agtgactgaa ctaagaagag caaaacaaca tgtgactcgg cgttacgcag 126480
gcacacacag cgcggccgcc ccgccccgct gcctcgcatt ggcgccgcgc cccccgacgg 126540
acggcgcgct cggccaatcg gcgcggcgct cgcgggggcg ggccgcgcgc ccccgccccg 126600 ccccccttttc tccccgggcc gcgtttcccg ccgtcccctc cccctcccgc gaaggccccg 126660
gcccggccgg gcggggtggg gcggccccgg cctcattaat cagcggcttg ttgtggatgc 126720
cggcggagga gatgccaccc agggcgggaa aaggggcgcg gaagaggggc ggggcgggcc 126780
acggcgcgca gggcccttcc ctcccgcctc ggactcaatt aattgggctt gagcttccgc 126840
cggggagggg gcgccgggcg gggccgcggc tgggcggggc gggggatcgg gatcggcggc 126900
gggggctgcg gccttgcagt ggaagcatgg gcggcgagcc gggccgtgct ctcggggcgc 126960
ggggtcccca ttttgggcga gggcggccgc tcccgcgctc ggggtgggcg cgccccatcc 127020 ccgtccccg tttcccgtcc ccgtctcccg gccgcatctc cgtcccccg cagccgcgaa 127080 acgcggggag gttccagggc ccgcggccgc gggttcgcga gcaccgcgct ccagatcgag 127140
agcggcgcgc gcccttccgt ggaggacaga ggggcgcgga gggggcgcct gtgtcccacc 127200
cgctcgcggg cgctttacgg ggcgtcctct gcgccattca cttgtcagct tgtcgggaag 127260
ttgaaatcgc gtttgggagg taataggaga aagagatcgg ggacggcagg cggagaaagt 127320
gcggtttcca tagcgccggg gagagggcgg acccgcgagc cagcggtccc tgagccggga 127380
gaccgcgcgg gcgtctctcc agccccgca ggagcgccgc cttccttccg caggggcgtc 127440
ctctcccccc accgctgcag gagcaccccc ttccttcctc ggaagcgtcc tctcaccaca 127500
ccgcttcaag agcccccct tccttccaca ggggcgtcct ttccccctcc gaggcaggag 127560 cgccccttt ccccccacag gagcgccctc cccaccccag gagcgccctg cgcccagcag 127620

-continued acgggcaggt gggcgggcgt ccactacctg tgtgcgcggt gcgggcggtg actgccaagt 127680
tggagatgcc cttggagaac tgcttcgaat tcatgtatct actgggcttt tgtgactttc 127740
aaagcctata gcaaataagc acccctgcaa ttacgtctcc tcaatgacca agtcagggtg 127800
aggtgagggc ttcctgagtt cagatcccag caagctcccg atcctgcgca acgaagaaaa 127860
ctcaacaaaa caggctttgg ctgtttattt tatttttttt ttaattgtgc cttcatgaaa 127920
taatttacag caataattta tcttataata ttggttattg tttttaagtc ccggatgttt 127980
acttttggat gtcctctata attcatagaa gtatcttaaa agtaataaaa tcttaatcta 128040
agagaaaata agtgtaattt ttgaaagagt gatatatatt ttaatatgtt tttgtaacat 128100
gtgacttgaa gattgtgttg gctaatttta tgtgccaaga gagccctgac tagtacaaag 128160
attatagcgt ttttattttt agcatgtata cagttaggat tattgatcag tagcctgaat 128220
ttgggaagaa taatcattgt ggcaaatatc acccagtgtg cctcaaaaag gtgtgtttaa 128280
agttgatctt ccatttttaa atcatacctt aaaaaaaaat acctcaagaa atgccatttt 128340
aagtctgtgc acctatgtgt gcatgtgtgc gtgtttgttt atataataga ttgtgtgatt 128400
gtgtgtgtat aggtatgtgt gtatgattgt gtgtgttggg ggcgccacct ttatgaacat 128460
tatgcttcgg cgttcttttt agatcttgtt accttttctt acgttcacaa atgttgccta 128520
gcaatatgtc tagtcaggaa agatgaaggg attcttatct tggtgcttga agaaaatgtg 128580
gtgtagtttt attggctttg tgatcactta catcccactt ttatgaggat gtaaatgggc 128640
cacctctatg ttcctgtatg ttgccagcca tcagtagaca atgctaaagg aaccaccact 128700
tttaaacatc atgtgatggt ttcttctgag aaagtatatt ttgcaatctt tttctttttc 128760
atgttgactt ttattatgca gttgcatttt catatccgta ttgaacattt acttgctgtg 128820
cctgtcacac gctagcaggt gtcatctttt cctgtttgct tgtttcttgg ggccatccta 128880
gtgttaaagg ccagtgtttt taaggtgtca gcagctctgg attggcagtt agcactttcc 128940
ccatgtactg cctcagttac cagactgggg acaaaagaga gaaggttaaa gaattatcac 129000
ctatgtccgt ggtattctgt catagagagt ataaatttcc tacagcaaac tggaaattaa 129060
ttgcaattct gcagttagaa cctccaaata caaatgtgga tgatacaatt tcaattctca 129120
ttgagagtca gcccatgaaa caaaccaaca gtaagaaact ctgtaattag aagtatccca 129180
gtcctcttcc tcaaccgagg aacttgtttt ctttcccccct ttctattgcc agataagcta 129240
tttatttatt taaagcttgt tctacacctt gtgattttcc aactgttctt ccatactttt 129300
tcaacaaaag tcagctaata acatctgcca acatgctctg cacgcaggac tggctggggc 129360
tggcatggcc tcttgccagc aaacagcctg gttgaaattt tttctcatgg tccaagatct 129420
ttccttggaa gctttctttc ctttcacagc taataaaatg gccatatctt tcagcaggga 129480
gttttttctg tttgtttgtt ttttctattt ttaacagaat catatacaat aatgattatt 129540
ttattagaag tcttctgaaa taattacttt tcaagaaaga atcaattata taaaagtgta 129600
gagatttaaa aatatgttac aggttcacaa tacaaatact agtagcacta ccaataatga 129660
acatcactaa ttattttctt tgtttcatat aggaaaggca agtatgggag gagaaaggtg 129720
aatagcattt tattgcttgt gaaattttct ttcttttttt agttctttgc cctgtaggtg 129780
tttgacagta ttttgtattt aggtgagctc aatctaaaaa ctaagcagat taagtggaat 129840
gctatataac tagttagaat agctttaatt taaaaggtat tttaagaggg aaagattttt 129900
aacttcacag gtttctgtca aaggatatat ttaatcttta aaatgagtgg caccatttca 129960
ttatatttca ttttattaga taatgttgtt cagtagctca tttgagaaat tccattcctc 130020

-continued tgatgaacga actgtggaca gacttttcct catctagggt ttataaggaa acttcttgca 130080
ctttaccagc aaatttattt gctaatgttt caactgaaat ttcacaagag ttttgtaaca 130140
tgctaactct gtgtatgggc aacagaatga cttacatgag agaatataac tgctgtttgg 130200
atcatttgct atgtatggca ttgcaaacat ttaaagtatc aggatttgtt aatggaattg 130260
atcagcccct tggaaattat aaaggctttc tacttgtgtg tttattattc ttgttaaaaa 130320
tatggatcag tctctttcct aaatgttcat tttatgaggg aggattttct aaaataaatg 130380
attatttaat gtgcatatat gatagaacaa actactataa ctttttttaaa gtcttatcaa 130440 ttgaattaat actgtttaga aaaatatgtt gtagttacaa atgcagctaa tccagtattc 130500
tcaacatttt ttcattataa atataattat gttgaagaaa tacataaatg cccaattaaa 130560
aagtgactgc ggttaggagt tgaaaatatt tattaatatg cctctggatt ttgttctgtt 130620
tgaattttga gaatgtgttt ctagatttaa gaagcaacac aagctttttt tcccagaagg 130680
cttcctatta ttgaaatgga aattatacat taatgactgt ataacactag tagatatttt 130740
taaaatgcaa gagcatcttc ttagatcatt acttttcctt ggaatgcttg gcccctgtaa 130800
tataatacac cggtattttg catgatgaaa ttgatgtcct gtgtgttgct tcatgttgct 130860
atcctagctg ccgattaaaa cgtttttttt ttttcatgcc agagcagaac aaaattgtct 130920
gcttctcaat ctgcacatca taagcagatg acattaaaaa tgtctgtaag atgacacagc 130980
tatattttct gggagagggc gggaggatgc tcagcgaggg tggcccggag tgtccttgta 131040
cagagtacag atgttatgaa gtggggaaga ccagcctgtg ttcattgatt cacctattga 131100
ttccaggagc aagctcaccc tgtttcatac actgctcagg aggtaaacag gaggaaggga 131160
gccagcctgg ctttttttgcc acatgctctg ctgtttggta gaactgtatt atagtcagaa 131220
accttccgct tttctgcagt tgtttgcatg ctgtttccaa ggctagccct ctgagtctgt 131280
tttctagagt tgttttgaaa ttcaacctaa agataacaga ggaaatgtga ccctctcttg 131340
tgaatgctgc caccaactgg caatgtttct tcccaaggca gattcagggt tctggcatga 131400
gttgtcacaa atacagtggt ggttgctttg agagaaaggt gcttacaacc tgacataaat 131460
ttgctttgca tgaaacttta aggaaattaa tagaagtaag attaaacaaa gaaattttga 131520
tagtgagtga ctaagagcaa tatcagatga caaatgaggg aagagaacat taataagtgc 131580
aatactttat tttttatggt tgaattaagt atcaagcaaa tatgttcata ttttctaatg 131640
caatttatat cccaatttgc atagttactt atacagttta atagaaatgt atatcactgc 131700
ccacttaaga gtttagaata ctagccaaca aaataaaaac aagaatctaa attcagtatt 131760
attttagaat gtttacctaa tcaaaaataa gttataatca agatttgctt atctggcaag 131820
ccaagtgttt tttaattgta tttctcccct acattgacct ttaagtctca cattcttttt 131880
aggataagcc aaagtcatct tgaaagattg aaaagcaaat tggaaaaagt aagataggaa 131940
agaaaacata ctctgaaaat gacacataac aaaaatgtat tttaaaaaca taaataacaa 132000
atggcaataa gcatcgaatg tcactatctt tttgattgcg taaaattatt tgaacttaca 132060
tactcattac taatttggca attctaaatt tacaaattac accttccttc ttaactgctt 132120
tattctcaat ctttaggcat tgcaaataga agatattcaa gttagtcaaa gtgttcagag 132180
ctgttattca atagagtgaa gggatctgaa aacttatttg ctactgaaca tgtcgttgag 132240
gtacttttat ggatgaaaaa aagttgatat ataaaatatc aataatagta atagcttgtg 132300
agagtagttt gtcagtatac tcacaaagat catgaatttg acgcttacta gtatgaggga 132360
taaataaaaa acattttata atatgtagct accataaaga tacgattatg acacaactga 132420

-continued gaattgagcg gtcttttaat tctccttttg agtaatcttt accaacctgt cctctgagcc 132480
tccgtgtata tgctatgttt aagaccaatg attagctatt tatacatgaa ttttccattt 132540
ttccttgttc aaaacacttt tgtcacacaa ataatattaa ctaaactaaa gtgacttgag 132600
ggagtatgga ttaatgaggt tcacaagaaa ataaataaag caacaacttg tgaaatttag 132660
ggcagatgcc atttattgcc atttcccgct gactgttaag tagagatttc agttcagata 132720
aacacattct aagaattact actgaaagtg taaacatcag cctgcatttt agtacttgct 132780
ggttctttag taaaaatttc gaatgtcagc ccaaggttgt cttgctaaaa gagaaaaaaa 132840
ataggaatta tatattgaaa acatcttaaa attatatttt atactacaaa aatttccttt 132900
taggtagtaa aagtgagaat ttaaaaacat gattctcact gctactaaaa gcacacagaa 132960
aatgaaatac atatttttga gacttgatac ttacctgttt tattttgata aacttgtacc 133020
tagttttaaa gtttcttcac actaaaagta caccacaatt tcaaaatggc acccttgtct 133080
ctcacaatat aaactttaaa ggaaattaat atctagatca tcattttgct ttgttgtttt 133140
aaatatcatc atgttttagt tacagaataa tacaaaagtg ggctcaccct ttatcgtgaa 133200
ggtgcattta tggcattttc aattcaaaat ataaaaatcc gcaaacattg ttactaaaaa 133260
tgtgctagat atttgttaag cctcaaacgt atactaagaa ttacccagaa cataggtctt 133320
tgccccatta gctttctgtc taagtaataa ggcactattt tcctcaacta tttctttcct 133380
caaatatttt tttcttgtgt cttttgttac aatattgcca cacataattt gaagataaaa 133440
attgccatat attataacca tcatctggct tttttaaaaa aactttctta gtgcttgatt 133500
ttaatgtcca atgctgcaat tttaccttct tcttactaat ggtgtagagt agagaaagtg 133560
acttttatct ctgagctgag gaagtttcta aatttcattt cacagaaatt agttttaatg 133620
agtcaaacag taattctatt tcttttattt ttaggttgct tcctttagaa ggtaccgttt 133680
tggactcttg acgctgcctg ggtccatagt gtgaggaccc atctgtgtag tagagaataa 133740
tactcaatag atgtagtgat gtagttatgc tgtgtggtgg taaattcatt ctaacccagt 133800
gaaatgttgg attcggtcaa atttatcaac gtttcttaag cacctacttt gtactagaca 133860
ctgatcctgt ggacatcaaa atgcaaaccg accacaacca ctcagctgtg tctgctggga 133920
aaggccctcc tctgtgcgtc tctcctgctc ccacgcctgt tagtgggtca gtgaaatacg 133980
caagaccctg gctttgcttt actcaagcct tttttaaggg ttgtgcttgc agcaaaccac 134040
actaagaggt gaggtcgcat tccagaacaa agtgcgggcc tgcttatttc ctgctacaaa 134100
aatggtggat tacccaagtc ctttgtgtca gccgaaacac agcccactgc aggcgtggca 134160
tccaacaggc cccgccctgt tgccccatgc tgcccgggaa gcaagaggaa tagaggcaag 134220
tcatgccact ttctgtgcca tgagtctctg accggaaagg cttacatcct ctgccagcat 134280
ccacctaacg gtgacgggct aacattactt tctaagggaa agggagtaaa atctcaaacc 134340
ctgacagtgt gcttaggaag ctcacaaatc agtgggaggt ggagaaccta catgaacata 134400
gccaaatcaa aaggtcagtt gtatttggta cagaactaaa tctagataca agggacaaag 134460
catattataa agctggcagt ttatttcatt ggaggataag agattattca gtaaatgggg 134520
ttggcagaac cagaaaatat acctgtagac acataaaaat tagatgcctg tgtcctttca 134580
ctaaaatgtc aggtgaagca aaaaattaaa tattaaaaca tgaaaccata aaaccaagta 134640
gaaaagtaaa gaaatattga taaacttgac tttctaaaat aggattctgt agggggaata 134700
cagtaaaaac aaaacaaaaa cagtaaaagc aaagttaaag tagaagctgg aaggaaattg 134760
cagccagtat catagatgaa gtgctaatga tgcttattta atactttaaa agagcgctgt 134820

-continued aaaaaataag aaactaaaaa cattctaaaa attggtgaat gacctgaata caaatttcac 134880
aataatgaaa attaatgcaa gaaaggctta aatgtgtgaa agtttgctta acctttcttg 134940
taataagatg aatgcaaatt aaaaccacaa tgtggtagaa tagttcacct atcagattgg 135000
cacagatcaa gaagtttgat aacacggtgt gtttgccaga atgttgggaa acaggttccc 135060
acccaaggct gctggtggta cagactgaac agcatctata caatttggct gtatctgtca 135120
aaacgacaaa tgtctcatgt tccttgaccc acaatctaat ttccaggaat tactcatgtg 135180
gatgggaaat gacttcttta taagggtgtt cattgcatta ttgttaggaa tagaaactta 135240
tacacatgat tacagtattg tcttgtaatg gcaaaggttt gaaccctatg caactgtaac 135300
acaaacgagg cagctctgtt tatactgacc cagaataata tttgactgta taatgtgagg 135360
tgggaaaaca agcttcagaa cagtgtgtat agtatagtac aaccattttt tttattttta 135420
aaacgtgtgg gtatgtgcac agatacctac tgcaagtgac ctcacaaata tggcaatgcg 135480
aggagccaac ctggcttcct ggggaaggga cgggttgggg agaggactca cgtttcatcg 135540
tgttactttt cggactttcc gaattttgta gcacaagtat gtatcaaata tttaacagtg 135600
taaaaataat tgactttaat ttctaaaggc tcagtagcac ttggtgatga tttgggggta 135660
ggggaggaag agaggacctt cagtgtcctg cactgtcgct gggtgatgac aaggtcttct 135720
cctgagatgg gggagggaga gttaagagat ttattttgga cacacgaggt tggacataat 135780
agaaatctga gagaagatgt tggataggct gttggagagg cttggaatgg agatattaat 135840
ttgggattca tgggcatcta gctgcattta agtccctagg atttgccgaa agtgactgtg 135900
agagatgaga ttggagcacc tgggattgga cccaactact cttaacattt agaagtcagg 135960
gacagaaagg taatctagca gagaaaacgc aatgaaaggg cacagactag cttgctgaag 136020
aaccacggga gtggacagca gagagcattg cagcagggac tggccagcca ggggtaacga 136080
ggatgagtgg tccaggcagg ggacctggtg acatgggagc catgttgatc tagtgcgtgg 136140
tttcctggtg tgaggaagag gggaatgcag cctggagaag gcatgacaga tggggcagga 136200
tccatgagaa tgaactttca ataaatgaag tctttgcatt atgaattcaa agtgctattt 136260
agcagaaaca ttggagaacg agaagaatcc gaaggaaaat ccaggggcaa aataagcatt 136320
atcctccggg agcagaagag tcagtgtccc caggatgcag ccagctttca ggaaaggctg 136380
agactcagaa agcatgggag tagtgttgca atggaaagga cacttgagag aagacactgg 136440
aagtgtttgg gaggtaaagg agtgaaaaag ggctgggtga aaggaaaaca tcagttagga 136500
taaccccatg ggagaaagtg gatagctcta agggcttcta ctgtgggcag aaatatgacg 136560
catggtaggt tgagttgttt gtttcgtttt gttttgagac tgagtcttac tctgtcaccc 136620
aggctggagt gcagtggcac aatctcggct cactgcaacc tctgcctccc aggttcaagc 136680
aattctcctg cctcagcccc tgagtagcta ggactatagg cgtgcaccac cacacccagc 136740
taatctttat tgtatttttt gtagagatgg ggtttcacca tgttggctga gttggtctca 136800
aactcctgac ctcaagcaat ccacctgcct cagcctccca aagtcctggg attgcaggtg 136860
taagccatcg tgcccggccg gtaggttgag ttttaatggt gtctgtgaag atgcaagttc 136920
agctgtagcc tggaagtgtg acctggcatc tgagaggagc actgcagcac cccttttctg 136980
tgctgcttgc attggcatcc atggtgagtg cagcaatagc tgtcatcagt gagcaaagag 137040
gctccagcca ggggccctgt ggtgcctaca gggagaggca gagatctggg tgtccccagg 137100
tttttctgct tgagtcaaag cccctgggag cccaggtatg aaaacctagg ggcttccatc 137160
atgtccggat ggtgggtctc catcattcct cttaatctca tggttttctt gcaaagctga 137220

-continued agaagcccca ttatgggctt ttcctcaaat tgaatgtcat cttgcaacat ctcttcagct 137280
ttgcattttt ggaacatgga tcagaatctt tcctttcctt gactcccttt ctagcagctt 137340
gttagaatgc attcatgtag caactgggaa tgaatgcgac acatttacat ttaacacctc 137400
ccttccattg acttcagctc agacctttcc agagatttct ccattagagg actgttagat 137460
gccactagac gtgtgagacc aaatgatgtt ggcatcatct tggaatagag acggagactg 137520
gggtctggcc tttcttctgg tcctcagtcc tgcaggctgt cctttctcca ctgcacctcc 137580
tcaaggagca ttcctggtag cctctggaac ctgccctggg tgtgttttgg ttcactctct 137640
atgcttgata ggctttctca aagaacctgc tgcatcgtaa gtgctcaaca cactcttttc 137700
aggattgttc ttttatgttt ttagattaca attttatgta atttttttct gattaaatac 137760
tttttgtgtg gctacggaaa agttcacata aattaacaca ttaaagacct ttgaaagctc 137820
ctgactggca cagtagacac agccagtaca tattggctat gatcgtttgt gttctgtatc 137880
agattggttt acaggccaca aagatggggg ccctacggat cctctctgtt caagcagtga 137940
agagctggta tctgaggata aaagaagctt gtgttgtaat gatgtggaaa ttccagaggt 138000
tgtgatggaa tgaatgacct agaatagaga agagcaaagc atgttgggag cagggaggtg 138060
gaaaagggag tataggaaga ggggaagagg ggtcccagtt ggcctccagg tttctggaag 138120
taccaatcct agagtcttct tggtgaaggg agttggccaa ggcaaggaaa cctgagccct 138180
ttgtgaagga gtcagaggag gtttatgact aaaaaatgac aaattatgcc atattacgta 138240
ttctgaacaa atatgtgtaa atacatgatt tagataaatt aggtatttat taaatatttc 138300
aagatttggt tccagaagag tacaatttgt ctcttcacca ttgttagagg gaaaaaaaca 138360
ggtaaagcca atcaaagaaa gatgaaagtt tttagaggaa aaaaaaatct agttttgcag 138420
caaagaggat taatctgtaa agtctcatct tatagatgtg ctactgtagt aatctagaat 138480
ttgtttcttc ttattcttca tttcccaaca gtattaagat gaagtgtgta atctttagaa 138540
ctagagagaa gtctgtttgc atctgtgggg ttaatgcaga gagggaggtg agaggtgatt 138600
cttgccatac ttggtcactt gaataaaact acctattccc atggctttct ctttagggag 138660
tagaaaaccc tcatttcaat gaaatcagtg tttttcataa ttggaagcct accttccaag 138720
agctaatggc atataatgga aatgaattat cccttgctac ctaaacactt gcttcctaaa 138780
ctcatattta actgtgtaag gatatttata ttaatttagg aagtttatat ctaagcaggg 138840
atttcccttt aacgaatgaa acaatatgca tactggcaag gtagaaaatg ttttcaattt 138900
gcattttgtt gtttggaggc ctatttaatt cattgcaatc ttatttattc agtgatgtat 138960
attaaacata aatgtattaa aaatctacca ctagaaagta ctaattgtca ttgaatggca 139020
cattttaaaa tgaataattt catgttatgt aaatgctgcc taaaaactat aatagaactg 139080
ccatgattaa gacattatgt ctacacagag aaggttaaag taacaatacc ataactactg 139140
tccttttata aataaacaaa taaaaacata atatttattc caaaggacat tcttgtgtcg 139200
aaagatgaaa cagaaagaaa gtggaagata gtaacagaga aagtggaaaa aaggacgaga 139260
agggatagac atgcaaaact ccagcattcc aaagttaagg gaaagagaat aaccatgttg 139320
tgcctataac cctagaagat tacaaaaatt atttctagca aattgacaac ccttctttct 139380
gaaggtagct ttgggcaaaa aggtgctgtt ttgagctttt accctgaatc acctggggtg 139440
cacttgaaaa gaagccattt tgccaatgca ttaaaagtgt ctgagtgaaa gctgccactt 139500
gattgtccta agaggctttt aaccccagcc acataattat ttcataacaa acaatcagga 139560
acatttctct tcctcatcag tttcccagac tacctcatag cacatgcatg atacaatgtg 139620

-continued

```
tgattttgca gccttccatg taacatcgga gtcctaaaga gatggacttg aagaggctca 139680
tggtgatttt aattgcattt tgaaatgcca cacatattct aagagatgtc attctaagag 139740
atgtcatcaa tctcttaaaa catgattttt aatggctgca taccattctt ctaccccatt 139800
gtaccatgat tcatttaacc acctcttaat acttgcttcg ttttggtgtt tctaatttct 139860
tgcaaataaa aatttaactg cccttgctaa tgattatttg gtaggtgatt cttaccttga 139920
taagtaggtc accatctatc cagttgtgca gctggaaacc tggaaatcat tcttgcaata 139980
gttttcaccc cgaatcccaa tccattgcca aattctgtca attttctatt cttagtatct 140040
ctcaagctta ttcacttctt tccacccctc ataaatattt ttgccgtaat atttctgaat 140100
tccttattgg ttcagcaata tactaggtat ttattatctt ttatttttca cacctatcca 140160
ttgttactct tcttccaatt tttctctcaa atttttgatg aaattcagtt tatttacctt 140220
aagaactttt atttttact tattggattt ttatattgtg caacatagta cacacataca 140280
aaaagatatt taacatatat gtaagttata aataataata ctttaaaatt ggcatagtca 140340
agcctaaaaa gtaggacatt accaatattt attttgaagt ccactgacta gccttatcac 140400
aatctgaaat tttgtgatta ttgtcctttg gctgtcttca tgattttact ggatatgtat 140460
gtaaacattt tgcattgtac ttaaatttaa gcattataca aatattatca tcctattaat 140520
attcttctgc aacttgctca acagtatggt tttattattg agatgtaact tagataccat 140580
aaaaatgtac aacttaatat tttttagtat aatcacaagg ctgtgaaatt gtcatcacac 140640
tctaagtctg gaatatcttc atcaccccaa aaagaaaccc caagaaactt tgtgcccaca 140700
gcagtcactt ttgagttccc ctcccttcac ccctggcggc cataagtctt ctctctgtcc 140760
ctgttcatcg ttatgttttt gagagaaatg tattacgatt tctgaagtcg tagttcatct 140820
ttttcagttg taataaatat ataactgttt ttcacttctg ccaatagaaa tttaggttat 140880
ttgtagttgt ttttaaaatt tctatttgaa catgacttgt ttttttaaaa agtatgtttc 140940
acaattacac accttttaac aattaaagtg ccttttaaca attatttatg catacatata 141000
tattcttagg cacactgttt tagacagaag aatagaattg ccagtgttaa ttctgtccac 141060
ctttaatttt aatgtgtaat aaaaatcatt ttcgaaagta agtgtacaaa ttgaaaattc 141120
caccaataag gtgtcattgt cttttacaat ttttcccatt ggattgtagt cattgtttat 141180
agaggccatg tgttaatctt ttataaaaat cgatttgtca aatttattat ttgcttttta 141240
ttttctttat gttttctttt gaatgaacat caattttaaa ttttaactga gtaaaattta 141300
tcaagtttac cttttgagtt ttgtgccttt ttcattttgt tttaattttt ttctctatcg 141360
ccaaattttc aagtacttac tcctgtattt cctttctctc tctctctttt tttagcttta 141420
attcacctgc attatatgtt tgtgcatggt gtctgatagt ggctcaattt cagttttttt 141480
ttaaattgtt tccgaggcgt gtttcaaata tttgactttt tcccactggt ctgaatagtg 141540
cttctcagat acggcaagtc tctaggtttg catgagtcag cctctgtgcc ctctgttctt 141600
ttccccgatg ttctttttgc ttcttcttat gctattacca cactgtctta attactatat 141660
tttattaaca aatctcactt tctggtagac catttccttc acctacttct tcactttcct 141720
tcaggaatgt cttggatatt tgtaactctt ttccttatga tttagcatca gcttgacaag 141780
tttaataaac cttgttagga ctgagataaa attagaaaga ttggacatct ttaaggtact 141840
gagttctcct agccaggaat gtggcacgtt tccctatttc tttagggaat tgtaaaatgt 141900
ctttttataa cgttttataa ttttccccat agagatcttt aaaatatttt gttagattta 141960
ttcctagcac cttatatatt ttgttactct tgtaaaaagt atccttttt tttttttttt 142020
```

```
ttttagaaac ggagtctcgc tctgtcgccc aggctggagt gcagtggcac gatcttggct 142080

cactgcaagc tccgcctccc gggttcacgc cattctcctg cctcagcctc ccgagtagct 142140

gggactgcag gcacctgcca ccacgcccgg ctaatttttg tatttttagt agtagagacg 142200

gggtttcacc gcgttagcca ggatgttctc gatctcctga cctcgtgatc cgcccgcctc 142260

ggcctcccaa agtgctggga ttacaggtgt gagccaccgc gcccggccag tatccatttt 142320

taaaaactac attttctctt tgttgcttgg gtagagaaat aaaatcaatt tttaatttat 142380

cttatatctg atcattttgt taaaccctca tattaatttt aatgctttaa agatgtttag 142440

agggaaatat tttataaata cacaaataat accatttcat gtgtcgctta cagatttttct 142500

catcttattg aactggctag agccaccaat gtatgctgta aaagcaacct tgttttaatc 142560

ctttttgaaa gggaatgttc cagattctac catgtggtac catgtttgtg ctaagatttt 142620

ggtaggttca attttttca gtttaaagaa gttctcctct agcccattat gccaatgaat 142680

ttaagctgaa tggatataaa aattaatcaa atattttta gtgcctactg aggtgatctt 142740

acgcctttct agtttgattt ataagtaggg ctaactatat taattgattt ttcaatgtta 142800

aacaaaattt acatttctgg aatagattta acttggtcgt tctttaactt tgcgttcccc 142860

ttaaaaagga ccttgagaga agggctcagc gtctgatagt tccagcatct ggctgtggag 142920

ctgtatggct gagtcatcat ctgttggttt gtttgctgac ttccaacctt tgtgcctaga 142980

tattgaagtc accttctctc cctttgaagg gcagagactt tgtgtgtttg tcctttcact 143040

cagcatggct cttggagttt ctggctgcat gagaaggtcc tgggagactc ttcccttcca 143100

agagcctcca tgttgtcttc tgccttttgg ggctactgaa accgcagcac aaggtgtagg 143160

gaaattacca ggttccccca gagccgtcgt tccttgcacc gcctttccac gatgtgtgtg 143220

ccccttttg ttttgtcccc tgggatttct cctacactct tgcgaggtca ttatgaactt 143280

aaaaggatgt ggatttttat tttattttat accttagagg tcttttatag cagagatttt 143340

tcagggcatc aagactagac gttttgccca aaagggaaaa ccagaggctt tcaatttttt 143400

tttgaattc                                                         143409
```

<210> SEQ ID NO 19
<211> LENGTH: 143409
<212> TYPE: DNA
<213> ORGANISM: Homo sapiens
<220> FEATURE:
<221> NAME/KEY: misc_feature
<222> LOCATION: (1)..(143409)
<223> OTHER INFORMATION: Reverse complement of AL162497
<220> FEATURE:
<221> NAME/KEY: variation
<222> LOCATION: (12936)..(12936)
<223> OTHER INFORMATION: Position of polymorphism (a). At this position a polymorphic variant of the wild-type would have A instead of C.
<220> FEATURE:
<221> NAME/KEY: variation
<222> LOCATION: (15012)..(15013)
<223> OTHER INFORMATION: Position of polymorphism (b). These bases (AT) would be deleted in polymorphic variant (b).
<220> FEATURE:
<221> NAME/KEY: variation
<222> LOCATION: (16359)..(16359)
<223> OTHER INFORMATION: Position of polymorphism (c). A polymorphic variant has C instead of wild-type A at this position. SEQ ID NO: 19 shows the variant base.
<220> FEATURE:
<221> NAME/KEY: variation
<222> LOCATION: (33392)..(33392)
<223> OTHER INFORMATION: Position of polymorphic variant (d). This variant has G instead of wild-type A at this position. SEQ ID NO: 19 depicts the variant residue.
<220> FEATURE:

<221> NAME/KEY: variation
<222> LOCATION: (47315)..(47315)
<223> OTHER INFORMATION: Position of polymorphism (d). Variant (d) has G instead of wild-type A. SEQ ID NO: 19 depicts variant residue.
<220> FEATURE:
<221> NAME/KEY: variation
<222> LOCATION: (49053)..(49053)
<223> OTHER INFORMATION: Position of polymorphism (f). The wild-type would have C between these two positions. SEQ ID NO: 19 depicts variant having deletion of this C.

<400> SEQUENCE: 19

```
gaattcaaaa aaaaattgaa agcctctggt tttccctttt gggcaaaacg tctagtcttg     60

atgccctgaa aaatctctgc tataaaagac ctctaaggta taaaataaaa taaaaatcca    120

catcctttta agttcataat gacctcgcaa gagtgtagga gaaatcccag gggacaaaac    180

aaaaggggc acacacatcg tggaaaggcg gtgcaaggaa cgacggctct gggggaacct    240

ggtaatttcc ctacaccttg tgctgcggtt tcagtagccc caaaaggcag aagacaacat    300

ggaggctctt ggaagggaag agtctcccag gaccttctca tgcagccaga aactccaaga    360

gccatgctga gtgaaaggac aaacacacaa agtctctgcc cttcaaaggg agagaaggtg    420

acttcaatat ctaggcacaa aggttggaag tcagcaaaca aaccaacaga tgatgactca    480

gccatacagc tccacagcca gatgctggaa ctatcagacg ctgagccctt ctctcaaggt    540

ccttttaag ggaacgcaa agttaaagaa cgaccaagtt aaatctattc cagaaatgta    600

aattttgttt aacattgaaa aatcaattaa tatagttagc cctacttata aatcaaacta    660

gaaaggcgta agatcacctc agtaggcact aaaaaatatt tgattaattt ttatatccat    720

tcagcttaaa ttcattggca taatgggcta gaggagaact tctttaaact gaaaaaaatt    780

gaacctacca aaatcttagc acaaacatgg taccacatgg tagaatctgg aacattccct    840

ttcaaaaagg attaaaacaa ggttgctttt acagcataca ttggtggctc tagccagttc    900

aataagatga gaaaatctgt aagcgacaca tgaaatggta ttatttgtgt atttataaaa    960

tatttccctc taaacatctt taaagcatta aaattaatat gagggtttaa caaaatgatc   1020

agatataaga taaattaaaa attgatttta tttctctacc caagcaacaa agagaaaatg   1080

tagtttttaa aaatggatac tggccgggcg cggtggctca cacctgtaat cccagcactt   1140

tgggaggccg aggcgggcgg atcacgaggt caggagatcg agaacatcct ggctaacgcg   1200

gtgaaacccc gtctctacta ctaaaaatac aaaaattagc cgggcgtggt ggcaggtgcc   1260

tgcagtccca gctactcggg aggctgaggc aggagaatgg cgtgaacccg ggaggcggag   1320

cttgcagtga gccaagatcg tgccactgca ctccagcctg ggcgacagag cgagactccg   1380

tttctaaaaa aaaaaaaaaa aaaaaggata ctttttacaa gagtaacaaa atatataagg   1440

tgctaggaat aaatctaaca aaatatttta aagatctcta tggggaaaat tataaaacgt   1500

tataaaaaga cattttacaa ttccctaaag aaatagggaa acgtgccaca ttcctggcta   1560

ggagaactca gtaccttaaa gatgtccaat ctttctaatt ttatctcagt cctaacaagg   1620

tttattaaac ttgtcaagct gatgctaaat cataaggaaa agagttacaa atatccaaga   1680

cattcctgaa ggaaagtgaa gaagtaggtg aaggaaatgg tctaccagaa agtgagattt   1740

gttaataaaa tatagtaatt aagacagtgt ggtaatagca taagaagaag caaaaagaac   1800

atcggggaaa agaacagagg gcacagaggc tgactcatgc aaacctagag acttgccgta   1860

tctgagaagc actattcaga ccagtgggaa aaagtcaaat atttgaaaca cgcctcggaa   1920

acaatttaaa aaaaaactga aattgagcca ctatcagaca ccatgcacaa acatataatg   1980

caggtgaatt aaagctaaaa aaagagagag agagaaagga aatacaggag taagtacttg   2040
```

-continued

```
aaaatttggc gatagagaaa aaaattaaaa caaaatgaaa aaggcacaaa actcaaaagg   2100
taaacttgat aaattttact cagttaaaat ttaaaattga tgttcattca aaagaaaaca   2160
taaagaaaat aaaaagcaaa taataaattt gacaaatcga tttttataaa agattaacac   2220
atggcctcta taaacaatga ctacaatcca atgggaaaaa ttgtaaaaga caatgacacc   2280
ttattggtgg aattttcaat ttgtacactt actttcgaaa atgattttta ttacacatta   2340
aaattaaagg tggacagaat taacactggc aattctattc ttctgtctaa aacagtgtgc   2400
ctaagaatat atatgtatgc ataaataatt gttaaaaggc actttaattg ttaaaaggtg   2460
tgtaattgtg aaacatactt tttaaaaaaa caagtcatgt tcaaatagaa attttaaaaa   2520
caactacaaa taacctaaat ttctattggc agaagtgaaa aacagttata tatttattac   2580
aactgaaaaa gatgaactac gacttcagaa atcgtaatac atttctctca aaaacataac   2640
gatgaacagg gacagagaga agacttatgg ccgccagggg tgaagggagg ggaactcaaa   2700
agtgactgct gtgggcacaa agtttcttgg ggtttctttt tggggtgatg aagatattcc   2760
agacttagag tgtgatgaca atttcacagc cttgtgatta tactaaaaaa tattaagttg   2820
tacattttta tggtatctaa gttacatctc aataataaaa ccatactgtt gagcaagttg   2880
cagaagaata ttaataggat gataatattt gtataatgct taaatttaag tacaatgcaa   2940
aatgtttaca tacatatcca gtaaaatcat gaagacagcc aaaggacaat aatcacaaaa   3000
tttcagattg tgataaggct agtcagtgga cttcaaaata aatattggta atgtcctact   3060
ttttaggctt gactatgcca attttaaagt attattattt ataacttaca tatatgttaa   3120
atatcttttt gtatgtgtgt actatgttgc acaatataaa aatccaataa gtaaaaaata   3180
aaagttctta aggtaaataa actgaatttc atcaaaaatt tgagagaaaa attggaagaa   3240
gagtaacaat ggataggtgt gaaaaataaa agataataaa tacctagtat attgctgaac   3300
caataaggaa ttcagaaata ttacggcaaa aatatttatg aggggtggaa agaagtgaat   3360
aagcttgaga gatactaaga atagaaaatt gacagaattt ggcaatggat tgggattcgg   3420
ggtgaaaact attgcaagaa tgatttccag gtttccagct gcacaactgg atagatggtg   3480
acctacttat caaggtaaga atcacctacc aaataatcat tagcaagggc agttaaattt   3540
ttatttgcaa gaaattagaa acaccaaaac gaagcaagta ttaagaggtg gttaaatgaa   3600
tcatggtaca atggggtaga agaatggtat gcagccatta aaaatcatgt tttaagagat   3660
tgatgacatc tcttagaatg acatctctta gaatatgtgt ggcatttcaa aatgcaatta   3720
aaatcaccat gagcctcttc aagtccatct ctttaggact ccgatgttac atggaaggct   3780
gcaaaatcac acattgtatc atgcatgtgc tatgaggtag tctgggaaac tgatgaggaa   3840
gagaaatgtt cctgattgtt tgttatgaaa taattatgtg gctggggtta aaagcctctt   3900
aggacaatca agtggcagct ttcactcaga cacttttaat gcattggcaa aatggcttct   3960
tttcaagtgc accccaggtg attcagggta aaagctcaaa acagcacctt tttgcccaaa   4020
gctaccttca gaaagaaggg ttgtcaattt gctagaaata atttttgtaa tcttctaggg   4080
ttataggcac aacatggtta ttctctttcc cttaactttg gaatgctgga gttttgcatg   4140
tctatccctt ctcgtccttt tttccacttt ctctgttact atcttccact ttctttctgt   4200
ttcatctttc gacacaagaa tgtcctttgg aataaatatt atgtttttat ttgtttattt   4260
ataaaaggac agtagttatg gtattgttac tttaaccttc tctgtgtaga cataatgtct   4320
taatcatggc agttctatta tagtttttag gcagcattta cataacatga aattattcat   4380
tttaaaatgt gccattcaat gacaattagt actttctagt ggtagatttt taatacattt   4440
```

-continued atgtttaata tacatcactg aataaataag attgcaatga attaaatagg cctccaaaca 4500
acaaaatgca aattgaaaac attttctacc ttgccagtat gcatattgtt tcattcgtta 4560
aagggaaatc cctgcttaga tataaacttc ctaaattaat ataaatatcc ttacacagtt 4620
aaatatgagt ttaggaagca agtgtttagg tagcaaggga taattcattt ccattatatg 4680
ccattagctc ttggaaggta ggcttccaat tatgaaaaac actgatttca ttgaaatgag 4740
ggttttctac tccctaaaga gaaagccatg ggaataggta gttttattca agtgaccaag 4800
tatggcaaga atcacctctc acctccctct ctgcattaac cccacagatg caaacagact 4860
tctctctagt tctaaagatt acacacttca tcttaatact gttgggaaat gaagaataag 4920
aagaaacaaa ttctagatta ctacagtagc acatctataa gatgagactt tacagattaa 4980
tcctctttgc tgcaaaacta gatttttttt tcctctaaaa actttcatct ttctttgatt 5040
ggctttacct gttttttttcc ctctaacaat ggtgaagaga caaattgtac tcttctggaa 5100
ccaaatcttg aaatatttaa taaataccta atttatctaa atcatgtatt tacacatatt 5160
tgttcagaat acgtaatatg gcataatttg tcattttttta gtcataaacc tcctctgact 5220
ccttcacaaa gggctcaggt ttccttgcct tggccaactc ccttcaccaa gaagactcta 5280
ggattggtac ttccagaaac ctggaggcca actgggaccc ctcttcccct cttcctatac 5340 tccctttttcc acctccctgc tcccaacatg ctttgctctt ctctattcta ggtcattcat 5400
tccatcacaa cctctggaat ttccacatca ttacaacaca agcttctttt atcctcagat 5460
accagctctt cactgcttga acagagagga tccgtagggc cccatctttt gtggcctgta 5520
aaccaatctg atacagaaca caaacgatca tagccaatat gtactggctg tgtctactgt 5580
gccagtcagg agctttcaaa ggtctttaat gtgttaattt atgtgaactt ttccgtagcc 5640
acacaaaaag tatttaatca gaaaaaaatt acataaaatt gtaatctaaa aacataaaag 5700
aacaatcctg aaaagagtgt gttgagcact tacgatgcag caggttcttt gagaaagcct 5760
atcaagcata gagagtgaac caaaacacac ccagggcagg ttccagaggc taccaggaat 5820
gctccttgag gaggtgcagt ggagaaagga cagcctgcag gactgaggac cagaagaaag 5880
gccagacccc agtctccgtc tctattccaa gatgatgcca acatcatttg gtctcacacg 5940
tctagtggca tctaacagtc ctctaatgga gaaatctctg gaaaggtctg agctgaagtc 6000
aatggaaggg aggtgttaaa tgtaaatgtg tcgcattcat tcccagttgc tacatgaatg 6060
cattctaaca agctgctaga aagggagtca aggaaaggaa agattctgat ccatgttcca 6120
aaaatgcaaa gctgaagaga tgttgcaaga tgacattcaa tttgaggaaa agcccataat 6180
ggggcttctt cagctttgca agaaaaccat gagattaaga ggaatgatgg agacccacca 6240
tccggacatg atggaagccc ctaggttttc atacctgggc tcccaggggc tttgactcaa 6300
gcagaaaaac ctggggacac ccagatctct gcctctccct gtaggcacca cagggcccct 6360
ggctggagcc tctttgctca ctgatgacag ctattgctgc actcaccatg gatgccaatg 6420
caagcagcac agaaaagggg tgctgcagtg ctcctctcag atgccaggtc acacttccag 6480
gctacagctg aacttgcatc ttcacagaca ccattaaaac tcaacctacc ggccgggcac 6540
gatggcttac acctgcaatc ccaggacttt gggaggctga ggcaggtgga ttgcttgagg 6600
tcaggagttt gagaccaact cagccaacat ggtgaaaccc catctctaca aaaaatacaa 6660
taaagattag ctgggtgtgg tggtgcacgc ctatagtcct agctactcag gggctgaggc 6720
aggagaattg cttgaacctg ggaggcagag gttgcagtga gccgagattg tgccactgca 6780
ctccagcctg ggtgacagag taagactcag tctcaaaaca aaacgaaaca aacaactcaa 6840

-continued

```
cctaccatgc gtcatatttc tgcccacagt agaagccctt agagctatcc actttctccc   6900
atggggttat cctaactgat gttttccttt cacccagccc tttttcactc ctttacctcc   6960
caaacacttc cagtgtcttc tctcaagtgt cctttccatt gcaacactac tcccatgctt   7020
tctgagtctc agcctttcct gaaagctggc tgcatcctgg ggacactgac tcttctgctc   7080
ccggaggata atgcttattt tgcccctgga ttttccttcg gattcttctc gttctccaat   7140
gtttctgcta aatagcactt tgaattcata atgcaaagac ttcatttatt gaaagttcat   7200
tctcatggat cctgccccat ctgtcatgcc ttctccaggc tgcattcccc tcttcctcac   7260
accaggaaac cacgcactag atcaacatgg ctcccatgtc accaggtccc ctgcctggac   7320
cactcatcct cgttacccct ggctggccag tccctgctgc aatgctctct gctgtccact   7380
cccgtggttc ttcagcaagc tagtctgtgc cctttcattg cgttttctct gctagattac   7440
ctttctgtcc ctgacttcta aatgttaaga gtagttgggt ccaatcccag gtgctccaat   7500
ctcatctctc acagtcactt tcggcaaatc ctagggactt aaatgcagct agatgcccat   7560
gaatcccaaa ttaatatctc cattccaagc ctctccaaca gcctatccaa catcttctct   7620
cagatttcta ttatgtccaa cctcgtgtgt ccaaaataaa tctcttaact ctccctcccc   7680
catctcagga gaagaccttg tcatcaccca gcgacagtgc aggacactga aggtcctctc   7740
ttcctcccct acccccaaat catcaccaag tgctactgag cctttagaaa ttaaagtcaa   7800
ttatttttac actgttaaat atttgataca tacttgtgct acaaaattcg gaaagtccga   7860
aaagtaacac gatgaaacgt gagtcctctc cccaacccgt cccttcccca ggaagccagg   7920
ttggctcctc gcattgccat atttgtgagg tcacttgcag taggtatctg tgcacatacc   7980
cacacgtttt aaaaataaaa aaaatggttg tactatacta tacacactgt tctgaagctt   8040
gttttcccac ctcacattat acagtcaaat attattctgg gtcagtataa acagagctgc   8100
ctcgtttgtg ttacagttgc atagggttca aacctttgcc attacaagac aatactgtaa   8160
tcatgtgtat aagtttctat tcctaacaat aatgcaatga acacccttat aaagaagtca   8220
tttcccatcc acatgagtaa ttcctggaaa ttagattgtg ggtcaaggaa catgagacat   8280
ttgtcgtttt gacagataca gccaaattgt atagatgctg ttcagtctgt accaccagca   8340
gccttgggtg ggaacctgtt tcccaacatt ctggcaaaca caccgtgtta tcaaacttct   8400
tgatctgtgc caatctgata ggtgaactat tctaccacat tgtggtttta atttgcattc   8460
atcttattac aagaaaggtt aagcaaactt tcacacattt aagcctttct tgcattaatt   8520
ttcattattg tgaaatttgt attcaggtca ttcaccaatt tttagaatgt ttttagtttc   8580
ttatttttta cagcgctctt ttaaagtatt aaataagcat cattagcact tcatctatga   8640
tactggctgc aatttccttc cagcttctac tttaactttg cttttactgt ttttgttttg   8700
tttttactgt attcccccta cagaatccta ttttagaaag tcaagtttat caatatttct   8760
ttacttttct acttggtttt atggtttcat gttttaatat ttaatttttt gcttcacctg   8820
acattttagt gaaaggacac aggcatctaa tttttatgtg tctacaggta tattttctgg   8880
ttctgccaac cccatttact gaataatctc ttatcctcca atgaaataaa ctgccagctt   8940
tataatatgc tttgtccctt gtatctagat ttagttctgt accaaataca actgaccttt   9000
tgatttggct atgttcatgt aggttctcca cctcccactg atttgtgagc ttcctaagca   9060
cactgtcagg gtttgagatt ttactccctt tcccttagaa agtaatgtta gcccgtcacc   9120
gttaggtgga tgctggcaga ggatgtaagc ctttccggtc agagactcat ggcacagaaa   9180
gtggcatgac ttgcctctat tcctcttgct tcccgggcag catggggcaa cagggcgggg   9240
```

-continued

```
cctgttggat gccacgcctg cagtgggctg tgtttcggct gacacaaagg acttgggtaa   9300
tccaccattt ttgtagcagg aaataagcag gcccgcactt tgttctggaa tgcgacctca   9360
cctcttagtg tggtttgctg caagcacaac ccttaaaaaa ggcttgagta aagcaaagcc   9420
agggtcttgc gtatttcact gacccactaa caggcgtggg agcaggagag acgcacagag   9480
gagggccttt cccagcagac acagctgagt ggttgtggtc ggtttgcatt ttgatgtcca   9540
caggatcagt gtctagtaca aagtaggtgc ttaagaaacg ttgataaatt tgaccgaatc   9600
caacatttca ctgggttaga atgaatttac caccacacag cataactaca tcactacatc   9660
tattgagtat tattctctac tacacagatg ggtcctcaca ctatggaccc aggcagcgtc   9720
aagagtccaa aacggtacct tctaaaggaa gcaacctaaa aataaaagaa atagaattac   9780
tgtttgactc attaaaacta atttctgtga aatgaaattt agaaacttcc tcagctcaga   9840
gataaaagtc actttctcta ctctacacca ttagtaagaa gaaggtaaaa ttgcagcatt   9900
ggacattaaa atcaagcact aagaaagttt ttttaaaaaa gccagatgat ggttataata   9960
tatggcaatt tttatcttca aattatgtgt ggcaatattg taacaaaaga cacaagaaaa  10020
aaatatttga ggaaagaaat agttgaggaa aatagtgcct tattacttag acagaaagct  10080
aatggggcaa agacctatgt tctgggtaat tcttagtata cgtttgaggc ttaacaaata  10140
tctagcacat ttttagtaac aatgtttgcg gatttttata ttttgaattg aaaatgccat  10200
aaatgcacct tcacgataaa gggtgagccc acttttgtat tattctgtaa ctaaaacatg  10260
atgatattta aaacaacaaa gcaaaatgat gatctagata ttaatttcct ttaaagttta  10320
tattgtgaga gacaagggtg ccatttttgaa attgtggtgt acttttagtg tgaagaaact  10380
ttaaaactag gtacaagttt atcaaaataa aacaggtaag tatcaagtct caaaaatatg  10440
tatttcattt tctgtgtgct tttagtagca gtgagaatca tgtttttaaa ttctcacttt  10500
tactacctaa aaggaaattt ttgtagtata aaatataatt ttaagatgtt ttcaatatat  10560
aattcctatt ttttttctct tttagcaaga caaccttggg ctgacattcg aaatttttac  10620
taaagaacca gcaagtacta aaatgcaggc tgatgtttac actttcagta gtaattctta  10680
gaatgtgttt atctgaactg aaatctctac ttaacagtca gcgggaaatg gcaataaatg  10740
gcatctgccc taaatttcac aagttgttgc tttatttatt ttcttgtgaa cctcattaat  10800
ccatactccc tcaagtcact ttagtttagt taatattatt tgtgtgacaa aagtgttttg  10860
aacaaggaaa aatggaaaat tcatgtataa atagctaatc attggtctta aacatagcat  10920
atacacggag gctcagagga caggttggta aagattactc aaaaggagaa ttaaaagacc  10980
gctcaattct cagttgtgtc ataatcgtat ctttatggta gctacatatt ataaaatgtt  11040
ttttatttat ccctcatact agtaagcgtc aaattcatga tctttgtgag tatactgaca  11100
aactactctc acaagctatt actattattg atattttata tatcaacttt ttttcatcca  11160
taaaagtacc tcaacgacat gttcagtagc aaataagttt tcagatccct tcactctatt  11220
gaataacagc tctgaacact ttgactaact tgaatatctt ctatttgcaa tgcctaaaga  11280
ttgagaataa agcagttaag aaggaaggtg taatttgtaa atttagaatt gccaaattag  11340
taatgagtat gtaagttcaa ataattttac gcaatcaaaa agatagtgac attcgatgct  11400
tattgccatt tgttatttat gtttttaaaa tacatttttg ttatgtgtca ttttcagagt  11460
atgttttctt tcctatctta ctttttccaa tttgcttttc aatctttcaa gatgactttg  11520
gcttatccta aaaagaatgt gagacttaaa ggtcaatgta ggggagaaat acaattaaaa  11580
aacacttggc ttgccagata agcaaatctt gattataact tatttttgat taggtaaaca  11640
```

-continued

```
ttctaaaata atactgaatt tagattcttg tttttatttt gttggctagt attctaaact  11700
cttaagtggg cagtgatata catttctatt aaactgtata agtaactatg caaattggga  11760
tataaattgc attagaaaat atgaacatat ttgcttgata cttaattcaa ccataaaaaa  11820
taaagtattg cacttattaa tgttctcttc cctcatttgt catctgatat tgctcttagt  11880
cactcactat caaaatttct ttgtttaatc ttacttctat taatttcctt aaagtttcat  11940
gcaaagcaaa tttatgtcag gttgtaagca cctttctctc aaagcaacca ccactgtatt  12000
tgtgacaact catgccagaa ccctgaatct gccttgggaa gaaacattgc cagttggtgg  12060
cagcattcac aagagagggt cacatttcct ctgttatctt taggttgaat ttcaaaacaa  12120
ctctagaaaa cagactcaga gggctagcct tggaaacagc atgcaaacaa ctgcagaaaa  12180
gcggaaggtt tctgactata atacagttct accaaacagc agagcatgtg gcaaaaaagc  12240
caggctggct cccttcctcc tgtttacctc ctgagcagtg tatgaaacag ggtgagcttg  12300
ctcctggaat caataggtga atcaatgaac acaggctggt cttccccact tcataacatc  12360
tgtactctgt acaaggacac tccgggccac cctcgctgag catcctcccg ccctctccca  12420
gaaaatatag ctgtgtcatc ttacagacat ttttaatgtc atctgcttat gatgtgcaga  12480
ttgagaagca gacaattttg ttctgctctg gcatgaaaaa aaaaaaacgt tttaatcggc  12540
agctaggata gcaacatgaa gcaacacaca ggacatcaat ttcatcatgc aaaataccgg  12600
tgtattatat tacaggggcc aagcattcca aggaaaagta atgatctaag aagatgctct  12660
tgcattttaa aaatatctac tagtgttata cagtcattaa tgtataattt ccatttcaat  12720
aataggaagc cttctgggaa aaaaagcttg tgttgcttct taaatctaga aacacattct  12780
caaaattcaa acagaacaaa atccagaggc atattaataa atattttcaa ctcctaaccg  12840
cagtcacttt ttaattgggc atttatgtat ttcttcaaca taattatatt tataatgaaa  12900
aaatgttgag aatactggat tagctgcatt tgtaactaca acatattttt ctaaacagta  12960
ttaattcaat tgataagact ttaaaaaagt tatagtagtt tgttctatca tatatgcaca  13020
ttaaataatc atttatttta gaaaatcctc cctcataaaa tgaacattta ggaaagagac  13080
tgatccatat ttttaacaag aataataaac acacaagtag aaagccttta taatttccaa  13140
ggggctgatc aattccatta acaaatcctg atactttaaa tgtttgcaat gccatacata  13200
gcaaatgatc caaacagcag ttatattctc tcatgtaagt cattctgttg cccatacaca  13260
gagttagcat gttacaaaac tcttgtgaaa tttcagttga aacattagca aataaatttg  13320
ctggtaaagt gcaagaagtt tccttataaa ccctagatga ggaaaagtct gtccacagtt  13380
cgttcatcag aggaatggaa tttctcaaat gagctactga acaacattat ctaataaaat  13440
gaaatataat gaaatggtgc cactcatttt aaagattaaa tatatccttt gacagaaacc  13500
tgtgaagtta aaaatctttc cctcttaaaa taccttttaa attaaagcta ttctaactag  13560
ttatatagca ttccacttaa tctgcttagt ttttagattg agctcaccta aatacaaaat  13620
actgtcaaac acctacaggg caaagaacta aaaaaagaaa gaaaatttca caagcaataa  13680
aatgctattc acctttctcc tcccatactt gcctttccta tatgaaacaa agaaaataat  13740
tagtgatgtt cattattggt agtgctacta gtatttgtat tgtgaacctg taacatattt  13800
ttaaatctct acacttttat ataattgatt ctttcttgaa aagtaattat ttcagaagac  13860
ttctaataaa ataatcatta ttgtatatga ttctgttaaa aatagaaaaa acaaacaaac  13920
agaaaaaact ccctgctgaa agatatggcc attttattag ctgtgaaagg aaagaaagct  13980
tccaaggaaa gatcttggac catgagaaaa aatttcaacc aggctgtttg ctggcaagag  14040
```

```
gccatgccag ccccagccag tcctgcgtgc agagcatgtt ggcagatgtt attagctgac  14100
ttttgttgaa aaagtatgga agaacagttg gaaaatcaca aggtgtagaa caagctttaa  14160
ataaataaat agcttatctg gcaatagaaa gggggaaaga aaacaagttc ctcggttgag  14220
gaagaggact gggatacttc taattacaga gtttcttact gttggtttgt ttcatgggct  14280
gactctcaat gagaattgaa attgtatcat ccacatttgt atttggaggt tctaactgca  14340
gaattgcaat taatttccag tttgctgtag gaaatttata ctctctatga cagaatacca  14400
cggacatagg tgataattct ttaaccttct ctcttttgtc cccagtctgg taactgaggc  14460
agtacatggg gaaagtgcta actgccaatc cagagctgct gacaccttaa aaacactggc  14520
ctttaacact aggatggccc caagaaacaa gcaaacagga aaagatgaca cctgctagcg  14580
tgtgacaggc acagcaagta aatgttcaat acggatatga aaatgcaact gcataataaa  14640
agtcaacatg aaaaagaaaa agattgcaaa atatactttc tcagaagaaa ccatcacatg  14700
atgtttaaaa gtggtggttc ctttagcatt gtctactgat ggctggcaac atacaggaac  14760
atagaggtgg cccatttaca tcctcataaa agtgggatgt aagtgatcac aaagccaata  14820
aaactacacc acattttctt caagcaccaa gataagaatc ccttcatctt tcctgactag  14880
acatattgct aggcaacatt tgtgaacgta agaaaaggta acaagatcta aaaagaacgc  14940
cgaagcataa tgttcataaa ggtggcgccc ccaacacaca caatcataca cacataccta  15000
tacacacaca atcacacaat ctattatata aacaaacacg cacacatgca cacataggtg  15060
cacagactta aaatggcatt tcttgaggta ttttttttta aggtatgatt taaaaatgga  15120
agatcaactt taaacacacc tttttgaggc acactgggtg atatttgcca caatgattat  15180
tcttcccaaa ttcaggctac tgatcaataa tcctaactgt atacatgcta aaaataaaaa  15240
cgctataatc tttgtactag tcagggctct cttggcacat aaaattagcc aacacaatct  15300
tcaagtcaca tgttacaaaa acatattaaa atatatatca ctctttcaaa aattacactt  15360
attttctctt agattaagat tttattactt ttaagatact tctatgaatt atagaggaca  15420
tccaaaagta aacatccggg acttaaaaac aataaccaat attataagat aaattattgc  15480
tgtaaattat ttcatgaagg cacaattaaa aaaaaaataa aataaacagc caaagcctgt  15540
tttgttgagt tttcttcgtt gcgcaggatc gggagcttgc tgggatctga actcaggaag  15600
ccctcacctc accctgactt ggtcattgag gagacgtaat tgcaggggtg cttatttgct  15660
ataggctttg aaagtcacaa aagcccagta gatacatgaa ttcgaagcag ttctccaagg  15720
gcatctccaa cttggcagtc accgcccgca ccgcgcacac aggtagtgga cgcccgccca  15780
cctgcccgtc tgctgggcgc agggcgctcc tggggtgggg agggcgctcc tgtgggggga  15840
aaaggggcgc tcctgcctcg gagggggaaa ggacgcccct gtggaaggaa gggggggctc  15900
ttgaagcggt gtggtgagag gacgcttccg aggaaggaag gggtgctcc tgcagcggtg  15960
gggggagagg acgcccctgc ggaaggaagg cggcgctcct gcgggggctg gagagacgcc  16020
cgcgcggtct cccggctcag ggaccgctgg ctcgcgggtc cgccctctcc ccggcgctat  16080
ggaaaccgca ctttctccgc ctgccgtccc cgatctcttt ctcctattac ctcccaaacg  16140
cgatttcaac ttcccgacaa gctgacaagt gaatggcgca gaggacgccc cgtaaagcgc  16200
ccgcgagcgg gtgggacaca ggcgccccct ccgcgcccct ctgtcctcca cggaagggcg  16260
cgcgccgctc tcgatctgga gcgcggtgct cgcgaacccg cggccgcggg ccctggaacc  16320
tccccgcgtt tcgcggctgc ggggggacgg agatgcggcc gggagacggg gacgggaaac  16380
gggggacggg gatggggcgc gcccaccccg agcgcgggag cggccgccct cgcccaaaat  16440
```

-continued

```
gggacccccg cgccccgaga gcacggcccg gctcgccgcc catgcttcca ctgcaaggcc  16500
gcagcccccg ccgccgatcc cgatcccccg ccccgcccag ccgcggcccc gcccggcgcc  16560
ccctccccgg cggaagctca agcccaatta attgagtccg aggcgggagg gaagggccct  16620
gcgcgccgtg gcccgccccg cccctcttcc gcgcccettt tcccgccctg ggtggcatct  16680
cctccgccgg catccacaac aagccgctga ttaatgaggc cggggccgcc ccaccccgcc  16740
cggccgggcc ggggccttcg cgggaggggg aggggacggc gggaaacgcg gcccggggag  16800
aaaggggggc ggggcggggg cgcgcggccc gccccccgcga gcgccgcgcc gattggccga  16860
gcgcgccgtc cgtcgggggg cgcggcgcca atgcgaggca gcggggcggg gcggccgcgc  16920
tgtgtgtgcc tgcgtaacgc cgagtcacat gttgttttgc tcttcttagt tcagtcactc  16980
ggtgcgcgat gtgttactca ctgtgcggcg gggaccgcga cgagcccggg tcgccgttgg  17040
cagcagcagc agcaacacca gcagcagcag cagccccggc ggcggcgcgg accccgagcg  17100
cccgggcgca ccccggcttc ccggagcgcg acgcggcggc agcagccccg gtgcggccgc  17160
gcgcgcctta ggctcggccc cgcggctcgg ggaccccgac tcccggccca gcgagcgcgt  17220
cccccggcgc cgcccgagag cccgaggagg cagcggccgc aggcagccgg ggaggggggc  17280
ggccaccgcc cgcgccgggc atcctcagga gccccagagc gcggagggcg cggcgccgcc  17340
gagcggtgct ggcccccgcg ggcctccccg gaccttcccc accgcctggg cccgagggac  17400
gcgtgatcgg gcgggcggcc gggcgcaagg gtgggaggga gccgcccccg cccgcgcccc  17460
ctccgcccct cgccccaacc cctgggcgcc gggcccgggc cgcgcggcct gaagcgcccg  17520
cgatggcgag cccgccgcgg cacgggccgc ccgggccggc gagcggagac ggccccaacc  17580
tcaacaacaa caacaacaac aacaaccaca gcgtgcgcaa gtgcggctac ctgcgcaagc  17640
agaagcatgg ccacaagcgc ttcttcgtgc tgcgcggacc cggcgcgggc ggcgacgagg  17700
cgacggcggg cggggggtcg gcgccgcaac cgccgcggct cgagtactac gagagcgaga  17760
aaaagtggcg gagcaaggca ggcgcgccga aacgggtgat cgctctcgac tgctgcctga  17820
acatcaacaa gcgcgccgac gccaagcaca agtacctgat cgccctctac accaaggacg  17880
agtacttcgc cgtggccgcc gagaacgagc aggagcagga gggctggtac cgcgcgctca  17940
ccgacctggt cagcgagggc cgcgcggccg ccggagacgc gccccccgcc gccgcgcccg  18000
ccgcgtcctg cagcgcctcc ctgcccggcg ccctgggcgg ctctgccggc gccgccgggg  18060
ccgaggacag ctacgggctg gtggctcccg ccacggccgc ctaccgtgag gtgtggcagg  18120
tgaacctgaa gcccaagggt ctgggccaga gcaagaacct gacgggggtg taccgtctgt  18180
gcctgtctgc gcgcaccatc ggcttcgtga agctcaactg cgagcagccg tcggtgacgc  18240
tgcagctcat gaacatccgc cgctgcggcc actcggacag cttcttcttc atcgaggtgg  18300
gccgctcggc cgtcacaggc cccggcgagc tgtggatgca ggcggacgac tcggtggtgg  18360
cgcagaacat ccacgagacc atcctggagg ccatgaaggc gctcaaggag ctcttcgagt  18420
tccggccgcg cagtaagagc caatcgtcgg ggtcgtcggc cacgcacccc atcagcgtcc  18480
ccggcgcgcg ccgccaccac cacctggtca acctgccccc cagccagacg ggcctggtgc  18540
gccgctcgcg caccgacagc ctggccgcca ccccgccggc ggccaagtgc agctcgtgcc  18600
gggtgcgcac cgccagcgag ggcgacggcg gcgcggcggc gggagcggcg gccgcgggcg  18660
ccaggccggt gtcggtggct gggagccccc tgagccccgg gccggtgcgc gcgcccctga  18720
gccgctcgca caccctgagc ggcggctgcg gcggccgcgg gagcaaggtg gcgctgctgc  18780
cggcaggggg cgcgctgcaa cacagccgct ccatgtccat gcccgtggcg cactcgccgc  18840
```

ccgccgccac cagccccggc tccctgtcgt ccagcagcgg ccacggctcg ggctcctacc 18900
cgccgccgcc cggcccgcac ccgcctctgc cgcatccgct gcaccacggc cccggccagc 18960
ggccctccag cggcagcgcc tccgcctcgg gctcccccag cgaccccggc ttcatgtccc 19020
tggacgagta cggctccagc ccaggcgacc tgcgcgcctt ctgcagccac cgaagcaaca 19080
cgcccgagtc catcgcggag acgcccccgg cccgagacgg cggcggcggc ggtgagttct 19140
acgggtacat gaccatggac aggcccctga gccactgtgg ccgctcctac cgccgggtct 19200
cgggggacgc ggcccaggac ctggaccgag ggctgcgcaa gaggacctac tccctgacca 19260
cgccagcccg gcagcggccg gtgccccagc cctcctctgc ctcgctggat gaatacaccc 19320
tgatgcgggc caccttctcg ggcagcgcgg gccgcctctg cccgtcctgc cccgcgtcct 19380
ctcccaaggt ggcctaccac ccctacccag aggactacgg agacatcgag atcggctccc 19440
acaggagctc cagcagcaac ctgggggcag acgacggcta catgcccatg acgcccggcg 19500
cggccctcgc gggcagtggg agcggcagct gcaggagcga cgactacatg cccatgagcc 19560
ccgccagcgt gtccgccccc aagcagatct tgcagcccag ggccgccgcc gccgccgccg 19620
ccgccgtgcc ttctgcgggg cctgcggggc cagcacccac ctctgcggcg ggcaggacat 19680
tcccggcgag cgggggcggc tacaaggcca gctcgcccgc cgagagctcc cccgaggaca 19740
gtgggtacat gcgcatgtgg tgcggttcca agctgtccat ggagcatgca gatggcaagc 19800
tgctgcccaa cggggactac ctcaacgtgt cccccagcga cgcggtcacc acgggcaccc 19860
cgcccgactt cttctccgca gccctgcacc ccggcgggga gccgctcagg ggcgttcccg 19920
gctgctgcta cagctccttg ccccgctcct acaaggcccc ctacacctgt ggcggggaca 19980
gcgaccagta cgtgctcatg agctcccccg tggggcgcat cctggaggag gagcgtctgg 20040
agcctcaggc cacgccaggg cccagccagg cggccagcgc cttcggggcc ggcccccacgc 20100
agcccccctca ccctgtagtg ccttcgcccg tgcggcctag cggcggccgc ccggagggct 20160
tcttgggcca gcgcggccgg gcggtgaggc ccacgcgcct gtccctggag gggctgccca 20220
gcctgcccag catgcacgag tacccactgc caccggagcc caagagcccc ggcgagtaca 20280
tcaacatcga ctttggcgag cccggggccc gcctgtcgcc gcccgcgcct cccctgctgg 20340
cgtcggcggc ctcgtcctcc tcgctcttgt ccgccagcag cccggcctcg tcgctgggct 20400
caggcacccc gggcaccagc agcgacagcc ggcagcggtc tccgctctcc gactacatga 20460
acctcgactt cagctccccc aagtctccta agccgggcgc cccgagcggc caccccgtgg 20520
gctccttgga cggcctcctg tcccccgagg cctcctcccc gtatccgccg ttgcccccgc 20580
gtccgtccgc gtccccgtcg tcgtctctgc agccgccgcc accgccgccg gccccggggg 20640
agctgtaccg cctgcccccc gcctcggccg ttgccaccgc ccagggcccg ggcgccgcct 20700
catcgttgtc ctcggacacc ggggacaatg gtgactacac cgagatggct tttggtgtgg 20760
ccgccacccc gccgcaacct atcgcggccc ccccgaagcc agaagctgcc cgcgtggcca 20820
gcccgacgtc gggcgtgaag aggctgagcc tcatggagca ggtgtcggga gtcgaggcct 20880
tcctgcaggc cagccagccc ccggaccccc accgcggcgc caaggtcatc cgcgcagacc 20940
cgcagggggg ccgccgccgc cacagttccg agaccttctc ctccaccacg acggtcaccc 21000
ccgtgtcccc gtccttcgcc cacaacccca agcgccacaa ctcggcctcc gtggaaaatg 21060
tctctctcag gaaaagcagc gagggcggcg tgggtgtcgg ccctggaggg ggcgacgagc 21120
cgcccacctc cccacgacag ttgcagccgg cgccccttt ggcaccgcag ggccggccgt 21180
ggaccccggg tcagcccggg ggcttggtcg gttgtcctgg gagcggtgga tcgcccatgc 21240

```
gcagagagac ctctgccggc ttccagaatg gtctcaacta catcgccatc gacgtgaggg  21300
aggagcccgg gctgccaccc cagccgcagc cgccgccgcc gccgcttcct cagccgggag  21360
acaagagctc ctggggccgg acccgaagcc tcgggggtct catcagcgct gtgggcgtcg  21420
gcagcaccgg cggcgggtgc ggggggccgg gtcccggtgc cctgccccct gccaacacct  21480
acgccagcat tgacttcttg tcccaccact tgaaggaggc caccatcgtg aaaggtgagg  21540
aggccctttg ccttggcgtc tggcgggaag gaggggcggg gcgctgaggg agcctcttgg  21600
gtttcactgc tcccactttt tggggacctt gacccagaag ccgacagcct ggcactggct  21660
ccttgttttg tttttctgcg ggctgccctg ttctcttcct tcagagaact tgccaggaac  21720
attcgtcttg gagttgaatg tgacgttttc cgcgtgggag ggagactgat tttttgaggc  21780
cccacccatt cacccattct gtgcgtccca cagccccctg tcccttaaca cagtggaagt  21840
tctcccagac cggccacact agaggccgcg gggcacccga ctgtcttcat ccggctgcgt  21900
gggtccgtcc ttctggaagg acctcgggtc cggaccgctg ccctcagccg cagctttcac  21960
ctttccctgt gttcctggag ctgggctccg cctgattctt ggtgagcttg aaggttcaga  22020
cctgaaagtc atttaagaaa tgagcatcca ttttgatggc tgctaatagc gacagttaac  22080
catttccgtt ttacacacaa actgtgggag cttttccatc agaggcattg tttttctcgg  22140
aaggggtgaa acggtaaggc tgcacacagc ctaatgcagt ggtgttcaac ttgagcatat  22200
gtgggagtta cctggaggct ttgctgaaac atggatctct ggcctgtgtt aaccccgcag  22260
tttccgatgc tgtagctttg ggcgcggcc caggctgtgc atttctagtg agtctccgca  22320
taatgccgat gctgctggcc gggggaccac cctgtgagga ccctgcccca ggtgagactc  22380
acctggggag gattgaaaaa ttacctgttg ggcctcaccc cagacccgtt gaagtgaaac  22440
atgagatggc taggaggcag ggacggacat ttttcagagt tgtccaggtg atttgaatgt  22500
gcagccagga tttacaatca gtgctttgga gaaaacaagg gaaagacaaa aaacacaggt  22560
cttctcaaga acaattggat aggagggtgc ctggtattgt tcttcccgtt ctgatcaaat  22620
atccatgagg agagagagct gatgcagaat gcagctggtg gtgcattctg gctgtctaaa  22680
ctttgaatgg tgtttggggt cggggagatg agagggaaag gtgaatgctc aattcgggag  22740
actttattta attttgtagc tgttttcttt gtagggttcc tagcaggata gaggctttgt  22800
gggaacagtg aaacatatag taaaatttgg atgctggatt agatgtgagc ctaaggtgta  22860
aacagtcttc aagggtcatg agatgaggat caaggtgggc tggagattca cagccttttg  22920
ttcttaaata gaccagttta gtgctatcta aatccagcat ctgttttata gtatacttag  22980
gactgtcggt ccatgggatt taaaattata gctgtggggt gaactccctg ttattctagt  23040
gtaatagaga aaagctattt cctttattaa aaccgtatac tagaagatga agagtcacag  23100
agaattatca ggagtgtggt gcttcagcat ccaattaaat cattggaagt cgccagaatg  23160
tatcctgtga acagtgattc tcagctgaag gtcactttgg ttggagttac ttatacacta  23220
ttgctagtgt gtcagaaagt tgaaggatta gctgccttat aagacacaga ccattataaa  23280
cacagcagca gcagcagcag tataattgag tggggaaaaa cacacatatt tatggtctgc  23340
acaaatgggt atatgccaga gtgaacatga aagtaaatta catcttaccc gaatctgatt  23400
ctaatcagaa aacagccaag aacataacac cttttcctgc tttcagtgga gctggtggga  23460
caaacctgga ctgggtggag ctggggcccc agcagtgggc tctgccatag caggcgccat  23520
aagctggaat ttgtgcctcc aggcctggag ggacgcaagg cgtttctgat gaagccgata  23580
cattcagaat tggggtccaa ataggaaata atgccctttt caggctagtg aaaatgttga  23640
```

actctaagag ataagtttat ttagagactg gattgagctt ttgtttaaga tttcccacct 23700
gcgtaaaatt cctttcagcc cataggattc ttgattctga agtccagaca gaagcctgtg 23760
ttctgtagct gctgaacaaa gatgagagat cactggggct gctgtttgtc cgaagtttgt 23820
gtgggtatca tgatgaaccc tcttctaaga agtaaaagga tcttttaaat caaaatagac 23880
aactgcagtc agtccaccat gcccaacgac atttaaaaaa aaagaaatat ctgcccatt 23940
gggtttctag taaagtaagt tgaacacaga gaacagcaga ataggaaagg ctagtgtcac 24000
cttagtccac gtagcaccaa agttgtggtc cgttgagaca gaaaggaagc atttaggaac 24060
ttgggataaa tacccacttt tatttaactc atacatgcac tagaaatttg tttgggatgc 24120
tcataaatac agagttcaca gtagatcagt gtcctttgag gaaatgattt gtagaaggcc 24180
gacttgcaaa gcatttcttt gaagatgaaa tagagaaagc acttcctggg cggccccctg 24240
ccctgcctgg ctcttagaag tggcctgtgt ttccaccctg agctcttcct gttctgcatg 24300
ggaagacctc gttagtgatg ctgatgcaga ataattttgg ggttatgtgg gtaatgtttg 24360
gtatttgcat aagtgatagc agagaggtaa ggttccagcc atgtctggca cttgtttaca 24420
atagaatcgt gaatgggggt gggctttcag tgcaagagcc agttaaaaag tatatctcag 24480
gtacatctgt ttttattagt ccagagcaaa ctcaaaatta tgcatcttat ttgagggcag 24540
gttaaggtta cttatcatgt gtttttggtg tgtgtgcatg tggaaaactc taaccaattt 24600
gttaggtttc gttgttgttt gggaattgga aagacgctac tgaatttcct gtgctttaaa 24660
actgattttt aaaattaact ttatatgttt ttgtgttagg atggtagatt gatgaatgcc 24720
ataaaatttg ctgttttagt attccttttt agtgatttta gggattttat tctaaaattg 24780
gcgtatatat atgtatgtat gtataagaca gattagatca gaattactac tgaaagtatc 24840
catatttaaa ttttgttgaa taaaaggatt atcatttctt aaggggaaag aatgataaga 24900
gatatgtttc caaagggaca ataaaatcac gatttatgtt gaaaagtttt gccttttgaa 24960
gtcgtaaagc agagaatttt cctaaattca gaaatccagt gaggtgattg acaaaccaca 25020
caagtttctt gtttgctgtg gcgggtgcta gtttgcttta gttggctggc tctggccata 25080
ataagacaat agcgtgcact gctgctgccc tattcgcagg agcagacaac taaggtgcta 25140
atgaaaacac acaccggctt tcgtgaatga aagtcacatg acttgttctg tttcctttat 25200
tgaaagagaa acctttacaa aaatagtact tcatagaagg aagcatagta tgtggaacac 25260
taaaccagga atcaggaaac caggtttcta gttgctgatc ttaatgagtc attgtgtgtc 25320
tatgggagag ccacttaatc ctgccttctc actttccctg tctgtaaaat gggggtaatt 25380
ataatcctcc cctttctgtg tcacaaggcc gctggaaggt aaatgaggtc ataaacatca 25440
agagtgtttt aagctcttct aaaggaagat gctaataaat ccagttgttg atacttattg 25500
ctttgaaacc atgaatgtat acaggaaaga cacttttgta aatgggtgct cttaaattga 25560
aacaaacagt aacagcatag tctgaaaatg gagccagcac cttaaaaatt gcttaccttt 25620
actgcttatt gctagttccg ctccaggctc ccaagagcca ttgttttccc cctttatgta 25680
acttaagatc tgttcataga tatttatgaa cagattgtaa caaagtggtg ttctaaatta 25740
catagtaaag taacaattag ggaaaacagt atggtaatcc tgaaactatg ttaagactga 25800
acttctgatt accttttatt actggttttt atattaagag atgttgacaa gatgaaaatg 25860
tataattaga atatacattt taaaaatcgc ctcttaatgc cgaatgcatt gaaagaaaaa 25920
cagaaccctg aggttgtttg actactcatt gtttagtctg gggttcatt ctttggggtc 25980
gatttaatga gggtggtcat tcctgcagtt ttgatggtag cactgtgctt atcaaacata 26040

-continued

```
gtaggaaaat gcgtgattct tttgtttttc taccacccaa aaaggaatct tagtagagaa  26100
ttgatatttt attttcttta gaagtatgag tatttaaaat gaggctcttt tttctgaaga  26160
gaagaacttg gaaaagtttt agtaacagca tgagtataat gggttttctg ttaaaattcc  26220
cactaatgca ttttctttag aaacgtagtt ctaagagcta attttggtat cagatttggc  26280
aagtagaaag ggtttttgtt tgtttgtttt ggttttttc tagggggagt agcacagaat  26340
caagtgttcc catttcacct tataaactta agggaaaatg taactttatt ctttcatctg  26400
cattgccaag tagaatgagg aaaacactgg gtgaggcaaa gtgctgtgcc ccccgccccc  26460
catcctgcat ttggacagct gtaatgcagg tggattctct gtttcatttc tctagtacgg  26520
atgacagcag aatgtatatt tctatacaag atgaacaaaa cgttttaatg ttggcgtttt  26580
aatgaacaaa tgaaaacaaa attttctgaa tgtccaaaag tattggttat aaacacatta  26640
actgtcagat catgattttt gtgaaaagaa tgctgtccaa gtttagatag ggacactctt  26700
tctatattta gtttgagtgg gttcttcaag actgcagtgg ttattctgac tcatttcagg  26760
tagattattg tacacagagt tcagtgctag acttttctga agaaaactag taaagtcatc  26820
atttggcatg gaggagatga tggggttgat gattgctact gatttcaatt tctttcaaga  26880
tagctacaga gacttacatt aactgggtgc taaaatacaa tgcataggtg aaggttagtg  26940
tagaaagagt tggagtatat gttgtatacc aacattttgc tctgtaggtg caaataatgc  27000
aagatgcttc tgtgtgttat agctttatta cttaagtgaa ttcattacat aagaattctg  27060
aaatagattg gattaaaact tatgggttac atgtttacaa atgataaaat agtcaatttg  27120
gtggttctga ttaattttct attagactag gaaaatacta agtttgtata gagtcacttt  27180
tatgtgtcca aagacactgt aaaacttgaa tgggtaaagg tgaagccttg gaaactctgt  27240
ccagttttct tatgtcatat atgatatcta tatacacaag gtttataaaa tattccttgc  27300
ttactgtgtt tttactgaaa tttggaatat ttgatcaaat attttgaccc acgatatatt  27360
ttttaaagat aactgatcac acgcattgca ccctgtaaat gctgggtttt tttcttttt  27420
ttttttgag acggagtctc actctatcac tcagtctgga gtgcagtggt gtgatctcgg  27480
ctcactgcaa cgtccacctc ccgggttcaa gcgattctcc tgcctccgcc tcctgagtag  27540
ctgggactag aggtgcatgc caccatgccc tgctaatttt ttgtattttt agtagagatg  27600
ggatttcacc gtgttagcca ggctggtctc gatctcctga ccccgtgatc ttcccgcctc  27660
agcctctcaa agtgctggga ttgcaggcat aagccactgc gcccggccta atgctggatc  27720
ttttaatatt cattttaaag agtatcaggt tttccagcaa caaatatttg ggctggtgt  27780
gtgtgtgtgt gtgtgtgtgt gtgtgtgtgt gtgtgtgtgt gtttccataa tatctcatcc  27840
agtcatgctc caggaggctg gatatgatat ttttctccat aactgaaatt caaggattaa  27900
tgatgtgttc tttgttcatg ttgaaacttt ataacttaag catagtctac tgctacttta  27960
tccctataca gttagtacaa atacttgagt cagttattac ggtgtggtat gaaatttcaa  28020
ttgttttcaa tgcataaaaa cagatattat gatatagttc attatactat gtgattttgt  28080
tactttacaa tcctattata ctgtgtgatt ttgttacctt aaaatcctta tgtttatgtt  28140
aagaatgatt cattcttgga tgagcttggt ggctcatgcc tgtaatccca gcgctttggg  28200
aggccgaggt gggtggatca tctgaggtca ggagttcaag accagcctgg ccaacatgga  28260
gaaaccccat ctctactaaa aatacaaaaa ttagccagcc atggtagcat gcacctgtag  28320
tcccagctac tcaggaggct gaggcaggag aatcacttga accagggagg cagaggttgc  28380
agtgagctga gatcgcgaca ctgtactcca gcctgagcaa caaagagtga aattcagtct  28440
```

```
caaaaaaaaa aaaaaaaaaa agaaagattt tgcatagtat taatgcttaa tctttaatat  28500
ttaagaatat gatacagtgc tttctgtatg cattctatgg acttaaataa gtcaatcttt  28560
ggcctccaaa gtataagtgt aacagataat cccacaactt ggtagacaac tggcaactga  28620
agattttgaa agaatcttat tgaagttgaa tgcaatgacg atgtaccatt attctgatca  28680
atattgacgg ataactgcct gccactcttc tcttggggtt aaaagagttg tgtaaaattc  28740
aaagggtgtt tttcttccct ttatagtggt aagacatttt cctatataca atatggtata  28800
atattccaaa aaatcctatg gcataggcag aaccaccatg aaccccattc tttggaatca  28860
agaacctaca gtgtggagag gccagatgac ttgctccaga tctctgagcc aaaaggagaa  28920
ggagtgtcgg gttcaacctc ataacatctt ggtatcccta gcccagttct ctaatgtcat  28980
attgtctgct tgggaagctc atatgcaata attacattag gattttatcc tagacccttg  29040
cctcaagcaa catttaagtt aatattttgc tggagtgata gttaatcatc tcccccttt  29100
tcttccactg ggtatcaatt caaaggaaaa tggggaccat tgaggaggaa gactggtagg  29160
aaagcgctct atttattgaa atcagttttt acatcctccg gtttggagag tttagtattt  29220
gatactattt tcaaggctgt gatgttacta gtgaatttta aagttgacca tcaagttggt  29280
gatggatctg ttctggggac tccagtcatg cttcctggac ctctagatgt gtcaacaaag  29340
tggaaaactt agattgctct ggctgtcttt cattacctct tggtaaagca aactgtatat  29400
gatacttggt aagatacctc cccaccaccg ccaccatcaa atacattaaa actcttgcaa  29460
ctcaggtggt gacaatacga aaaaaatata caagggtgtt ctgagaagga agagttgaga  29520
accgttgata gaatgtaact tagttattta aggttgtgaa aacagaggct gtgtgaggtc  29580
cggagtctta gtcaaggtca ctgattcaat tagtggtaga gttgtttgta gatatcatca  29640
agaaagagta ggagaatgtg atacaaacaa tgacacatct cagttggttc tttgtatctt  29700
gatgaataac tttctcccag gatacagcct atgctcttta gaacaactta gtatttgtgg  29760
aaatgatatt agtcttttta ctttggaaca ttttagtaac tttcttcatc catagactaa  29820
aagaaaccct gaaagccaga aatagagaat gcagaattcc ttaatgaaga aacgcgttat  29880
aaatcagaga aatatggctg ttcatgacta tgtggacggt gtctactgag tggggagaag  29940
atttggcaaa tatttaaggt catgtattta ctttatcaaa gaaaaggaaa caaagttatt  30000
gtttcatgaa gacccccagt gaaatcgaaa ggcctagatt atctagcaga attgaaggcg  30060
gctctgtgta acaggttcag cctgggcggt gacacagtga tgagtcagcg ggtgcattcg  30120
gtcactgctc tctgtgtctc taagacaggt gcttgttcta taagtgaaat atcatatatt  30180
ccccattatg gataagtcca ttaacatttt tctaagaaat gagtcattaa cctatttaat  30240
gagtttattt gaaaactaat caatttagaa tttgcctaag gaccaataac taactaatca  30300
gttgttgcta ggtggttatc ttctggggaa ttgagtattt tgtcagtgcc tttttatttt  30360
taacagccct tgtttttttc ttttttttta attctcagga aaaaaatcat ttagctggat  30420
ttttatatga agataaatag ttttcataca aatttaattt cacagaagct gccattattc  30480
taatgacgtg ggtataacct cactttcaaa agcagaaaga aacactttag caaacacata  30540
aaaattctta agatattcac actttaaaaa atgtaatagg cggccgggcg cggtggctca  30600
cgcctgtaat cccagcactt tgggaggccg aggcgggtgg atcatgaggt caggagatcg  30660
agaccatcct ggctaacaag gtgaaacccc gtctctacta aaaatacaaa aaattagccg  30720
ggtgcggtgg cgggcgcctg tagtcccagc tactcgggag gctgaggcag gagaatggcg  30780
tgaacccggg aagcggagct tgcagtgagc cgagatcgcg ccactgcagt ccgcagtccg  30840
```

-continued

```
gcctggccga cagagcgaga ctccgtctca aaaaaaaaaa aaaaaaatgt aataggcaaa  30900
tctgtggcct ggaactcttg tgggcagtgc agtgtttgct ttgtgcaagc tgtcaggcct  30960
ctcagcatca agagacagta cctccttcct ggccagcacc cccaacggtg agcgccgtga  31020
cccaccaaac agcaggtgag attggagacc tggctggatg agcaaagcag gaaagcagtt  31080
ttgctatccg ggcgaatgga gttacggacc ttcttccagg ttaagaagaa agccacgttc  31140
ggagcgccct gtgttgcagt gatgggtttg ttgagcaccc accaatttag tcaggaaaac  31200
tgatgcagac gtgtggtctg gggtcttca tgaatcggcc agaagccttt tccccagcaa  31260
ggtttgggtg cctctgggaa cttttgcctt ctgcagagga cctgggaaga gcgtgcacct  31320
acctgcaccg ctccgtgcta tgaaccaccg aaaataggga ctgaagtcag ggaccatctg  31380
accacgtgaa ttcccgggtc tgcggcagaa gccgcccccg atcccgtcat ctcagtggcc  31440
accctcaccc atgactgccc tgcgctgcct gggcccagcg catgccgggt gagcctctct  31500
gccctccttt ctttgttcgg gacttcccat acccagatgg atggataaat aaggggaatt  31560
gtgaagcagg gagaaaagtt ttggaaatag gccagaattt ctttactaaa tttaaaaacc  31620
atgcacataa tcctttagaa actccacgca ataagcagga ttaagcaagt cgtggattag  31680
agtgtattga gcagagactg tttctgtttg aagaggtcag aaatggaggt actgggaccc  31740
tagtttactg tggacattgc agggcttctg aacttcccag acagcagaaa ttcctggaaa  31800
agtagagtct tgtggtcagt ttcttacccc acacctttgg tgcattttaa aaaaataaat  31860
tactaaagtg ctttgcttca gttttattct ggtatgatag taggtattca ctttttattg  31920
tcttcctgca taaaagcaac ctaaaataac gttttacata cgcaaatgaa acagaaaaca  31980
aatccataag ctacccatac cctcttccag ttctatatat caggtgagtg tgctgagact  32040
tgtacaaata acttatgttg tcaagtagac atctactaaa tgtatagttc aactgaaagt  32100
atatttgagt atgctttagc aaaatgtgtt agttgcaaaa gtaccaaatc tctttttctc  32160
ttttaaagta ttataaatcc aggattgtaa atttatttta attgcagttt cagaaaacta  32220
actttaattt agctggctga gaaagcaaaa gagaaaaaaa ttaaatatta atattgaact  32280
gcatgaaaat actagataca aaggctacac aaaacccttt tagatataaa catccatgaa  32340
tttgcattca ttgatgcaaa gacattgttg agattatttg ttctgacaag ttttttaaat  32400
gagaatttct cctaaaggtt ttgtagcttc tacatgtaag ggcattttgg tgtttgggga  32460
cagatgaaag tttcagtggt ccagtagaaa ggacacacct tggttcagtt tgccgtctta  32520
ctgttatttg cagcttagct tatcagtgtt cctagttcga gatgaaataa tcactgcaat  32580
gaaatgtcca agttttccca gcagggagca tttaatgaag ttcttagaac aagtctgggt  32640
gatacacatt catctgtgtg agtcttgatc tgtccaggtt cgctgggctg tttagaatca  32700
ctgggtcttc agccatttcc aaaacgcaga acacagttga tattttaagc caatcaatgt  32760
attgagagtt cagcgtgtgt cagcacaaga gtagatgtcc tgggagatgc agaagaaatg  32820
tgaagcctgg cctctgttcc ctaggtgcct tcagagtcaa cttggcagca tcccaccggg  32880
caccattttc tgggcagccc ctctgatcct tttcataagt gtccaccccg caggcaatct  32940
tggctgagca cagagaatgg gatgtttcac gggatgtctc tgctgcgaca gtggatatcc  33000
ttgctggaac attcacagta ctggtcccat tcacagctgg gaccactcag atgtttcacc  33060
ccttcacccc tgcgtgaacc tggggtgcat cagatgaggt agtgtttgta agttttcttc  33120
tctgaaaaat agtagctttg attctgctgc tatcccgatt cctagatgtc agcttgccct  33180
gagctcttgg cggccttgcc tccaagctct cctggtactt cattctgtgc tcagtctttg  33240
```

```
ttgtaaatgg tagtattcca gaaacttccc cattgtcagg tttcttggct ccttttttgta  33300
ggcagcccca aaggctgcgt taagggtatt gatcacattc tttctatagg catccctagc  33360
ctgttcagga aagcccctc ctttcctgcc agccacagcc cccaccggct caaagggctg  33420
cttgccgctc ttggcctccc tgccctccat ggtggtggcc agtgtaggcg aaagaaggaa  33480
gtcccattgg gttggggagc tccaagtcac ccacccgtga ggctgatggg ggagttagtc  33540
acagatgagt ctcctcccat tctcaccttt tgccaccttt tgcagttttc agaaaaaaag  33600
aaaaatagga actttactta tgggttgctt gagaaaggta gaaagttggg ggcagaaagg  33660
acgatggcaa aaatggtgag atctcccttt aatttttaaa tgtattcaaa ctgttaaatt  33720
tctgcatgtt ttcattacaa agatgacaat tgttgcatat agactatctc aaaaatactt  33780
catccatttg agcaatatga aagaataggc tagagagaaa cagatttggt ttttcaagct  33840
aaaaagaata acagaaagtg ggcgagtctt cagtgagctg tctgcctttg aaacctagga  33900
agtaaactta atttggatgt gcatttagga gatgaagcac tacaggtggt gaaatgctct  33960
agcaatgaag cagggaaggg agaggggga aaggaaattt gagccaagca acctgaaggt  34020
caggggaagc cggtcttaca gatgttaagg gaggaatcca agtaggcaaa ggggatgaac  34080
agcagtgcaa aggctctggg gcagcaggtt gcccggtatg ttccagaaca ggaaggaggc  34140
cagtgtggct ggcatggaga gctaaggctc aaaggagaaa gtgaagagaa agaggtagta  34200
agggaccagg aggaattgag cccggccagc cgtgctactg atgttagccc acatgtcaca  34260
gtgtgtgagg gagatagagt ccttgggaac aataaatatgc agagctttta aaaactttca  34320
tactgtagcc atcaattcca tcatcatggt ggtggtatcc ctgggtggtg gtggttactt  34380
ggtagagtat acgtcaactc gaatttcttc ctcaaaagta tataaaattt gaaaagacct  34440
agaagtgatc tagtggaatg aagacgctga ggtaccattg aggttgggga aactactggg  34500
acgtgcttac aggataaact gcaaaacaaa agcacaagtt tgtaatcatg gaatgacatg  34560
ccttattctg aaaacttaac gtttgtagcg taccttataa ttcataagac atttaaaaat  34620
ggtattgaat cccaataacc tatgcgtagg gttggatctt gttgttatcc ctgtttttta  34680
atggaaaatc tgaggcctga agatggtagg ccatgtatat gcctgccccg ccgttgagcc  34740
tggctcctgc tgttggagaa actttcccag tctgtagaga gaggatgtgg tcctggcaag  34800
cctggctcct gcctgattct gtatcttctg gtaacacaca gccgtcattt aaaaaaaaaa  34860
agacaaggtc tttccctctg acagactaaa agctgaatcc gcttatttcg aactctgcct  34920
tgaggcggga tgccccgtgc attatggtta actaggacct gctaaccatc ggcttatcaa  34980
acaaatcaat ttcactcttc agctaatttg gaaatgaaaa ttatagaagt tagaaaaaat  35040
gtgcagaaaa agtattattc caatgtatta ttccatttgt ttcatagaga tcctggcttc  35100
acaggaaaga gccaagggca tgggttttgc tgagggcgta agagcttggg gaaggtgagg  35160
gctaggtgtg tacgggtgcc ctgatgtcct cttagcctgc tggtgaggaa agtgcatgtt  35220
taataaatgg gctccagcca actgtgtgca gttatttgta gcctgcataa ttttaaaaat  35280
gtggttgagc atttaggtct atcttcagaa tttaggctcc atttgactta gttttcctga  35340
aatatgtaga aaactaatgg tgaaagagga cctaattctt gaattatctg cttgaactgt  35400
gttgctagtt attccaagta gaatttgtaa aatggtccat cattctctaa gcaaaatgag  35460
ggaaataaca attattttct agaaatttca tatatattga atattacaaa atcatgtaac  35520
tagaaatgtt taaatggtca cactgggcca ggcacggtgg ctcacgcctg tgatcccagc  35580
actttgggag accaaggctg gtggattaca agatcaggag tttgagacca tcctggccaa  35640
```

-continued

```
tatgatgaaa ccctatctct actaaaaata gaaaaattag ctaggtgtgg tggcgcatgc  35700
ctgtagtccc agctgcttag gaggctgagg caggagaatc gctggaaccc gtgaagcgga  35760
ggttgcagcg agccgagatt gcaccactgc gctccagcct gggcaacaga gcgagactcc  35820
atctcaaaaa aaaaaaaaaa aaaaaaagga aaaatggtcg agctgatttt ccagaatgga  35880
atatcactgc gtgatgctct ctgggaagag aaggcattaa gtctgtaaca cacaggacag  35940
aactactgtc tattctgtac gcatctgctt gatcctcagt tttgtcacct tggttactaa  36000
caaggtggtt agaaagttac atctctcttg aatccattct taaaggcctt caaggactca  36060
ggcacagcct tgggaaacca ggaaatgtga ctgtgtcaat caccacacag tccaacttcc  36120
ttttcgtgta ggaaatgttt tctttatcat taattgatca gttctcccct ttccaaactt  36180
ctggcaattt gggaaatgga atctttatgt tgctgggtat tttctccttc cacacctcct  36240
tctccttgct ggacaggagg ggagggcaga agacgtgttt gtggccacat tcccggtgtg  36300
gcccgcctgg acaggagcca gggtgcacac tgacctgcac agcctctggc ctctgtccct  36360
gggcctgaga ggcaggagca aggggcctgt cctcactctg aatccaactg ctggtgactc  36420
agggcaccct gctggaccct ccaggagaag ttggggccca cgtttctagg ctgcccactc  36480
atccaaacct ccctccatgt ccctgaccaa agcatttcgc agatctgggt cctctggtgt  36540
gtgaggctcc tcccagccca tgagcattgg aaaatgtcta caagatcttt gccattttag  36600
gttctaccga ggctaaagaa tgtatgtttc ctctgcttag acttaagttt ttgagtaact  36660
ttatagacac tttggcattt tggctgaaag ggcatgtgca gtaactgaat atgacttgtg  36720
cactgtttca gtgccagtgg gtcacatgca ggggagtcag agccaaggtg gatgaggctg  36780
ggatatctac atgcttggtg gggagttgga gtcagggtgg atgaggctgg gatatctaca  36840
tgcttggtgg ggagtcggag ccagggtgga tgaggctggg atatctacat gtttggtggg  36900
gagttggagt cagggtggat gaggctggga tatctacatg cttggtgggg agtcggagcc  36960
agggtggatg aggctgggat atctacatgc ttggtgggga gttggagcca aggtggatga  37020
ggctgggata tctacatgct tggtggggag tcggagtcag ggtggatgag gctgggatat  37080
ctacatgctt ggtggggagt cggagccagg gtggatgagg ctgggatatc tacatgcttg  37140
gtggggagtc ggagtcaggg tggttgaggc tgggatatct acatgcttgg tggggagtcg  37200
gagtcagggt ggttgaggct gggatatcta catgcttggt ggggagttgg agtcagggtg  37260
gatgaggctg ggatatctac atgcttggtg gggagtcgga gccagggtgg atgaggctgg  37320
gatatctaca tgtttggtgg ggagttggag tcagggtgga tgaggctggg atatctacat  37380
gcttggtggg gagtcggagt cagggtggtt gaggctggga tatctacatg cttggtgggg  37440
agtcggagcc aaggtggatg aggctgggat atctacatgc ttggtgggga gttggagtca  37500
gggtggatga ggctgggata tctacatgct tggtggggag tcggagccag ggtggatgag  37560
gctgggatat ctacatgctt ggtggggagt cggagccagg gtggatgagg ctgggatatc  37620
tacatgcttg gtggggagga ggagccaagg tggatgaggc tgggatatct acatgcttgg  37680
tggggagttg gagccaaggt ggatgaggct gggatatcta catgcttggt ggggagttgg  37740
agtcagggtg gatgaggctg ggatatctac atgcttggtg gggagtcgga gtcagggtgg  37800
ttgaggctgg gatatctaca tgcttggtgg ggaggaggag ccaaagtgga tgaggctggg  37860
atatctacat gcttggtggg gagttggagc caaggtggag gaggctggga tatctacatg  37920
cttggtgggg agttggagtc agggtggatg aggctgggat atctacatgc ttggtgggga  37980
gttggatcca aggtggatga ggctgggata tctacatgct tggtggggag ttggagtcag  38040
```

ggtggttgag gctgggatat ctacatgctt ggtggggagt tggagtcagg gtggatgagg 38100
ctgggatatc tacatgcttg gtggggagtt ggagtcaggg tggttgaggc tgggatatct 38160
acatgcttgt tggggaagag gagccaaaga tgtggatttc ctctgtctcc acatccttgg 38220
gcaaggactg gtgatcagct gctgctgtct tattttattt gcttctccag taaatgaact 38280
ttatatagtt ggtagcttgg cgttttccat tttgcattac tgaaatttca ataaatagtg 38340
ctttagttag atgtaaatct ctgtcatttg tggcagagga acttaaatgt cggcctgcat 38400
tttagggcac ctttttgtat agagcagaga gaagggaagt gctgtccccc agtggcctgg 38460
accaggcgga gcccagcctg ttgatgatgc attgtgtgtg cttggcatgt gtgacgtggc 38520
aagggattca tgttctctgt gggcagctgc ctgagtagta gacatgtgag gccccttccc 38580
gggcattttg tcctgtcctc aggacatgaa gaaagcagct aggcaaaggc actctttgca 38640
gctttaaatg gcctagagtt acccccagaa aaacaattct acttctgttc cacttctgtc 38700
caattaaaac aagtttgttc attttatttt aggagcaatt tgccattgtt tttgtgcatt 38760
cggcagttgt ttatttgctg cttgcagttg tggttgttcg tggtatcatt cacgaataca 38820
attttgaacg aggaagagct gtgatgacaa atgcactaag agacaccact gtggctctcc 38880
acaaattagc cagaacataa gggtgggagg agcctgtctt tccctggcag cacagggctg 38940
cctggtctta agaagtctgt agttgagaac acagcatgtg gttacatgta tacattattt 39000
gaaggtgcac aaagcaaagg gaagccaacc acaaaatgcc agttgtgcta gtagcatgtg 39060
cttctttatg aatgaaagaa catacgcatt tttggtatta attatttata tattttatac 39120
atgaaatctc atttgacagg ttccctgtga ctccactggg gaattcaggg tgggagaggt 39180
agtgccccca tcttcataag agggagcaga cttagagaca tagctgtaga gattacacag 39240
ctggtaagaa gtggttccta gatgctagcc ctggggaccc ggctctggtg tggcgacagc 39300
gcctttcaca cctgtatcct gagagtcgtg ggaatggcat gtagtttaaa gtacagagat 39360
gggggcatgg agtcattcct aggctcccag ggaagagcag gatgtttttg atatggccga 39420
ttaggaagaa tgggcacttt gatctctgca aagagagcct gcgcttcagt gactaagtag 39480
gatttgaccc ttcaaccttg actctagtag atggctcagt taaaggctac gtggtgattc 39540
ttaggaggct tttaaattag atagatggat ttgtccctgg agagacaaag ctgaaatcct 39600
atatcacata gatgttatag accgaggagg ggggatttac ctacagttat ttaagctttt 39660
aaagtagaaa aaaggtccag ttgaaatgat atataacaac aggctatctg gagatggata 39720
tattgtgaat aaataattat tctacattct cttaatttgg cagcaaaaat ataattaggt 39780
tttataattt ctgatataaa caatataaac attgttatgg tgtacataaa attttttttag 39840 attagtaaga aaaccatacg tataaacatg tgttaagtct gaggaaagaa ttacgtcgtt 39900
cattggctat ttgcgatttt aatgcacctt atatcacttg gcccaaatac tcttagggca 39960
gaagcataat gcttacattc acattctcaa atgacccaag aaagagaaaa gatttggacc 40020
cttaatgagt tgtagatctc atatataaac ctttacttct gttaaaggaa gaatgctagt 40080
gtaggatgta tttagcaatg attagattta ttgagcactt ttgtgttatg catgaaaaat 40140
caaatagaat agcggtagct aagagaaatt cattccaaaa gtgtgctggc ttcataaatg 40200
attttgtgat gtgtgtcctc tttttcagta gggtctgtaa caggatagtg tggtttttag 40260
tagatagtat tgcatttcta aagtacgtaa gcttgcagat aattttcaaa gggatatcaa 40320
ttagtttccc agtataacac acagatggaa atatatggtg tttttctgac aaatttgcct 40380
gtttttcttc gcattgtctt ccttagtaaa ggttgccatg ttcatgtgct ccttgaagga 40440

-continued

```
ttaacaaaca ttctgtgaaa ggtcaggtag taaagagttt aggttcattg ccatgcagtc  40500
tctgtcacag ctgctccact ctgcttatgg tgtgaaagca gccatatgta aatgcgtgag  40560
cacggctgtg cccaaataaa actttatttg cagagacagg caagccagat ctggccttac  40620
tttactgacc tctgcttgga acgtcactct ccaagtgggc tggaaagggt tttcttttct  40680
tctgggtctc acgcagtcct aaagcttcgt tctgttttag aaaactttgt tctcttttag  40740
aaaactttat tgagcatttc tgcctgtgag aaatggcatg aaccacatgg ggttttcgct  40800
tcaatttaat acctataagc tttactaagg acctgaccag caggctgctg gctgctgggg  40860
acagggaggt gagaaggcag ggcctgggca tcagctggca aggaagacca accatggagc  40920
acaccctcat cgactcacag gcttcactga atcttgtgac atgctagcat gctgtttaat  40980
gtccttcgag gagagtttta taaagagcta gtggttcact gtggaagttg acactctggg  41040
gccccaggtg acagttgcag gtgtctctgc tcctgccctg tcccacccat ctcattgtca  41100
ccaaagggga gcagagagga aagtgttctg ggagaagttg aggaccctgt tcttccacag  41160
actggcaggg aggcttcagc aagttgttcg tgcttcctgg tctgggtttt aactaaaaag  41220
ggtctaacat ttcataattt aaaagaaagg gtccacccgc aattcttgga actttttgta  41280
tctcaggtgt ttgtgcagaa gaatcatcga tactgtttct cctatggcat tggcggctgc  41340
tgcaggggca gtgggcaatt cttgccatag acgaatagct cacttcatgc acatggcagg  41400
gtttttaaca ataacactca gaaaagaacc gtgtacattc tgtgttacac aatctgctgt  41460
agccgtgcac tgtaaaattt atacaggctc ctgtatagga aagttgaatg tgtagaggga  41520
attggaagtg cagtaggtaa aagtttagga ggcctgattt tcctagtttt ggatgattaa  41580
gaccaggtct tatgtgcagg attaaacagg agttaaaggg ggagatacct tttactaaat  41640
ccagcctgtg agacaactag attgtctcat cctattttgt attgtgtcat taacatcaag  41700
ttgcaacttg atattcggaa tttttttttac taacaagcat tcaaaatgaa atgattttaa  41760
ttgtcagtgg aagtgatgag ctcatagaaa agaatgtttt cagtctttct caaggagggc  41820
agcaggaaag caagttattg cccctgtttg tcatggggaa cttattcttc catattttcc  41880
ttttaagtta gtttttttttc caatttaaaa gaaaagttca agtaaccgtt tttcctagaa  41940
tctctggctt ttgttatcat acccaacctt acctttttttt ttttttcatg ttcttagagt  42000
gtcttgcttt agtaaagtct ggagatacta aattatcggg tttatttttc tcagaattgc  42060
tcctgcaact gaaaagtcaa ttttcccttg taattctgtg tttaacataa aaggctgaaa  42120
ctgggcactg agatgtacct gtacgatatg tttgagctca tggaaggttt ccttgctttc  42180
ggaatcacat ttgctactag aaatacaaat tttaatttta agaagtgtat cgtttcattt  42240
tgtcaagtac atcagtattt gtaacactcc taattcagct atggctgaaa atgtgaaagc  42300
atctttacct actccatgaa tttggcctct gggtggtcca gtgttgctca ccaaaggcct  42360
gtgaggcccc atgtcccaca gccgtgccat ggggccctac gtggtggccg taagcccctc  42420
tgcagagagg accggggcct ccctgggcag agctgccacg acccaggtgt atatcctgga  42480
ttttgaacat cgaaatgtaa cattggaggc aaacatgtcc aaacccaaat tgtcaggaga  42540
aattatgaag aaaaaggatt ggtgagtcag actgtgtgcc gaaaatgctg cctgatttta  42600
ttggctggag caaattgacc ttatttccaa catgttctag gcttgatgcc cacttcagtt  42660
ttctgtaatg tgattgcagt catggtgccc agctccgtgt gacatgtcat tgttgggaca  42720
ttgttccata tattacaagg aagctttcct ccttgtctta atcacaatgt tttctagtga  42780
tttgttttct ttcctccttt ctctctttcg ggggagtcaa gttgagcagt ttgaaggtgg  42840
```

agcttttact gacagctctc tccttcattt gcattctgat tgctcttgta agtggaggag 42900
aaaaggggag gaattattgc ccatctgcag ggcattatgg tgagtggcac aggggactgt 42960
atcccacgta tgaatgtcat ctgtcacaag cgacagcaga aaggagatgc ggagtggata 43020
cactgcacga catgtcacat ggaacaactc tcatctctgc taaaagtgtt tttgtttgtt 43080
ggttttattt gctcaaataa ctctacgtgg atacgtctgt ggatggattt cctcacaaag 43140
caacgtctaa gggacagagt agtacagtgt gtaatgagcg atgtgacaaa ttcaatgagt 43200
atcagtaagt ttacattttt tatatagatt acctgtagca gcagaactgg tgtgtggtgt 43260
tctgtcattg tgttcatgag caacacgtga gtcttattgt tttctttttg gttttgccat 43320
tacagctgat gaattcagaa aatctcttcc ttcttagtga atattcaggg tagaacagcc 43380
ataaaattaa taattctttg cttctactaa aatgaacaca gataatacaa caaataaatt 43440
tttgctggaa tctcatcttc aggaagcctg aagtttgatc atatttaaag gttgaggatg 43500
tcagatgatt agtgttagaa aattgttggt gtgttttttt cccctggtca ggatgaacca 43560
ggctgatttt cagggtgagg gataacttca gttactttga aagtaaatga atataaaggc 43620
aaaagtttac tctcattcct aggtttgaat ctctggagtg ttttccagct ttcttcttcc 43680
tggggtaggg gagtgtcact gatgagtggg tggctgtcag gtgggtggta ggtatcgtgt 43740
tgccgtggtg gtttcaacca ggggcaccag ctcttggtgt ttggtgtctg aaagctgtgt 43800
gtgaactaca gagagccctc ctgagccctt gcacgtgtta atcatttagc cctatgcctg 43860
gggcctttaa tagtatgtgt ggcaaagatt ctaccaccag ctcaattgga aaaaggtatt 43920
tgagacatca gttcaggcag atggcttctg tcttagacct tctttctcta acaaatgaat 43980
aaaaatgata cttagggttt caaaacagat ccctttttttc caccataaat tcttagtact 44040
gatgcttctt aggtctctgt tgtatcccaa tccctctgct gcggctggca ggtcctagtc 44100
atctgggtcc aatctgaggt gtgctccagc cttttcctcg ctgccctttt gcacctccgc 44160
aaaggattgt ttctgctggt taattctgtt taaatcaccg cgagcgcttc caagcatccc 44220
aaagggtcac ctggaatcag cctcagcctc ctggggtggg gggatgtcta agcaagcagg 44280
tctgtgagag gcagggcact ggggagcaaa accacaggcc tgtgcccgct gagcacaccc 44340
agaccacagt tctcgcttta ccgtgaaagg aggcggccgt tgaaagcggt tgtattaacc 44400
taacaggaga caggctaggt gagacacatg cacgttgtgc ttgctctggt gcacgtgtgt 44460
gcatgtagat gtgtgtgaaa cgctgcacag ctgacacccc catgcctggc tctgagcggg 44520
tggtcatcct gtttctggtc tccctcacct cagctctctt gtgtcctttg agtgtgccat 44580
taacaggttc atcttcctgt aataaccctt ccttcctccc ttctccttcc ctttcccctt 44640
cctccctcct tctttttttt tctttccttc cccttcctct tccccttcct cttcctcttc 44700
cgcttgccct tcctttcccc ctttccttct tttttttttt ttttttgtca gccatcttcc 44760
cccaagttat cagtgaggcc ttgcaccaga gtagaattaa aaaaagaaaa ttgttgaaag 44820
gtcattgcat gaataaatgc atggatgaat tacttccttg ccatttatca gctcttttct 44880
tgcataatgc taatgcttag aaattaacgt tttgataact gtattctact tccaaaaaat 44940
aaaattacat gttcaactta attggagctc gcaaagatgt aatgataaga gttgaatatt 45000
acagcgatac agcatcctaa aaaaaacaat gaaaatgtca gtggcctcat gaaatcacaa 45060
atgaaaatgg aaagtaattt ttttcagcaa taatttaccc gccatttata tgacaaagtg 45120
cttaagtttg agaaactgaa gaacttacta gtttagctgt tttcaaaata acagacttag 45180
agttaacatg agataattca gccacattta gctaattgtt agtgtcaaaa taaaataagc 45240
aattgattag aaattcttct gtcaatggat ttgcagagtc tcagttacct gcttgtggtg 45300
gccatgggat tcttcccaaa tcagggtctc agggacaaaa tgcaagctca ttttagggtg 45360
aattacaagt ctcaaggtgt gttttagcaa atgcctgttt ttttttaggg gatacaaaca 45420
attagattct cactgaagtc tcctgggatt gaaaatcaca acaataatga atcagataac 45480
tcaaagacag atctttcctt aggaagaaat taattctgtt aaggttcatt ggcagaacat 45540
tgtttactta ttaaatttat aatggacata aagcttttta aaaataacaa gataggccgg 45600
ccgcagtggc ccacgcctgt aatcccagca ctttgggagg cctaagtggg tggatcacct 45660
gaggtcagga gttcaagact agcctggcca gcatggtgaa accccgtctc tactaaaaat 45720
acaaaaatta gccaggcatg gtggcacgta cctgtaatcc cagctacttg ggaggctgag 45780
acacgagaat tgctcaaacc tgggaggtga aggttgcagt gaaccaagat catgccactg 45840
cactccagcc tgggtgacag aataagactc catcttaaaa aagactaata ataataataa 45900
ataaaataga taaaacagcc tcagaatgtc gcgttgtagg gaattttaaa atgtccactt 45960
tgtatattga caagtatttt ttctgtaaag cttttggggt ttttgggggg ctatagcatg 46020
tagtgcctcg agttcataag gagatgtggt tttgagggac tcactctcag cttcagggca 46080
cactggaagt ttctgtcttg ttgagttcag tcctctaaac ttaagatgga gagaaaagaa 46140
tttggttcac aaaaaagtaa gtcagggagt atgataagag gctaggatca gaattctaaa 46200
ggattttaga agagtgtcca gaaatgcagt tggtataaat gcatctgcaa aggaaggaaa 46260
tgtacctgtt tgagagcaaa gcggtgctca ccctcatgtt gctgagtgat gaaaatgaac 46320
agtatgtcat tttggttaaa aagccaagaa gcttagaaag aagaaaacag cacgctgtga 46380
aaggtcaaaa tcttccaatt tgttctgtcc cttgaagaag gaatatatca agtaaaaata 46440
ggcctaaaac actggaaatt gagaaaggtt aaagaatttt gatccttcat cctggaaggg 46500
aggaagcaat tagatctggc cacgtgtcct cagtccctgt cccctctgag cacagcgaaa 46560
gggtaaatta cttaaactgg aacatatgaa agtttgagtg gataaaaata accctttcct 46620
aatgttgagg gttatgcaac aacacatgag gccgtgcagg aaccttccat tgctgggcac 46680
gttcaaaaag aggtagatga tccggttgga agttttctga gggcagaagt gtggagttat 46740
tagttactcc actttcataa cataatgcac atttgtagaa taaacatagt ttacagagca 46800
ttgtaatgtg tgtcatagtt tttcatctct gcagccctgg gaggaaggca agtggattct 46860
gtgtatccca cacaacacag gaagcatcaa ggcctaagga gttacagggg tcattccatc 46920
acacagacac gcagtgcaac ctaggaactg gcccttcttt ttctatcttg ttcgacagaa 46980
tgattcacaa aaacacatgc gaatattttt cttaaattga aaatacgaac ctaactgtct 47040
agacaactca ccatgaacct aacagctctg cttccaggaa aactcagagt tttcccactg 47100
aactcacctc tggaaaacag aatgaataca tgtttctttc tcaaaggtca tcagtttatg 47160
aaaatgaccc aggtcctagc tgtgggttag aggggccctt tctggaactc cagagattgc 47220
tctgttctcc tgagggtctc tgctaacttc cctcctttct ttttcagagt gaagatctgt 47280
ctggctttat caccaggatg tcacatgtca gagagtatca ttaaaagaag acgctcagca 47340
ctgtttcagc ccgaagctgc ttgcagtttt cttttggatc tgagcaatga ctgtgtttgg 47400
aaacatctgt ggactctgtt agatgaggca ccaacaaggc aaggtcacct gcctctttcc 47460
cttgttcccg gatggggcat tcatcattgt gctgtttgcg ttttgttttg ttttgtttta 47520
acaaaattag ctgaagaagt tattctcaag aaaattggat gttttcattg gccttcttaa 47580
attgtggcca gtgtctttta atttcttctt cttttccttt tggcaaagca gatataaccc 47640
tcagcatgct aggagagtgc acccgtacct atggaagtgg taaaatctgg tatttactgg 47700
cttacactca aaacgaccac agtcctacct cagttcaagg taaagccgga tttccgtggc 47760
gggggtccca caggacctcc tgtagtagcc cctgcgctgt gtgtctggag cgcggtcctc 47820
ggccttattg aaatggtcca agtagacagc tgcttgttgg attccagtgc aggtacctgc 47880
gatgtttacg tccacaccga gcccagtgtg ggactgacat ttctcaatgg aagtgaaatt 47940
tgggattgga ctttgaagac ggattactaa ataataatta ttatatgtaa ctgaagcaac 48000
ctacttttga aaatcaactg tattgggtag tgggaggtgg gagggaaggg ctttgggaag 48060
gggatgaata tctcttttta cctttaacag acttgtttaa tcttctcgat gtagatgttt 48120
atgtaggtac ttcacattgc aaacgccttt tattctattt acaagctcag atgtctctgc 48180
tctcctgaat cttgggcatg cctttctgta accaaaaatc cctgtaggcg tgctagcaat 48240
tccagggtgg tccgggtttg gcagatttga tttttaaaaa acgtattatc tttaataaaa 48300
tgttattatg tcaaccagtg aggctgccct gaacaaaaaa aacaaaaaga aaaaaaaaaa 48360
aggaaagaaa gaaactgata aaaagaggca ttccagcccc tatgttattg atggaaaaag 48420
aaaaagaaga aaagcaatct cgcagtacat gttacttgtc gaaaaaattc cggacaagac 48480
tacccttgtt ttatgttttc agtattctga aaataccagt gtgtggcagt tctcgcagat 48540
gttacctaaa actgctgaac ttgaccggca gaatgttctg ccgttttctg ctccctcgac 48600
acttgattgg agggctgtcg acctctcctc ccgtgggggc ttccccagtg cctatcttct 48660
ctgatagtca tggagaggtt acactaattc attggagatg taagttgttg gttttgtttt 48720
gttttgtttt tagaaaaata tatataaata tataatagat atctatcgct atagaataat 48780
gcattaataa aatgaggctt ttttagagga agaccaaaaa attcaatgtc ttaaaaatat 48840
atttaatggc aatgcaaaag tcttcctgct tccgtgctga actttagaac agaggattgt 48900
attgcaagac aaagttgaat gtaaagtgat ctccctgaac atttttaagg ttttactttt 48960
ctgaaattat acatcacagc agtgcatagg ccatataatg ttagctggaa ggtcaatttc 49020
agtgtatgat atactttatt aagatgtata aaaatcctga agtttttatt tagttttggg 49080
aataggcatc aatgggtggt atttgctttg taactccccc caggtacgat agggactgaa 49140
tatggaccct gctgaaagca gtgtattgac gcatatttaa ctcgccctct atccgtagag 49200
tagtcatgac actatacaga tggttcgtgt tcatactgca gcttaaaaca agcaaaatac 49260
acagatgata atatgctaaa ttttcctcta tcctgtacat ttcacaaaaa ggcatatgca 49320
atatttacat ttttaattta gtttacagaa tggaaccaaa atgtataaat gttatgtttg 49380
ctaaaacttc acaatgtata ttgggtcttt gtacattttg cctgacttac cttaaattta 49440
aaatattttt tgctatataa actttaacag ttattaaaca gtgttttctt tttgggtacg 49500
tattgtttct ggatatcaag atgttaaata tatttcttgc tattgtgata tgacaagaga 49560
cttaacttat cttgctctgt cttccactgt acacgctgta tataggggtc aatgtgatgc 49620
tgctggagac gagaataaac tggactagaa tagtgcattg tatttagtct gtattgatca 49680
tggatgccct ccttaatagc catatgcaat aaaataaagt acattattta tgaaatgaat 49740
acagtcctga agattttttc tgtacgaatt ctctgtttaa cataaagcca atctactttt 49800
agagtttggg agtaagtgag gaaatactag gctcctaaaa atacttggat accccttta 49860 attttaaaac ttttattctg gaagccaaaa aatacctgcc agataacaac atttatgaaa 49920
agtaaatgtg ttatataaca aaacagaaca ttcgatgtac tctacaaaac agagtcctta 49980
tgacgtgctg gatgccattc taaatacata acaaatatta acttcttgat agctcatgac 50040
aatcttagga ggtaagaatt gtcatcctca ttctacagag gaggagcccg aggtacaaaa 50100
atgctaagag acttgtgtga gagcacacag tccatgagtg gtaaaaccag gaccgctccc 50160
cagctctgca gtccagaatc tgcttatgca cctctgctta gtgctccctt cctgatgtgc 50220
acacagaaga tacaccaacg tgtacatcaa gaatgctccc tccatgacat gcacacagaa 50280
gatgtaccaa tgcatacatt aagaatgctt cctccggccg ggcgtggtgg ctcacacctg 50340
taatcccagc actttgggag gctgaggcag gcagatcacc tgaggtcagg agttcgagac 50400
aagcctgacc aacatggaga aaccccgtct ctactaaaaa tacaaaatta gccaggcgtg 50460
gtggcgcatg cctgtaatcc cagctactcg ggaggctgag gcaggagaat ggcttgaacc 50520
cgggaggcag aggttgccgt gagccaagat aatgccattg cactccagcc tgggcaacaa 50580
gagcgaaact ccgtctcaaa aaaaaaaaaa aaaaagaaga agaatgctgc ctccatgaca 50640
caaacacaga agaagacata ccgatgcata catcaagaat acaaagaaga aaatcatcag 50700
atccaggaaa atgcaattca ggaagcagaa aatagaaaat tgatgctgtg aatttttatc 50760
caggagagtt ttacctcctt gcttgaaaca tttgtccgtg catccacttt gccctaaaat 50820
gatagtcatg taataatgtg tgtgttatct tttgaacaaa taaaatcagt gcaatttgga 50880
aggtgatttt taaattacgg ttgttaagtc agcaagatgg actcacactg tggtgtggaa 50940
acctgtgatg ggatagccac aggctgcatc ccctgtttgt gcctggatgg tttgttctgg 51000
gggagcctgt tagtcacaca gagtaagagg cctgatctgc aagtcttgat atacctgaaa 51060
tctgataacc atttcaacaa tgaaagggca aatgatgcag tcattccaca ggcctcatct 51120
aaggcaggaa cggacaagtg atttatctga aagagccatt gtggagaaag tacagcaaaa 51180
tggagttgtt tcaaaggtcc acagattctg gaaataccac tcaaaaccaa tgcagggcct 51240
tttccagaat gttaagtgtt atatgacaag atgagaagac tgcaggctgc aataattttg 51300
gaagaatttg gttctaaccc actgatggcc tcgacaggca gcttgcaaga ggcaccttag 51360
ctcatggtac tgtcatgata tttgagtccc atccttgagc tgatctgcag ctcgtccttc 51420
ctcaaacctt ccttaagcat tgcttcacag attagatggg ttgctcatta gtgcatatca 51480
ctgtgagttg accaggggta atagcatttg agtgaagcta gcattacttg acatagcaac 51540
ttttggatgg caccagttga aggacagagg ggacgattcc tccactgaga atgtgcagtg 51600
tctcttccct gtcattgccc cagtagtatt tctctgaatt ctataaccaa gtgaaatctg 51660
atgtttatgg gtcttgcttt ggcaatgata cacagatgat agacctagca tgctgcagtt 51720
gatagcttga aaacattaag catcccttca ggagctcctt ttagattttg accctcacag 51780
ctgtgtcttt cctcttgtct cttcagcctt gtttccctct gcagatccca atgaccctaa 51840
atagcaattt ggtggtttct tgtcctctta tcattagtgc ctccttcatt tcacactggt 51900
cccgctttcc tacctgagcg gtcagatgac tcacagcctt tccgctgcat ctggagactc 51960
tgtcctattt taggcacttg gttcctctga caggagctct gtctgagttt gtgcctctga 52020
acttttcttt ttctgcattt caaaatcctc tcctttcacc ttggaactca aaaagttcta 52080
aatttttacg aaaattactt ataccccagg aaacctaccc cagctctttt ccagcctgtc 52140
tgggtgtgtc aaatacatat caggaactgt acaacgtgct cctgtctctc cagatctttc 52200
tggttatgac acttaattct cagatgacat tgacagaaaa catactgatt gatagatttt 52260
tctagaaaag atgcataaaa caataaagga gctgtattaa ttagcatgca tttagctgca 52320
agtaattgaa acctcaattc aatggctctt agctgatctg agctgctata acaaaatgcc 52380
atagactggg tagcttatag gcaatagtat tttttttccc tcacaattct ggaggctgag 52440
aagtctaaga acaagctgct ataatgtggt gtctggtgaa ggcctgctgc ctgcttcata 52500
gatggtactg tctcagtgcc ctcccgtgac agaagggttg acctagctct ctggggtccc 52560
tttcataagg gcactaatcc tattcatgag agctctgccc tcatgactga atcacttcct 52620
aaagaccccc acctcctaat accagcactt tggggattca aattttaata taggagtggt 52680
gggaggacac agacattcag actgtagcaa gctcagagca gtagttctca aacttcagga 52740
cttcttagaa ttatctggag gggcttgtta aaaacagatt gctggactcc actcctagac 52800
tcttctcagc aagtctgggg tagggcccca aaatctgcat ttctaaaaat ttccagatga 52860
tgctgatact ggtctgggac cacacagtga aaatcactaa attgcaaagg gatgtgttaa 52920
ctcacacaac aggaagccca gggctggtta attaggcagc taagtggcgt gcacagaagc 52980
cctggatctc ttcatctttc tactcagcca tcctcccgat ctttgctttc atttcagacg 53040
cttggccccc tgtgtttcta agatggttgc ggcagctcca ggcagcatgt catctcataa 53100
caatgtccag caaagcagtg tctcttcctg gggtgtcttt ttggaatgat gcaaatgacc 53160
ccagagccac cccaccacca gctgcctctg cctcacttcc attgtctggg attgggtccc 53220
aagctcctgg ttccattgat tatgaggaag gagatggctg atttacacta aaagagatgc 53280
accctccagg gctgggaggt gtccacatcc catgaagaga cagttgaaca aaagctgggc 53340
attggaaacc aggaaaaagg agtactgtca cttcagtagc aactaacagt gtctgctata 53400
acagcagaaa atgaaagggc catccttttc aaatgcaatt atatctctaa tgtatgatct 53460
ccatctacag cgattttgaa agggggatt taaaataggg taaaagtaga acaaaattat 53520
gaatctagca tggtcaaaaa gaggatggcg tcattgcttc actataggct tcacgtatct 53580
ttgcttttgt tattaaattt tgtgcaacat gggaagctgt tttataaaag atcaagatat 53640
aaaggattgg aaaattggac atttgaaggt acatcaaaga gctaggacta tttagactgg 53700
aaaagaggaa actacgtggt gattgattag cattgataac attaggggct atagataaaa 53760
taaagattag tcagctgacc tcctcaaaag atgataaaac cagagaaagg ggtagaatac 53820
aattagaaaa atgtgtccga tttccataaa aaataatttg ataataacga gggttattaa 53880
atatcaactt tgaaataatt gttgatttca ttgcctggag gccttaaaaa ataggacttt 53940
gcagctgtct ttcttcgtag tgatgggaga ggggacatag accacataat ctcgaccagc 54000
cccttccccc aggggctcag catcgcacag ctgaggaggc agccaccccc tttgttgctc 54060
atgtcaacag ctcccctgga cttgcacagg gcatggcctg aagcctgaga tcctggcttc 54120
tctgaggata agagaactac tgagcatgga tttaatcagc aaaaagaatc accatagttt 54180
tttctgccta gtttagtctg taaagtgttt accaaagtag tatttaggaa tctgaaggaa 54240
agatctgaaa tttgaaggaa ggatcagagt atgaggtcca tcctgaatag tccagattca 54300
taagattata agatcataag atcatgctga tagagcagct ctaaatcatg ttgcttaaag 54360
aggtttttaa atacaggaca gccaaagtga caaagtgatc tttatcaaat agccgggccc 54420
tcttgctggc acctgtagtc ccagctactt aggaggctaa gttgggaggg tcacttgagc 54480
ccaagagttg ggggccaaac tgcacaatat agctagatcc tgtctcaaaa aagaaaaaaa 54540
aaataaatgc atgtataatt caaattctcc ttcctcccca ctcacccatt atcttttagg 54600
aaaagtcaaa gttcctgaac gtggtaggcc tgagacataa ggcactatat gaactggctt 54660
ctgcctaatt ccccagacac atcttcaagg ccctgtccct cccgctccac ccctccctgt 54720
gtctgcacct aagccttcct agagcacata aagtgcacct agctcaagta aggaggagaa 54780
cataaaatga aaagacaaag aattgctgaa cctaaaaaca aatgtttatc taccaagagt 54840
tactatttcc taaaagatcc cttgaggaaa ggtatgcaac aagttagaag catttttaaa 54900
aataccattt aaatgctata cagcattgct tcacttcttc ctttgaaatc tgaggacatt 54960
catcatctca tttccattca cctctccttt ctccttttc cccaccttaa catttgtcag 55020
ttacattatt ttctgcattt tcaaggtaaa aaaatacatt ttttctgtaa tgtaattcct 55080
atgagtttaa aatacttatc cttcatttac attgatccat ttcatgccac ccgttctttg 55140
aacatgctta ttttttaacc atctattaat tgcttggatt ttgttactga aaacaaacaa 55200
ctcaaaactt ctttccagac actttttaat atgctctgtt ccctgagctc tctcatattt 55260
gagaggtaat ttgcctgttg tctttataga tgagcaacaa attggctatg tagatcactc 55320
ttaggtccca tacgcctttc caaagaagtt tgtgacattt ctccagcctt cttatttatt 55380
gaatcaggag attttgatga gtggttttca agttcaaatt actctgggga aattcacctt 55440
gcacaaaggt gccctaaata tacaacccta tctacctaac cagactcacc ttctgccttc 55500
taccacccca tgaacccagc gttggtcaca gttgcactga tcctatcacc aaattttaat 55560
ccttttatga ctcggctttg cataaaaatt tcatttgccc tagagtgttg aaacctcttt 55620
cttcatctag agacttgtac tgactcttca agacaactct accatgtgtc aggagaagga 55680
aaactggaaa tatccagtga atgcttccaa tgactataat gcaacctgat ttcaactcac 55740
ctaaacagag ctagtgaccc acttctccag attctcaaac cactctgctt acccttctgt 55800
tacggcacct tccaagtttc actgtattat ctgtttatct gtgtttctcc cacgaggggg 55860
ctccttgatg gaaaggatca cattgcagac atggtagcta gcaaaactgt gttactgtaa 55920
ccgctgagca actctgttca gacatttatc tacctctcat tccatattca cacacctctg 55980
agaactaagt gctattaaga aaactgaagc tcagaaaggt taaacacctt gctcagggtc 56040
acaactaata agcagtgagt cagaattcaa agcatttatt ccaattccag ctctttccta 56100
ctgtgtttta gtgaacctaa cacaatacac gacacatagt agtaggtact caacaaatat 56160
ttgttgaata tttgaatgaa tgcatttgtc ttgtatacat ctagaacact cgcaggctaa 56220
gagactaggt tgccttgaat gattgtattc tatatttgca caatttcttc aacaattacg 56280
ctgttttatt ggctttatga aggcataaca ttgctcagag aagtaaagtg cattcgttga 56340
attataataa gtgactaaaa ttgaatccca atggttctct gatatatgta taggaaacct 56400
ttaactatat atagcagaaa agccaaaaca acaatggctg gaacatatat aatgttttat 56460
tctctcagat gaaactagac agatgtgggc attccaaggc tggcacgggg tttccatcac 56520
ttcccaggac ccaccttccc accgtcattc agctttagca ttttcagtgc acacctttct 56580
gtcttcaagg tgcctcatag tccaacgtgg ctcctgaagc tccagccatc acactggctt 56640
tatccacaag aaaggtgaaa ggggaaagta taaaaatggg tgcctctgct gggcgagtca 56700
gctactttat aagtgagtct tccacttaag tcttgtacgc tgcatatttg aaacacctca 56760
ctgagaacat ttcctttctc catgattgat ttctgcgact aatttctatt gcattctcct 56820
cctcatccga tatgcttctg gatactggag atcgagtgga gaggaagcct gagtgcctgg 56880
acttataagg ccttcttctg gtgatcagca agtaaaacaa atatgaaaca caagatgaag 56940
ataagaaccg ggaggaatag cccaggcgtg gggagagaa ggctggtttc caggggatgg 57000
tcagaggcgg cctctcggag aaggcaacac ttgatcagag ttcccaaagg gcctactgtg 57060
gggacctgaa ggaagagcag cgcagcaggt gcaaaggccc cggggtggag gcatacttga 57120
catggtggag accaggaagg agggccacga ctcggtccct catctctcat tccacttttt 57180
aacagttctc tatttagaac tcccatgttt caatgagaac ctattataga aacagtctat 57240
caaagtcttg ccatttaagg gtgatcatta agagctttgc tttacttctt cacacagaga 57300
aggggtggga gaggaggaag gacagtgtga agcagacaga cagaaactcc cctttggctt 57360
tgaaggtgta ttctttgggg gtgccgacat attccacaag acaaggcagg gcacagggag 57420
gctgggcgtt cacgtagaca gtgtgtcttc cagcagaagg tgtgcgtgac gcccgcctgc 57480
acaggaacgg gtgcaagcac tcaatacctg gtttctatcg gggcactgcc tgggctctgc 57540
tgtttcaaca atgcacttgg cttcttccat gacccagagt tgctgcagaa accactgctg 57600
agagtacgat tgattctctg tatgccgacg tgtccaagga cagttagtag gagcggaggt 57660
ttcagggcat caaggagtac tgtccttgca cacgggcaag gtactgataa gctgttgtct 57720
gaagcccgag agccggtgca ccctgccgtg accaggcgca gctctgtgct gcaggataac 57780
gcgagctatc tcatcactgt ctcatcactc aaaaggcttc tgatgaaggc cgtggctgaa 57840
tgggttcggt ctcatgctaa caaaatcttg atgcggatgc accctccatc ccatgtttaa 57900
gatctttaat tttatgggta cgagtaataa aaaataatca ggctgtgtat tttctgtatc 57960
cactgatata aatgttggca tcagcattat tataatctta attaccatca ttggttacac 58020
gtgctaaaaa tgttcacgcc gtctaaaaga aaataaaaac aagcggcggc aggacccctg 58080
ctctcacaca gtaaagggca ataaacattt atcgacatgc tgaggagagg agattgtcat 58140
atcctattaa aataaccaaa gataaggttt taaagaattc aacctgtcgg gctgtctttt 58200
catacgaagg ccagagactt cccggaaacc gcgatgtccg cagtggcgtg gtaggatctg 58260
gttggtaact gtgcaccgcg gggtatgtga gcgcaggcgc tcccggagca gcgacacaga 58320
cctgttcatt tgaaaggcat tagaggagaa actcctgcgg tcagccttgc caacctcctt 58380
tgtccccgtg gatgtgtctg gacacccttc atcaccctcc ctcgggggac gggaagcctc 58440
agttaagagc gaggcccagt gccctccctc caggaaaccc cataaccttc acttccaggg 58500
taaggggctt cgtctacaca agctccaccc gtcagcccca gcagcctttg agctagagct 58560
ggcggagggc accgcctggc tctgcttctc ctccaccgcc ctgcccttca gagagccagg 58620
ccagggagtg gaggcatgag gggcgaaccc taggggcgtt tgcctgggat tctgctgttg 58680
gcctccctgc tgggtgtggc tgaggcccga tgcccactgc tgcatggcgc cacggcagcc 58740
cttgccccgc caccccatcc acagccctaa ggaggcttcc tcagccgctc tgtggagctt 58800
tcgaggatcc gcttgaagat gtcagcacac tcctccctgg ccggcagcca atagtttgtt 58860
tattgctctc aaagcacact cacactcttt cctcccgtcc agtccatttt ctgaaaacac 58920
tgagctcttg gctcacggtc aatgccttct gcttttatct gctcggcctg aaacagtgac 58980
gtccagccaa gaggccagag ctagggctcc tccgatgctc ctccgatgct ccaacggtgg 59040
tggccctgct cctcgatgag gccggttccc gcaaggccga tgcttaggca tttcagagag 59100
atgcactctc cctcttctta tcgctttccc cttctgcttt attaaaatta ggtgactttt 59160
caagactcca tgcaaaaggt ggcatgcata gctctggcca tgcaatagaa actaaagtaa 59220
ggttcccgtg tataatccaa tcacacagct gccccgcctt ggtctcacac caggtctgca 59280
agatggcagc ccctttggtt tgccctccag ccttctctta agtcctggag ccgctctggt 59340
aattgagcct tccttctggc atcctctgga aggctaattg aatacagcag gaggcagtca 59400
cagagctttt tagcatttct acttcctttc atttgcacac ttttccaata ggaagcaaag 59460
ctactcaatt caggagagaa ctcccctctc ttcctactta acctttctcc tgcatacaca 59520
atcgggctac tcaaaggtat gctgtttcct ttccgctaaa agtttcctcc taattacctc 59580
gaggcatcca ggtgtggctg aaaatatgct caaccccggg tgtaaatatc tgcacctaag 59640

-continued ggcagtgagt agcagagcaa aacagcttgt gcagggcgca gtgtgcttaa aacaacctgc 59700
agctatttat cgggtgactc agacaggatg caggggccag atggttagca tcttgcaaag 59760
gctgacgggc actttcattt gattgtttaa gaataagttc acaccggaaa ggggatttca 59820
cacgtcctct tccattctgg attttcagtg tttcattaag ctactttata aactattatc 59880
ttggagaaga aacaaaaaaa cttttaatta tgtttccttt gcattggcgg tcaggcagac 59940
agatgaaatt tttaattatt gaactgctcc aaggtgtgcc tgtaagtata tctaaaatat 60000
gtcttgaaat agttattgta ccttttteta gaaaatgata acttctatgt tttctttgta 60060
aaataaaaac ccacttgtga ctggtataca aggaagaagc tgacctgaag ctgtctaaat 60120
aataaaggca aaactagtag acccccaaaa acgatagagc tcactcttct ctgtctctgg 60180
cacgtggaga aggcatgaaa ctatcaaagg ccccaggaat tgaacttggg aaaacttggt 60240
tcaagtcggg tggggcagtg ggcaaagggt tgatgttgtt gaatgtcatg gacttcataa 60300
tcagtaggca taaggatatg atcgcttaga tgtttagcgt ggcagtgaaa tagtaaaagt 60360
gcataaaggt agtctttaaa gagtgagcga agcaccatgc cgggtaggta ttgaagccat 60420
gtcagttact aagctgaaca tcaacaattt gctttggtgc tttggcacat acctaaaatt 60480
gtcaagtgag tcctttattg aaaggtaagg atgcttgttg tctagtttct ttggatgttt 60540
ttatttggaa aaccttgggt gaagtgtcat taaataatat atgatactgc ttttccttct 60600
ttccttcctc ttccccttct ccttcctctc tctcttcctt tcctctttct ttcttgacag 60660
ggtctcactc tttcactcag gctggcatgc attaggtgct atcagagctc accacagttt 60720
cgaaatgcca gactcaaggg attctctcac ctcagcctcc tgagttgctg ggactacagg 60780
catgcaccgc acctggctaa tgtttaaaaa tgttttggcc gggcgtggtg gctcatgcct 60840
gtaatcccag cactttggga ggccgaggcg ggtggatcat gaagtcagga gtttgagacc 60900
agactggcca acatggtgaa accccgtctc tactaaaaat acaaaaatta gctgggcgtg 60960
gtgtcacacg cttataatcc cagctacttg ggaagctgag gcagaagaat cgcttgaacc 61020
tgagagatgg aggttgcagt gagctgagat catgccactg cattccagcc tgggcaacag 61080
agtgagactc catctcaaaa aaaaaaatat tttgtagaga tggggtttct tttgttgccc 61140
aggctggtct tgaactcctg gcctcaagcg atcctgccca ccatggcctc ttaaagtgct 61200
cggattacag acgtgagcca ctgtgcctaa taatgctttt caaatgtcaa catgcacaca 61260
aatctctctg gcgatctcgt taaaatgcag agtctgattc aggaggttgg gtggagattg 61320
agagcctcat ttctaaccag ctcctgggtg atgctgatgt tgggctgggg cacgcatttc 61380
ggacagtgag gggtgggtga tgtgaagcag acagtagaca ggaaatgcat gttgagaaga 61440
ggagctaaat cctgaaagtc agtggccctc accttattcg ttcttcctca aactctgcct 61500
tacccagggg gcacagtaat acgccttaca agtcctgagg tggaacagga ggatggactc 61560
acagacatgg caggaaggga gctgggaacc agaactgtct gggctctgag gctggagtgc 61620
tgagggcctc cgccctgact aggggtgtct ggtggaggat ccagcacaga cccactggct 61680
ggaaggatcc ctgtaaaatc cctgaaagag aggaggagcc tcaccccaaa tgaatgcctc 61740
ttctctaggc ctctctgcag ccacccatgc atgccagagg tccatgcaag atttgccttc 61800
tggagcttgg ggagaagtaa ccagaagtca tgtaaacatc atggtcttga ttctttccct 61860
tcctgctgat cctgtctcac tccagtgtgg ccctcaatga ctttccttct ccttttctgc 61920
aaatgtacct gacggcttgc cagacagaat ttccatgctt ggttagaaag gacgatgcag 61980
ctgagatgtg agatatttat tgcctctcga ctggagtttg tgtgacaccg cacctttcat 62040

-continued

```
ccgcacgttt gtctcccatc tcataaaggt cagagttctc atctgtgcac cgctctcttg  62100
cttgacaccc cttccccagg tgccctcatc cccccatgac ttcagctccc tcatctacat  62160
cctcaacttt gacttccacc ctcacatcca ctgctgcctg cgcggcaact cccagggctg  62220
tgccatggat gccccatgcc tagcttctca aacagaaggt ctcaccctgc catggcctgc  62280
tcctcctgct gaatctaagc cccactcagc cattgcagcc aaacatactc tgcctcttcc  62340
gaacaagacc tgggctggca tctcacaaga tcgcatggcc tgagtccatc tgcatgccga  62400
tggcactcaa atccactctg catctccaca tgcctagcct gcacatgcct caaaaccaac  62460
atgatcaaag cgtggtcttt cctgaacaga cccacccagc ccacccctaa ggtgccctcc  62520
caccagcctt ctctgcaccg ataaacggca ccaccagccg tccacacact caggccaacc  62580
agccgagcac tcgccaggac tcctccatct cacagcccac attccatcct tcagcaactc  62640
tgtcgccttg acctcagagc atatcccggt ctcagtccaa cctcctctca tcccttcccc  62700
tgatagaaaa gtcgccatcc tttcttgctt gggctacaca gcagcctcct aagtggcctc  62760
cccctggcat ccttcccctc attccactcc attctcccta ctacagtgca gcgtcagcca  62820
gttcagatcc ctcccatgtc ttccagcaca cttgaagcag aatctgccct cccttccagg  62880
gtgcacaaag gcctactgtg tgtcacgtcc attcgtgcca atattgcaca tccattcacc  62940
tttaaatgtt gttgggctga gggtacgact gggaaaggag aaaataaaga tctaattttg  63000
attaggcgat tcatgttcac acaatcattt gaactgaaaa tgcccatctg aatgcccaca  63060
cagacgtcat ctatatgaat tggtataatc agcacatgag aataaaagtc cttgcctgca  63120
ctttcctctt ttcctttata acagcagtgc tcgcacattc aattccggca cggtcacctc  63180
tgactcgctc gtcactgccg cttgccatca caggtgtttc ctggtcagtc actgtccact  63240
ggctgcatcc catggtgcaa gctcattctg gaaccttgtc tttgagctgc ttcctctcgt  63300
tctatcttct gcagatacca ctcctctgtg gtctggggat tttctctgcc aagaacatca  63360
tgcagtttgg gggtgcagtt cccatttgtc tcttgacaaa gggaaacaca agtggattga  63420
aagcaaaaac ataagggctc tttccccgaa gccattcctg aatcctgaaa ctgaaagagg  63480
ggatccagag gaagtgtgga attagttatc atggaaaaat ccagggtgga aataaattag  63540
gctaatgata aaataattga acaacattct tgggtctgac ttcttaagcc acagtgttag  63600
aagttggcat agaatctgat ccccttatgtt acaggatcat ctatttcatg ccgtataata  63660
tagtacagta ggcataatcc ttttggggat agacttggat taaataaaaa ttatgaaact  63720
taatgtcact gtgtcttcaa tcattttctt ttcctttctt tattattatt ttgagacaga  63780
gtctcactct gtggcccagg ctggagtgca gtggcacaat ctcggctcac tgcaacctct  63840
gcctcctggg ttcaagcgat tctcctgcct cagcctcccc agtagctggg attacaggcg  63900
tgtgccacca cacgctacta attttcgtat ttttagtaga gacggggttt tcactatgtt  63960
ggccaggctg atctcaaact cctgaccttt tgatctgccc gcctcagcct cccaaagtgc  64020
tgggattgca ggcatgaacc accatgccca gcccgatcat ttttcttttt aatcacttac  64080
aaaacattaa ttttcaaaag gagaaaagaa ggtggggtag actaggatcc aggagaaaag  64140
tgtgttcacc tgtgtgggac tcagcaaaca tttgacctct cggggcctca ctttccttct  64200
acctgaatca tctcacaggt gactgaaata gattaatgca gcaaatatct atactgatca  64260
cctaccttct atcagtgccc ctatgcccca aggcatgggt ccttcataca attcttttaa  64320
aataaattat tacaaattga tatcaaatta ttatttggag acagggtctt gctctgttgc  64380
ccatgctgga gtgcagtggc atgatcatac cttattgcag ccttgacctc ctgggctcaa  64440
```

gcgatccttc cacctcagcc tcccaggtag ctgggactac aggcacatgg caccacgcct 64500
ggctaatttt ttggattttt tttttagtag agatgaggtc ttgctatgtt gctcatgctg 64560
gtctcaagat cctgggttca agcaatctgc tctcacaaag tgctgagatt acaggtttga 64620
gccaccatgc ccagccaatt agataaaatt attataaaat aaattaattt tataataaat 64680
gacaaccatt caaaataaac cctgaagatc ctttacccaa ttcactaagt tacattgtat 64740
atgacagatt atagtatcaa acggcaagtc tcagggccat acactaagcc ttatcgggaa 64800
ctgaaagtga tccatctcca agattttgaa cacagaagtt cccctgcttg gccacagcgc 64860
ccctcttccc ttgtcctttt ccccttcctg gagcatcctg gggtagactg actgtcaaaa 64920
cagcccacgc gttccgctgt cttgccctgc cctgcatcca gcctgcggtg atgtcacttt 64980
gtggctcttc tcatctggaa gtagagggta tttctctgca ctcctgagtc tggccagcct 65040
tgcaactcac tgtggccaat ggaatgtgga ggaagtggca ggtgcccgtc ccaaacctat 65100
cctcagaagc tgtctgctgg gaaacaagcc caggcaaatc tgcgagatga agagagacca 65160
cacggagccg gcaccagtcc atccggttgt ctcagacacg taggaagccc agcaggatga 65220
gccgtcgcca gccccccatc ccgactcaca gacttatgag caaaggtcaa ggtgtgctgg 65280
tgtccgccat gaggttgtgt ggttgttcag tcccgtgtcc aggtgatgga cacctcctgt 65340
ccctcccctc ttcctcattc tcccagccca tctccgttgc acagtctcac gtacctttct 65400
gtccacactg atcctgaggc agctgtgtga gcataaactg aggcaagaga ccagcccaga 65460
aaggctgaca gatttcaaat ctcagacccc aggtgacctt gtggtaaggg acattcctca 65520
ccctgggtgg caggtgacac tacaagtcaa gtcggtaatt ctaatctcaa cttaggtccc 65580
attgatgttt tgttattcct gtctctttaa atgacacctc aggtgactca atacatggac 65640
tttttcactc cctccccttc ggcccactta cctgctacta ggcctgctcc acacaagtga 65700
tctcatatcc aggaggtggg gtgccccaag caggagtccc cctcctctcc ctcctctctt 65760
ctttaagctg tccctgctcc tcctcacaca ccccagcttc ctgcattttg cttcatgctc 65820
agagctagcc agctgttcag caagcactcg atcagaggct gttctacgac aagggcatcg 65880
ttcctgcctt gagtcactct caagctaatc agcgtgggtg gctggtggaa aacatgcctg 65940
tgagaaagca aatgagtgga tggcatcatt gggacctcat ataaagaaca aagactcatg 66000
gagacactag aaaatggaac cgccccaggg aagctctata gagagaaaat ccagctacac 66060
cttggaagga aaaagacctt tgtccagata gagaaaggaa aaaatagaac atccatctac 66120
ttcttgcctc gccacttatg ccgtgctcct ttgcaatatg gactctgcca ccctcagccg 66180
ttgacagggc tgtgttgaca accttctcga tgccaccgtt gcaagagctc ccaaccccct 66240
gcagcagcag ctcactctgt tgactccttc ctgcctaata aaggtcatag gcaccattcc 66300
ttagtgctag ttgtcacaag accttgcacc aaacacctta cgtcttattt caccccttgca 66360 acaactccca tttacaatgc agagaagcgc tgacagggcg ctcagataga tgtcccaggt 66420
tacaagacca cactagcaga atcatggctt caccctgagt ccggctaatt ccacatctat 66480
gcgcagccac cctgcccctc gccttccctg cagggcgagt ggctgaacat tttctttggc 66540
tagtgcaatg gccacccctt ctttctccct ctgctctcta aatgtccttg accctcaact 66600
tcccaacaat gacttcccat ccctcacttc cttcctgtgt gatctccttc tctggagatc 66660
ccttactgcc tttctctctt tgcagccacc tctcaaatcc cagaagccag gatgttacat 66720
gtgcaatttc cctgcaaggt gccttaattt ggttttccta atggcatctt aaattcaaca 66780
tgtccagaat ggatcagtgt cttccctgaa aaccaattcc atctcttgac cattttctct 66840

```
aagtcactgg ggctaaaatt tagagggcca cttatttctg acagctccct ccccacatcc  66900
ttgggccctc cccacatcca atcaactcct gtctgaaatg tgacttgtaa ccgcccctcc  66960
cttgccattc ccactgatag cactttactt attacttgtt acttcttgct gggccacaga  67020
aacggctgga ctcaccttcc tgtctctggt ttatgtgcca ttcagagaaa ctctgagaca  67080
tcacctgacg aatcattgtg atgctcagct tgcaggatcc cacttctcta ctcagggacc  67140
cccagtactt ccccgttctt actgaataaa gtccaaattc tacacttcag tgttctagcc  67200
ccttatcacg tgggcggtga aacctttggc tgcatctcgg acagctcatg ggcaggtccc  67260
ctctgctgtc acacccagag ttaggaaggc ctcaaattca ctccctgcac acttgcttcc  67320
ctgtctcctg gcaaactgct ttctctttgt tcttaactct gcctgggaaa atcttcccca  67380
tccttgaagg cctttctcca ctgttacccc tgcatgaaga cctcactgac cccccaaaaa  67440
gtgtttgacc cagaacactt tggcttttgc ttataatatt tacctctgac ttggggcacg  67500
tgtttcattc tctatttgag tgtatgctct ttgagggtag gaatgagtga ctgtctggcc  67560
taccctgaat cttgactctc atgaatcaag ttttataaat tgactcaaaa taataagtta  67620
gagttacaag aataaggtgg taacggtggt tttataattc agaaataatc cttttaaaaa  67680
tgtaaaaaat actctaaaaa agtcagctgt agaggtttgc tcgtggttgc caaggagcaa  67740
agactttcag agagcttaac tccagtgggt ttgagcctct ttctgattaa agcatcagtg  67800
ccaatagcat tggatccctc caagaatgtg gtgtttggga ctttaccatc atttgtttgt  67860
ggaattgtgt gtaggtctga aaattcaggc ctgtggggaa ctaactttga attttgataa  67920
atgactttcg tggtcagttc gggtcaccca gctacactct gttgtgtata ttttggcaca  67980
tctgctcttg aaagatatga ttatatgtaa ctccaacaaa tatatcaaaa gtgtgtttta  68040
attttttttgc cttttagatt taatgaacca gttcctaaga gaaccctaca tgtttcttta  68100
gaagacctaa ccaattgata ctgcattatg acaaaccctc taccagaatt tcctcattca  68160
ttcaaaatta tgtttaaacc cataatgtcc acattctttt ttttttaac atgaggagac  68220
atcataagaa atgaaacaac agtttgagtc agggcaacag agtccaagtt tccttccaag  68280
aggccaagtt gttttagcag aaaaggacat tggcgccaaa acccacacta ggtccaccgg  68340
cagcaaacac agaatggtgc cctcactcta ggaagctggc tgttccatat ttttatacta  68400
gatttaaggt tcaaaatttc atgttggtgt tcataaatgc aaacacacaa gccagcaaag  68460
aaaaaggaga gttatttagt ttatattttc ttctcccatc ctttctctct ctctttctat  68520
gcaaatgttt caatcacata ggtttgacca aatagctgcg tcttacacca ttctcctcta  68580
tgtaaagatg taaagcaact ctgcactttt tttttttttt tttttaagac aaagtctcac  68640
tctgtggctc aggttggagt gcagtggcac aatttcggct cactgaaacc tctgcgtctt  68700
gggttcaagc gattctcctg cctcagcctc ccgagtagct gggattacag gtgtgtgcca  68760
ccacacctaa tttttgtatt tttattagtc agggggttca ccatgttggc caggctggtc  68820
ttgaactcct gacctcaggt gacctgcctg cctcagcctc ccaaagtgct gggattacag  68880
gcctgagcca ccccgaccgg ccatgcactt ggttttgaga gcagcacagt ggcggtctgt  68940
tctccctgcc cgcctgctcc agggagagga gttgcttgct cccttacagc cctcacctcc  69000
catgggaccc tgcaggtgct gagggctcag gcgcagctgc tgccagtcgt cacagccatc  69060
tcatccattc cagagttgta aataggctga tgattccgtt ttttgttccc agagctgtat  69120
atccagtggc ctcctggagt cacctactgg gatggctgat gatctccaaa agtgtcaaca  69180
ctgtcccaaa ctgagcaccc cgccccacag cagagccctg ccccagcgcc tcctgttctg  69240
```

gctctatggc aattccctct tcccagcggc cgcagcaaga gtcgggtccc ctgcgccctg 69300
gcccagcccc tgccgcccct gcctggcctg gatgttggca atggtggttt cccagtgccc 69360
tgcccccacc ctttccctta cccctttcag cccgttcctt actaagaagc caccgcaatg 69420
ttggtgagaa agtgggtcag atgtgccaca gccttaggcc gcttcaaagt ctaaccacgt 69480
cctgaaaacc ttctggtttg gttcccagct cctgctccga tctcgcctct atttgaaaac 69540
caccatcccc acatcggcca cctctcagtc accccatcct ctggctcacc cccgagaccg 69600
ctgccaattg gggggacccg tccatagcac ggatggcgct gcttccggca cctgcgccgc 69660
ccgagggtct cctggccatg gcctgggggt gccacgcagc cgtggccacc gcatcctccc 69720
tcagtgctcc ccacggctct caatgcgctc cccaagtgct gaccacgcgc gcccccacgg 69780
ctccccgaca gctccgccac gccctcccca cggctctcca cgctctcccc aagtccccaa 69840
cggctccccc aagcgctgcc cacgctcccc cacgactccc ccactccctc tccacgtgct 69900
ccccacgtgc tcagaggagc ctggacaggt ggatccgggt tgccccgggg actcattcag 69960
gggtgagcac accttgtact tttccctcgt tgtttccctc cttcccctcc tggaaatgcc 70020
tcctgcggaa accactcaaa cccttgtctc aggaccatgg caggggtctc ctttcttaca 70080
gggctggctg cttcctcagt caaggcttct ttggctattt acttatctaa aatgaaaact 70140
ccagccatat tctcagtatt tcatagcctc cttttccatg ttgttctcat tctttaaagt 70200
actacctatt tcacctactt gtagtgttct ctgtatccct ctcctaccag aatgtgacat 70260
ggacggtaat gtcagccttc ttcactcctg gttaagcaga cttgagaaaa gggcctggca 70320
tacagtaggc attcagtaaa tgctttgtga ctctgtcgag aggtgacagc atgctggcag 70380
ccctcacagg ccttgctcgc tctcggtgcc tcctcggcct cggcgcccat tctggccgcg 70440
cttgaggagc gcttcagccc gccgctgcac tgtgggagcc ccctcctggg atggctgagg 70500
caggagccgg ctccctcagc ctgcggggag gtgtggaggg agaggcacgg gcgggaacca 70560
gggctgggag cggcgcttgc gggccagcta gagttccggg tgggcgtggg cttggcgggc 70620
cccgcactcg gagcggccgg gcagtgaggg gcttagcacc cgagccagca gctgcggagg 70680
gtgcgccagg tcccccagca gtgccggccc accggcgctg cgctcgattt ctcgccgggc 70740
cttagctgcc tccccgcagg gcagggctcg ggacctgcag cccgccatgc ctgagcctgc 70800
ccccgcaccc ccgccgtggg ctcctggcgg cccgagcctc ccctatgagc gccgccccct 70860
gctccacggc gcccagtccc aacaaccgcc caagggctga ggagtgcggg cgcacagcgt 70920
gggactggca gacagctcca cctgcagccc ccgggcggga tccactgagt gaagccagct 70980
gggctcttga gtctggtggg gacttggaga atctttatgt ctagctaagg gattgtaaat 71040
acaccaatca gcactctgta tctagctcaa ggtttgtaaa tgcaccaatc agcactctgt 71100
gtctagctga tctggtgggg acttggagaa catttatgtc tagctaaggg attgtgaata 71160
caccaatcag cactctgtat ctagctcaag gtttgtaaat gcaccaatca gcaccctgtg 71220
tctagctaat ctggtgggga cttggagaac ctttgtgtct agctcaggat tgtaaacgca 71280
ccaatcagca ccctgtcaaa acagaccaat cagctctctg taaaacagac caatcagctc 71340
tctgtaaaat gggccaatca gcaggatgtg ggtggagcca gataagggaa gaaaagcagg 71400
ctctccgagc tagcggtggc aatctgttag ggtttgtgtc tgtcgtgtgg aagctttgtt 71460
cattcgtctt ttgcaataaa tcttgctact gctcagtctt tgggtccaca ctgcttttat 71520
gagctgtagc agtcaccacg aaggtctgca gctgcactcc tgaggctagc gagaccacga 71580
acccaccggg aggagcgaac gactccagac gcgctgactt aagagctgta acagcttacc 71640

```
gctaaggtct gcagcttcac tcctgagcca gagagaccag gaacccacct agaaggaaca  71700
aactccggac atgccgcctt taagagctgt aacactcacc gccagggtcc gcagctgcat  71760
tcttgaagtc agtgagacca agaacccacc aattccagac acactgtcat caaaaagtgg  71820
gatatctttt taaacagaga taacattgca gaatcttgga gttggaaata gacctcagct  71880
ggggtttagt cctgttttct cctcagagca gaagtcctgg gatgccgttc tggactgatt  71940
gtcagttttt tctcctgtcc ttgagctatt ctaatgccag acatctgtgg ctttacacag  72000
ccaggctttc agttagagaa cttggttagc tcaggtcaac aaatgctgct ctgagaacac  72060
tgactcccat gtgggagac tctgcacctg gagctccggg agagccggct caggcctctt  72120
cctgctatcc agggaactgc agtggcgttg gagggccttg ctggggctgg ggctggggag  72180
aagggattcc aaccctactg ataattcgtt tggaaacacc gggctgtgga tttcagaagt  72240
tcttgggcag cctgattacc actggcagtg agccggggac gaagccgaag ctatgagtga  72300
cagacggaaa gaactggggg ctttggtgaa ccagagaaca cttagctcct ccagccctga  72360
agcaggcgtc accgcagggc ttatggtcct aagagccact tagtttcctt attcattaaa  72420
ctagtttaat ttgggttttc tgcatcctgg aggacaccaa gtcggtgtgc ggagggaccc  72480
tgtagacacg tgtgcaaaga ataagccgac gatcatggaa tttctgatga cgccactgac  72540
acgtgggatg gaggcctcct tcccagggca cccctacact catgacaatg aatcctggct  72600
cttattcacc cctttggatt tcacaagcaa gtagtaagta gaaaaatagt ttcattttat  72660
tttcagtaca tcaactgaat gtgctaatac ttgtatccac ttccacatgt aagaactctg  72720
ttacataaat ttgagaataa tctgctcttt gctattttga ctttattttc actgcagatt  72780
accaattgtc cctacaattt gcgttttata gtttacatca tcgtacactt gattttatag  72840
ggaacaaaag gttctcaata attacaaaga aatgtgttga tttaacatac tccaagaatc  72900
tcatgaacac agtccaaata ataattcaaa attgaaggtg gtatattggg ctaaagtgtc  72960
cagcaactaa ggaactaacg atgacttaac ttttattgtc ttgggtcaca gacacataaa  73020
attgactaga aaattaatcc tggtatatct tttgtatctt caacatcact atgaatattc  73080
tactttttaa gtgacatgga aacattcaaa ttgagacatg gagtctgaga gtgacacggg  73140
ctgctggagt ccacaccctg ttgaccaaat ccacaccttt ggtggccagc tccgttttgg  73200
ttttcaaact ttaagctcca ttgtatcccc aaaatatatg aatgaaaaca aatcaattta  73260
tttattttca ttttagttat ttatttgaga cagggtcttg ctctgtcgcc caggctggag  73320
tgggttgttg tgatctcgcc tcattgcaac ttccatctcc tgggtttaag cgattctcct  73380
gcctcagcct cctgagtagc tgagattaca ggcacggacc accttgcccg gctaattttt  73440
gtactttagt agagagaggg ttttgcaatg ttggccaggc ttgtctggaa ctcctgacct  73500
caagtaatcc tcctgcctca gcctcctaaa gtgctgggat tacaggcgtg agccaccaca  73560
cccggcccaa gtcaacgtat ttataatatg tgaattgttt gcacacctat ttcaagcact  73620
ggaaaagaaa aaaaagaaaa gaaacaggtc catgaatgag gtaagcagag ttggacccaa  73680
atacttcaat gccttctcaa caatttcttc taaatggctt cccgaaatta gctctgcacg  73740
acctatcttt cttggggggt ggggaagcga ttacttttta aaagccacat taaagtgtgt  73800
gttctatatc acgatggcag ttaagggagg ggaggcgtct acagctgacc tggggaagtt  73860
ttaatcattg aactatgcac aagtggggcc ggggcgggaa gcggcaggaa aatgaggcac  73920
cttctgcaga acctagccag cctgcaggcg ttcctgatct gaggaaaaca ctttaattaa  73980
tatgtaaaac agcagtgggg agaaaagcaa ggttaatttc caaaccacat cactaccagc  74040
```

```
ggtatttggg ttatgaaacc ttgggaaact tctaggagat cctgtttgaa ggcacagagg  74100
tgcttttgtg tgtgagtagc ttctgagatg ctcaaaagct cttttatctg ccccctgcag  74160
tggtattgct ctttctgtgt ttaaaaacac tgcctttgac tggcaggctt ttgtttttaa  74220
tttgcagtgc atcctccatt tttgtttgga acttgcctga aagcagcgtt taggggagag  74280
agagctgttt gatttccttt gttgcggctt tcttagctgc tggctacctt tggaatgtgt  74340
gacacaggcg tctctcctgg ttaggaaaat gttctgtact tgcctggggt gagactgtag  74400
ctcatttcct gggttgagat ctaaaatcct gagcagagtt aagtgtatca aatagtggct  74460
gtgccaagga tcagtgtctg gtggagacag cggattttcc aaggtcatgg aagtgaagaa  74520
acagctgaca agtctttccc tagcttgagc agaaacagct ccattcagtg cgtgaacaat  74580
taactcaatt agagaatgtg cagctttcta aagacgcgtc cactgtgagt gcgtgtgcct  74640
gcgtttcctg cctccctctc ctcacagaca cctcaaaagc aacatatctg aaaagtcctc  74700
ttagctaccc tgtctaggag aagtcagagg cttgaggacg atactgtgtt cctcccaccg  74760
cttggtatcc caccaacacc cgctcctggc cattagacac tcaagcatct ttcaagtagg  74820
gagatgactt ttttgggggt catagactcc tttgagaatt aaagtttacc ccaggaggaa  74880
aataatatct gcacatacca agatcagcac acactttcag gggttttccc atacctactt  74940
taagcccaat taggatttct gtactaaaat caatccctct gtcccatttc ctctgccaca  75000
gccgtatgtg cagccccacg cgttacttac atctagcctg gagggttaac tttgacttcc  75060
cagcttctgg cacaatttcc ttctccatcg caggccggag tggtctccac attccccaag  75120
ggctcaccca tgacctttag aagaaagtcc aagcactagc ttggcactca aagtctaagg  75180
aattcttcat cccgtgctcc aggcacatga aatgcctgtg ttttcgtgag caaacgtttc  75240
tcctgtggcc ttccagtttc tcccagtaca tcctgtggac tatcgtggag gatttgcatt  75300
gcagtgtgtg cctctcaggt ccatgttgga gtgccctgcg tccgcctccc tctgcgcggt  75360
ccactcagct gggtggcgtc actggtgact gggcttctgc ctccttcctt tcactgggag  75420
actcctcagt cagagtctgg gtcttcatct ctaaaccccc cggggcagca gcagtccctg  75480
attttgacat aggagattag gactgcagct tgtagggagg tggtgatcca cggaggggct  75540
tcttctgaag ctgacttttg tagcaagcac agtgttccaa cttacattaa atacacgtgg  75600
ggtggcttga tatgacgatg gagaagatcc cacattgcac aaggtgggag ctaaagcccc  75660
agtcctcgcc ctgcagctgt agtacacagc ttcacagtta cgtgcactgc cacatgtatg  75720
taataatctg gtatgtaaca ggtgcttgtt gaatatttgt tggatgaata gatgagtgac  75780
cctagaaaaa cacaatgcag acctatgggt agaagaagaa aagaacctgg agtttcctgg  75840
aagttagggg ttccagccca cctctgtcca cagccatgtg atctcacaca cacacacaca  75900
cacacacaca cctacacctg cacccatgag cctccccact ttgtcaggga tcatgattca  75960
caggttatgc tgcatctcct aacttttcca tttctttgca ctcacttttt cactccattt  76020
ataggcacac agcaaccccg tctcctgcaa tgacccctgc tccaggcctc acataaacca  76080
cctgctatct gtactcggca gccctggtcc gaaggcaaac acagtcctgg ttgccccacc  76140
tgacgcaatt gctcctagca tttcttattc actctccagc tttcgcttgg ctctaccctc  76200
tgctgaaaca gctaaccctc ttgcctggca gagtcaagga aatttttgag tccagggcct  76260
tcaaccttgt gtcttcagga gcctctgcaa agctgggtgc catgtaggtg ggctctctcc  76320
ttccactccc tgtcgtcttc attctctagc cctccgtatc acccttctgg gcaattcttt  76380
ctcagctcac ttagcgaatg taaggaagtg tttcattttc agtctttcaa atcttttttc  76440
```

aaatacttcg tattcaatca tttcctcttc ttggatagag ttttgtgttt taagtacagt 76500
gttatccaat ggctagatcc gcacctctag ccagctcacc actctgtggc ccagactctc 76560
tttgccaact gtttaactct cgtgtataaa tgacaggcag ctgcatatgt ccatatgtcc 76620
agctgtctgt tctgcagtgg gtcacttatg ggatcagatt gtacatctgc ctgtttcact 76680
tcaaattgcc tcttctttgc aagcatccag gggtgtcttg cctcacatac aaacaaacac 76740
agaacaaaac taaaaacctc aaaggaattt ctgtgttgaa gaggttttaa tggtaaaata 76800
attaagttta cttgcgatta aaaaataatt gtaaattttt attaaaaaac cctcaaaact 76860
atcttgctgt atttttcttt tattataatc aaagtttagg caagaagagg ggtatctatt 76920
ggctcatgaa gtttaacagt tccctggatt gacctagaac agtgcttttc aaaataagca 76980
tcaggcccat ctagagagct tggaaagaga tctcactgag tcagctccat cttccagagt 77040
ttgtaatgca gtgagtctgg gagctgaggt tgagaattcg catttccagc aaggccatga 77100
ggctgctgct gctgctttgg gggccccact ttgagaactc atagcgtcag gcaccacagg 77160
acccagatgg tcaatgatat ccggagaatc aagtctcgct ttccccagtg acacagaaag 77220
ttcctggcac tcccaggcta acatcctctc tggagttggt aatttccaaa agagatcttt 77280
ccaacttcca taaaaacttc aaaaatatga ctctggtgct acatgagcta cctgcttacc 77340
cctgggccaa tcactgatgt tccctgtggg gtaacctgat tctctggcct gggtcacatg 77400
actcgccttg tggtgggcag gctcccttcg tgactgacag ctttcctgcc cgccccacat 77460
tcagaatcct atctaaagca aggaatgtag ggcaaacaga gtgtttttaa agtatatttc 77520
aatctctata tctatctacc tgcctacctg tctgcctacc cacctattga tctaggccag 77580
ttacgtaatc tctctgaacc tcatgtttta tttatccaga taagtgattc cataatactt 77640
acctttcagg ccattgtgtg gattagaaat atcacctgct tcaaacagcc agcatattgc 77700
ctgcatcaac tatgtagaat aaatgatagc tagatatgaa gaggaaattg cttcatcctt 77760
gaccctgtct cccccagtaa aggtggttca ttaggtgtct ggcgccagat agggtggggc 77820
cagattgagg atgctcaccc tatcactttt ccccactcat ctctaactcc ttgaccagtg 77880
actatgacct ctccatgcac tcatgtgtat atggaggttt tccattggaa aatgaggcat 77940
atattacaga aacacccatc acatatctgt atccctttgg tgagaggtgc aggggcacgt 78000
ggagtactcc ttcctgctgc taagttcatt tttgtgtggc tttcaccgtt tgttccctgt 78060
tgaagccttc tccaagcttc gggtgttcac aagtctccaa gggctctgtg agattagaac 78120
ttccttcctc tttcagctga taattacagc tctgtggttc tcccttgtag gtctttcctt 78180
gagctccaaa acagagtttt cctgcagtgg agcttctatt cggataatta gggcactcag 78240
ttgtattgga ggagggttga attaactacc tctgtctcct gtgctacttg gttctgggct 78300
tctacacatc acagctacct ggaggataat catcatgata ataactatta tttactgagc 78360
tgatgatgcc ctaggcaaga ttctttttcc attgcattct cccaaagcct agaaggtagc 78420
tattcaattt tacagatgag gaaactaagg ctgtgtgagc taaatgcctc cgctaaaatc 78480
acacagcagt acaaagcgtg gcagggtggg gaggcccgca gagttgcgac cccagcccag 78540
cctgtgaatg cagactttct gtgtgaactg cgctgttctt gcagctctct ttggacctgg 78600
attgaagttt tcccatgaag aactggggaa cattgaattg ttgatgttgt tgttgttgtt 78660
gctctgaatt ggattacata taaattctct tttccttcaa tattcagtga gattttggca 78720
gtcaatggag actcattgcc taatggttgc catgggtgat tttctcaaat cactgctccg 78780
ggcccagggc catcagagca attcaccatg ctgaagagac gcctttgtta gtccaaaggc 78840

-continued

```
aacctcaggt aatcaactgc ttgacccacc tctgatttta agcaccaaat taattttaga  78900
cgttgcatag agaaaggtcg atcctcctgt tttctctggg agtggcaagt gagcagctca  78960
gctggagcgc ggcagggttc tgcctgtgtc cctgtcctca ccccatctct gctttcacca  79020
agcaagagct gcatttgggg ttggccgggg ctttctcacc tctggagatt cctggtccaa  79080
tgtcattggc aagcacgtga cctgagagaa cctgaagatt aaaacactgg ccttcgaatt  79140
ctgagaagtc ctgtcatcat ctatcaggga acttagcaat accacttctt ttcatagcag  79200
atatatttat gtgcttgact tacattttaa tggtttataa aagctaaaag caatcgcagt  79260
ttggggggcc ctacgtggac ttccctgcaa ttctgtgatt gtcccttaat gaagtcaaca  79320
aacacaatgg gcagatgaat gaatgctccc aacctaatta aatctaacat ttgagaataa  79380
aataatacta aatatgtaat ctcatttcca tttggaacca actagagctt ctttgaaatt  79440
tggggctatt tggaaagcat tatagatcac aaatagatgg aaccataatg gaaacacatt  79500
accgctcaag aagattgaaa atagccctcc cgtaaaccta gtgttgtatc tctgtacttg  79560
tgaaggaaaa gactctactt tgacctgagt gggctctgtt gaataatatt gaaaatgcac  79620
agctgaatga ggctgcatta gactgtccca gcgggagaac aaatcagaag ttatgttgtt  79680
gatgcaaacc gttttgtctg gccacctttc taacgtgctt gtttttcatt ttcctctttt  79740
tctgtctttt ttgggaggct ggggggtggg gtattaccta gggagagggg aagccaatca  79800
ccatttgact gtgtgttgaa tttaaggacg cctagaggtg aaaagaggaa accttatgat  79860
tgaattttgc ctactaatga aagttcatat aaatcaaggc tcacatagct cttatatgaa  79920
taaaatatta tacctggagg caggaggatg tgatctattt tactatcttc attaatctgc  79980
aaatttgctg ttcaaggctg tggccacata tcactgtgga gaaaagacat tcccttctgc  80040
actgctgttt tctcaggtcc agaacatgct ctttctttag tatgacacat gtcttttttc  80100
tgataatcac ctggcttcac tttttgtaag gtttacaaaa ttcattaggc atattcaggt  80160
tcagaggttg gtgaagtgct tgaaccatat ctttaggtga ttactatccc gcatgctgca  80220
ttttgtaatg atgatgcttt actcagttat agtcaggtca aacaagtgac aatgataaag  80280
accattgtgg acgcagcaca gtcactgact ggacctacaa acacactggc agggctgtgt  80340
ttgccttaca atctgggctt tataattaaa ggaaacatca gtgcttaagc ccagaccttt  80400
ggtggggcag ttatcatgaa ctctggaaga ttcgatccat taaatatttt ggtttgttcc  80460
aatcaagcag tgttcatgac ctactttgac aggtatttgg gatgtgcagt caggtgattt  80520
ttcttttaaa ctatcttatc aaccaagcag attcttccat gtggccatct gctcagtttt  80580
gcagccctca gctgttcttg gagctagaaa aaaattctcc tgtggaaaaa tcaatgtact  80640
tctctcaagg agatggagat ttaatatgtt acaggaatag atgcagtaga aattgataac  80700
ccttgttata tctccatttg attgagagat cttagggtaa ataaaatatg gctcaattta  80760
cagtcagatt acttaggttg ttattttaat aactaattca gtaattttag aaagtaggag  80820
agtaaactta tagcattttt acactaaaat agatttcaga catccttcat gtaggtaatg  80880
tcttgttgag actattttcc tggtgttttt gaaactgtgg ttctgtttgt agtttcgtaa  80940
gagctttgaa tttggctcca tttggggttc agcaaattag tgtagtttgt tctggttttt  81000
atttgaggtt ctgctcggga tgagtcccag gaatggatgc catgtttgtg aacagggccc  81060
actttcatct gagcatgtca ataacaggaa aagccagatg ggcagcaagc ctccaccagc  81120
acccccacca catctgcact catacccacc cctccgtgtt ggctccagag gtgagagctg  81180
ttttctttgt tcaccatttt agggtgagcc cagtgaaagg caggcagggt gtccatcggt  81240
```

ggatacatat ggagatcaag atgcctgact tccattccct accccagcac acctgctggc 81300
gggatccagg cacacagctc tcagcactgt gtttgccctt gaaccagtga ggggtctcag 81360
tcgctgactg gagggggcgg atcacgatcc agcaaggcct ctgagtgcca gacagtgtgc 81420
taagccctct gtacagttag gagatccctg tggaaggtga tatcaccccc atttttatgt 81480
tcaaggaaaa gcagtcccag aaaggactcg ggtttgagtc ccgcggcagt aagtgctgga 81540
ggtaattcga gcgcgttttg gcttcctggc tgttctgtgc tctgtcctgt agcctccata 81600
aatacaggta gttggtgacc taaagattgt aatctttagc atttttacaa gccaaacatc 81660
tgtgaaaacc acagtagtat cattataaaa atcccatgta agtataaata gtatagtaaa 81720
attaaataac agcaactcct cttatttgaa tatagcagta tttttaggcc aagggttgtt 81780
ttggtcaaac atgatcccta tatctggaaa acctggtatt tttgggacat agtttccctt 81840
attcttgctg caagaatgac tttttctgga ttaaaaaata gactatggga ctactacctt 81900
gtttttctgt ttacagaagt aggctgactt acggatgtgg gggaattatt catttacgat 81960
tatttcatga agccattcat cttcaggtct tccttccaat aaggaagacc tgaagttcaa 82020
ttagtggctc ccttacaatc tgagcataac atgaaattta cataaatctc tacttctctt 82080
ttgctttgga ttaatgaaat caaacaggca actagaatat gctgccagtg cagaatatga 82140
ataaaataaa taaagtattt accccagctg tgattgttaa ttttagtgta tagtgagact 82200
cctacagtgt ggtttgttat agattttttt tctttttggt tccttttttt ttttaattga 82260
ggaattatgt tttctgtttt tatctctttt tttatgtgtg ttttgtggtt tatactcctg 82320
gattttccta ttagttttac ccctcctaaa attctagctc atcgtactta gctatgtttc 82380
aatatatgat tacagtgacc ctttaagtga acagaatgat ccctttgaac cgtggaatag 82440
gtgaacgacc ttttggaata cacacagact ctggtgcaat gtagccagaa aaaccaaaca 82500
aattgacagc cagatgaaaa gcgattggtt caattgaggt acacctgcca aatcagggct 82560
gccagctggg aaattcttac gcattttcct aagtggctgt tacataaaat attgagcctg 82620
cgtgtatctg ttaagtcatc atggctctga tatttaaaga gccttgttct tttatttttt 82680
ccttcctgga atggggaatc aagagaccag ggtttacata ttgaaaacaa gaaaccaaat 82740
caaacagtgg cttattcttt aaagtaaaca gagcaaaggc tatcagtggc agatgtaacc 82800
aagagctggc tctatgcaga caaagaggag attatgaaaa caaaaatctc ttccactgaa 82860
ataattatgt ttaattactg atccaggaac tgcatttaac gtttttcatt tgcacaaatc 82920
ttaagggtaa atgaggctga caaatactaa tcaggagaca ggggagatta tttcatggtt 82980
ttgggtggga tgagcatcta aaagcctatc cttctctctg gttttgccgg cctagaccct 83040
acgtctccct caaagatctg ctgagaccag aactttgagc cccactcttc ggggagtgcc 83100
agcccattct ttccaacctt ctttcttctg catttctgaa aaccacaaaa ttgagttatc 83160
actgcggcaa caccttgtca cttggctgag ctctttctct ttagctgata acttggggga 83220
acaaagcctg gttccatcca gggttcatat ttgaaaacta aataacaaaa catagaatac 83280
ttgaatgaac tctattctgt cttgtatatt gtccctggca taccatctgc actgaaagct 83340
gctcagaggc agggatactt catgtctctt ttttcccagc tcccagcagg atattgagtc 83400
aatcgtgaat gatggatgga tgggtggatg gatgaatgga cggatggatc tgggatcgtg 83460
tccaagtgat tgcactgtgg ttcttaaagt ttattcagat atttggaaca agatcataga 83520
ctatctccta cagatagtaa aaaattcaat cctttagcca actggtggaa ggagatcaag 83580
gctatccatc tgtaagattg ctccagagtc atgcctgatg ccatttcaca gagaatgtca 83640
accctgctct tgctttactg tgcgtttccc gtggcagggc tgatctctga gaactgtgaa 83700
gtagttgttg attgttgttg tttggttgtt agagtctgac ccttgttgga gtcattccgt 83760
gttctaaaaa gtctccactc ttttagagaa aatcacagtg ggcaagggtt acaatggcag 83820
cagaatgttt cctgatgaga tcaatgcacc cttcaaaatc ccatgactga cccttcacca 83880
aaggtcctaa acagaatacc accaaggagt taaggactgt ccagtaacgc aggtattgcc 83940
aattcacttc tttaccctaa aaaacaattc ttgctttgag actccatcag cagtccctgt 84000
aaatattaca caaagcacta attttcttct tctacaaaag cagtaatttc tgtctccttt 84060
actctttttt tatgaagttc tatggagaac tgttaaatat ttaattcctg ctgtgtatga 84120
gagatcagct ctgatttcta agtacaaaac taaacttcag caagctataa gaatagtctg 84180
tagtcctggt gattgacact gtgataatat atctctaaat ggtgactgtg tgaacacagt 84240
attacagtct taagaaatag atttggtaca aataattatt actagcttgt gtggtatatg 84300
ttgcatgtat gtgatacatg gtgtcacgtg gtgtatgtac atagaccata tatgatgtgt 84360
ttatataggc gtatatatgt gtatacacac accctttca gcctttttgg atatggtctc 84420
gatttctttg caaaacatat ttattttttc atcccaagaa aatatttgtc ttgcagaagt 84480
gcactggaaa tacttaggtt gttgattcaa aataattatc cttgaaaaaa gcatgatttg 84540
tgttcagtct cacagcacca tttgattgct tcccatgccc tacagaacta tatttataaa 84600
aggattttgt ccttttgccc tttccataac tcaccatcaa ctgtgaatca agtttcagta 84660
acaatggagg ctgttttcct gaatcaacag gcaagcttta ttgctttttc tttttcaggg 84720
cttctttact tgctcatttt ccagagttct gctgttctag actctcattt atattaatca 84780
gtcagagtcc ctcatctgct tactgaattt gctgttgcct ggaagaattt ccaagtactc 84840
ttttgcaagg aaaacaacat attttgtagt aggaagtaga agttgcccac gggccactta 84900
caatccaact ttcaatcagc agcttgaatt agatatttgg agttagattt ttttgtgtgt 84960
cttgtttatt ttataaaagg acattcttat ttctcatttt tgagtttaag ttggctaata 85020
aatgtataat gtgactttcc taagaagtca caatattact taatatatat tactatatta 85080
tatagtattt atatattata tagtattata tatattataa taagtataat aaatatttac 85140
ttattatgta tttattagcc agtaaggact tctaaatggc tttctaaata aagcagattt 85200
tcttttcttg tagtaaaagc aaataaaata agaccaaaaa tatttcagag tattatcaaa 85260
tatccaccac acctatactc cctcagaagc ttctgtttct ccctccctgc tatcaattta 85320
gttacaatgt aacctcatta aaaataggtt cctttcctct ggggcacctc gtaggatggc 85380
ttcctccagg aagttcccaa aatatgggga tggatagccg gggtcatctt ctgccagctt 85440
tggtctctac atgcttatac ccacttcagc caggtcccac ttcctctagg actttccgtg 85500
gcttgatgcc taggctggct gggtcatcgt gaaggggcca gaacacagaa ttgcaggtag 85560
gaaaaaccct aaggtttatg tgtgggtatt acctgaaggc tttgaggcag gtgcctcttc 85620
tagatgatct cagtgagtct ccactccaac tctggcacag cccactgtgg caggtcttaa 85680
gcttcagaga ggtttaggag ttggcctagt cgcagacagc aggtgggcaa gatgggcatg 85740
actgcaggtg agcacgagcc tgcctctctg cagctttctt cctggtccca atccttctgg 85800
aacagaggtt cttgccctgt cctcctatcg ctgtggtctt agacctgcag gctctcgaga 85860
aggctccttt tatacatctg ctgtttacct cccgcagatg cttggagctc cattggtcac 85920
ttgccccatc cctgctggag gtaaatcctt aaggctcctc atatcctgcc caccattcac 85980
tcactcattc actcattcac tcttgtagcc tcttacccac ttcaagtcat ttattacatt 86040

```
cactcactca ctcactcatt cattcttgta gcctcttacc cacttcaagt catttattac  86100
attcactcac tcactcactc attcattctt gtagcctctt acccacttca agtcatttat  86160
tacattcact cactcactca ctcattcatt cttgtagcct cttacccact tcaagtcatt  86220
tattacattc actcactcac tcactcattc attcttgtag cctcttaccc acttcaagtc  86280
atttattacg ttcactcact cactcattca ttcttgtagc ctcttcttac ccacttcaag  86340
tcatttatta cgttcgaggc actaggaaag aatttcccat ttcaaagaca tgcagttttc  86400
tggagtggat gacctctgct ctaaacatga tactaataat agttgttatt attacctata  86460
tcaacagcag tatggattga attgtgtctc ctccaaattt atgtgatgaa atttgaaact  86520
cccagcatca cataaatatga ttatatttgg gggacagggt ctttagagag gtaatcaagg  86580
tcactatggt tgctgtcctt agcgaaaggg gaaagttgca catagacaca agcatagagt  86640
aaagacgatg tggagagact cagggagaag ataggcgtct acagccaggg agaggcctgg  86700
agcagagcct ccctcacaga tgtcagaaga agccagccct gccaccacct ggatcttgga  86760
cttctggccc acagaaccgt gagataatca atttctattg tttaagccac caagtctggg  86820
gtactttgtt gtgacagcca tggtaatgta atacaaatag gaataatata tatatggaaa  86880
tgtaggcctt cgctacgtgc aaggtatggt gaaaattgct tttagtgcag aatcttactt  86940
aaatctcacc caaaccttca tattaccagc actactaaga tttaaagatt aagaaactta  87000
tccaagacca gacagctagt agatgagaaa cccagggttc aaacccacac ctgtgactct  87060
ggagccatca cctttaacca tcactttgtc ttattttccc ccaggctgaa aaagtccttc  87120
ctactcactg gatgtgagtc ctgcgtgtcc cattgtaaac tgtccctctg cctcaaatgt  87180
caacagcaac attgaaacaa cagtattttt tttttcaaat cagtataata ttcagaggac  87240
attaaattaa gtaggcattc tcatattctt ggtctccaca tagcagaaaa atctgttaga  87300
atgaagaagg taatctcatt agtgaggtat tacgttgacc tgaggagcaa atgctgttgt  87360
tgtttctggc aacagaggat tttgtccctg aacaaaagtt agcctggcac tgtgaagtag  87420
gcttttatat gaacaggtca ctccttgcaa cagcaacaag tgttgcttca gaatgagcct  87480
ggctcctgcc atgtgggtca gggctgacag cagggatttc acatgtgaca gatgactaag  87540
ggtttatgtg gacatggaag atttgaggct cctttctgcc cccatcctct cactgaggca  87600
attgaagatc tttttctcct agcagaccta gaaattgttt gccagtgggg gcagaatgag  87660
ggaggggctt tgaaactcag ttgctacaag ttagcgtgta cgtttagatg aactcatgtt  87720
aacaatatac ttttccagtg gatccattcc agattaaact gtggtctttg agtttctcaa  87780
cttccttttt cttattgttt gatatttatt gctttttaaa aagatttgct aatcttacac  87840
gcaaaacttt cagacaaaga cttcagggaa taatctttca tacaaagatt tcaggcaata  87900
aatttctagt gtttatacag ctagcgaata gaacttcttc ctaaaattgt ttgaagccca  87960
aaatctaatg gcaagagatt ggctctcatt tttggtagcc ttgattgaag ccgattgatt  88020
gaattgctgt tcctgtcaat cttgtgacat tcttacacta atgaggtaaa ataaatgctg  88080
agtcctgagg tcacaccagt cctcgctgca catgtccttc acctgacttg atattttgaa  88140
atttttatcc ataatgagaa gttgagatct atcgcccctt tttgtgtgtg tgaaaatatg  88200
gctggtttta ctcattggtc tgtccttgta aacaattaca ctttctcaac aattgagatt  88260
ccaaactgtg agccgaccct tgcttccaca gagagaggag atggtagaga ggcaggaagc  88320
catggagtcc tgtgggataa cggcccccag aggacaaggc gacgttaaat gatggcatgc  88380
atggtaccca tccaataagt tctattctag ttttccccat cgatgggctt gactatgacc  88440
```

-continued

```
agggaatcat acagctttgg aacagaaaag aatcatctag ttgtggtcaa atgtcacact  88500
ttttgggaga aaaacctaga ggtgagggag acacagtgac ttgttcaagg tcacataact  88560
agtaaatgtc aacgctggga tgataaaccg agtcttttgg gcatgagttc agtatttttc  88620
aacagaattc acatactgct atttcacaaa ttagacccag tttactaatt gttgccttat  88680
gctagatctt gagaggcaac agctgtgttt gtccttatcc tttgacaccc agagcctagc  88740
acggtacctg gggcacaaga gaaactcaaa tgtgtttgcc aaattaaagc actaaggaat  88800
aagcacattt cctcttaatg atcactttca aaataaatct actattcatt taggaatact  88860
aatagctttg acccttcact tgctcacgat tatggttgcc taaggttaaa aataaggtaa  88920
ggtaatgaat gtaaattcat ctctgtctgg ctctttgtta ttggtgatag tgaaaagttt  88980
catggcaaaa gaagatacaa atcaatgaaa aaaatggagt ggggagatac cttctgtctg  89040
tgctgcgtgt gttccccatg atcataaatg gagaagtgga ggcaatatta acgaaatgtg  89100
cacttacaaa gcctgtgctc agcaactttt gataatattt aagtccatta gggcctaccc  89160
atacagtcat agatccgaag aggtcgatta aactttgaag agcttgttta gctttgttgc  89220
ctccaggaag tccgtaggaa aaagtatcag aaaagcataa aacaaaaaaa agttaaaaaa  89280
aaattatttc ttctatgtgg tgtggttcca agaaaggact ataacaggct tctgccctaa  89340
attgatcagt gtaagctgac atttgaagat aaagcataaa tactctaaga ctgtaacata  89400
ctatacccag agtagtaaga acaattaaaa ataggctcct ggggaaaaaa aagattccta  89460
aaactgaaga gaaattctct ttttctatta tataagctat ataccaatgt ccctcaactt  89520
atgatacagt tacatctggt atggtttggg tctgtctctc tgccaaaatc ttattgcaat  89580
ccccactgtt ggaagagggg cctggtggga ggctattgga tcatgggggt ggatcttccc  89640
cttgctgttc ttgtgacagt gagttctggt tgttgaaaag tgtgtggcac ctcccgcttc  89700
actctcttcc tcctgctcca gccatgtgcc tgcttcccct tcgcccgcac atgattgaaa  89760
gtttcctgag gcctcctgag ccgtgcttcc tggagagcct gtggaactgt gagtcaatta  89820
aacctctttt gtttataaat tatccagtct caggtatttc tttatagcag tatgagaatg  89880
gactaataca cattcctata aacccattgt aaactaaaaa tgtaagtcga aaatgcattg  89940
aatacaccta ccaaacgtca tagcttagcc tagcctaccg taaacgtgtt cggaatactt  90000
aacattagcc tacagttggg caaaaccacc tcacacaaag cctgttttat aataatgagt  90060
tgaatatctc atataattga ctgaacagcc tcttgaaaat gaaacacgga atggttattt  90120
cagctctgga aatacagttt ccactggatg tgtgttgctt ttgtgccatt gttaagtcaa  90180
aaaatcctaa ggcagggcac atctgggttt tttttttttt tttttttttt gagaaggagc  90240
ttcacaccat cgcccaggct ggagtgcagt ggcgccatct cagctcactg caacctccgc  90300
ttcccgggtt caagagattc tcctgcctca gcctcctgag tagctgggac tacaggtgcc  90360
cgccaccatg cccgactaat tttgtatgt gttagctaga gattgtagct gtgtgagtgt  90420
ggtttatttc atacggaaca gaaatgtttc ttttagtaga gacagggttt caccatgttg  90480
gccaggctgg tctcgaactc ccgaccttgt gatctgccct tctcggcctc ccaaagtatt  90540
gagattacag gcgtgagcca ccgtgcctgg cccatctggg gttttttgta gtgtatctta  90600
gttgcaatct agaagaatct gatgagtttt cactgtgtag gcttattaag acttgctata  90660
tttttactgt gtcctttacc ttcttaaaat gcatttataa tttaaaaagt ctgatctcat  90720
gtatataaac aatcctcaga aataatttga atatgttcta agtaaagtta ataattttca  90780
attatacaaa ggccaatagt gggtttattt tgtttgtatt ccatgcagac ttaagttgct  90840
```

tgcaagataa tctgggaaat tgtaggcttt ttggtggtgt tatagaatcc agaatttggg 90900
agtctccact gtagaccaaa tgctctggag tacgtgaaat ttgtctatca gcaaatcaac 90960
agactagtta acctttctcc aggcagtgtc tcccctccag ccctcaggca ttttgcctaa 91020
atcccatttc tttttctctg ccggctgtct gctaatccct cggaaagtgt tagctgataa 91080
cttaaggtgt gaccactctc aggagtattg catttcaaaa gaggcctcca agatagaaaa 91140
tacttcactt aaaggagcta gacaaggaag gaaggttgtt attttttaac ctgcttgtaa 91200
gttgagttcc aggccattta actcagtctt tagcgagatc ctctgtgagc ttccccactg 91260
catgaatttc cctccaattc tgagagccag tgactctgga cggcacttcc tcacttgaaa 91320
gcatcacatc acaatcattt cggcctaaaa cttattactc atctgtgtta gctagagatt 91380
gtagctgcgt aaatgtggct tatttcatcc agaacagaaa cattaaaacg attcgactcc 91440
tgcaggacat cttaatagtg tgtgaaagga agaattcata tttccagaac tctgtacctg 91500
ttacagctca ggcggtctat gctttcataa acatagtgac atattttatg cattgatctt 91560
aaaaccctat tacaaattct attccatatt ttcttagaca tttggacaca cttaaagctg 91620
aagcaaccat gtgtcagggt tcgctcatta aggttttctg ctcaaatctg tatgaacaat 91680
gtatagatga catataccta tatatgtaaa tatgtatata gattatgcca gtatcttcca 91740
tttattctca tataattaga gttataacaa caatgattta tatgttcaaa agcaaacatt 91800
tattgagttt attctgtggt cagcggatac tagacattag atgtgcagat agaaatgtat 91860
atagttcagg gcccggtgca gtggctcatg cctgtaagcc cagcacttcg ggaggccgag 91920
gcaggcagat cacgatgtca ggagatcaag accatcctgg acaacgtggt gaaacccagt 91980
ctctactgaa aatacaaaaa ttagctggtg tggtggcgct cgcctgtaat cccagctact 92040
tgggaggctg aggcaggaga atcgcttgaa cccgggaggc agaagttgca gagagccaag 92100
attgcgccac tgcactccag cctgggcgac agaatgagac ttcatctcca aaaaagaaaa 92160
aaaaaaaata acagagcttt aggttatgag gggttttgtc tcctcatccc atttcagttt 92220
ttctgaaaaa gtgaagacac ttaactatgc tcacaatttc aggaaatatg ctcagttttc 92280
agtttcttca gctcttacag ttacaactat ctaatcttta tttgggttgg tcaaagactg 92340
cagccaacaa tctgagaata tgcttcctaa agtggctttg tcttgtatat ttaattgagg 92400
aaggtatatt ttatattcac acatgcacat gtgacttcta tcttcagata tcaatggtca 92460
aacttaggaa gtgcagcaga ggtgaaggag tagtcagctt tcttcccact tgctcttgca 92520
aattggttgt gatctgtacc catgggtaaa catctatttt ggcacacata caaaaataaa 92580
atcagaatct agagttggta aaatttgatg aatgattcct agtaatttag ttttcactta 92640
caactctaga aattttttaa atcttttctg cataacaata ttgtttttta agttttgggt 92700
ataaaaaaat gacattctcc ctgaaacaag caggcagctc tccattcagc agaaagttat 92760
gcaataagat ataagggatt gcagagacgt tctccatcct cctctctctc tctcccttct 92820
aaggggaaaa cctcctaagt taccttgggc aggtgcctac atttggtact cctggacagc 92880
tcagccatct gccaagaaac aattctatat agatgcctga cctgctcagt tcagaaggag 92940
ttttcttctg actgctgcta aataagccga ctgaatgata catttatttg ttaatggata 93000 ctctttttttg gctctcaatt taaaaacatt ttttaatggg caattgaaaa atatacagat 93060
gaagaggcca tggtctaatg agaagccatg gagtcatcac ccagcttcag cagctataaa 93120
ctcaggatca gtcttgtttc acctagagct acagtagaga aacaaagtgt ttggaaaact 93180
ggagaatcaa caatcttggt gagcagtgtg tgtgtgtgtg tgtgtgtgtg tgtgtgtgtg 93240

```
tgtgagagag agaaatctgt aggtttgggg ctttattgtt tttcctaata tgtaatatag  93300
cttgtgcatc catataatat tattattgga agtatggctc caaaaaattt taggcctata  93360
ttttaatttt aaacttaatg actaaatgtg tatattttca agatatcaga tatccacatg  93420
taaacaaaaa atacggtcaa ctttctggaa gttcatatct ctagatagct atctctgtgt  93480
ggataaaaca tctagtttat gtttaacaat gaatgaagaa tgggctctgg tcatagctga  93540
acagggaacc tggggtttgg ccacttcagg gtgacctcag gcaagtcatt aaatcagtta  93600
cttgggttta tactttcctg tttctttcat ttatttatta aacatatatt gagtggatta  93660
ctttctacca ggcactgcag agaacaaaac aaataaatcg cctttctaga tataaagtgg  93720
ctccagtcca gaggggatga gagtagaggc tggatattct gtccctaacc tttttggcac  93780
cagggactgg tttcatggaa gacaactgtt ccacagacca ctgggggtgg ggagatggtt  93840
ttgggatgat tcaagtgcgt gctttatttt tattattatt atatcgtaat atataatgac  93900
ataattatac aagtcaccgt aatgtagaat cagtgggagc cctgagcttg ttttcctgca  93960
actagacagt cccatctggg gatgatggga gacagtgaca gatcatcagg cattagattc  94020
tcataaggag tgcacaacct agatccctcg catgcacagg tcacaatagt gtttgtgctc  94080
caatgttcct gaatctaatg caagtgctga tctgacagga ggcggagctt aggtggtaat  94140
gctccccgtg gcttgtggct catcttctgc ggtgcagcca gttcctaaca ggccatggac  94200
ctggtaccag tccatgccct ggagctcgcg gacccctgct ctaaagctac ttccggcgct  94260
ggtagtatgt ttttaattat ttcttttatg ttaattttat tttccaaata attccctatt  94320
ctccaataat tacaggataa aacctttagt ctaatatttg agatttacca cactgttgtt  94380
caaatctgcc ttcccaactt acaattctac ttctcccctg ctaaaattat tctctctagt  94440
tacaatgagt tgtggacagg aagtttgctt cattcatctt tgtatccaca atacctaaca  94500
taatatctga cccagtgtag atgctcaata aatgattaat gagtagtaga taaatggaag  94560
cctcagtcta tctcctttct tgtcttataa tattatacct tgagtatgtg gaaaaaagta  94620
ctgaaaatct ttgattcttt caaggtgccc agggtatgat ttatctagag gatcttgaat  94680
taatagctag atttcatttc caatttatga aacagatttc agggtctttc aggaactaat  94740
aatttttgaa aattacttac tcagcttcca aaggttttat cagtcatgat aaaggtatac  94800
tatgatactt gctgattaca tacaatttca agtatttaga tgtttggaaa tacgtggatg  94860
ttattagtac tatgtacata aaatttgttt ttgaatgtcc ttacaatctt gatagttctt  94920
tagaagaaaa tttaaaatga ttttactaac tctgcttcat ctaacataaa atcctgaaaa  94980
cctcaaatga tagtactcct tgtgcctaga gctgctggaa agcacctctg aagcactgtc  95040
atggagtttg tgtttttcga accttataat gaacagcgaa gtgggaagtt tccaggctta  95100
ggtgttcttt cacgaggagg aagttgggtt taacacccgt cttagtagtg ctgtacagag  95160
agcaataaac aagccataat gtggtttatt tgggttaacc tattagccat gtaacctaaa  95220
agcttgaacc acatggaaaa tagacatgat gaggtgagaa gcaaatatga caaccaagaa  95280
aagacaggga ttgtgacagc cgcagtgatg gacggcgggc cttgaaacac agtgaggtgg  95340
cccgaagctg gccccgctgg gcctcaggct cccggcccag cctcttgggg cttttgtttc  95400
ctcttccatg aagcagagga ttgtgccgat tgctctgcgc cttcatatgt gtgaagctcc  95460
catgtcagtg cctggcacat ggctggtggg atatgttttc ttttattact gtacaaatga  95520
atttgataac aggctggtta ctcagagcca gctttgtgac accttacttg tctgtatatt  95580
ttgctctttg ttcagttcat tcattcatcc atagataaac attttaaata actattcaat  95640
```

-continued

```
tgcatatcat gaatatttat tatctgctct gtaacagcag tgtgtgaggt gctacatctt  95700
ttatgtaaga tctggagagt gactctcccc acctgggctc cgtaggttat gggagggtca  95760
ggcacagcac tcccaccaag ctatctgctg gggcatgagc tggggtaacc tcgaggagag  95820
gcccctgctc taaagtacac acctaccatg tggctgtcat tctgctcaca gtcgcccctc  95880
cctgctggcc tgggagtttg ctgctcacct gctgtgacag tcaccaagct ggccatgctc  95940
cctgggaaac agggaaggga ggagacactc ccatcctgtc ctcactgcct ccagcctaga  96000
gaagggctct gaagacgacg gggctctgag gatgtgatcc cacgtgtcct cgtcctgagc  96060
agatgttcta ttcgtgtcca actgcagcct cccttcccat gacacacaga cgtacacaga  96120
tatcctgaaa tcagcattgc ctttgtatcc caacatggag atccttgcct gcaataatgt  96180
ctcgcttttt tcttcaatca ctggaacctg acttttcttc tgaaccacgc tatgtgtcca  96240
tgaacttctc aagaggttct ccaccttcct ctgcaacggc tcagctccac tcccaggcct  96300
ctcttgagaa tttccgcacc agctgcagcg tgccccccctc ctctctgtga atttctcctg  96360
tgacaagatg cctatcgctt tgctttgcat caggttgcat catatgatgt cagaaaagct  96420
gaaagaaaac aaagtgctgt ccctggggag tggggcactc acaacacaga aaggagcctt  96480
ggggaggggc cgcgcttggg tttcacctgc agaacaccca cttctggctt caagtaacca  96540
ttctttagtc ccacattcta tattgccatt tgtttttcat gagcattaaa aacgcattct  96600
tagttcttag gtgttttctg ggactcagag ttcattctgc tgtttcattc aaggttcagt  96660
acacttcttg attttatgtc cattgtattc caaggataga tgattaaaat atcatcaaca  96720
atctagggca ctttgtgaaa accttcaccc cagaactctt atccactgat gactctcctg  96780
gtctgctaaa aactcactta ttgtgaaaga ctttcctggg atcaaatgtt ttgaaataaa  96840
aatttatatg taaagaaaca ttgttttgtt taaaacagag gtaacagtat gacttgaatt  96900
ttattcgttt cttaatcatg attttttttt ctaatgatga cctttgatta aattgtataa  96960
aaggaccttg aaattgaatt gacacatctt ctccggtgag accttggtcc agctgctaag  97020
gtaggatttc tgacagtgcc ggctgtccag tggaactggc tgacaccttt tctcagagga  97080
caaggcacag ctgtgaggtt ctttggagga actgtgcgcc tgccccattg ccagtgtggg  97140
gcccggtcca caggaaggcg cccctaatgt gctcagcgtg tgtgaagatc agaagcacac  97200
agatgcaaac atgggttagt aagtcacaca ccgtaactga ctcgaactca cagctctaaa  97260
acaagagtaa agaagatgaa attcatccag ttttgtcacc acctgtgcat ttccaccaga  97320
gaggaaacca ggcagttgtg aaatcgaagg ggctgggctg cccactcctg gcccacaggc  97380
ccccctaccc tgagggaggt cctcaaggca aaggacagga agcggtgggg ttgggagctc  97440
tgtctgatgc tctgttctcc caaaataatg tagacttttc cactggattt gaggacgtgt  97500
tctcaagtgc atttcaggct tgggacaact ggaggcagtg ttggtggaca gctaaggagg  97560
gtgcaggaga atcactcagt ggaggaccct cattttgctt gctttggctc tgagcatgtc  97620
tgggagaatt tttttttttt tttttgagat ggagtctcac tctgtcaccc aggctggagt  97680
gcagtggcac gatctcagct cactgtaacc tccaactccc gggttcaact gattctcctg  97740
cctcctgagt agctgggatt acaggcgtgc gccaccacac ctagctaatt tttggatttt  97800
tagtagagac ggggtttcac catgttggct aggacggtcg caatctcatg acctcgtgac  97860
ccgcccgcct cagcctcccc aagtgctggg attacaggtg taagccaccg tgccaggcct  97920
tctgggagaa ttaaattcca cagttgaggg tggggccgct tggaagaagg tggggtaacg  97980
caggaaggga gccgggattc ggtccttggg cagagctggc acctggggct cacaaccctt  98040
```

gcctccttca gcctgtggat catgagtgcg tcagctgaaa ggggcatgaa accaacccta 98100
gcaggcatca gattttgtaa tcttatgtgc tctgtgccag agctgccgca acagtatccg 98160
ctgccggccc ctcccatttt tcctctcctt ccctttagag cagggagaca tggccacgcc 98220
tgacaaacgc aagccttccc tgccctgcca aagcccactg tctggcatct ccttatgcct 98280
cttgttctct ctccgttctg cagccctgtg ggctttcttc agttgtttaa acacagatgc 98340
tcctgtggcc tctggctatt tgcagacacc attcattttg cccggaaaga aaattaactt 98400
cctcttccac caggtgcttc ctatggttct tcaaaactca cctcgagcat tactccttca 98460
ggaatctttt tttttcagtt tcaaagtagg caaatattct ctttggtgat gtcaccgtgc 98520
catgtacttc tcgagttgtt acgaaatagg gcaaacagtt ttgagataca ctgatgtaat 98580
tttatgcttt gcatttcccg gtatatgggc ttctcctacg caacctgggc agcctcctgc 98640
cctacaggga ggagggtgac ctgccaggat gcagacagcg ggtttactca tacggggaag 98700
gatgggcagg ttctgcatgc taatgaagct atctgagttc acagaaacac acgaggcccg 98760
aaggccaagc tttgtagaga aagaaaaata tttcccagtt tgggaagctc cctttttggc 98820
atattcaaag ctaggcaaag tgtaattgat catagagttt tgtgtctgga aggtgtggtg 98880
gaacagaaag agaagaggga tggcctgtcg ggtgccacac catggggcag ggaaggcaaa 98940
gcagagtgta aagcagcaca gtgccaggtc ctgtccacgc caagtgtggg gccttctcct 99000
caaggttgat gggcaggatg tggggtgagg gtgggagtgc atggcaaaaa tccagaaaga 99060
tggagggtcg cctgtcaagg gcagaggggc agtgcacaaa tacggccttg taggatgccc 99120
ctgctccggc acttcagggt ggtcttctca cagtgctagt gactgcacag ctcaaatagg 99180
tagagtgagg atctgagctt gctgtccttg tcactgtggc atggaaagca tcaagacatt 99240
cccacaggta catggagggc atggaaggag gctgagaaca ttccagaggt catctctgtg 99300
gcaaagggtg cctgtacctg gaacccaaca gaagtcactg acaacctcag ggggtccatg 99360
gggccagtga gagtaagacc cagtgggcac gaggaatggc tggtggttcc caggaaaaca 99420
gcctgaagcg aaacagaaca gctgttcagt caccacaagg tgtagttgtg aatggcaggg 99480
aagcattagg aggggtcttc aaagtggctg ggattgacgg tttggcaacc tggaagcgtt 99540
atggaaagct tggagcccga agagagagag agcacatgtt ggtgggtagc atgttcatag 99600
tgaccggctc tgtgttcaga tatacattag caacttggat ctaccacatg caaagtagat 99660
aacaataggt atgtttttaa aactctgtga ttctcaattt gctcattggt agaaagtcat 99720
ttagttgtga aaatttaata aagtaagtaa agcagagaga acagtgccct tggatagaaa 99780
gcacacagat ttgcattgtt gtcctgctgt tagtattttt agaaggtaag cttcaagatg 99840
gcaactcata tgtatctttt tcaccaaagg gttttcagtg gctagtacaa ttccatgatg 99900
taatagagac tttacaaaat attcctggag caaatgtata aatgaacgat ttgaagcctt 99960
aagttagatc agggtgattt attttttaaa atgtcatata cctgtgttaa tagcagtgaa 100020
tgatgccaaa agtaatatgt gtgtgtgttt cagaactctt atcaagaaga tcactcatga 100080
taatatacag taaatataaa tggtcaaac ttcctttaca aaagatattg tcatattaaa 100140
ttttatatac acatacatgt gtacgaagca aaatgacata gaaaatagat gagtaaattc 100200
ttaaatgtaa gacaaaaaat aaaatgaacc ccaaagtgca atattaatat catacaaagt 100260
ggaacttgag agaaaataag gaatgagcga gggctacttt atattaattt tctaaagtat 100320
aatttattat gagaatgtag tagccagaga tgtttaaaaa ccaaataaca gcatcaaaag 100380
acataaaagt tgttataaat gcaataagaa actggcaaag cacagtctta acaggctact 100440

-continued taacaatatc tctacttttt atgttatgta cataaacttt acagagaact gaataattaa 100500
tatgttttat ttactcagta tttctttaaa gaaaatgtct tcaaatgtgc atcgtatagt 100560
taaacattga ttatagcttc tgtgtcaaaa aaaagctcaa tacaaagcat tcccataagc 100620
catattttga caataaacaa tagaatttaa gtaataaaaa gtttaacacc aaatctaaaa 100680
ccatgtggaa actaaaaata ctccctgaat aatccatgag ctgttaactc aaagaaaatg 100740
atagagaaaa ttaaaactga ataaagagat tgtttagaag atgccataat atatggaatg 100800
taacccacat tgtgctagga gaaaactttg taagttttca aggtttttat aagaaagttg 100860
caaatgaaat atccatgtta ctgcagaagc aaaaaataat ttaaaaagcc ccaacaaaag 100920
catgagtaag aaaacgaaga tatagtagaa attaatgact tagaacctga aaaactataa 100980
caaatatagt aattcaaacc tttattcttt gatattaaat actactgatg acaaatcttt 101040
ggaaggctaa gagaaaagca gagaacatac aaatattcag cattagaatt caggacactg 101100
gggagaggca tagtggtgag agcagtccct tagccgaggc acactgggtt gacttcaccg 101160
gtactcagct gtgtgatcca ggaacgctgt ccagccttct tgtctcatgc cttggattcc 101220
cacggctcat agtgctgtta aaaaaattac attgagttac catttgtgat atggtttggc 101280
tgtgtcccca cccaaatctc atcttgaatt cccacatgtt gtgggaggga cccagtggga 101340
ggtaattgaa tcatgggggc aggtctttcc catgctgttc tcgtgatagt gagtaagtct 101400
cacaagatct gatggtttta taaagaggag ttctcctgca ccagatcgat ctctctgcct 101460
gctgccatcc gaggtgtgac ttgctcctct ttatcttccg ccatgattgt gaggcctccc 101520
cagccgtgtg gaactgtaag tccattaaat ctctttcttc cgtaaattgc ccagtctcca 101580
gtatgtcttt atcagcagtg tgaaaactga ctaatacaat ttgtcgagta cttttataac 101640
agggtttcaa aaagaaaata tgtatgtgtt tcttatgtaa aacaagcaat atggaaagga 101700
ggttgcagtc cacagccatg agataatcca ttttgatatc tagctgaaat gaatgaattt 101760
ctaggaaaat atattaccaa atatgactta agaagagaca gaaaacttaa tttgtcagtg 101820
ctacaggaga tactgaagaa agtttgaata gagctatact tctgatggta gaaaggcata 101880
tattttgcat tcacgcattc atttaacaaa tattgattaa ttacctacta tgtgcctgat 101940
gctgctttta ttccactaaa agtacgataa tttttttaat ttcaaaagaa atttatactc 102000
tgttaaaaaa tgagagtatc aagtggtgaa gattaaaagc aaacatcttc acctcctcta 102060
ctccccaatc tcagctgtct gctacgtatt ctagatattt ttaaattcct ctctctctac 102120
ctacctacct acctattatc tatctatctg cctatttgtc tagttgtgcc tgtgtatgtg 102180
tatttaagct cagtaggatc ctattatcca tttgttttgc aacttgtttt tcatgtgatg 102240
gatgtccctc cacgtcagca catggtatta taattatgca tattttattc tctttgaaac 102300
aaggtgaata aataaacctg tagcaaggga aacgctatct gtcaccaaaa ctcccactac 102360
tcgaagcgtg acctaaggcc aagatctgcg ggaccttttt cacaaccttt gtgcgtcttc 102420
ttagcttctg atggcagcca ctggttccta cacagcatgt tgtccccttc tgtgttgtgg 102480
gagcttttag agtttttctt ttattttggg gtctataagt tttatcaggg gacctgtggg 102540
tggacacaca gccctcagtg gatcactgta taaggaactt cagctccaga aaagaggctt 102600
caatcatttc tcctagtatt tctttctaat atttttgttc tctatttgta aaagtctcta 102660
ttagtttgac cctcctgaat atatcttgca agacttttag gtttttattc attcgtctgt 102720
ttatttttcc ttttagatct gggaggtttc tttggctcga ccctctagct gcctggtctc 102780
catggtggaa cagcccctct tctggacagc cagcttggca gttccattta attttcattt 102840
tgtcagttaa attttattta ccatacctct tcctttttcg taagtgctgt tatcttctta 102900
ttccctgttc cttaccctcc ctacctcctc ctcctcctaa ttgtagctaa ttctaatttt 102960
atgggtgcaa tttcctctct aatctctcag tatcaagttg gatttttatt attattatta 103020
cttctatttc ctctcaggtg agctgtttta tttgttcaca ttatcctcca ccctggtatt 103080
tgcctcctgt attgggtggc acttgatttg gttctttttt atgaatgaag atggggttga 103140
ttgcttgtgg gtttcctttg cagccaggca catctgtttc ctgctcagcc tcctccctgc 103200
ctggctaact acaggcctgt gtctgtggat gaggctccaa cagcaggaag aactatccag 103260
cagcctgggg acctcctcct gcccacgccc ctcctgggcc agctgccaag ccaggagggt 103320
ttttctttcc tgagagccga taactacagc acagagactt cctcgctttc ttggttcaag 103380
tctctatcat tgtttcagta attttttttac agtggcccta ggccagagca acttcttaac 103440
agttctgtgt ataagtagtt agagccaaac gacataatta tgcatgccct aacaacttag 103500
taactgtttg aaaaaccaat acatatacct ttaaagaaaa aacaaacaaa aacaaaacaa 103560
aacaaaaaac aacccatctt ttcttttgct ctgaaattcc catcacttag cagcgctgca 103620
cgcgcctgct ggggacagca cagcctcacc taccttggca tgagattgga gagccctgct 103680
gcgttttctg ttccctgctg gttttcatac ggggcctgct ttttatcaga gcacctgctg 103740
aacatccagc cagggcctcg tggaaagtaa agtagcgctc ttgagccttg gatcggtggc 103800
tttgctagag cagacgtttc atggaggggc tgatggatgt ccaagaggtt gtgtttctct 103860
caaaaatgaa gaaactccac agcgcccctg tgggtttgcc ggggcgaaga tctgctgtgc 103920
ttcttttagg ccctgtaagt tcaccgacaa attaattttc tttaaaaact agtctttggg 103980
ctttgtcttt gggagaaaca atttctccga ccgtcatttt tcgactctat tttgggggat 104040
tggtggtagg agctgtagtg agccgttcca gctctcgccc taatgtttga ctcatggcaa 104100
ggtctttgcc tccttgactt tgctctcaga gctttttcta ggcttgcttg ggaagaagct 104160
ttcaacattt ctattccatg gctattttca tttttctctt ttccagtaat gttatgtttt 104220
catttatatg tattattttt ctcaaaagta acttgaggaa tagaaaaatt ggagccaagc 104280
cagctcctcc atcagccatt tgaatttgct tgagcttcta tattgggctg gacatcagtt 104340
ttaattctta aaattttatt tgaattagaa tggtgaactt tgaatcatac tgactctttg 104400
tggattccac attttatgtt gtcagttatt atccagctct acttgaattc taaatcacaa 104460
aacaaaacta ttcaaaccat catggtttct gcacttttaa tgtaagtatt tgaggttcaa 104520
agttagctaa tcatacaata tattccagag ttagtgagaa tggacactga aaaattactc 104580
ttttctggga taaggatgac taagaaccac agggaacaga gttcctctaa aatgagttgt 104640
tttcaaacgg aaataaaaaa accacaaaac attgcagaat tgctcatttt atcagatggc 104700
tgaaacttac atttgtaaaa atgcagtttg attgattatg atggctaagc cagggtttgt 104760
tgaccttgaa gaataaaagc ttggcacata cttattggaa agtgtgagcg acatgaaaaa 104820
gatataacga gaaatctttt aaatttttgc aataggactc aagaaataaa agatgtcata 104880
tcaacacaag gtaaggcttt gcctagcagc cacttggtgt ggaatattta caaattgttg 104940
acagttgtat actttaatac gtatgtgcct ttccaaaata tgaaggtatc agaattttag 105000
atgaggtaga atatttttca tacttcttct tttagtatgt cacagaaaca agttatttga 105060
tattatctct tttatatgta tagtacatcc atggatagca accacagtag gaagtaaaat 105120
taccagcaaa actcttgcca gggattgtaa ttagttatta aaaaataatg tctccctacc 105180
ccatattctc ctcctgagtg tattttgggt ttttcttcca ctgccaaagc cttaaagcaa 105240
atgtctagac aaacctccta cactctgata atttcaaacc tgctgatttc gagtgataga 105300
cctacatctt gatgtcattc tatgaatggc aaggcctgaa tttccaaagg ctctctggac 105360
atctgggcag tcatcagaac tcaccgtgcc ctaatctgat gggccttcct tccctgctgc 105420
cttttctcct gtatttcaca tttgagctgc tgataactgc agctgtccca gctgccgggt 105480
aggaacgtca gcctctcccg cgggacgtca atccctagca cggacctgtc tgacccttcc 105540
cctataccac gtcctcttgc ttctccctct gaaatatctc ccaaatcctt ctctctgcct 105600
tcttttccta ctctcctcac tcacatgact gcctcgggcc ccattttcct tcacttggat 105660
ctttttgtga tggtctcttt acaaagacac tgttgctgga accccttccc agaagctgag 105720
gtagaatcat accgctcctc tagaacctca gacactctca gtgcatttaa agacataccc 105780
aaattctggc aacatgacac aagtctgcac cctgtcctgc ctcatcttcc acttatttat 105840
gagctgtgtg tcactgagct ttccaaaata taccttttgt tttcacagcc cattcttctc 105900
ttatcctgaa atgaacttct cttctatgcc tctgacacct actcacgtat gaatgtcctg 105960
ctaacacacc acttccgcca ggacccaagt ttgctcatga accctcttgc ccattccagt 106020
ggctacttca gaactcgcca gatctttctc tcgttcccat gttattgatc tgccgtcttt 106080
gtttgctttt cacactcctt ctcttatcca agaaagattt tcacagcatc acactcattt 106140
aaatgtctat agctttagtt ctagactagt ttatcttctt gctatatttt tagagacaaa 106200
tttccatcca aatttactat gcaaaataaa attcttaagg aatctctaaa tcagaaagca 106260
attttggcat gtttgcattg tgtatttttt ttattaactg agatttactc agaaagaatc 106320
aaatgagcca aaaatttgga gctgaaatgc ttgacattta acccttctgg aaagaataat 106380
gttggtctta caatgaatta attgtacatt tttgaaacgt gtaagatttt taaaaagtta 106440
tatgttctag ttgttaagcc attagaaagt ttgggtaagt ggccccttttt gtaggaaatc 106500
ctgtgtgcct cacagtctct ccatagcctg gtgagtagca agtgagaaat attttgcaat 106560
agaaaacaga aaagtcaagg ctgaggaaaa atagaatttc caccacaaat atctgataaa 106620
tttatctagg agccaaattt ggggagctat atgggtagtt caaaatctgt ttgtattctc 106680
ctactggaca gaaagaggaa agtaaatgga ttaatcaggt agattggcat ctactgatgt 106740
aagcaacagg tagataaatg ggatgaatcc agtcatcctg gttcttactt ttctgtgttg 106800
ggatagaaga tggttttctc tcataagtgg atgtaaggga aactggtggg gataatgtgt 106860
tgattgaaat ttaaattttc ttatggaaga cttgttgaag aattcaattg ttttattcca 106920
acaatctggc agtttggatg cctgccatag ccttaccgtg cattagctgt gttacctcaa 106980
acaaaccagc tagtcttcct tggcctcagt ttccttagct attgaatgag ggtttggact 107040
gggcgatcac atagatctct tttggtggcc aaatcctgtg gctttgtgat tctgtgtaca 107100
gcccagttgc ttattctgtg cagttagacg atagcatcca gactcatgca ctaggggtgg 107160
aaaccgttga ctcctttctt ctttcttcct ttagtttctg aagcactcct ctgtgactac 107220
acattatcag tttcttcttt ctctctatat gttttttttct ttttttccag ataatgcagt 107280
tccccttgac tctaatccca aactgctttt ttcctccctg accctacata cagttcatcc 107340
aagacaactt catctgtaca catgcattca actaccatac tgttactatt agcttggggc 107400
tctttccgga gcttcagact cctgtcttcc acccccatgg acatctttgc ttcaatgccc 107460
tgtgagtgtc tctaactcac tatgtacaga gctgaattca ttatctgttg cccttaattg 107520
atctttcttg ccatggaata ctaattgact tccttctctt ccatgtaacc acctccaatc 107580
catcttcaat ctgtcaacag aatgatccta ctaaaaccca gatctaatca tgtctgtctc 107640
atgaggaaaa atttttagtt tccctattgc ctccagaatg catttgaaac ctctttctag 107700
ctctgtacag ccctgccacc tgcttcttga gtctttatgc actactgcat gggcccttca 107760
gccattcagt aaaattgact tttttctttt tagtgcatag gtctatcaat tttgactcat 107820
atatagattt gcgtgatcac taccacaatc aggttacaaa caattccctc acccccaaaa 107880
ctccttgggg ctatcccttt ataggctcac cctcctgaat tctgacgcca gcacccacta 107940
ttctgtcctg catcactgcc gatgtatctt tccaatgctg tcataccagt gcaatcatac 108000
ggccctcacc tattgaggtc agcttcatta gctcaccgta atgcctgtaa aatccatcta 108060
agttgttgat tcatgtttgt cccttgctgg gttgtattcc attgtgtgga ggagccacag 108120
ctgattattc actcactttt ggaggggcat tttagctgtt tccagtttgg gacaattatg 108180
aacagagctg caacaaacat tcatgtacag gtttttgtgt gaagacatat tttcatttat 108240
ctgggataaa tacccaggag cagaattgtt gagtcatgtg gtaagggcat gtttaccttg 108300
ataagagcct gtgaaaccat ttttgagagt ggatgcttgt attttttaaa caagattcat 108360
agttgactct gaggcccagc caggtttggg agccagagcc ggaataatca cttacatgtt 108420
ggtcgttcgc acacactaca ggttgcttaa caggactctg tgcctgcatg tttgtgtcat 108480
ctctgcaacc tcaaagccta gtgaagattt catcttaact tgattgctat gtgtttgcat 108540
agttgaataa ctaagagaga gtgctcacag cgtggctgct cccactaagg tgtagtcaga 108600
acatgtgata tacagtacag atgattttcc acacttctct cctgcacgta acaaaattac 108660
ttttagtaat gatcatgtaa gactcagtag tagtaatgac tttctttaat attatttatt 108720
aaatatttta ttataatatt tatatttata taatatatat ttatatttat ataatatata 108780
tttatattta tataatatat atttatataa tatatattta tatttatata atatatattt 108840
atataatata tatttatatt tatataatat atattatata atatataata tatattatat 108900
aatatatatt tatatttata taatatatat tatataatat atatttatat tatataatat 108960
atattatata atatatattt atatttatat aatatatatt atataatata tatttatatt 109020
tatattatat atatttatat aatatatatt tatatttata taatatatat ttatatttat 109080
atatttatat ttatttatat ttatatatat tatatattaa atatatgtta tatataacta 109140
tatattatat attaaatata tgttatatat aacatatata ttaaatatat attatataac 109200
tatatattat gtattaaata tatatattat ataactatat attatgtatt aaatatatat 109260
attatatatt gtatattaaa tatatattat acataactta tatatgatat atatatatta 109320
tatattatat atgaaatata tattatatat aactatatat tatatattat atatgaaata 109380
tatattatat ataactatat attatatata actattatat ataatatata ttatatatta 109440
aatatatatt atatattata tattatatat aaatttatat ttatatatat tatatattta 109500
tatttctttt aatattaaaa tgagtagaaa tcagttaaaa ttatacattt ctatttttaa 109560
aaaaattttt cagattcagt aaaatgtttt atgaactgac atttgcattt actaaacaaa 109620
aatattacat tgtgcagttt gtcccctgtt gcactgtttt agattttaag cacaaacttc 109680
caaatggtcc cctctgatga ctgaattaaa ataagtcaag ttgtgttcct ttattttgac 109740
aggcactgtc ctgtcacgtt taatttagaa tctaaggttt aagtgcgaga atatgtatta 109800
tccccggggt tggagaagca cctggaacca gtgttaatag tttactccat ccagctcctt 109860
ccgttcacat gaaggcgggg ggctgggtgc ctgtgtgcca gggtcagctg aataacttgg 109920
agttttctgg aataactttc ctgtagagta tgatgtttat taagtgataa agatacaaat 109980
gaattgattg aagcttgcat aggtgtataa gtttcgccag actgctgtca caaatgacca 110040
caaactgtgt ggcttaaaat aacagacatg tattcctcat ggttctcgag gctggaggtc 110100
tgcagggctg gttcctttgg aggctgggag aaggaatcgg ccccctgcct ctctccagct 110160
tctggtggtg gctggggcca tcggggtact gcttggctct cagacacatt gcctgatctc 110220
tgctccatgt tcacatcttc cacattctct tgtgttgtct tggttttctt cccctcttct 110280
tatcaggaca ctagtcactt tggatgaagg acccaccata cttcagtatg gtttcatctt 110340
aacttgattg cttctgcaaa gaccccccac ttccagataa agtcaccttc acaggtacca 110400
ggggttagga cttgaacata gctttttggg cgatgcattt caacccatca cacacgcgca 110460
cacacgtgca cgcacacaca cacacccaaa tatatgtaat gaaaactcaa cagtcacaag 110520
agcaattatt tagaactttc atcaacaaat gattgtgtgt gtgtgtgtgt gtgtgtgtgt 110580
gtgtgtgtgt gtaggactgt ttcatcacta actgtgtttg gaatgactct cttgttggga 110640
taaaagcagg ccagttttgc ttggcttact tatcgtgtat gaattatctt ttaacagaaa 110700
ttttctgtac cccaggcaag accattccct tcatcccagc ccaggtagct gctgtcccca 110760
aacaccctca gtgggcatga ggtggtcctc ataattcctg gtgatgtcca tttcttcttc 110820
catgttttca aacagcggta tggcactttg aggtgaaata tggctctatt taatgtcact 110880
ggtttcttga agctctgagt tttctgggac cacaagtttt acttgaaggt aagcaattta 110940
aagtatttta atataaacat aactacagta taaagtgtga tgcgtatatt acatatatct 111000
ttagaactaa acatgagatg aaaaaatatg aacatggttg cagggccctg aaatttcttt 111060
cctctgttac tgtggtaaac aaagcaaagt aaactaagac agtggaaagg gttcatttca 111120
aacctgtaag atatgtccta tctctaagtc tgacttgatc atttgtttgc tctgatgcat 111180
aaatggcaat ggaaataata ccaccttctt cttatcccag taaacaagtt tgtgagcaaa 111240
taatttaata tggggaaaga gcttctgagt tctcagagga tcgccatttt ctcagagcta 111300
ggagatgact tagtgcgggg ggtgagccat cttttcggcc agttcgtgaa tgtcttgggc 111360
tttgtgtggc agaccttctc cgatcaaaca actctgccgc tgcagcttga aaacaaccac 111420
agacaacaca cacacaaatc cagcgtggct gtgttccgac gcaatttgac aaaaacaggc 111480
actggccaga cttggcccat ggactgcagt ttgccagcct ctgaacttag aggaaaaaaa 111540
ttggaagaat ggagtgaacc ttgagcacag ggaggagcag gcactgaagc tgtctgtgtg 111600
ctcttttcct gtcttgatgg agaacaagac atttgtatgc tttcacaaaa caaagacaag 111660
tgtaactgtg agttcaaaga ttacatcatt gatttcagta gtgttgatac tttaagcatt 111720
tgctatgttt cctctgagct attgggacat tacactgaga tgcagtcggt ggtatgggga 111780
ggtgctcagg ggttctcctc tctgccctca ctgcttggtg cttacagaca gctactgaag 111840
cagtgccttt catgctgggg agcctgacta tttgcaggtt gttaaatcaa tttaatgggt 111900
cgtggtctgc atttgaaaga atagaactgg ctcaacttcc ttgggctaga atggaaaatc 111960
acaaggtaca tcctttatag tattttgtga atttttgttg tacacttgaa catatataaa 112020
catatatggg atgcatacat aataaagaac tattagggga aaatcaagct gttttttgta 112080
aagttaaaac tttggaaaga gtatagtcga gtcacaaact tttctctgtt aagttatacc 112140
tagatgtgat gattgtgaaa aattggcaaa caaaaactct agaaaaagtt tgcattcaga 112200
ttgtttccca atggcttcct aagttactga aagacatctc aactagaatt taggaataga 112260
cactttcagt gttatgtatg ccaaataata ataataataa taagtgccga actctaatcg 112320
actgatccat ttctgttgcc caggctggag tgcagtggca tgatcttggc tcactgcaac 112380
ctccacctcc tgggttcaag caattctcct gcctcagctt cccaagtggc tgggattaca 112440
ggtatgcacc accacacccg gctaattttt gtatttttag tagagatggg gtctcaccat 112500
gttggcaagg ctggtcttga actcctgacc tcaggtgatc cacccatctt ggcctcccta 112560
agtgctgaga ttacaggcgt gagccaccat gcccggccct gatccatttt taagaaaagc 112620
ctttatcctt aaagcaaata ttggtgcatg agtatgtaat gtatgaacac gtgatgttta 112680
tgatttccaa cttgcagtca ccttttcttt gaactgttct aatattttgt tcagtcctca 112740
tttgtatctg ctgaacctcc ccttgagggg attgtcaggt accctccttt cgcctgtgag 112800
ctgagggaaa ggtgagaatg actttagggg aagagaaggg tgaaaagtac caatttccaa 112860
ctcttcctcg caatcttgaa atgtttgatt ttgatctcat ctttgcactt tcccctccct 112920
gccgtaaaga gagacacaca gttctgtgct gggctaaaag catgtttgaa aagtaaagaa 112980
attggaatat aagatatata tcagtccaca ctggactgat gtggccaggc aaggcaactg 113040
acctcttcta acgttttcct tcttccagca gagcacgtct ctgtcctctt aagaggccac 113100
atgtcaggtg tgtggctctc tctgactctg tcctaatggc agtgccttcg tattttttgt 113160
ttgtttgttt ttgttttgag atggagtctc actctgtcac ccaggttgga gtgcagtgtc 113220
acgatctcgg ctcactgcaa gctccgtctc ccgggttcat gccattcttc tgcctcagac 113280
tcctgagtag ctgggactac agacatgtgc caccacgccc ggctaatttt ttgtattttt 113340
agtagagacg gggtttcaca ttttagccag ggatggtctc gatctcccga cctcctggct 113400
ggtgatccac ccgcctcagc ctcccaaagt gctgggatta caggcgtgag ccaccatgcc 113460
cggccggcag tgcctctgtt tttatggcat gagggcagcc ccggtgaact ggggttcttc 113520
gtggaggagt gtgcccgtgc gtgacggaag catgcgcctc ctctgacctg gatgcaggct 113580
gggatgccat cggcactggg gctaccacat ggtgctaacg ggctcagaag aagccagcac 113640
agggtgattt aaacagtggc cagtgatcca gggtcgccag tgctgaagga aggaaaaatc 113700
aatgttgaat aatatacttc acagccctaa agtagactca tatgtaatgt tgagacaact 113760
aacaatttgt aaagaggaca gtactaagca gaagagacga cagaaatacc ctgctttggt 113820
ttcgtttgat gaattttctt gaggagggat ttctagggca gttcaaaaag aaaacagaaa 113880
gcaggtgaca ctcaggtgaa atattcagca tccatctcct ttgtgtctaa gccctggtga 113940
gtctgtgtgc aatcagctaa gggccttagc ccatggaccc caggctgcag gcagcccttg 114000
ctcactgaga ctggggacca caccagctga tggcctccac tgggttacat gcccacaggc 114060
agctgctgag tctcaggata gcgggaagaa aggtcctgcc acaagaagac atcaattaac 114120
aaaaaataga taccataatg taaagcaatt acgtggcctg ccttttggaa acttctgggg 114180
agaggaggga ggaagtctaa acatgaattg caaatgctgt acatgaaaac agtatgcaga 114240
tatatttagc tctatcaatt agttgaagtc acaacatcca gggatgtttt cactaatgca 114300
tttcattagt aaatatctat tactattggg tatttattgt taaatatatg catgcgaaaa 114360
gacagactaa ggaacactca agtcctcacc tctcagcttt gctgtatctt agcattttgc 114420
cacattcgcc tcagatagtt tttaaagaat taaaacatta gatgctatgg aagcccattc 114480
tacctcttac tgtgacttct aagatatttt caatgattta agaaaaattt tgaaaagcaa 114540
tgaagtcaaa cagttaaaga cactgctgcg tggaggtttt ccctctgatg gtgagatgca 114600
gacgctgcac tcagaggaac atgagctggg aaatggggag tctgaagaga agagctgagt 114660
tgcaaacaaa tgtccttttt gcttccagcc ttagctttgg ttttatgatg gataagatgt 114720
atttgcatat tatgtcctct gtccaatagc atattccaga caggggtttc tgggggcatg 114780
attaggaaat aaaatatatt gctgtacagt tgactatggc aagcaaagac tgcagacctc 114840
aatcacttaa cttaatataa atgttggagt tatcacagtt ggacaaggat tatggtgatg 114900
ttctctacat ttctatgaaa aagtcactat ctggtagtgg ccaccgagct tttattaatt 114960
ttgttattgc acaggagaag gaagtcattt cgaggcaagt gtttgcgccc tgatattagt 115020
aaaacttcag agggctcagc catcccctcc cactgccata tttttaggag aaacagcagc 115080
tgaggcctgg agagaggtga tgtgagattt gtagtgagag atggaaagca tcctggagtt 115140
attccaaaaa gtgatcaggt agaacctcta tgcccacgac atagtgtaaa tcctttgtaa 115200
aaccaacacc caaagcattt ggggttttgc ggtgctagtt tcaccacgca gtggcttgat 115260
tttgaacact gccctttgca gacctagcac catggaaacc caggcctttg cggaggacaa 115320
cgcggcctgc gtgctcccat cctggctact gttcaccaag tgtgggtgac cctgggaggc 115380
tgcccttgct tgtttacttg tttttcctgg ctgttgattt caaagaaatc tcggtcaaat 115440
gagaaacccg ccaacaattt tgaggaaata cagggatgag ctttggcagg aattaggtac 115500
gttctcaaag caggccttct gcccgaagtc acagtgaatt tccaacacca caggagctca 115560
tctttctttg tccctggtgc agggaaagta aataagagca caattagtgg aaaccataaa 115620
gagaatgctt tgaaacttgc atctgagatc aagccaacag gagtttctgg tagaggtgat 115680
attggaattt tgaaaagaca gaaatgttca atccaaagga ctttgacttt gtgcttatct 115740
cataaaagaa gtcatttgga ggctatttaa atgtgtaaaa ggtacaaagg ctttgtggac 115800
caattagttc taggagggtt aaagagcaaa ccctgcccag agccggtgca cctgctggtc 115860
cctcttcctg cttcctggaa tgctcttgtc ccagatagct gtgtgctttg ccctgaattt 115920
ttctttcggt ttcccgttta aatgtcactt tatctgcaag gccatccctt accactctaa 115980
gaagaatttt tctttctgtc cccttgatcc tgccagtttt caataacact agcatctgac 116040
attttatttt attaaatgca tattgcattg tttatctcct gtttatccct tccagaatgt 116100
aaattctctg tgaccaggca cctgtttttt tttttgttc ttgcttttttg agtcagagtc 116160 ttgccctggt tgtccaggct ggagtgtagt ggtgccatca cggctcactg cagactccgc 116220
ctcttgggct taagtggtcc tcccacctca gccttccgag tagttgggtt ggcaggtggg 116280
caccacaatg cctggttaat ttattattat tattttttg agacggagtt tcactgtcgt 116340
tgcccaggct ggagtgcaat ggtgcagtct tggctcattg cacctcccag gtttaagcga 116400
ttttcctgcc tcagcctcct gagtagctgg gattacaggt gcatgccacc atacccggct 116460
gatttttgta tttttagtag agacagggtt tcaccacata ggccaggctg gtctctaagt 116520
tctgacctca ggtgatcagc ccgcctcggc ttcccaaagt gctgggatta caggcgtgag 116580
ccactgtgcc cagctccaat ttctaaattt tttgttgggt ctcactgtgc tgctcaggtt 116640
gatcttgaac tcctgggctt aagtgatcct tccacctgag ccccacaaaa tgctgaaatt 116700
acaggtgtga gttactatgt ccagcatcct tggtatgtgc ttaataacca ggactgaacc 116760
aatgtttgga gtagaattag tttgctttaa ttattcactg aatgaatgat tacataaatg 116820
actaaataga agttttaaat gctaaatttc tagactccag agtttagagt gaattagtgt 116880 ttgtttttg tttgtgttgt atttaagcaa cttatttata cctcttcaaa agggtatctt 116940
tggtgtctta taaaatgtac atagaataat ataaaaatag atcctgaaat cagagcaaag 117000
agaaaaataa gagtggcttc attcttgtag cagaaaatct gtattctaaa aatacatttc 117060
taatatagtc taagacagag catgggaagt gaaaaacatc acaggacgat ggttctccaa 117120
cttgattcct gtggaaaacg tgtactctgg aggctgaacc tggggtttta ctattaaagt 117180
gagataatga tcgtttccag gtgcacatac aaggttgaga aaagggatag gctttttca 117240 atttaaaaag ttccccaata actttttctt aaatctttgg aaattctact gcttctctgc 117300
tggaaagcac ttaaattgat aagaaaaaca gtgaacaagt accaaactct caaccgagta 117360
ccttggaaat agctacctga gttagcctga cagctggatt ttcatggaca gctgtgctca 117420
tagttgtgaa tttgtattgc gtgattttaa tgttgccata cttttaatcg ctaaaataac 117480
cctagttcaa aaaacagagg taaacattga tattttatca tgtttcgtaa ctttctgatg 117540
tttcattccc taagtaattt taagaaccct tgtttagaca tctggcttta tgggacaatc 117600
aaaaatatga tttgagttct ttatttcagg acaatttatg cacataaatg tgctacagaa 117660
aataaggagg agtaggtttt acttaagccg actttgtttt ctcctgtggg atgaagagca 117720
gctctttcca ttgatctgat tgtcccaaat aatgtttcag tgcttcagtt cattttgacc 117780
acgtggtcac accccaaaat gtcagccaca acattacact gtacacacaa aagtccagat 117840
ttaccgctgt acctttggtc caacaacatt tatatttagc ctccaataaa ggctcaactt 117900
gctccaagag atttttaatg aagagcacca taacattccg gttgcaatta tgcagtgaat 117960
ggcaaattcc agaagcataa gtaaatcaat ggagaaagca caatgatccc ttctacacta 118020
gcatctggat ttttaaaaat ccacatagcc tcttccttcc tttctccctc cctcccactc 118080
ctccttccac cctctcccct gctgggcatg tgaggcttgc tccaagcttg attctgagtg 118140
gagttttcgc atttctaacc tgcacagagg ccgggtccag ccttaggtgg ctgtcccatg 118200
gtggacttgg ggctgccata cccagttcat tttctcaacc cttcacttca ttttcgcccg 118260
ttgacacagg cttagtgggc tccggatttt atttttttta attccaaacg gttgcctaac 118320
tttccccttt cgcctaaaca cgatagagct gtctttcttc gctggagctg cttgcacggg 118380
cacggtggca tttgctgcta tttcagctct ttccacgcag caaatctgct ttccccagcc 118440
ccgaagtaaa catcaccttt tccctagttg acctgcctct gctgaaaaca cacccacccc 118500
ttcctgctcc aattacaaac ttagacttga ctgtgggcca agttgctttt cccacaggag 118560
caatgtctct gcctcacact tggtttttcc aagggaggcg gtgactgagg ccagcacaga 118620
caatgctcca gcctttgtat ttgctgggcc acagagagcc acgtaacatt tattcagatc 118680
cagtgaaacc taatgcgagg aagccaaggg gaaggtggtt tctcctgcgt gccattttca 118740
aaagtgtgcg agctgtctgt ccaactacac atctcttttt aatcatgtct gctgaggtct 118800
gacctagatg tgtcccatcc ctcacttcct cttggggtgc ctaagagggt taccatttgg 118860
ggcgatgaca ggtgtgtcct ggaatgggcc ctgttacaca ggtggattga cctgatcctg 118920
ggtgtgtgag caaagcccag tgctagcaga ttagttatgt cataaaacat taggaaatat 118980
tttatacagt ggagataagt cggagaactg caggctgctg ggttaggcca aatcgttctg 119040
gaagcagggt caaatgatct tatatactgt gtttgcctga cttggtggag ttgaaactaa 119100
tgactcttct tcgctttgtg gagcaaaact tccaaactgc attatatttt tggctctgac 119160
cttgcacctg ccaccccaca gccccaggca tcattagaca ccagcacaag tcattttctg 119220
aagacgtgaa ctcctgttgt ggtttatttg ctttcatgac ccaaagacct gtcaggcttt 119280
gagtttttct tggtagcgag tgttccctct ctgcacctca gcttgtagag ctcttccatg 119340
ggaagtcaca gagtttatac ccagggatgt ggctgcattg atgctgctgg caggggctgg 119400
ggggaggggt gtcctgtttc agcttctaga aagctgcctt tcccattgcc tacaacggtc 119460
attgcatact ttcaccattt tcattttccc ccaactccta ccttatccct tccccaccct 119520
ccacactgaa cacccaactg tgattttgac tttttaaagg aaacagatac atcaggacaa 119580
accccctcaa ctttcaggtt acttttctac caactcattt ctacctgttc acatacctgt 119640
tttaagctca tatcagagaa gttattcctt ttgcttttca agaaggcact caatactgct 119700
ttttttccta tcaatgtatc aacgaatctg tcatcttccc tctgttttct accctttttgc 119760
cactgtctta aaaagtcaag aaaaaacctt ctctaaacct tcaatgttaa atttctcctt 119820
aatccttcat ctcctccttc tcctcctctc tgtatttctg tttatcactc attttctaca 119880
ctcaaaactt tattaccgtc atcacgatgg tacttgccat tttatattca tctaacacat 119940
ttattgagca ttttttttta aatgtcaaaa atggggttgg atcttggggg atagaaaaga 120000
aaaagctaca gttgtgaagc atccatcatt ctcagcaatt atcttgttta tttatacaat 120060
tgcctatttg cgagcatcga agtcacagag cctgtgcttt cactgctgta tgttgggagt 120120
gctggctgtg ggataggggc tcataaaaag cttttgaagg aatgaccgaa gccatcacca 120180
ggagtttacc gtagaggaga catgagcacc tgatcacagc tcaactgtgc ttgtgatggg 120240
gtgtggggaa tgtcttcaga actgcagtgg agaaagcact ctgactttgc ctacgggtgg 120300
tgggaggttt tcctggagct acatctgaaa ggatgaaaag gagtaagtcc agtgaaggag 120360
gaccgaggga atgggaacat tctaggcaga gaaagggagc agaaagctca tgagtgaggg 120420
gctgagaaca aacttgatgc attcagggac tatttagctg aaccaagctc ggggaggaca 120480
agatggccag gtgtggactg gagggaggga ggtaaaaaag gtgagcatgg gctttgtacc 120540
tcgtgagtat gggagcatgg ggaaaggagg cacgtgttgg cattggtgga gcccctcatg 120600
agtatgggag catgaggaaa ggagactcag gttggtattt gtgaagacac tcttgatttc 120660
agtgcagaac tcattaaaat agtgcaagat taaagcaggg tgacctttct aggaagccaa 120720
gggagggcta atgatggtgg gagcactgtg atggtgggag cattgacagt gatggtgcaa 120780
ttggagggaa gatgacaggt tcaagcaacg ttgggctaaa aacagactga ccttggagag 120840
atgaagggct cactctgtgg ggaaggcgag acgtggagga cacacgcctc tgctgtattt 120900
tggaatgagt tttactgtca aaacaattga acctatgtta tttatcactg ttttttcttt 120960
tcttttttttc tttcacaaaa ccagttgctg tgctctagtg ggtcaggtga gccagctcct 121020
aggtaaggag agttgtgtgg ggctcctccc tcaagccgcc tgcgcacttc attccagcct 121080
ctgcacaagg ctgtggattg tgtttcccgg tccaggtctg ctgtcctttc ctgtcaccag 121140
catctcccag agtctggcag ggggtttgtg gatcgacagg tccacctgtc tgtgcttgtg 121200
tttttatcct tttctgtgct ttcctactta ctctaggaag gaattggaag tgtttgagcc 121260
aggcactgtc agatactgtt ttagttctga agtaccctct gcttgaaata acgttggggg 121320
gagcttgtaa cttgtagaag aaaaggagga ggcactaaag tgaaccgctt ggtgttcaga 121380
acttcgcagg ctctgtgctt atgtgtatgt gtgtgtacac accagcactg gctatgtgca 121440
aagaatgcag tgtttgggga aaagcataga atttggaatc ataaacctga ggtttgtcag 121500
ctatgtaatc gcagtgtttg gccactctaa acttcatttc catcagctgg aaaataagat 121560
gaataaatca tcagtcccgg acatctatga ggaagacatg aaataactat tgcatggtaa 121620
gtgtttagtt cagtgggtga tgacaatgat tatgacatac gattatggaa aaagcccctt 121680
tccttccaaa atccccaaaa tgaacaaata catacgttgt tatggtataa atctggtttt 121740
catgttatac aaggagttat tagaacaatt tggaaattct ttccaaatta aagctctttc 121800
tgtatgttga tctaatttta aaaattttct gtttttatgt ataaaaagca atcagggcca 121860
ggtacggtgg ctcacacctg taatctcagc actttgggag gccgaggtgg gtggatcacc 121920
tgaggtcagt agttcaagac cagcctggct aacgtggtga aacgctgtct ctactaaaaa 121980
tataaaatta gctgggggtg gtggtgcatg cttatgatcc cagctactag ggaggctgag 122040
ccaggagaat tgcttgaacc cgggaggcgg aggttgcagt gaatcaaggc tgtgccattg 122100
cactccagcc ccggtgacaa gagtcaaaac tctgtctccc gcctcccccc caaaaaaaac 122160
gcaatcagcc atgattataa aaaaggaaaa atgtgttact gaaatttact taaaatgttg 122220
acaaaaagat gacaaaataa tactctggaa tacaagccta gtataaatgt ttttatttgt 122280
tgcatttaca atttaaagca gaaacttgtt taagtttttg catcgcacat agccaaaagg 122340
aggatgtggg cgaagtggcc aatgtcattg tttaggccct gtgcctggaa tgtggcgctc 122400
ccactggtcc tgctcacagc tctgccatgc cccctgacct tggtgtgctg tttcacaaga 122460
gcatgccctg gtgcaggatg agggacaggt ggctggagag gatgggcagt caacacagtc 122520
catccttgtg tttggaaaca catgttcact tgtgtgcaat gttgggattc gtggagaagc 122580
tggctggaaa gttggtaaag tatccagaag acaaggtttt gccccagcta ctcatcatct 122640
gaacagccag gtagattcta ctttgcagac tgagcctaag ccttgaactc tatcgggaaa 122700
taaacagaga tggtgaactg cgatggaacc caagtgcagt tagttacagc aaacacatct 122760
catgtgaata cataactccg ttgtgaatac ataactctgt tttccaccct taatacccat 122820
cacatctaac cccaatacat ccaggaagta tgtagggtct ccacgacaca gaccatcatt 122880
gatgtccttg tctgatgagg gcaggggaag agctgataaa acacctggag acaattctgc 122940
ttggagaagg tagcttggag acccttgcct tgcttctgag catgacaacc agcaccactg 123000
ctctgggccc taatggcaca tgccccccatt gctgaacctt ggctctatgg ttcataggtt 123060
acaattagca ctattgtgta attctgtgtt ttctagttaa ctgcacaccg tcttggctct 123120
tcaccatgta cgatattcct tatttagtcc ctggaccttc tcatctggac ccgttattac 123180
ctcttcccct ttcgtgtccc atctctgctt cctaagccaa tcaaagctcc ccatatgggc 123240
tgaggcttca gcttctccac aaggttccct cccagaaagt accttatctc cataaactga 123300
agtgctattc catcctcaaa tccagtccca gatgccctcc actcaggagt cagctctttt 123360
tttttttttt tttttttgg tagaatttgc ctatatctct cttatggtat tgatcatttt 123420
atagctggtg gggttggtat ttgtggatgt gttttggcat tccttctgga ctgtaaactg 123480
ccaagaacat gaccatgtct tggtttttta aaatactttt caacatttat cacactgttt 123540
ttcccattat aggtgcttag gaactttatt gtagggatgg caaggtcgac tcctttgttc 123600
ttgcctcagt ctgagtgttt atgccataaa aacaatgtct gtgcaacaat ggcaacaaca 123660
acaagaagtt acacacagtt ttatttcctt ttttagtctc tacctaaaaa gtttgcactg 123720
aaaattggac catagaatgc ctaaaattca ttcattcaac aaatacatat tgattatgca 123780
cctactatgt tccaggtaca ttaacgtatg cctcccccgc cccttcaaaa aaaatccctg 123840
ccttattaaa cttatattct ggaagaagaa gacagataat aaactataga cataataagt 123900
acataatgca gtatggtaga atatcataaa tattgtacac acaggaaaac aaagatatgg 123960
gtgatgcgct aagggcaatc ttaagcaggg tggtcaggct gaacctgatt gagacaatgt 124020
gacaattcag atacagagag aggtgagcaa agtttgcatt taatatgata attgttcaga 124080
ggcataaatg gaaaagaatt tctatttgga atgtaatttg taaataaggc ttgtgggttt 124140
tcaacattag ctactttttt ctttagcctt tataagtctg ctagaaataa tgaaatcaat 124200
tgaataatga ggtagagttt ttattataaa ggggagattt atgaacccac aataaatggc 124260
tttgaatctt agttttcaat caaggaccag agtacctaat atttaatctg tctgtctgtc 124320
tatctatcta tctatctatc atctatctat ctatctgagt ggattctctt tagtcttctt 124380
tctcatctct aatctacctg gatgttgttt tgctatttta gtttcctaga atagcatttc 124440

-continued ctctttgact tttcctttta actctgcttt ttgtctttgt ggtgactaat tgatgtgtta 124500
aaaaaataat atttataata tttgtattgc atttcatcac agctctgtag ttaaaaagta 124560
taaaaattgt tttcaaaata aataggttta ataatacata aagccaaggc tcgagatgac 124620
tatttttcat tacaaaaata gtcatttaga taattgactt ttcatttaga taattatttt 124680
catttagata attgtagatt cacctgcagt tgcaagaaat aatacagaga gacttgaggt 124740
acccacttgc ccccatggtg atattttgca aaaacatggt ggaactatta cagccaggat 124800
atgggcgttg acacagtcca ctgattttat tcagatttcc tcagtagtgc cagtagtgtg 124860
tgtgtgtgtg tgtgtgtgta tgcatgtgta tttgcgagtg tgtgcctgca tgtgtataca 124920
tgtgtgcaca tgcatgtgtg tacacgtgcc tgtgtgcaca cgtgtgtgca tgtgtatgtg 124980
tgtgtctctg tgtgtgttaa gttctatcca cttctctcct gtgtaagttt ttatattcac 125040
taccagagtc aagacactga acaattccat agcctcttcc ctctcacccc acttccccca 125100
tccctaactt ctgggtaccg taatctgtct tccatttcta aaactttgtc atttcagaaa 125160
cgttacaaaa aaagaatcat atgtcatctt tgagaattag atttttccac tcagcataat 125220
tttctgaaga ttcattcaac gtgttgtatt agtacttggt tcctttgcgt ttctgaacgg 125280
cagtcctcag tagggaggta ccatggttta tttcaccaat cagctgttaa ggatgcctgg 125340
gctgattcca ccattgggcc attgggtgat gatgaataaa gctgctccgt acattcctat 125400
acagctttcc atgtgataca taacatttgc tttcataatt actcttgatt aagattcaga 125460
atttgaatgt tgaccttgaa ttttaacata atttctctgt ccttatgtaa aattggcttt 125520
agtaaaattg gttgccaatt tgtgttcaga tgtatatgga taaggaaact ttccaaagca 125580
aatatataaa atgtttgaca gaagtacaga agtattaatt acattttaaa tttttataga 125640
gaacctcaat gaatgaaatt ggggatttta tagcattagg taggaaatta tataacaatg 125700
gaatttgttt ttaaatagaa acattgtcat aactgttctt aaattaaggg gttgaattgt 125760
gtcccccaaa atgctgaagt cctaactctc catgctcact caccagtgtg acctcgctta 125820
gaagttgagt ctttgcagat ggttaaggtg aggccattag agtgcctcta gtagaatatt 125880
actgatgttt ttatagaacg ggaaaatttg gacacagaga cacctgtaga agaagatgat 125940
gtgaagacac acagagagag gacagccacc tacaagccaa gggaggccaa ggccagaaga 126000
cactgggaga gcacggggaa cagattttcc cttggaagga tccggtgact ttttttttt 126060 ttttttgaga caaggtcttg ctctgtcacc caagctggag tgcagtggtg caatcatgtc 126120
tcgctgcagc ctccggctcc caggctcaag ggatccttcc acctcagcct cctgagtagt 126180
ggggaccaca agtgttcccc aacattcctg gctaattttt gtattttttg tagagacacg 126240
gtctctctat gttgcccagg ttggtcttga actcctaagc tcaagccatc tgtttgcctt 126300
ggcctcccaa agtgctggag ttacaggtgt gagccatgct gtctggcaga tccaacacct 126360
gaatctcaga cttctagcct ctagaactgt gagacaatac atttctgtca tttaagcctc 126420
tagtttgtgg tactttatta tagaagggtc aggaaacaaa tatgatatat tattctgcat 126480
gtatagaaac tttaaatttc tgactagtct atcaaagcaa cactttttac tttatctgtt 126540
ctcaagactt aaaaaataac cttgcatgta tggaatttgg attggagttt ctccttccca 126600
tctctttagg aatctttctc agtagcaccc ctgctgtgtt tctctgttgt tttacctata 126660
tatttagaca gatcccaaat tatgaggaaa agacaaaaca ataaaaaagc aaaaagaaaa 126720
caaaagacta acttttgatt tttgccatcc cccaatttac agccaatccc ttatcccttc 126780
ctgcccattg atggttggaa tttttttttt ttttttttga gattgagcct tgttctgttg 126840

-continued ccagggctgg agtacagtgg cgcgatctcg gctcacttca acctctgcct tctgggctca 126900
agcgattctc ctgcctcagc ctcctgagta gctgggatta cagccatgtg ccaccacacc 126960
cagctaattt tctgtgtgtg tttttagtag aaacggggtt tcgccatgtt ggccagtctg 127020
gtcttgaact cctgacttca aatgatctgc ccgcctcagc ctcccaaagt gttgggatta 127080
caggcgtgag ccaccatgcc tagcttttgg atttcttaat aaataatctg tcccaacatg 127140
aggcagagga agctgaggtc taccagatgt ccgttttcct tcctaggtgc agaattctca 127200
gtgcttagct gagtgcgtca tcatctggga taaaggctgc atctcctagt cttgcttaca 127260
cttatttgtg gtcttctgat taaatcatgg ccagtgagat gggtgtggga gtaagcgtgc 127320
ccgtaaaaag ctatgagaac taggtactgt aatttgggaa ccatagatct atccactgta 127380
gtttgggaac cataggccta tcctctgcag tttgggaagc ttggatttat ctactttctt 127440
atcatctact caccccatct ccttgaatga ctgacgttgc ttgctgagtg tcactaggaa 127500
ccacattact gcccagtctg atggctttct taatctatta gcctctgcag tttctgcaga 127560
gtctgaccca gtggaaactc tccatttccg gaaagctcca tcctgaggct cttttgcttc 127620
atctctcttg cttccactgg ttctttttct ccttcccaac ccctaaatgt tgttctctca 127680
ggcttttccc ttaaccctct tttctcatct agtctttcct caatctaagc caattgcatc 127740
cattctaaga tgtcaacttt cattctaggc aaacgacttc cacatcccca gtttaatccc 127800
tctgactgct gaaccctagt ccatgttttc aactgcacgg tatccatctc cacctgaacc 127860
cccacccttg cctttgacat aaactattca aagcatttga actcaacctt gctttcaaat 127920
gagctcccct tttacctgtt tcttgcagaa gccttgagcc cttgctgccc aattctcggc 127980
ctgagagtta ccccagtgcc tccccccaac cctcccattc ccttctctct gtttcaccct 128040
cattccaacc ccatctgcct ttgggttccc ttgattcaca gatgggttgt acctctaact 128100
cctggctatt cttttctacc tccagttttt tgtttctcca atccatccct gccagatcag 128160
attttctgaa atgcagttct aatctgattc tccctagcaa aaccttactt caagcccagc 128220
cttttcaccc tattgtgtga gcttctctct tcagttctgg caggatctat aatgtgcacc 128280
accaacggga ggtgtgcggc ctgagtcttc tcggctcagc acgtttgctt gtttgtcctt 128340
cctccagccc aaaattacca caaaagttgt tttttatcca acaaacacct tcagagccac 128400
ttattatatg ccaggcactc ttctaagcaa tttgtaaata tgaatttttt ttaatcctca 128460
taacagccta ataccagaag ttctattgtt attcccattt tacagagaac actgaggtaa 128520
agagaagttg aataacttgg cccaggtccc cagtgttctg taagtggcag agctggggtt 128580
ggagcacgaa cccatactgt taccagtgaa agcagtgtac caaaatttta agtagagatc 128640
actgttctgt aactcattaa gttttttaa aaaaatagta attatccctt aaaaccatta 128700
caaaaacaga gaatgaagaa ttaaaaaaaa atagatttgt tgtaaatccc cagaaagaaa 128760
attaagcagg tctccatcaa agactcataa tagaggaact caaaattttg gtcttctaaa 128820
agaagacatg gactttggtt actattattg tttaggtttt tctccagtgg tgatgaagta 128880
aaaggagact ttgacctttt catagacctt ataagttggg ctctggcatt tactgtttaa 128940
tgctctaaag gttcaatata caaaatgtag aataaaaaaa tcatcttgcc ctgggttgcc 129000
atctctgaca gctgtgcttt gattattgtg gcagtgctaa gaggttcatg tggaggtggg 129060
agtgctagga caagacagcc tgagttaaat ttcaatcctc acacttacca gatctgtgta 129120
caggtgtcat cacctgtcaa atagaggtga taccagtggc taccttactg aggaatggga 129180
gagttccact gaggtaatat gagtaaaaca gctcttaaca ggcataagca cttaaaaacg 129240
gtaattatca tcatggcgtg atgtatttgc ccatgttcac actgcttgaa agatactacc 129300
tgagactggg taatttataa agaaagaagg cttaattgac tcacagttct gcatgactgg 129360
ggaggcctca ggaaacttac aatcacggtg gaagatgaag aggaagcaag gcaagtctta 129420
catggcggca ggagagagag agcgtgcagg gaaaactgcc acttttaaac catgagaact 129480
cactatcatg agaacagcat gtgggaaacc tcctctgtga tccaatcacc tcccaccagg 129540
tatgtccccc ccttgacaca gggggattac aattagagat gagatttagg tggggacaca 129600
gagccaaacc acatcacatg ctattcaata ataatagaat tgctctgcaa aataaaaaaa 129660
atgaagctaa caaattttgc ttataacttt gcaggagtat tggaagtttt tattcctact 129720
gccaacaaag actatttatc tggtatactc atagtgcctt taaaaaatta cacagcactg 129780
ccctgtttat ttttagtttt gtaatagaat tcatggattg gttgttcata gtctttacta 129840
tggcatcatg agccttaagg aaagaacaag gagatttctg agagtcccag cgggttatac 129900
tgtgaatttt actcatgtta ttcttacact gggaacagca aggaacttga cttgactttt 129960
accctggcag acaatcttga aacagttttt caaataaaag atgttatttt taacaggaaa 130020
caactgatac taaagatctg actcagactt tactctcctt caaatgatgt ttgaagttca 130080
gcttgtctgc agctgttcat tatgtgccta ctatgtgcag gcctggaggt aaacaagact 130140
cagccttcat tatcaggggc tcatactcca gtggagaagc cagattcatc aacagatgat 130200
ttccaagaag tgtggggagc acacatggtc ccagaaactg ggaatccagg agatactcat 130260
tgcactgtcc tttaggctga aattcaagtt ggagcttcct ccttgagtcc cttgtcagtt 130320
tctgcttcta tgtagctgac tgtccatctg agaggacgca tcccctatct gaggtcatca 130380
aaagacctgt ggcagccagg attcaagccc aagtgtcctg tctcctagct ctatgcttgg 130440
gcacaccaag catagagctt gggtagagat gttgggacaa aaaccaagtc aaataaacaa 130500
aaaacccagt tcttacattt aaggatccgt agagcctaca acatagtttt gtgtctcaaa 130560
tttaagccac aaagttctgt taaccgtcat tcatctagca tatagttgtt aaatttctcg 130620
tatgtggcag gcattttttt ccaggtccta gaatttagaa gagggaacga tgaattaatc 130680
agagattgct gagatagaga caaaccaacc aaccaaccaa acaaccagcc agccagcaag 130740
caattagccc tcgctgtgca catccttcag tgattatggt cagcagaatg tggaaggaat 130800
tcatttgttt atttcttttg agggatgaga gagttgagga ttagcctctc caggaattgg 130860
catcaagaat caacagggca aagctgaagg ataagccaca attaggcagg atgcagaggt 130920
gagactgaag ggagagaggt cagaacccag agaggaatgt atgcatggat cattaaggac 130980
tggaactggc aaacatcttt gtagataata atgggaaact aggtataaac aagggaaaac 131040
taggaaacta tacaggttct aatagagagt ccgttgtcgc cctgggaagt gtgctttttt 131100
tctttgactt aaccaccgta gagcggctca caaggagcac agatccactg aaatgcctga 131160
cgattgggag agacgaaatc tctgttgtct gtttatattc ttattttatt aggtctgttt 131220
catgtcttca agatccacga gtgtaggaca cgatgccatt tcccctgtat gtcttcggtt 131280
tctaagcaat taagaaatat aatttctttc tcaacattta ctgatgtgga aatttgggga 131340
tctgagccag ggggcttgcc atcatccggt cattggaaaa gtgcataagg gaacacaaag 131400
ctagagtacc taggttggga aatctgcttg cctgcaaatc cagctcaagt tggccaggaa 131460
accctgccct atagatggca aaatgtaaat cccctgagac tagttaaaga caaacacatt 131520
tcattgagtt ggggttttgt tacaaaatag gtaaacgtgc atggtttcca ggccaacgtt 131580
attcagacta ctaaggtctt gaccaagttg gcagttcttt ctagaggcct tagttccact 131640
ggaattagca ggttcattaa aactaaaact caaagaggga catgtcagct agccaggaaa 131700
ctgagttgac taggtcctct tgaaggtttc attgtaacat tgggtaccca tccaagtcct 131760
agtggccttt gtctcagatt gctgcataaa agtggctcaa catgaaggcc aatgtgaaga 131820
catattggat aagggaattc atttctgttt ctttctgcca ccgcccctca tttattttat 131880
caccataaag atgtaattca catatcatga taccaacttt taaaaggagt gtagttcagt 131940
agttgttcgt gtattcacag agttggcaac catcttcacc atctaatttc agaatgttct 132000
atcatcccaa agagaagccc catagccatg acaccccatt tctcttgact cctagtccct 132060
tacaactact agtccacttc ctgtcatgat tgacttgggt actctggata tttcatataa 132120
atggaatcat acgttatatg ttgtgtctgg cttctttcac ttaacgtaat gtttaaaggt 132180
tcatgcacgt tgtagtgtgt gctagcactt catttctttt ttatgactaa ataatattcc 132240
attaaagaga tatataccac attttgtttc ctcattttct aacttttcag taagaattta 132300
aaaaaacaca ccaatacaat atgctgtctt ttaacatgct agccctaaca tggtaatgcc 132360
tggaatattg tccacgaatt tctctggtgt ttctttggtg acttgtttac ttcctcagtg 132420
atgttgcact gttgtgttct gaccctgtct gagtcctgtc tgttctctgg cttgagagtg 132480
gctttgactg agctttggga taggactgct gttggtctgc agttatcacg ttcagacttt 132540
atctgagatg cggactttgg gccagataaa tgcaggattt tctgaactca ctggtgagga 132600
aaagcatttg ctaccgctgg ttcttcgaca gcatataact ttccctaagt caggagtgcg 132660
tgtgtgtggt tgctgggtgt gggtgaagat aatcaatttt atgcttctga taacctttca 132720
agatttgcag caaaagaact tggtggccct gaagactctt tttcctcttc ccattcctgg 132780
gtctaacagt tacagtcatg gctgttctga agctgagcac ttggtggtgt ccatgacttt 132840
aataacatgt gctgggagcg gtggctcacg cctgtaatct cagcactttg ggaggccgag 132900
gtaggcggat cacttgaggc caggagttcg agaccagtct ggccaacatg gtgaaacccc 132960
gtctctacta aaaatacaaa aattagccgg gcttggtggt gggcacctgt agtcccacct 133020
actaggaggc tgagggaggt gaatcgcttg aacccaggag gcggatgttg cagtgagcaa 133080
gatcttggca ttgcactcca gcctgggtga cagagcgaga ctccgtcaaa aaaaaaacaa 133140
caaaaacaaa caaacaaaaa acaaaaaaaa ccctaaacag tgctggggac aggcaccaca 133200
acttaacagg gcatctgccc tgtgaagcca cagaggtagg tggtgggtgt cttgaggtgg 133260
ggggagaaag gcaagattgc tgctgggcaa agtggagaca gtgaggttca agccaccatg 133320
cgtcccagca ggtgtggagg tcacaccact cagcaggtgg aggatgcacc gtcacccact 133380
gtgaggcagg gaccttcctg tgggttcaca gaggagccct ccagcaatgg agtaacactg 133440
cagctggctg ctctgctcag ggtcgcagcc cagggtagag tggaagacag aggagcaggc 133500
tggtgaggac aggctgctga aggcttccac tttagtcttc acatctaact cggggcggct 133560
tcatagcagg gagatagtca gcaagaactt ccaaatcatt ttcaaagtct atcaggaaca 133620
tttctggctc agaatctcac gctccctcct ttccagagct acgttccttt gtattttcta 133680
tagaagcaga cgtaggatct aagcatatgt ctctgagggt gcctggacta agaaatccag 133740
gagattcagt gaagaattgt gttatgtttt tttttttttt tttttttttt tttttttttt 133800
tttttttttg tcgtatgctt ggcagagagc aggtaattgg gcccatcatt atttagggct 133860
aaaaatttgt tgatttgaga ttttttggga ttggctaaaa cctacttcag aacaacatgg 133920
gaaggaaaag aaaagctatc tttgtttcag gaatgccggg cttcagcttc cctggtgagt 133980
aaatgaagaa actgcctgcg actgcttggc ctcagactgc cttgcgaagg ctccttctgg 134040
cacaatttgg gctttgaact tctcccttaa tttctgaatc tgtgttgtga taattggctt 134100
tggaaaggtt acgagaggtt gactctggcc tgacacggag gctctagcca atgccagaga 134160
ggtaggcttg gtgccagagc tcacctcaga cccacatctc cagggagtga caggaacaga 134220
aaatcagcca agctactgtg acccagtcgt tcagcaaatg tcggagcgtt gcaatgcctg 134280
cccccaccct accccagagc aaggctgggc acctgaacac tgtgtggggt actctgcgtc 134340
tgtgctctgg ggaagggggc tgtgaaattc acctggagat ctgttttaag acctgcgctt 134400
tcgaaatgct ctcaaactct tttatcaaga cagtacagct tggacaaatg tccacaatag 134460
agaagcagtg acatcccttg gacctccggg aacagcagcc ctgtctgtct ctgaacgggc 134520
cttcctccct caggctcctc tcacccctcg gggctgccct caggggagga tggcctcacc 134580
cagtgaaggt taactgggcc ctttgtttgc aaatggcagg acaggagctg gtgctagctg 134640
atcatgaggc tttttacagc atcaaagtgc tgcagtttac taagaaatca ggaaagcata 134700
ttccaaaaca gggttgtctt ctaggaagga acagagagga ctctgccttt ctactttcag 134760
gcatccagcc ctgtatgctc caccagggta tctgtgagga gaggcagcgt gagcaggccc 134820
agtggaagca gggatggaga aggaggggtc tcccataact cactgcagat gctgagtata 134880
attaaaatgt gaattacatg tgtctaacat ggtaaagagg ctcaggtaac tgagcgaggt 134940
tttctccttg aaggtagaaa tgtctgtgta aggaggtcat tccacctttt gggctacctt 135000
taaatgagtg tttttgaagt ggtattcttt aaaaaaaatt tttttaaatg caatctgtcc 135060
ttgttctctt taaagcaaat atctacagag atgtttatca cattatcata cctctggttg 135120
gaaacaatat ttttgacttg atggatttta tattttcact attagaagct actcctttat 135180
tcccaagtat aaaattctag cttcaaagta aatgcttggc caatcaacac caaataaggc 135240
aggaaaaaaa aaaaaaaaac gcagaaaact cacaaagcct cagattataa ggggcctagt 135300
caggtttcag aaactctagt ccaaacaggc attcctaacc tagcccaggc agctcttacc 135360
tcaggcactt agcaacgcgc aggccttttg aatttgctta aaactattaa gaagtaatta 135420
agtagttaga gggtcttttt cagccctgag gtccaggagg tgggctaaat gaaagaaaac 135480
aagcgcaatc gctcagcctt gtcttccttc tagctgacct tgcacgctaa taaattcatc 135540
ctgtattttt ctgctactgc caatttatgg cctacaggaa actaatcttg tacaataact 135600
accttcctgt acttagttcc taaatagagc caaatggatt tggtggcgga agagctcccc 135660
agcacttcct gtgaggcagt tgctgagccc agcaagatct gatagaggct tgatgcgctt 135720
atcgactctg acgatataat tatgttcttg ttttggctgc cctgcactta agcacagaaa 135780
ataaaaaagc aatcctctgt acaacgccta ccacaatgat ttaaacttca aactggaggg 135840
taagatgtgt atttgaaaca agccacgtag gcacagttat ggtgaattta gggagtgaaa 135900
cacacaggtg atcaatattt cactggagtc tttgatataa aatatatatc tgctctgtga 135960
tttcaaaata ttcacaaagg agtaaatttt ttaatgagct aatgaaagaa ctgtgttttc 136020
atttcaaacg ggaagagagg gagaaagaga gagagaatag aaatatagag ccatttcttc 136080
agtaatagtt tacaaccagt ttgccacagg cttggattaa agtaaggaaa ggctgtcaaa 136140
acgcagggta acctgtgtga tatcttttca gaccctcaaa tagctcaaat actacgctgg 136200
gaaaactcag agtttgtcct ttaaagaacc tgaaagtgtt taatctttga taagtgcagg 136260
ctcctcaggc tttgccgctt ccccacaccg gatttgcctg ccactcaccc ataccgatct 136320
gatgacttca tgtggacacg gatcggtccc gtatgacagc gtcttcttcc tgtgctcatt 136380
tattctagaa ctatagcaaa gctgctaatg caaagggaag ccttctacaa aaaggatgaa 136440
gaaatcaccc tgaccaagag accgaagcaa agatgaaagg aaggcataaa taatcgcagc 136500
tcgggtccga tgagacttat tgctggggct ttcagaccta gagaggtagc aggggcgggg 136560
tgggggtgcc tgtacgcggg ggcggggtgt cccacccagt tgacctggat tagagcccat 136620
ggggctgcat tccgggcttc cgtgtttccc aaagttatgt ggtggcgggg ggcctggctg 136680
ttaaggatct ggggatgtgg ttacctatgg cctctgaggg tgacaccagc tgtccagcac 136740
tgtgaaatca aacaatggta gtgggccaga aagatggctt agcttcctcc tgagtatgag 136800
caagtttccg taactgtgaa tcatccttcc ccaaccataa aagtgggcat attaatacct 136860
gtcttgtaag aatcctgtga agatcaggga taacaaatgc aacttaataa aagtaacctg 136920
ttatgtgttg gctggtgatg ccataaatgt attttgtaaa atctttataa tggtgactaa 136980
ccaatatatt attattaata gcaataggag tattgtctga ttcaaagggc gcatttagat 137040
tgtggtaatt ctgtgtgtgg ctggatggga gactggaggg ggctggaggt tttaggatga 137100
gtgggacagg gattattaga agtggctaat aaagagatca aagaagtaac tttgttccta 137160
atttttaaaa tcatcattct acctcactct cctaaaagtg atgaggatca taatatttat 137220
gccttacgtt tatacaggac tttatacttg aatatccctt ttacatctct ggtccgtttt 137280
agaaatttga gcctaaacat gggaagcaga aaaaaagtca atgtggaaaa gcactgtgcc 137340
catcccagtt tggccagaat gatttcagat tgttatcaag aaagggaata gcggcagcat 137400
ggtttggttt tcctctctca agaggactgg acacagggaa ggaacaggaa aaaacctcct 137460
gagcaaagca aggttccaga acagactagt tcaaagccta cacatggtta gtgctccgtg 137520
gaggtgccag ctcacggttg gtgcaccgtg gaggtgccag ctcatgctta gtgcaccgtg 137580
gaggtgccag ctcacggtta gtgcaccgtg gaggtgccag ctcacgctta gtgcaccgtg 137640
gaggtgccag ctcacgctta gtgcaccgtg gaggtgctga ctcatggttc gcgcacagca 137700
gaggctctgc gttttgggat tcgtctgttc taattgtagc ctttcactta ctgccctaag 137760
actggcatgg aaactatgtc tttgagtgat gaaagggcat ccggtgtgtg gaagctcctt 137820
gcagagtttc tccatattgt ctccttgata gaatgtagct tactgctggc ttgctttgca 137880
catggcagtc actcggtgca tgctggtgga ataattgaat ggaagctcca gggccatcac 137940
ctgcacacag tcccccggag gccctttctt ctctcatatc tcagcttccc actgctcagc 138000
ttgatgtcag ggagacatcc ttggtctcca ggaggtgaga gggaacagaa cactaacacc 138060
ccagtgaaac acagattgac ttattgttta gcagcaacca ggcaggcatg ggctccctcc 138120
ccgctgccag catccacacg cacctcctcc gtagccatgg taatatttcc cacatgccac 138180
aagtccgtga catggtccta atgaatagaa tgctttatgt ttagccccaa acgtggtcat 138240
tatccatata tttgaaagaa aaggctcaaa caaaaacaag gacgcctgat gcgaagctcc 138300
cagcctgtgg gttctttgcc atgggcctat tggatgggag gtttgggctg caagacaagc 138360
tgtgacttta cctccttgaa tgtgctgatt ctaaagagtc gatttcaatc taaggaagga 138420
cattgggggg attggaaaaa gtgaagagat tgtacagaag ctcacagcta gcaggtgatg 138480
gaggctgagc ccaggagtgc tttttccact ctcccaggct gcttaaaaaa taaattgtat 138540
ttgaatgtgc tcacattaat tttgctacca gtttactgtc gtcaaaatag tgtcaatgaa 138600
tgcaagttct taaaagacct gcaagtccca cctgggaggt ggggcagcac aggacatgag 138660
gagttggtgg tgaatgagaa tttgagaatg ttcaattcat ccctcattag ccatgtgatc 138720
tcaggcagcc cgctgatcat ttctgtgtct caggttccta ctctgtgagg gagagagaga 138780
gaataattgc acccccttttg aatgtaagca tctcccttag gagatgaata cacacggtgg 138840
agtgacagta gccaagtttt ttttttttta tactttaagt tttagggtac atgtgcacaa 138900
cgtgcaggtt agttacatat gtatacatgt gccatgttgg tgtgctgcac ccattaagtc 138960
gtcatttaac attaggtata tctctaaatg ctaccctccc ccctaccccc accccacaac 139020
aggccccagt gtgtgatgtt ccccttcctg tgtccatgtg ttctcattgt tcagttccca 139080
cctatgagtg agaacatgcg gtgtttggtt ttttgtcctt gtgatagttt gctgagaatg 139140
atggtttcca gcttcatcca tgtccctaca aaggacatga actcatcatt ttttatggct 139200
gcatagtatt ccatggtgta tatgtgccac attttcttaa tccagtctat cattgttgga 139260
catttgggtt ggttccaagt ctttgctatt gtgaatagtg ctgcagtaaa catacgtgtg 139320
catgtgtctt tatagcagta tgatttataa tcctttgggt atatacccag taatgggatg 139380
gctgggtcaa atggtatttc tagttctaga tccctgagga atcgccacac tgacttccac 139440
aatggttgaa ctagtttgca gtcccaccaa cagtgtaaaa gtgttcctgt ttctccacat 139500
cctctccagc acctgttgtt tcctgacttt ttaatgatca ccattctaac tggtgtgaga 139560
tggtatctca ttgtggtttt gatttgcatt tctctgatgg ccagtgatga tgagcatttt 139620
ttcatgtgtt ttttggctgc ataaatgtct tcttttgaga agtgtctgtt catatccttc 139680
acccacttgt tgatggggtt gtttgttttt ttcttgtaaa tttgttggag ttcctttctg 139740
agctttcagt ttctcatggc ccatatgaga tagtaacggt actcacttcc ccagactatt 139800
gcgatgatgg cacgcgatgg ggtgagtggg aggtttatca cacagaataa atgatacctt 139860
tggttatttt tagtgctgcc cttatcctgg gtcctaagat tctctgatct cttcctattg 139920
ggtgttcgtt tgactagatt ccaagaacaa aaattacttg acccacactg gtagggctag 139980
gcaatctttc cagccctcct gggttggcag ctgatggata tcatctgttg gtctcactgt 140040
cctttactga ggacactggc aaacttaggg gggttttcat catgatgcca tgcactgaca 140100
tcgtgaggca tacctgtctc attacagcag agactcatgt gacctgggaa ccactgcagg 140160
tcaaaactac agcgcatgaa agccaggagt ttaccaaatg ggtgcagagg ctgcccaggt 140220
gtttgggaat ttattttcat tggaaatttt tatcatttct tcacacataa ggatattagt 140280
tataagaagt ctgaattttt tttttcctaa caagtacaaa ctacttacaa aatagttgca 140340
aggacaacag aaataatttt ttttttgctg gaccttttga gagtaagttg cctgcatgat 140400
atcttgtcat ccctgaatac gaatacttta gtgtgtattt tgtaccaaca caaatatgct 140460
cctacacaac cacagtagag ttaacagaat cagataatca acgttgatat attcctaatg 140520
cctaattctc agaccctgtt catatttgcc cccagacatc cttaaaaaca aaaggaacca 140580
tctcagagct acatgctgca tttggctgtt gtgttttatt aggctccatt cacctggaaa 140640
agttcctcag tctttctgtg actttcgtgg ccttgacact ctaatggctc taggccagtt 140700
acattgcagg atttccccca gcacggggct gcctgatgct tcctcatgag cagattcagg 140760
tttagcgtcc ttggcaggag aacccaggag cgaccctggg accgcctcac tccgtgctct 140820
caggtcggca ggactgcaat ttgcccggtt actgacgatg ttcacactgg tgacctgatg 140880
gaggtggtgt ctgtggtttc ttcactcctt tcttcctttg taattaatta gtattacatg 140940
gaggactagc ttaaaactgt gtaaatactc tgctcttcat tcaacgttta atttattcat 141000
ttatgttgta tttatgtcag tatggatgtg tagttttcta tcttatttat tggattataa 141060
cctggaatta tcattactta tcttactgtt cacctttgct ggggtttgga agctgttccc 141120
actggcccgt gtgttgtcat tctctgagca ggtcctcaag atgtttctga gtcattgtgg 141180
accctgcctg ctctggatca tgggtcagct ggttctccaa aaagagctga atcccaagag 141240

-continued

```
gagaatgggc tttagatacc atgatctggg tgtacctcag tgcacagagc tggacagcat 141300
atgcatatag acacacacac acacacacac acacacacac acacacagat gtttatgtct 141360
atgtttgtct ctagctctgt ctatatggaa agccatgagt tggtgctaat atcttcagtt 141420
cactcaagca cctcagagtc caccccactt tcttcctttg tatatttgtg actctcattc 141480
acaccctgtg ccacccctgc cattttctat cagcattgcc acctcccccct gcacagtccg 141540
attccaaatt ctgtatgatc tctgaggcca ggcactggcc tgcatcccag gccagcatcc 141600
tccctgccca gtaatgctgt gccattcctg tctggaccat ccgcccacat gaaagcccct 141660
tttcctccct tcctacaccg aagccctcct tgccctgccc agaggcacac tttgctccag 141720
ctgcttcccc cttaaacccc attcattttt ctgggtgcct gccacccttc cattcagtcc 141780
cttcccctgc ttggacactc tctctaccct actcaggctg aaagtcccat ggtcctactc 141840
ctgcaggagc ccggtcctca ttgcactggg gctctgacac catgacccag ccatgtggac 141900
cgccaccgtc ccctaccaat gcccagctcg ggctcttgca aacctccccc aatcccatcc 141960
ttgctcacta tgttcctctg tggtcccttc catcggtgcg gatatccccc ttgtttggat 142020
acacacagtg gctttaggat cagattgttc agaaagtgga agacctgaaa aaatgtttta 142080
tagttagagc taacttctag aacacactgt cactagaaat tcatcagtga gccctagaga 142140
gtagcaggca ggaagatgag ccatgtccct caaatctgca tgtcactcag caaggtctct 142200
ggctgtggaa ccaggcatgg gagccaccct gtcccagctc ctgatagaga ctcagtggca 142260
gtgacccagc cagtaacctc catcaaagta ttctgcattt agatagactc taccacaccg 142320
agctattgcg ggaagcccca tggcttcttt cttactgttc ctcttcaccc actgggtggc 142380
tggtgatgat cccccgaggc aggggaaggc agtagtgtca gctcttactc cagggtggtc 142440
agggccctta gtgtcctcat ttcgtgcctg aaatctctag aggtgttcat cttgcatgtg 142500
ggctacgttg tgtcctccaa cttgcatctc cccagaaccc tgctttattt tctatctcca 142560
tttgaatttt tctttttaga ttccacatat gagtgagatc atgcaatatt tttcttactg 142620
tgtctggttt attccactta gcataatgtc ctctagcctc atcgatgttg tggcatatgg 142680
gatgatctca ttctttatga ggtccaaata acattctgtt gtacatatgt gacattattt 142740
attttagttt attattttat ttttccataa ggtattgggg aacaggtgat atttggttac 142800
atgagtaggt tcttttgtgg tgatttgtga gattttggcg cacccatcac ctgagcagta 142860
tacactgcac catatttgta gtcctttatc cctcatcctc ctcccagcct tcccccctaag 142920
tcctcaaagt ccgttgtgtc attcttatgc ctttgcatcc tcatagctta gcttccgtat 142980
gtcagtggga acacacgatg tttggttttc tgttcctgag ttacttcact tagaataata 143040
atctccaatc tcatcgagga atttcttcat ccatttgtct gtcaatggac acttaggtgg 143100
tttccatacc ttggctactg taaataatgc tgcagtgcac atgggagtgc caatattttt 143160
ataaggtagc catttcctct ctgttggata tatacccaga agagggttgc tgggtcttat 143220
ggtagttcta tttttcattt atttaaggaa gctccatttt gttttccaga atggctcttc 143280
caatctacat tcctaccaac agtgtacaag aattctcttt tctccacact ctgcaaacat 143340
ttatcacttg tctctggtaa tagccatcct aaagggtgta ggtgatatcg cacagtggtt 143400
ttgatttgc                                                         143409
```

METHOD OF JUDGING RISK FOR ONSET OF DRUG-INDUCED GRANULOCYTOPENIA

TECHNICAL FIELD

The present invention relates to a method for assessing the risk of drug-induced granulocytopenia by use, as an index, of a polymorphism of the human insulin receptor substrate-2 gene; to a method of detecting the genetic polymorphism employed as an index for the aforementioned risk assessment; to oligonucleotides employed for these methods; and to a kit for the assessment and/or the detection.

BACKGROUND ART

The mainstay of modern medicine is drug therapy, which employs drugs for treating or preventing various diseases. Almost all drugs employed in drug therapy (e.g., low-molecular-weight compounds) intrinsically are foreign substances to the human body, and thus administration of such drugs provides therapeutic efficacy, but may cause a variety of side effects. Such side effects often compel the drug therapy to be abandoned. Also, some drugs have encountered a situation where research and development have to be suspended due to severe side effects, although the drugs have been proved to be useful for patients with a certain disease. Moreover, the use of some other drugs is strictly regulated in order to detect the sign of their side effects by mandatory examinations.

According to the statistics published in the United States, the cases of drug-induced side effects account for two millions or more a year, and more than 100 thousand due to such side effects (JAMA, 279, 1200 (1998)). In Japan, 26,545 cases of drug-induced side effects (including redundantly reported cases) were reported, and 1,239 deaths due to such side effects only in one year of 2000 (Ministry of Health, Labor and Welfare, Jun. 6, 2003, House of Representatives, Responsive Pleading No. 55).

Among side effects due to drug administration, granulocytopenia is a fatal side effect. Particularly, a decrease in granulocytes tends to lead to an infection, and onset of agranulocytosis involves a very high risk for a serious infectious disease such as pneumonia or sepsis. Examples of drugs that are generally known to induce granulocytopenia include analgesic-antipyretic drugs (aminopyrine), antibiotics (Chloromycetin), antithyroid drugs (Mercazole), anticonvulsant drugs, antidiabetic drugs, and diuretic drugs. Occurrence of side effects caused by such a drug is less likely to be related to its dose, and is considered to be related to the predisposition of a patient (e.g., allergic predisposition or idiosyncrasy). Therefore, occurrence of such side effects is almost impossible to predict. In order to avoid occurrence of such side effects, doctors must handle respective cases very carefully, through detailed interviews with individual patients regarding, for example, drug administration records in other departments, and analysis of blood test results, etc. Notably, if and when a patient has onset a side effect of granulocytopenia, doctors must take immediate measures, including hospitalization.

Other drugs that are known to induce granulocytopenia include dibenzodiazepine (clozapine), which is an antipsychotic drug. This drug is expected to have high efficacy, but clinical trials of the drug have been suspended in Japan.

Other drugs that induce granulocytopenia include vesnarinone, which has inhibitory activities on PDE3 and K channel. This drug is an effective inotropic drug that is less likely to cause arrhythmia and other cardiac events (e.g., onset of heart failure and hospitalization). However, administration of this drug may cause side effects; i.e., leukopenia, granulocytopenia, and subsequent agranulocytosis. Therefore, the use of this drug is strictly limited.

Single nucleotide polymorphisms (SNPs) are the most frequently used genetic markers in human genetic analysis. SNPs have already been shown to be useful markers for an association study between genetic background and common diseases or drug response (see Non-Patent Documents 1, 2, and 3). As has been known, analysis of haplotype, constructed of multiple SNPs, is useful for analysis of the susceptibility of polygenic diseases (see Non-Patent Documents 4 and 5). In practice, some diseases such as Alzheimer's disease and hypertension have already been intensively analyzed by such an analysis method (Jeunemaitre, X., et al., Am. J. Hum. Genet., 60, 1448-1460 (1997); Martin, E. R. Am. J. Hum. Genet., 67, 383-394 (2000)).

In recent years, advances in genome analysis have led to development of toxicogenomics, which studies relationship between genes and toxicities such as the effect of a drug on cytochrome P450 (CYP) (i.e., a drug-metabolizing enzyme). Particularly, association studies of individual genetic background and sensitivity/response has been proposed as a powerful tool to elucidate the cause of adverse effects. So-called tailor-made therapy is expected to be realized through these approaches Non-Patent Document 1: Brookes, A. J., "The essence of SNPs," Gene, USA, (1999), 234, 177-186

Non-Patent Document 2: Cargill, M, et al., "Characterization of single-nucleotide polymorphisms in coding regions of human genes," Nature Genet., USA, (1999), 22, 231-238

Non-Patent Document 3: Evans, W. E., & Relling, M. V., "Pharmacogenomics: translating functional genomics into rational therapeutics," Science, USA, (1999), 286, 487-491

Non-Patent Document 4: Stephens, J. C., et al., "Dating the origin of the CCR5-Delta32 AIDS-resistance allele by the coalescence of haplotypes," Am. J. Hum. Genet., USA, (1998), 62, 1507-1515

Non-Patent Document 5: Tishkoff, S. A., et al., "The accuracy of statistical methods for estimation of haplotype frequencies: an example from the CD4 locus," Am. J. Hum. Genet., USA, (2000), 67, 518-522

DISCLOSURE OF THE INVENTION

Problems to be Solved by the Invention

A primary object of the present invention is to provide means for assessing the risk of drug-induced granulocytopenia by use, as an index, of polymorphisms of the human insulin receptor substrate-2 gene, or means for detecting the genetic polymorphisms employed as an index for the risk assessment means.

Means for Solving the Problems

In order to solve the aforementioned problems, firstly, the present inventors have selected, as genes for polymorphism analysis, 115 candidate genes, including cytokine-related genes, MHC region genes, G-CSF-related genes, TNF-α-related genes, NFκ-related genes, cAMP-related genes, and K-channel-related genes, searched for SNPs in these candidate genes from the database of Japanese Single Nucleotide Polymorphisms, and picked up 188 candidate SNPs for analysis.

Subsequently, the present inventors have determined the frequency of these SNPs in the genomic DNA of samples from the following two groups: a group of subjects with granulocytopenia induced by administration of a specific drug, and a group of subjects without granulocytopenia who have received the same drug. As a result, the present inventors have confirmed that SNPs with the most statistically significant difference between the aforementioned two groups are present on the insulin receptor substrate-2 gene (J-SNP ID: IMS-JST040476) (hereinafter, the gene will be referred to as "the IRS-2 gene").

Furthermore, the present inventors have conducted extensive studies on the relationship between polymorphisms in the human IRS-2 gene and drug-induced granulocytopenia, and as a result have confirmed that six SNPs of the human IRS-2 gene are intimately related to granulocytopenia induced by administration of the drug.

The present inventors have found that analysis of these specified SNPs enables assessment (predictive diagnosis) of the risk of side effects induced by drugs for various human diseases; particularly, the risk of onset of drug-induced granulocytopenia. The present invention has been accomplished on the basis of this finding.

The present invention provides a method for determining the presence of the risk of drug-induced granulocytopenia, a method of detecting a genetic polymorphism markers employed as an index for the aforementioned risk determination, and oligonucleotides and kit employed for these methods, which are summarized below in (1) through (19).

(1) A method for assessing the risk of drug-induced granulocytopenia, the method comprising detecting polymorphisms of the human IRS-2 gene of a subject, and determining the presence of the risk of drug-induced granulocytopenia of the subject by use of the genetic polymorphisms as an index.

(2) A method of detecting polymorphisms of the human IRS-2 gene of a subject for determining the presence of the risk of drug-induced granulocytopenia, in which the genetic polymorphism is employed as an index.

(3) An examination method for the risk of drug-induced granulocytopenia, comprising detecting a polymorphism of the human IRS-2 gene of a subject, and carrying out an examination using the genetic polymorphisms as an index for the risk.

(4) A method as described in any of (1) through (3) above, wherein the presence of the risk of drug-induced granulocytopenia is determined by use, as an index, of at least one genetic polymorphism selected from the group consisting of human IRS-2 gene polymorphisms described below in (a) through (f):

(a) a polymorphism that is C (wild type) to A conversion at position 4,587 upstream of the translation initiation codon;

(b) a polymorphism that is AT deletion (wild type) at position 2,510 upstream of the translation initiation codon;

(c) a polymorphism that is A (wild type) to C conversion at position 1,164 upstream of the translation initiation codon;

(d) a polymorphism that is A (wild type) to G conversion at position 15,870 downstream from the translation initiation codon;

(e) a polymorphism that is A (wild type) to G conversion at position 29,793 downstream from the translation initiation codon; and (f) a polymorphism that it C deletion (wild type) at position 31,532 downstream from the translation initiation codon.

(5) A method as described in any of (1) through (4) above, wherein the genetic polymorphisms is detected through at least one technique selected from the group consisting of direct nucleotide sequencing, allele-specific oligonucleotide (ASO)-dot blot analysis, single nucleotide primer extension assay, PCR-single strand conformation polymorphism (SSCP) analysis, PCR-restriction enzyme fragment length polymorphism (RFLP) analysis, Invader assay, quantitative real-time PCR assay, and genetic polymorphism assay employing a mass spectrometer (mass array).

(6) A method as described in (5) above, wherein the genetic polymorphisms is detected through direct nucleotide sequencing.

(7) A method as described in (5) above, wherein the genetic polymorphisms are detected through PCR-restriction enzyme fragment length polymorphism (RFLP) analysis.

(8) A method as described in (7) above, wherein the PCR-restriction enzyme fragment length polymorphism (RFLP) analysis is performed by use of the restriction enzyme Afa I for detecting A to G conversion at position 29,793 downstream from the translation initiation codon of the human IRS-2 gene.

(9) An oligonucleotide which can be hybridized with the human IRS-2 gene and is employed as a primer or probe for genetic polymorphism detection, the oligonucleotide being selected from the group consisting of oligonucleotides described below in (a) through (f):

(a) an oligonucleotide having a sequence including a genetic polymorphism that is C to A conversion at position 4,587 upstream of the translation initiation codon of the human IRS-2 gene;

(b) an oligonucleotide having a sequence including a genetic polymorphism that is AT deletion at position 2,510 upstream of the translation initiation codon of the human IRS-2 gene;

(c) an oligonucleotide having a sequence including a genetic polymorphism that is A to C conversion at position 1,164 upstream of the translation initiation codon of the human IRS-2 gene;

(d) an oligonucleotide having a sequence including a genetic polymorphism that is A to G conversion at position 15,870 downstream from the translation initiation codon of the human IRS-2 gene;

(e) an oligonucleotide having a sequence including a genetic polymorphism site that is A to G conversion at position 29,793 downstream from the translation initiation codon of the human IRS-2 gene; and (f) an oligonucleotide having a sequence including a genetic polymorphism that is C deletion at position 31, 532 downstream from the translation initiation codon of the human IRS-2 gene.

(10) An oligonucleotide, which can be hybridized with the human IRS-2 gene is employed as a primer for genetic polymorphism detection, the oligonucleotide being selected from the group consisting of oligonucleotides described below in (a) through (d) and (f):

(a) an oligonucleotide having the sequence of SEQ ID NO: 3;

(b) an oligonucleotide having the sequence of SEQ ID NO: 6;

(c) an oligonucleotide having the sequence of SEQ ID NO: 9;

(d) an oligonucleotide having the sequence of SEQ ID NO: 12; and (f) an oligonucleotide having the sequence of SEQ ID NO: 17.

(11) A kit for assessing the risk of drug-induced granulocytopenia, the kit comprising an oligonucleotide as described in (9) above serving as a primer or probe for detecting a polymorphism of the human IRS-2 gene.

(12) A kit as described in (11) above, which comprises oligonucleotides as described in (10) above.

(13) A kit as described in (11) above, which comprises the oligonucleotide as described in (e) of (9) above and the restriction enzyme Afa I, the kit being employed for detecting A to G conversion at position 29,793 downstream from the translation initiation codon of the human IRS-2 gene.

(14) A method as described in (1) above, which assesses the risk of drug-induced granulocytopenia attributed to vesnarinone administration by use of oligonucleotides as described in (9) or (10) above.

(15) A method as described in (1) above, which assesses the risk of drug-induced granulocytopenia attributed to vesnarinone administration by use of the oligonucleotides as described in (e) of (9) above and the restriction enzyme Afa I.

(16) A kit for detecting a polymorphism of the human IRS-2 gene employed for determining the presence of the risk of drug-induced granulocytopenia, the kit comprising oligonucleotides as described in (9) above as primers or probes for detecting the IRS-2 gene polymorphisms.

(17) A kit as described in (16) above, which comprises oligonucleotides as described in (10) above.

(18) A kit as described in (16) above, which comprises the oligonucleotides as described in (e) of (9) above and the restriction enzyme Afa I, the kit being employed for detecting A to G conversion at position 29,793 downstream from the translation initiation codon of the human IRS-2 gene.

(19) A method as described in (2) above, which detects a genetic polymorphism employed for assessing the risk of drug-induced granulocytopenia attributed to vesnarinone administration by use of oligonucleotides as described in (9) or (10) above.

(20) A method as described in (2) above, which detects a genetic polymorphism employed for assessing the risk of drug-induced granulocytopenia attributed to vesnarinone administration by use of the oligonucleotides as described in (e) of (9) above and the restriction enzyme Afa I.

(21) A method as described in (3) above, in which the examination is carried out concerning the risk of drug-induced granulocytopenia attributed to vesnarinone administration, by use of oligonucleotides as described in (9) or (10) above.

(22) A method as described in (3) above, in which the examination is carried out concerning the risk of drug-induced granulocytopenia attributed to vesnarinone administration, by use of oligonucleotides as described in (e) of (9) above and the restriction enzyme Afa I.

Effects of the Invention

According to the present invention, there are provided methods for assessing the risk of drug-induced granulocytopenia in a human; a method of detecting a genetic polymorphism employed as an index for the aforementioned assessment; kits for these methods; primers and probes for polymorphism detection, which are employed in these methods; and a gene relating to a risk factor for drug-induced granulocytopenia in a human. These are useful for examining or assessing the risk of human drug-induced granulocytopenia, particularly useful for examining or assessing the risk of human drug-induced granulocytopenia before administration of a drug which has already been reported to induce granulocytopenia (including agranulocytosis).

BRIEF DESCRIPTION OF THE DRAWING

FIG. 1 A schematic representation showing the structure of the human IRS-2 gene and the positions of polymorphisms of the gene.

BEST MODE FOR CARRYING OUT THE INVENTION

As used herein, abbreviations of amino acids, peptides, nucleotide sequences, nucleic acids, etc. are according to IUPAC-IUB nomenclature [IUPAC-IUB communication on Biological Nomenclature, Eur. J. Biochem., 138: 9 (1984)], "Guideline for preparation of a specification, etc. including nucleotide sequences or amino acid sequences" (edited by Japan Patent Office), and commonly employed symbols used in the field.

As used herein, the genomic sequence of the human IRS-2 (insulin receptor substrate 2) gene is included in the sequence reported by Mohammadi, M. at Sanger Center (GenBank Accession No: AL162497; version 20; SEQ ID NO: 18), which has a full length of 143,409 bp.

The IRS-2 gene, whose structure is estimated by the genomic sequence on the basis of the sequence data of IRS-2 mRNA sequence obtained from GenBank (accession number XM 007095) and the sequence data of the aforementioned AL162497, is a 32,730 bp composed of two exons and one intron. The IRS-2 gene corresponds to 93,673 to 126,402 bp in the sequence of AL162497. FIG. 1 schematically shows the structure of the IRS-2 gene. In FIG. 1, "Ex. 1" and "Ex. 2" correspond to the aforementioned two exons. Abbreviations with arrows correspond to the below-described alterations (SNPs). Notably, the SNPs are synonymous; i.e., the SNPs do not cause amino acid substitutions, and therefore the protein sequence does not be changed. The position numbers of SNPs as described in the specification or the figure correspond to the position numbers counting from A of ATG that is used as a codon for Met at N-terminus of protein when mRNA is translated into protein (translation initiation codon).

C-4587A: C to A conversion at position 4,587 upstream of the translation initiation codon of the human IRS-2 gene;

AT-2510del: AT deletion at position 2,510 upstream of the translation initiation codon of the human IRS-2 gene;

A-1164C: A to C conversion at position 1,164 upstream of the translation initiation codon of the human IRS-2 gene;

A15870G: A to G conversion at position 15,870 downstream from the translation initiation codon of the human IRS-2 gene;

A29793G: A to G conversion at position 29,793 downstream from the translation initiation codon of the human IRS-2 gene; and C31532del: C deletion at position 31,532 (in Ex. 2) from the translation initiation codon of the human IRS-2 gene.

As used herein, the term "gene" encompasses double-stranded DNA, as well as single-stranded DNA (sense strand or antisense strand) constituting the double-stranded DNA. Unless otherwise specified, the gene (DNA) employed in the present invention encompasses double-stranded DNA including human genomic DNA, single-stranded DNA including cDNA (sense strand), single-stranded DNA having a sequence complementary to the sense strand, and fragments thereof. The aforementioned gene (DNA) may include regulatory regions, coding regions, exons, and introns. The term "polynucleotide" encompasses RNA and DNA. The term "DNA" encompasses cDNA, genomic DNA, and synthetic DNA. The term "polypeptide" encompasses its fragments, homologues, derivatives, and mutants. The term "mutant" refers to a naturally occurring allele mutant, a non-naturally occurring mutant, a mutant obtained through alteration (deletion, substitution, addition, or insertion), and a polynucleotide sequence which does substantially not change the function of the polypeptide encoded by the polynucleotide sequence. Alteration of an amino acid sequence, which may naturally occur through, for example, mutation or post-translational modification, can be artificially performed by introducing mutations into the gene.

As used herein, the term "SNP (single nucleotide polymorphism)" refers to alteration of a single nucleotide in a gene or gene cluster, and "SNPs" refers to plural form of SNP. The term "haplotype" refers to the type of the aforementioned single strand marker constructed of multiple polymorphic sites of a continuous gene region or gene cluster.

The present invention has been accomplished on the basis of the finding that a polymorphism(s) including alteration at a specific site of the human IRS-2 gene (the entirety of the IRS-2 gene including the promoter region involved in transcriptional regulation), particularly, SNP or SNPs are intimately correlated with human drug-induced granulocytopenia, and the risk of drug-induced granulocytopenia can be assessed (pre-diagnosed) by detecting the SNPs as a genetic polymorphism marker at the specific site. The assessment method of the present invention involves detection of a polymorphism(s) (i.e., SNP or SNPs) of the human IRS-2 gene of a sample (derived from a subject).

The SNPs detected and analyzed by the method of the present invention (i.e., genetic alterations serving as an index for assessing the risk of drug-induced granulocytopenia) include the aforementioned six polymorphisms; i.e., C-4587A, AT-2510del, A-1164C, A15870G, A29793G, and C31532del. The positions of the SNPs on the IRS-2 gene are as shown in FIG. 1. Notably, the position numbers of the SNPs correspond to the position numbers counting from A of ATG that is used as a codon for Met at N-terminus of protein when mRNA is translated into protein (translation initiation codon).

The present invention enables detection of polymorphisms (SNPs and haplotype) of the human IRS-2 gene, which provides data or means useful for elucidation and understanding of the mechanism of drug-induced granulocytopenia in human, and for diagnosis and prevention of the disease. According to the present invention, when a subject having the risk of drug-induced granulocytopenia is determined, and administration of a drug to the subject is avoided, drug-induced granulocytopenia can be prevented. Moreover, when other assays are performed frequently in addition to the present invention to monitor side effects upon administration of a drug, effective measures can be taken against such side effects.

The method of the present invention will next be described in detail.

In the method of the present invention, polymorphisms of the human IRS-2 gene of a subject are detected, and the presence of the risk of drug-induced granulocytopenia is determined by use of the genetic polymorphisms as an index.

Detection of the polymorphisms of the human IRS-2 gene is performed through, for example, the following procedure: the genomic sequence of the human IRS-2 gene of a subject, or its complementary strand is prepared, and, if desired, the genomic sequence or the sequence of its complementary strand is determined, followed by detection of the gene polymorphisms.

Preparation of Human IRS-2 Gene Including SNPs

The human IRS-2 gene derived from a subject is prepared as a sample for DNA analysis. Specific examples of the gene having polymorphisms (SNPs) are as described above. The IRS-2 gene encompasses the above-exemplified complementary strand of the DNA sequence of the human IRS-2 gene.

The human IRS-2 gene, which has genetic polymorphisms, or its complementary strand can be readily prepared through a generally employed genetic engineering technique on the basis of specific sequence data of the human IRS-2 gene as disclosed herein [see, for example, Molecular Cloning 2nd Ed, Cold Spring Harbor Lab. Press (1989); or Zoku Seikagaku Jikken Koza "Idenshi Kenkyuho I, II, III" edited by The Japanese Biochemical Society (1986)].

Specifically, cDNA or genomic DNA is extracted, through a common method, from a subject (e.g., a patient with human drug-induced granulocytopenia who has SNPs of the human IRS-2 gene), and a target clone is selected through a common method employing, for example, an appropriate antibody, restriction enzyme, or probe which may include a specific polymorphism of the human IRS-2 gene [see, for example, Proc. Natl. Acad. Sci., U.S.A., 78, 6613 (1981); or Science, 222, 778 (1983)], to thereby prepare a target genomic sequence of the IRS-2 gene.

Examples of the source of the aforementioned cDNA or genomic DNA include various cells and tissues having the IRS-2 gene including SNPs, and cultured cells derived therefrom. Other examples of the source include body fluids such as blood (e.g., serum or plasma), saliva, lymph, airway mucus, urine, and semen. The aforementioned source material (serving as a sample) is preferably DNA or genomic DNA derived from a human subject before administration of a drug (in particular, a drug which has previously been reported to induce granulocytopenia). Isolation of RNA from such a source material, isolation and purification of mRNA, preparation of cDNA, cloning thereof, etc. can be carried out through a common method. In the present invention, various commercially available cDNA libraries (e.g., cDNA libraries available from Clontech Lab. Inc.) may be employed.

No particular limitation is imposed on the method for screening a target gene from cDNA libraries, and the gene screening can be performed through a common method. Specifically, there is a prepared probe including a polymorphic site which can selectively bind to the DNA sequence of target sequence around SNPs, and plaque hybridization, colony hybridization, etc. These methods are performed singly or in combination by use of the thus-prepared probe.

The primers employed for screening may be a forward primer or reverse primer designed on the basis of target nucleotide sequence data of the human IRS-2 gene. Such primers can be synthesized through a common method by use of, for example, an automated synthesis apparatus. The probe for screening is generally a labeled probe. However, the screening probe may be an unlabeled probe, so long as it can specifically bind to a directly or indirectly labeled reagent. The labeling reagent and labeling technique such a probe or ligand have already been well known in the field. Examples of the labeling reagent include radioactive labeling reagents, biotin, fluorescent dyes, chemiluminescent reagents, enzymes (e.g., luciferase), and antibodies, which can be incorporated through a known labeling technique such as nick translation, random priming, or kinase treatment.

The thus-extracted genomic DNA or mRNA including the human IRS-2 gene can be amplified through a gene amplification method. This gene amplification enables easier and accurate detection through the detection method of the present invention. Examples of the gene amplification method include PCR (Saiki, R. K., Bugawan, T. L., et al., Nature, 324, 163-166 (1986)), NASBA (Comptom, J., Nature, 650, 91-92 (1991)), TMA (Kacian, D. L., and Fultz, T. J., U.S. Pat. No. 5,399,491 (1995)), and SDA (Walker, G. T., Little, M. C., et al., Proc. Natl. Acad. Sci., U.S.A., 89, 392-396 (1992)).

Gene fragments amplified by means of, for example, PCR may be isolated and purified through a common technique such as gel electrophoresis. Alternatively, purification of such gene fragments may be performed by use of a column. The gene fragment purification can be confirmed through, for example, mass spectrometry. In accordance with properties of the thus-amplified gene fragments, the gene fragments are applied for detection of the human IRS-2 gene (SNPs) employed in the present invention.

Detection of Human IRS-2 Gene Polymorphism

In the method of the present invention, subsequently, the presence of a polymorphism (s) of the aforementioned sample is detected. Specifically, this detection can be performed through, for example, any of the below-described methods (1) through (8).

(1) Direct Nucleotide Sequencing

Detection of the IRS-2 gene polymorphism (s) can be performed through a direct nucleotide sequencing method, which has conventionally been employed for sequencing of such a gene; for example, the dideoxy method (Sanger, et al., Proc. Natl. Acad. Sci., U.S.A., 74, 5463-5467 (1977)) or the Maxam-Gilbert method [Methods in Enzymology, 65, 499 (1980)]. The genetic polymorphism detection may be performed through a combination of such a direct nucleotide sequencing method and a DNA amplification method (e.g., PCR). Particularly, a combination of such a direct nucleotide sequencing method and PCR or a similar DNA amplification method is preferred, since this combination needs only a small amount of a DNA sample, and enables simple and easy detection with high sensitivity and accuracy.

Basically, this preferred method can be performed through, for example, the following procedure: a PCR-amplified gene fragment or a purified product thereof is cloned into a plasmid, followed by direct nucleotide sequencing through the dideoxy method, the Maxam-Gilbert method, or a similar method. For the sake of convenience, the preferred method can be performed through nucleotide sequencing by use of, for example, a commercially available sequencing kit. Thus, the presence of polymorphisms at the aforementioned specific sites of the human IRS-2 gene can be detected.

In the aforementioned method and the below-described methods, no particular limitation is imposed on the PCR-amplified DNA fragment (i.e., sample), so long as the DNA fragment includes at least one of the aforementioned specific sites at which polymorphisms is expected to occur. The DNA fragment generally has a length of about 50 to several thousands of bp, preferably 50 to several hundreds of bp.

(2) Allele-Specific Oligonucleotide Dot Blot Method

Alternatively, detection of the IRS-2 gene polymorphism (s) can be performed through the allele-specific oligonucleotide (ASO)-dot blot method (Conner, B. J., et al., Proc. Natl. Acad. Sci., U.S.A., 80, 278-282 (1983)). This method can be performed through, for example, dot blot analysis in which a PCR-amplified gene fragment by use of a forward primer and reverse primer designed so as to sandwich a target is hybridized with an allele-specific oligonucleotide probe containing SNP site. Thus, the presence of SNP in the gene fragment can be determined.

(3) Single Nucleotide Primer Extension Assay

Detection of the IRS-2 gene polymorphism(s) can also be performed through a single nucleotide extension assay, such as the SNaPshot assay, pyrosequencing, or the point mutation detection assay disclosed in Japanese Patent Application Laid-Open (kokai) No. 2000-279197. In such an assay, a probe designed so as to correspond to a nucleotide immediately (or several nucleotides) before a target polymorphism (SNP) (i.e., a probe designed such that the 3'-end thereof corresponds to one (or several) nucleotide upstream of the polymorphism) is annealed to a DNA sample. Each of the aforementioned assays can be performed by use of a commercially available SNPs detection kit and the software attached to the kit.

For example, the SNaPshot assay can be performed by use of ABI PRISM SNaPshot ddNTP Primer Extension Kit (PE Applied Biosystems). Detection of SNPs can be performed through detection and analysis of fluorescent fragments generated after reaction by use of ABI PRISM 310/377/3100/3700 DNA Analyzer (PE Applied Biosystems) and GeneScan software.

Pyrosequencing can be performed through, for example, the following procedure. Specifically, genomic DNA is isolated from, for example, a blood sample through a common method; several tens to several hundreds of nucleotides (including a polymorphism) are PCR-amplified by use of a biotin-labeled primer; single-stranded DNA is purified by use of magnet beads; and the thus-purified DNA is employed as a sample. A primer designed to have a complementary sequence corresponding to several nucleotides upstream of a target polymorphism is annealed to the sample, and then each dNTP is added to the mixture none after another according to the sequence in the vicinity of the polymorphism input in software. Pyrophosphoric acid (PPi) released from nucleotide extension of DNA polymerase is converted to ATP by ATP sulfurylase, and luciferase generates detectable light using this ATP, which can be detected with a chemiluminescence detector, a CCD camera, etc. Thus, genotyping can be performed through analysis of the peak of luminescence obtained through addition of the dNTPs. This method enables genotyping in about 15 minutes for 96 samples.

The aforementioned method can use a generally employed reagent and apparatus. Examples include reagents such as commercially available SNP Reagent Kits (Pyrosequencing AB) which contain, as components, a mixture of the following four enzymes: DNA polymerase, ATP-sulfurylase, luciferase, and apyrase, a substrate solution containing luciferin and APS (adenosine 5'-phosphosulfate), and dNTPs containing dATP (deoxyadenosine 5'-triphosphate), dCTP, dGTP, and dTTP; PSQ96 system for automatic DNA sequence analysis (Pyrosequencing AB); and SNP software employed for the analysis (Pyrosequencing AB).

Alternatively, pyrosequencing can be performed through, for example, the method described in U.S. Pat. No. 6,159,693. Specifically, an isolated genomic DNA is amplified; the thus-amplified PCR product is purified; and the resultant product is reacted with pyrophosphoric acid by use of READIT™ System (Promega Corporation), followed by analysis of the resultant data.

(4) PCR-Single Strand Conformation Polymorphism (SSCP) Analysis

The detection method of the present invention can employ the PCR-SSCP method (Orita, M., Iwahara, H., et al., Proc. Natl. Acad. Sci., U.S.A., 86, 2776-2770 (1989)), in which an amplified PCR product (single-stranded DNA) is subjected to non-denatured polyacrylamide gel electrophoresis, and the presence of single nucleotide polymorphims is determined on the basis of the mobility difference.

(5) PCR-Restriction Enzyme Fragment Length Polymorphism (RFLP) Analysis

In the present invention, in the case where, for example, a nucleotide sequence including a polymorphims, which are targeted for detection of SNPs or haplotype of the human IRS-2 gene, contains a restriction enzyme recognition site, the detection can be performed through restriction enzyme fragment length polymorphism analysis (RFLP analysis: Botstein, D. R., et al., Am. J. Hum. Gen., 32, 314-331 (1980)).

Specifically, for example, there is employed a restriction enzyme which can recognize nucleotides around the polymorphism, in order to detect whether the nucleotide at position 29,793 is A (wild type) or G (mutant type), the position being counted from the translation initiation codon present in Ex. 2 of the human IRS-2 gene. The enzyme employed in the RFLP analysis may be any known restriction enzyme, so long as the enzyme can recognize nucleotides around the target polymorphisms. Specific examples of the restriction enzyme include Afa I.

The RFLP analysis is more preferably done as PCR-RFLP analysis; i.e., analysis performed on a large amount of sample DNA which has been amplified and prepared in advance through PCR or a modification thereof. Thus, the presence of polymorphism can be detected on the basis of the presence of a specific cleavage site.

More specifically, detection of SNP of the human IRS-2 gene by the PCR-RFLP analysis is performed through, for example, the following procedure. Firstly, the genomic DNA of the human IRS-2 gene is extracted from a human biological sample, and a DNA fragment of the region including a polymorphism of the gene is amplified, thereby preparing a large amount of a DNA sample. The forward primer and/or reverse primer to be employed may be a primer whose sequence is not completely identical to the genomic sequence, as long as is a primer containing a sequence for introducing a restriction enzyme recognition site. Subsequently, the above-amplified DNA sample is digested by use of a specific restriction enzyme (i.e., an enzyme which can digest either a wild type or a mutant type), and DNA cleavage patterns (e.g., the presence of cleavage, or the base length of cleaved fragments) are confirmed through a common method such as gel electrophoresis.

In the case of the polymorphism (A29793G) of the human IRS-2 gene specified by the present invention, which is associated with human drug-induced granulocytopenia, a specific recognition site (GTAC) of the restriction enzyme Afa I is generated by the SNP in the region including positions 29,793 to 29,796 of the nucleotide sequence of the human IRS-2 gene. Therefore, this polymorphism can be detected through the RFLP analysis.

(6) Invader Assay

Detection of SNPs of the IRS-2 gene can also be performed through the Invader assay. The Invader assay can be performed with reference to the following publications:

Lyamichev, V., et al., Nat. Bioltechnol., 17(3) 292-296 (1999); and

International Patent Publication WO 9823774 (Japanese Kohyo Patent Publication No. 2001-526526).

The Invader assay enables analysis of SNPs of genomic DNA without amplification of target DNA. For example, the Invader assay is performed as follows.

In order to detect the presence of target SNPs of the human IRS-2 gene, firstly, genomic DNA is isolated. To perform this assay, two oligonucleotides were prepared by use of, for example, an automated DNA synthesis apparatus. One oligonucleotide, the allele-specific probe, contains the complementary base of the SNP nucleotide to be analyzed, and extends to the upstream of the SNP. Additional non-complementary nucleotides, which are composed of 15 to 50 nucleotides (5' flap), were added to this probe on its 5' site. The second oligonucleotide having 15 to several tens of nucleotides, the Invader oligonucleotide probe, has a complementary sequence to the downstream of the SNP and the end of the probe is a non-matching base overlapping the SNP nucleotide to be analyzed. The two oligonucleotides and an enzyme (i.e., Cleavase for the Invader assay employed in the present invention) are added to the target genomic DNA, which is extracted from described above. This enzyme recognizes the specific structure composed of the two oligonucleotides and the target genomic DNA. This reaction mixture is reacted under the appropriate conditions.

When the genomic DNA of a sample has a target SNP, a first reaction proceeds; the enzyme cleaves the 5' flap. On the other hand, when the genomic DNA of a sample does not have a target SNP, the enzyme does not cleave it.

The 5' flap released from the allele-specific probe which has been cleaved by the enzyme is complementarily bound to a fluorescence resonance energy transfer (FRET) probe serving as a target, and the 3'-end of the 5' flap is invaded in the FRET probe. In a manner similar to that described above, enzymatic reaction (second reaction) occurs, and a fluorescent dye is released.

The FRET probe employed in this second reaction is formed such that it doesn't depend on a target to be detected, and contains the following two essential elements:

(1) a 3' region which is complementary to a product cleaved through the first reaction; and (2) a self-complementary region which forms a duplex for mimicking a single-stranded probe, which is hybridized with a target, and which contains a reporter fluorescent dye and a quencher fluorescent dye.

When the reporter fluorescent dye and the quencher fluorescent dye are bound to the same probe, the fluorescence intensity of the reporter fluorescent dye is quenched through fluorescence resonance energy transfer. Whereas when the reporter fluorescent dye and the quencher fluorescent dye are not bound to the same probe, the fluorescence intensity of the reporter fluorescent dye is not quenched. When the 5' flap released from the cleaved first probe is hybridized with the FRET probe, the resultant product acts as an invader oligonucleotide in the second reaction, and an invasion complex that is recognized by the enzyme is produced. Thus, cleavage of the FRET probe by the aforementioned enzyme separates the two fluorescent dyes, thereby yielding a detectable fluorescent signal. The signal can be read by use of, for example, a standard fluorescence microtiter plate reader, whereby the presence of target SNPs can be detected. A combination of the first and second reactions can amplify the signal by a factor of $1\times10^6$. Employment of two FRET probes having different fluorescent dyes also enables detection of the presence of SNP.

(7) Quantitative Real-Time PCR Assay

Detection of polymorphisms of the human IRS-2 gene can also be readily performed by quantitative real-time PCR assay (TaqMan assay).

This assay can be performed through, for example, the following procedure. Specifically, firstly, to confirm the presence of a polymorphism, a DNA fragment is prepared as a forward primer or reverse primer formed of, for example, 15 to 39 nucleotides. In this case, the forward primer or reverse primer is prepared so as not to contain the polymorphims. Subsequently, there is prepared a probe which has both a reporter fluorescent dye and a quencher fluorescent dye, and the probe contains, for example, a 15 to 50 bp oligonucleotide which correspond to a partial sequence of amplified fragment. The nucleotide sequence of the probe has to be selected such that a region with which both of the forward and reverse primer do not hybridize. The probe is designed so as to have a sequence complementary to an allele-specific sequence for detecting the presence of a target single nucleotide polymorphism. By use of the probe, a target DNA fragment of the IRS-2 gene of a sample to be detected is amplified through PCR, and fluorescence from the resultant reaction mixture is real-time measured. Thus, the presence of polymorphism can be detected. Employment of two probes having different fluorescent dyes also enables detection of both alleles.

The reporter fluorescent dye employed in the aforementioned Invader assay or TaqMan assay is preferably a fluorescein fluorescent dye such as FAM (6-carboxy-fluorescein), whereas the quencher fluorescent dye is preferably a rhodamine fluorescent dye such as TAMRA (6-carboxy-tetramethyl-rhodamine). These fluorescent dyes are known, and are contained in commercially available real-time PCR detection kits. In the present invention, such a commercially available fluorescent dye can be employed. No particular limitation is imposed on the binding position of the reporter fluorescent dye or the quencher fluorescent dye, but generally, the reporter fluorescent dye is bound to one end (preferably the 5'-end) of the oligonucleotide constituting the probe, and the quencher fluorescent dye is bound to the other end. The method for binding a fluorescent dye to an oligonucleotide is known, and is described in, for example, Noble, et al., (1984), Nuc. Acids Res., 12: 3387-3403 or Iyer, et al., (1990), J. Am. Chem. Soc., 112: 1253-1254.

The TaqMan assay per se is known, and apparatuses and kits for the TaqMan assay are commercially available. In the present invention, such a commercially available apparatus or kit can be employed. For example, the TaqMan assay can be performed according to the method described in Japanese Patent No. 2,825,976, or according to the ABI PRISM 7700 sequencing system user manual (PE Applied Biosystems).

(8) Genetic Polymorphism Assay Employing a Mass Spectrometer (Mass Array)

The mass array assay detects the difference in molecular weight between polymorphisms. Specifically, a region including a polymorphism to be detected is amplified through PCR, and then an extension primer is hybridized with a sequence immediately before the position of SNP, followed by extension reaction by use of a reaction mixture containing a ddNTP/dNTP mixture (e.g., a reaction mixture containing ddATP, dCTP, dGTP, and dTTP), thereby yielding a fragment having a length depending on the type of SNP. The resultant fragment is purified, and then subjected to analysis by use of, for example, a MALDI-TOF mass spectrometer, whereby the relationship between the molecular weight and the genetic polymorphism can be analyzed (Pusch, W., Wurmbach, J H., Thiele, H., Kostrzewa, M., MALDI-TOF mass spectrometry-based SNP genotyping, Pharmacogenomics, 3 (4): 537-48 (2002)). This assay can be readily performed by use of, for example, Sequenom Mass ARRAY high throughput SNP analysis system (http://www.sequenom.com/Files/applications/hme_assay.html).

(9) Other Detection Methods

Detection of SNPs of the human IRS-2 gene can also be performed through, for example, any of the below-described various methods, which have conventionally been known as DNA sequencing methods or mutation detection methods.

(a) PCR-SSO Method Employing Sequence-Specific Oligonucleotide

A method in which a probe for a mutation is immobilized on a carrier; a sample (gene amplified product) is hybridized with the probe; and a difference in hybridization efficiency is determined on the basis of the presence of mismatch.

(b) PCR-SSP Method for Point Mutation Detection

A method by use of a sequence-specific primer for gene amplification which is designed such that a nucleotide corresponding to point mutation becomes the 3'-end nucleotide, which method utilizes that a significant difference in PCR amplification efficiency occurs depending on the complementarity of the 3'-end nucleotide of the primer.

(c) PCR-DGGE (Denaturing Gradient Gel Electrophoresis)

When DNA fragment including a mutation is hybridized with a normal DNA fragment, and then the thus-hybridized product is electrophoresed on a polyacrylamide gel with gradually increasing denaturant (e.g., urea or formamide) concentrations, the product is converted into single-stranded DNA fragments at a position of lower denaturant concentration, as compared with the case of non-mismatched homogenous double-stranded DNA fragments. The single-stranded DNA fragments migrate at a rate higher than the migration rate of the double-stranded DNA fragments, and therefore single nucleotide mutation can be detected through comparison of the mobilities of the DNA fragments.

(d) PCR-DGGE/GC clamp method (Shefield, V. C., et al., Proc. Natl. Acad. Sci., U.S.A., 86, 232-236 (1989))

This method is a modification of the aforementioned PCR-DGGE, in which a region having a high GC content is added to a target DNA fragment for detection of a mutation. This method compensates for the disadvantage of the PCR-DGGE in detection of substitution, deletion, addition, or insertion of multiple nucleotides. This method requires a step of adding a GC clamp to a target DNA fragment for mutation detection.

(e) RNase protection assay (Finkelstein, J., et al., Genomics, 7, 167-172 (1990))

(f) In situ RT-PCR (Nucl. Acids Res., 21, 3159-3166 (1993))

(g) In situ hybridization (h) Southern blotting (Sambrook, J., et al., Molecular Cloning a Laboratory Manual., Cold Spring Harbor Laboratory Press: NY. (1989))

(i) Dot hybridization assay (see, for example, Southern, E. M., J. Mol. Biol., 98: 503-517 (1975))

(j) Fluorescence in situ hybridization (FISH: Takahashi, E., et al., Hum. Genet., 86, 1416 (1990))

(k) Comparative genomic hybridization (CGH: Kallioneimi, A., et al., Science, 258, 818-821 (1992)), (Spectral karyotyping: SKY: Rowley, J. D., et al., Blood, 93, 2038-2042 (1999))

(1) Method employing yeast artificial chromosome (YAC) vector clone as a probe (Lengauer, C., et al., Cancer Res., 52, 2590-2596 (1992)).

Thus, polymorphisms (SNPs) or haplotype of the human IRS-2 gene can be detected.

According to the present invention, when a test sample is confirmed to have a polymorphism(s) of the human IRS-2 gene through detection procedures described above, the sample is judged as a subject with a high risk of drug-induced granulocytopenia.

Thus, before administration of a drug, it is determined whether the subject has a high risk of drug-induced granulocytopenia. Therefore, granulocytopenia, attributed to drug administration or other causes, will be prevented by this test.

Particularly, detection of SNPs of the human IRS-2 gene according to the present invention is effective in detecting the presence of a risk factor for drug-induced granulocytopenia in a human. That is, screening of the SNPs enables detection of a risk factor for human drug-induced granulocytopenia.

Thus, the present invention provides a method of detecting a polymorphism(s) of the human IRS-2 gene of a subject who may develop drug-induced granulocytopenia. That is, the genetic polymorphism(s) of the human IRS-2 gene can be used as an index to detect a subject who develops drug-induced granulocytopenia.

Oligonucleotide

The present invention also provides an oligonucleotide serving as a primer or probe for genetic polymorphism detection, which is used in the assessment (detection) method of the present invention employing PCR. No particular limitation is imposed on the oligonucleotide, so long as it can specifically amplify a specific region including polymorphisms (SNPs) of the human IRS-2 gene. The oligonucleotide can be appropriately constructed on the basis of sequence data of the human IRS-2 gene and synthesized through common methods.

More specifically, the oligonucleotide can be synthesized through a generally employed chemical synthesis method such as the phosphoroamidite method or the phosphotriester method, or can be synthesized by use of a commercially available automated oligonucleotide synthesis apparatus such as Pharmacia LKB Gene Assembler Plus (product of Pharmacia). A double-stranded fragment can be obtained by annealing of a chemically synthesized single-stranded oligonucleotide and its complementary strand under appropriate conditions, or synthesized by using an appropriate primer and DNA polymerase.

Preferred examples of the aforementioned oligonucleotide serving as a probe or primer include partial oligonucleotides corresponding to a DNA fragment designed so as to contain a polymorphism of the human IRS-2 gene. These oligonucleotides have at least a sequence of 10 bases (generally about 10 to 35 a sequence of bases). The oligonucleotide serving as a primer pair may be oligonucleotides having two sequences which are designed and synthesized so as to sandwich SNP of the human IRS-2 gene (genomic sequence). The oligonucleotide serving as a probe may be its positive clone per se.

Preferred examples of the aforementioned oligonucleotide serving as a probe or primer include partial sequences corresponding to a DNA fragment designed so as to contain at least one of the following polymorphisms: C to A conversion at position 4,587 upstream of the translation initiation codon of the human IRS-2 gene (C-4587A); AT deletion at position 2,510 upstream of the translation initiation codon of the human IRS-2 gene (AT-2510del); A to C conversion at position 1,164 upstream of the translation initiation codon of the human IRS-2 gene (A-1164C); A to G conversion at position 15,870 from the translation initiation codon of the human IRS-2 gene (A15870G); A to G conversion at position 29,793 downstream from the translation initiation codon of the human IRS-2 gene (A29793G); and C deletion at position 31,532 downstream from the translation initiation codon of the human IRS-2 gene (C31532del). These primer or probe has at least a sequence of 10 basess (preferably at least a sequence of 15 bases).

Specific examples of the oligonucleotide include forward primers and reverse primers of SEQ ID NOs: 1, 2, 4, 5, 7, 8, 10, 11 and 13 to 16, and oligonucleotide primers for direct sequencing of SEQ ID NOs: 3, 6, 9, 12, and 17, which are described below in Examples.

No particular limitation is imposed on the gene-specific probe employed in the present invention, so long as it can detect any of the aforementioned C-4587A, AT-2510del, A-1164C, A15870G, A29793G, and C31532del.

Kit for Assessment

The assessment (detection) method of the present invention can be more easily performed by use of a reagent kit for detecting SNPs of the human IRS-2 gene of a sample. The present invention also provides a kit for such assessment.

A kit of the present invention includes, as an essential component, at least a DNA fragment which hybridizes with a partial or entire—nucleotide sequences or its complementary sequences—including six SNPs of the human IRS-2 gene, or which hybridizes with a sequence containing an ologonucleotide with one base or several bases before a polymorphic site. Another kit of the present invention includes, as an essential component, a restriction enzyme (e.g., Afa I) that specifically recognizes a sequence formed of several nucleotides (including the aforementioned polymorphic site).

Other components of the kit of the present invention are, for example, a labeling reagent, and reagents required for PCR (e.g., Taq DNA polymerase, deoxynucleotide triphosphate, or a primer for DNA amplification). Examples of the labeling reagent include chemical modification substances such as a radioactive isotope, a light-emitting substance, and a fluorescent substance. The DNA fragment per se may be conjugated in advance with such a labeling reagent. The kit of the present invention may further include, for example,—appropriate reaction diluents, standard antibodies, buffers, detergents, or reaction stopping solutions, to perform measurement conveniently.

Use of the aforementioned assessment method of the present invention enables provision of an examination method for the risk of human drug-induced granulocytopenia by use, as an index, of a detected genetic polymorphism which may cause drug-induced granulocytopenia in a human, particularly, an examination method for the risk of granulocytopenia attributed to administration of a drug (e.g., vesnarinone) which has already been reported to induce granulocytopenia (including agranulocytosis), before administration of the drug, as well as a diagnosis reagent and diagnosis kit employed for such an examination method.

The present invention will next be described in more detail by way of Examples, which should not be construed as limiting the invention thereto.

Example 1

(a) Screening of Genetic Polymorphism in Relation to Granulocytopenia Attributed to Drug Administration In order to find genetic polymorphisms in relation to granulocytopenia attributed to drug administration, there were employed subjects who had received vesnarinone (3,4-dihydro-6-[4-(3,4-dimethoxybenzoy1)-1-piperaziny1]-2(1H)-quinoline).

In Japan, vesnarinone, which is a commercially available drug applicable to chronic heart failure (mild to moderate heart failure), has been reported to induce side effects including leukopenia, granulocytopenia, and agranulocytosis, and therefore, administration of this drug requires observation of such side effects and frequent examinations of granulocytes.

Among subjects who had received vesnarinone, had orally agreed to cooperate with investigation of the cause for vesnarinone-induced granulocytopenia between May 1991 and October 1996, and had accepted to provide a blood sample, there were employed 84 subjects (male/female ratio=1.21:1) who had again agreed in writing to cooperate with genetic analysis according to ethical guidelines between July 2001 and December 2001. Genomic DNA was extracted from a blood sample (or a cell sample derived therefrom) of each of the subjects who had again agreed described above. through a common method, and was employed for the below-described tests.

(b) Classification Criteria of the Subjects

On the basis of the below-described criteria, the subjects were classified into the following two groups: a group of subjects with granulocytopenia, and a group of subjects without granulocytopenia.

Among the subjects, subjects having leukocytes or neutrophils which were decreased to half or less following vesnarinone administration, and having the number of leukocytes of 2,000/$mm^3$ or less, or the number of neutrophils of 1,000/$mm^3$ or less were classified as "subjects with granulocytopenia". On the other hand, subjects who did not decrease the number of neutrophils after vesnarinone administration for 90 days or more were classified as "subjects with granulocytopenia".

Each of these groups was further classified into two groups according to sex, to thereby become four subgroups; i.e., a group of 13 male with granulocytopenia (group A), a group of 17 female with granulocytopenia (group B), a group of 33 male without granulocytopenia (group C), and a group of 21 female without granulocytopenia (group D).

(c) Gene and Polymorphism (SNP) to be Analyzed

115 Candidate genes were selected from among, for example, cytokine-related genes, MHC region genes, G-CSF-related genes, TNF-α-related genes, NF-K-related genes, cAMP-related genes, and potassium channel-related genes.

Polymorphisms (SNPs) of these candidate genes were searched from the database of Japanese Single Nucleotide Polymorphisms (JSNP: http://snp.ims.u-tokyo.ac.jp/index-_ja.html), and 188 candidate SNPs were selected.

(d) Analysis Method

The SNPs were analyzed by the Invader assay. The Invader assay was performed with reference to the following publications (1) and (2):

(1) Lyamichev, V., et al., Nat. Biotechnol., 17: 292-296 (1999); and (2) International Patent Publication WO 9823774 (98/6/4).

In order to amplify genomic DNA regions including each of the candidate SNPs by PCR, a set of primers for amplifying these regions was designed on the basis of genomic DNA sequence data around the SNPs searched from JSNP, and each of the primers was synthesized.

An Invader assay reagent for determining genotypes of the candidate SNPs was prepared by a common method on the basis of genomic DNA sequence data around the SNPs searched from JSNP.

Each PCR was performed by use of genomic DNA (1 ng) as a template. A reaction mixture (15 μL) contained dNTPs (0.25 mM), the PCR buffer attached to TaKaRa Ex Taq (Takara) (1/10 of the total amount for reaction), a set of a forward and a reverse primer (130 nM each), and TaKaRa Ex Taq (Takara) (0.5 U). Each sample was amplified in DNA Engine PTC-0200 (MJ Research). The PCR was performed for 94° C. for 2 minutes; then 50 cycles of 94° C. for 30 seconds, 56° C. (or 58° C. or 60° C.) for 30 seconds, and 72° C. for 90 seconds.

Invader assay reaction was carried out mixing the Invader assay reagent with the PCR product that was diluted with a range of 10 to 1,000-fold. A reaction mixture (15 μL) contained 5.5×Invader buffer (2.75 μL), 10×Bioplex FRET Probe Mix (0.75 μL), Cleavase VIII enzyme (200 ng/μL) (1 μL), PPI Mix (3 μL), and the diluted PCR product described above (7.5 μL). The reaction was performed at 62° C. for 60 to 120 minutes.

(e) Genotype Determination Method

Genotype of each subject was determined based on the intensities of two different fluorescent materials detected as a result of the Invader assay reaction. Thus, the genotypes of the 188 SNPs located in the 115 genes of each subject were determined by the Invader assay.

(f) Statistical Analysis Method

The allele frequencies in the group of subjects with granulocytopenia were compared to that of subjects without granulocytopenia by the contingency χ square test. The odds ratio was estimated through the Brown method (Brown, C. C., Am. J. Epidemiol., 113: 474-480 (1981)). The 95% confidence interval of odds ratio was calculated through the Woolf method.

(g) Results

The results of analysis of the 188 SNPs in the 115 genes through the aforementioned method revealed that polymorphism with the most statistically significant association was located in the insulin receptor substrate 2 (IRS-2) gene (JSNP ID: IMS-JST040476). In these subjects, this SNP was in Hardy-Weinberg equilibrium.

The result suggests that the SNP in the human IRS-2 gene is intimately related to the granulocytopenia attributed to vesnarinone administration, and that the human IRS-2 gene is likely to play an important role in the pathogenesis of granulocytopenia.

The Human IRS-2 protein (translation product of the human IRS-2 gene) belongs to the insulin receptor substrate protein family (IRSs: IRS-1, IRS-2, IRS-3, and IRS-4). IRSs are activated by insulin receptor tyrosine kinase that phosphorylates tyrosine residues of IRSs. As has been known, Phosphorylated-IRSs are related to the insulin action that is to promote glucose uptake by accelerating translocation of glucose transporter 4 (GLUT-4) from cytoplasm to cell membrane via PI-3 kinase activated by phosphorylated-IRSs. In order to conduct further studies on the relation between the human IRS-2 gene and vesnarinone-induced granulocytopenia, another polymorphisms of the human IRS-2 gene were analyzed.

Example 2

Association Analysis of the Human IRS-2 Gene and Drug-Induced Granulocytopenia

By use of the subjects described in Example 1, polymorphisms of the human IRS-2 gene were analyzed as follows.

(a) Discovery of polymorphisms in the Human IRS-2 gene

In order to screen the entirety of the IRS-2 gene including a promoter region involved in its transcriptional regulation, the genomic sequence including the IRS-2 gene was obtained from GenBank (accession number AL162497, full length: 143,409 bp) by inquiring the human IRS-2 mRNA sequence, which is registered in GenBank (accession number XM_007095). The structure of the human IRS-2 gene was estimated through detailed comparison between the human IRS-2 mRNA sequence and the genomic sequence including the IRS-2 gene. Notably, a complementary strand of the above-obtained genomic sequence was employed for the comparison such that the above-compared sequences were in the same direction (from 5' to 3').

It is inferred from the result that the human IRS-2 gene has a full length of 32,730 bp including two exons and one intron.

On the basis of the above sequence data, primers were designed and synthesized.

For discovery of polumorphism, there were employed genomic samples from 12 subjects with granulocytopenia and 12 subjects without granulocytopenia among the subjects described in Example 1.

Each PCR was performed by use of genomic DNA (5 ng). A reaction mixture (10 μL) was prepared to contain dNTPs (1.25 mM), magnesium chloride (3.9 mM), ammonium sulfate (16.6 mM), Tris-HCl (67 mM, pH 8.8), β-mercaptoethanol (10 mM), a set of a forward primer and a reverse primer (1.25 mM), and TaKaRa Ex Taq (Takara) (0.5 U). If desired, DMSO (dimethyl sulfoxide) was added to the reaction mixture such that the final concentration was 10%.

Each sample was amplified by use of DNA Engine PTC-0200 (MJ Research) or GeneAmp PCR System 9700 (PE Applied Biosystems). The PCR was performed at 95° C. for 2 minutes; then 37 cycles of 94° C. for 30 seconds, 56° C. (or 58° C.) for 30 seconds, and 72° C. for 3 minutes with final extension at 72° C. for 7 minutes.

Each of the PCR product was employed to react with BigDye™ Terminator RR mix (PE Applied Biosystems).

On the basis of nucleotide sequence data obtained by ABI Prism 3700 DNA Analyzer (PE Applied Biosystems), genetic polymorphisms were detected and their positions on the human IRS-2 gene were confirmed by use of SEQUENCHER 3.1 (product of Gene Codes)

(b) Sample Amplification and Genotype Determination Method

In order to determine the genotype distribution, all polymorphisms identified by the discovery above were analyzed in the all subjects described in Example 1 by amplifying the regions containing the polymorphisms with primer sets and sequencing the PCR products under the condition described above.

(c) Statistical Analysis

In addition to the statistical methods employed in Example 1, a pair-wise linkage disequilibrium coefficient (D'=D/Dmax or D/Dmin) was calculated by use of the method by Thompson, et al. (Thompson, E. A., et al., Am. J. Hum. Genet. 42: 113-124 (1988))

(d) Results

The analysis results revealed that, in the subject groups, all the polymorphisms analyzed in the present Example are in Hardy-Weinberg equilibrium.

The analysis results also revealed that six polymorphisms were intimately associated with granulocytopenia induced by vesnarinone administration. Tables 1 through 6 show the results of statistical analysis on the six polymorphisms respectively.

TABLE 1

| Polymorphism The number of genotype C-4587A | subjects with agranulocytosis N (%) | subjects without agranulocytosis N (%) | $\chi^2$ (df = 1) | P | OR (95% Cl) |
|---|---|---|---|---|---|
| CC | 7 (25.0) | 29 (59.2) | 8.36 | 0.0038 | 4.35 |
| CA + AA | 21 (75.0) | 20 (40.8) | | | (1.56-12.16) |
| Total | 28 | 49 | | | |

TABLE 2

| Polymorphism The number of genotype AT-2510del | subjects with agranulocytosis N (%) | subjects without agranulocytosis N (%) | $\chi^2$ (df = 1) | P | OR (95% Cl) |
|---|---|---|---|---|---|
| AT | 7 (24.1) | 28 (57.1) | 8.02 | 0.0046 | 4.19 |
| ATdel + del | 22 (75.9) | 21 (42.9) | | | (1.51-11.64) |
| Total | 29 | 49 | | | |

TABLE 3

| Polymorphism The number of genotype A-1164C | subjects with agranulocytosis N (%) | subjects without agranulocytosis N (%) | $\chi^2$ (df = 1) | P | OR (95% Cl) |
|---|---|---|---|---|---|
| AA | 8 (26.7) | 29 (59.2) | 7.90 | 0.0049 | 3.99 |
| AC + CC | 22 (73.3) | 20 (40.8) | | | (1.48-10.73) |
| Total | 30 | 49 | | | |

TABLE 4

| Polymorphism The number of genotype A15870G | subjects with agranulocytosis N (%) | subjects without agranulocytosis N (%) | $\chi^2$ (df = 1) | P | OR (95% Cl) |
|---|---|---|---|---|---|
| AA | 10 (37.0) | 36 (73.5) | 9.67 | 0.0019 | 4.71 |

TABLE 4-continued

| Polymorphism The number of genotype A15870G | subjects with agranulocytosis N (%) | subjects without agranulocytosis N (%) | $\chi^2$ (df = 1) | P | OR (95% Cl) |
|---|---|---|---|---|---|
| AG + GG | 17 (63.0) | 13 (26.5) | | | (1.72-12.88) |
| Total | 27 | 49 | | | |

TABLE 5

| Polymorphism The number of genotype A29793G | subjects with agranulocytosis N (%) | subjects without agranulocytosis N (%) | $\chi^2$ (df = 1) | P | OR (95% Cl) |
|---|---|---|---|---|---|
| AA | 11 (36.7) | 39 (73.6) | 10.90 | 0.00096 | 4.81 |
| AG + GG | 19 (63.3) | 14 (26.4) | | | (1.84-12.56) |
| Total | 30 | 53 | | | |

TABLE 6

| Polymorphism The number of genotype | subjects with agranulocytosis N (%) | subjects without agranulocytosis N (%) | $\chi^2$ (df = 1) | P | OR (95% Cl) |
|---|---|---|---|---|---|
| C31532del | | | | | |
| CC | 9 (33.3) | 34 (70.8) | 9.93 | 0.0016 | 4.86 |
| Cdel + del | 18 (66.7) | 14 (29.2) | | | (1.76-13.39) |
| Total | 27 | 48 | | | |

In the Tables, a polymorphism with the symbol "del" corresponds to a deletion polymorphism, and the position number of each "polymorphism" correspond to the position number counting from A (position number: +1) of ATG (translation initiation codon) of the IRS-2 gene. A polymorphism shown by the position number with the symbol "−" is located 5' upstream of A of ATG (translation initiation codon) of the IRS-2 gene.

As shown in Tables 1 through 6, a subject having at least one of these six polymorphisms has showed association with the granulocytopenia by vesnarinone administration. In other words, these results suggest that one of these polymorphisms, "C-4587A", which is a polymorphism obtained through C to A conversion at position 4,587 upstream of the translation initiation codon of the human IRS-2 gene; "AT-2510del", which is a polymorphism obtained through AT deletion at position 2,510 upstream of the translation initiation codon of the coding region; "A-1164C", which is a polymorphism obtained through A to C conversion at position 1,164 upstream of the translation initiation codon of the coding region; "A15870G", which is a polymorphism obtained through A to G conversion at position 15,870 downstream from the translation initiation codon of the coding region; "A29793G", which is a polymorphism obtained through A to G conversion at position 29,793 downstream from the translation initiation codon of the coding region; and "C31532del", which is a polymorphism obtained through C deletion at position 31,532 downstream from the translation initiation codon of the coding region, is associated with granulocytopenia by vesnarinone administration. FIG. 1 shows the positions of these six polymorphisms in the human IRS-2 gene. In FIG. 1, "+1" corresponds to A of ATG (translation initiation codon).

Table 7 shows the results of analysis of linkage disequilibrium between these polymorphisms.

TABLE 7

| | D' | | | | |
|---|---|---|---|---|---|
| SNP | C-4587A | AT-2510del | A-1164C | A15870G | A29793G |
| AT-2510del | 1.000 | — | — | — | — |
| A-1164C | 1.000 | 1.000 | — | — | — |
| A15870G | 1.000 | 1.000 | 1.000 | — | — |
| A29793G | 0.956 | 0.956 | 0.957 | 1.000 | — |
| C31532del | 0.952 | 0.953 | 0.953 | 1.000 | 1.000 |

As is clear from Table 7, all the polymorphisms, which are intimately associated with granulocytopeniaby vesnarinone administration, are in almost complete linkage disequilibrium. Specifically, when the allele at position 4587 upstream of the translation initiation codon of the human IRS-2 gene is A (mutant type), each of the polymorphisms at the other five polymorphic sites has the genotype which shows association with granulocytopeniaby vesnarinone administration.

The results strongly suggest that these six polymorphisms of the human IRS-2 gene play an important role in the granulocytopenia by vesnarinone administration.

Recently, it has been reported that when HL-60 cells (myeloblasts) are differentiated into granulocytes by DMSO stimulation, the amount of IRS-2 protein is increased (Schacher, D. H., et al., J. Immunol., 164: 113-120 (2000)). This report suggests that IRS-2 is closely associated with granulocytic differentiation. Among the human IRS-2 gene polymorphisms analyzed or identified by the present inventors, three polymorphisms (C-4587A, AT-2510del, and A-1164C) are located in the promoter region, which regulates the transcription of the human IRS-2 gene. Therefore, it may be supported that the transcriptional levels of IRS-2 gene are reduced by these polymorphisms located in the promoter region, whereby a differentiation into granulocytes is also reduced.

Example 3

This Example is related to other methods for detecting the six polymorphisms of the human IRS-2 gene of the present invention. In this Example, these polymorphisms were detected through the below-described methods (a) and (b).

(a) Direct Sequencing

DNA fragments were amplified by use of forward primers (SEQ ID NOs: 1, 4, 7, 10, 13, and 15) and reverse primers (SEQ ID NOs: 2, 5, 8, 11, 14, and 16) described in Table 8, such that these amplified PCR products included the six polymorphisms according to the present invention. This operation was performed by DNA Engine PTC-0200 (MJ Research) or GeneAmp PCR System 9700 (PE Applied Biosystems) Each PCR was performed for 95° C. for 2 minutes; then 37 cycles of 94° C. for 30 seconds, the annealing temperature shown in Table 8 for 30 seconds, extension reaction at 72° C. for the time shown in Table 8 with final extension at 72° C. for 10 minutes. For each of the DNA fragments, as described in Table 8, the annealing temperature and the extension reaction time are 58° C. to 60° C. and 0.5 minutes to 3 minutes, respectively.

The component of a reaction mixture is as described in Example 2-(a). Notably, DMSO was added to the reaction mixture for detecting "A-1164C" such that the final concentration was 10% (see the column "DMSO" of Table 8).

G at position 23 of the reverse primer (SEQ ID NO: 14) employed for detection of "A29793G" described in Table 8 was a replaced base to create the polymorphic site that is recognized by the restriction enzyme Afa I.

The polymorphisms other than "A29793G" were detected by direct sequencing [the dideoxy method (Sanger, et al., Proc. Natl. Acad. Sci., U.S.A., 74, 5463-5467 (1977) or the Maxam-Gilbert method (Methods in Enzymology, 65, 499 (1980). Table 9 shows primers to determine genotype of each polymorphism (SEQ ID NOs: 3, 6, 9, 12, and 17).

TABLE 9

| | Primer for sequencing | Nucleotide position number in AL162497 |
|---|---|---|
| C-4587A | SEQ ID NO: 3 | 130343-130363 |
| AT-2510del | SEQ ID NO: 6 | 128581-128562 |
| A-1164C | SEQ ID NO: 9 | 126912-126929 |
| A15870G | SEQ ID NO: 12 | 110249-110231 |
| C31532del | SEQ ID NO: 17 | 94556-94537 |

(b) PCR-RFLP (Restriction Enzyme Fragment Length Polymorphism) Analysis

"PCR-RFLP (restriction enzyme fragment length polymorphism) analysis was performed to detect "A29793G". Specifically, a reaction mixture (20 μL) contained the PCR product (10 μL), 2 units of restriction enzyme Afa I (10 units/mL, Takara), and 10×Buffer T attached to the restriction enzyme (2 μL). BSA was added to the reaction mixture such that the final concentration was 0.01%, and the resultant mixture was incubated at 37° C. for 16 hours. Digested DNA fragments were separated by use of 4% agarose gel and visualized by ethidium bromide staining and ultraviolet transillumination.

When DNA extracted from a subject sample is applied to any of the detection methods for the six polymorphisms of the human IRS-2 gene described above in the Examples before administration of a drug which may induce granulocytopenia, there can be determined the possibility of an drug-induced granulocytopenia (including agranulocytosis); i.e., the risk of drug-induced granulocytopenia. Thus, according to the present invention, the risk of granulocytopenia attributed to vesnarinone administration can be examined or assessed by of the analysis of DNA from a subject.

TABLE 8

| | Forward primer | Nucleotide position number in AL162497 | Reverse primer | Nucleotide position number in AL162497 | Annealing temperature (° C.) | Extension time (min) | DMSO |
|---|---|---|---|---|---|---|---|
| C-4587A | SEQ ID NO: 1 | 131420-131399 | SEQ ID NO: 2 | 130318-130339 | 60 | 3 | − |
| AT-2510del | SEQ ID NO: 4 | 128930-128911 | SEQ ID NO: 5 | 127491-127510 | 60 | 3 | − |
| A-1164C | SEQ ID NO: 7 | 127837-127818 | SEQ ID NO: 8 | 126460-126479 | 60 | 3 | + |
| A15870G | SEQ ID NO: 10 | 110260-110240 | SEQ ID NO: 11 | 109859-109879 | 60 | 3 | − |
| A29793G | SEQ ID NO: 13 | 96209-96190 | SEQ ID NO: 14 | 96070-96091 | 58 | 0.5 | − |
| C31532del | SEQ ID NO: 15 | 94616-94595 | SEQ ID NO: 16 | 93139-93159 | 60 | 3 | − |

INDUSTRIAL APPLICABILITY

The present invention is useful for examining or assessing the risk of human drug-induced granulocytopenia, particularly useful for examining or assessing the risk of human drug-induced granulocytopenia before administration of a drug that has already been reported to induce granulocytopenia (including agranulocytosis).

The invention claimed is:

1. A method for determining whether a subject is at risk of developing vesnarinone-induced granulocytopenia said method comprising:

obtaining a sample from a subject;

extracting cDNA or genomic DNA from said sample;

detecting the presence of at least one polynucleotide polymorphism of the human insulin receptor substrate 2 gene in the polynucleotide sequence described by GenBank Accession No. AL162497 (version 20) (SEQ ID NO: 18), and correlating the presence of at least one polymorphism with an increased risk of developing vesnarinone-induced granulocytopenia in the subject; wherein said at least one polymorphism comprises a polymorphism C31532del that is G deletion between positions 94,356-94,357 of SEQ ID NO: 18.

2. The method of claim 1, wherein the polymorphism is detected through at least one technique selected from the group consisting of allele-specific oligonucleotide (ASO)-dot blot analysis, single nucleotide primer extension assay, PCR-single strand conformation polymorphism (SSCP) analysis, Invader assay, quantitative real-time PCR assay, and genetic polymorphism assay employing a mass spectrometer (mass array).

3. The method of claim 1, wherein the polymorphism is detected through direct nucleotide sequencing.

4. The method of claim 1, wherein the polymorphism is detected through PCR-restriction enzyme fragment length polymorphism (RFLP) analysis.

5. The method of claim 1, wherein said polymorphism is identified by a method employing a probe or primer which is an oligonucleotide having a sequence including a polymorphism that is G deletion at positions 94,356-94,357 of SEQ ID NO: 18.

6. The method of claim 1, wherein said polymorphism is identified by a method employing a probe which is an oligonucleotide having the sequence of SEQ ID NO: 17.

7. The method of claim 1, comprising assessing the risk of vesnarinone-induced granulocytopenia before vesnarinone administration.

8. The method of claim 1, further comprising obtaining a cDNA or genomic DNA sample from said subject.

* * * * *